US010653543B2

(12) United States Patent
Forsell

(10) Patent No.: US 10,653,543 B2
(45) Date of Patent: May 19, 2020

(54) APPARATUS FOR TREATING GERD

(76) Inventor: Peter Forsell, Bouveret (CH)

( * ) Notice: Subject to any disclaimer, the term of this patent is extended or adjusted under 35 U.S.C. 154(b) by 77 days.

(21) Appl. No.: 13/146,314

(22) PCT Filed: Jan. 29, 2010

(86) PCT No.: PCT/SE2010/050100
§ 371 (c)(1),
(2), (4) Date: Oct. 11, 2011

(87) PCT Pub. No.: WO2010/087773
PCT Pub. Date: Aug. 5, 2010

(65) Prior Publication Data
US 2012/0022561 A1 Jan. 26, 2012

Related U.S. Application Data

(60) Provisional application No. 61/213,813, filed on Jul. 17, 2009.

(30) Foreign Application Priority Data

Jan. 29, 2009  (WO) ................. PCT/SE2009/000051
Jul. 17, 2009  (SE) ...................................... 0900997
Oct. 12, 2009  (WO) ................. PCT/SE2009/051155

(51) Int. Cl.
*A61M 29/00* (2006.01)
*A61F 5/00* (2006.01)
(Continued)

(52) U.S. Cl.
CPC ............... *A61F 5/003* (2013.01); *A61B 1/04* (2013.01); *A61B 1/2736* (2013.01);
(Continued)

(58) Field of Classification Search
CPC ....... A61B 17/00; A61B 17/04; A61B 17/064; A61B 17/08; A61B 17/0469;
(Continued)

(56) References Cited

U.S. PATENT DOCUMENTS 245,533 A  *  8/1881  McChesney .............. A63F 9/12
                                                    273/160
393,816 A  *  12/1888  Chandler .................. A63F 9/12
                                                    273/160
(Continued)

FOREIGN PATENT DOCUMENTS

EP         1929957 A1     6/2008
WO      WO 0158391       8/2001
(Continued)

OTHER PUBLICATIONS

International Search Report for PCT/SE2010/050100, dated May 5, 2010.

*Primary Examiner* — Amy R Weisberg

(57) ABSTRACT

The present invention relates to a reflux disease treatment apparatus, comprising two or more movement restriction device segments adapted to form an implantable movement restriction device with an elongated shape that maintains cardia in the correct position. The movement restriction device has proximal and a distal end, wherein the distal end is adapted to stabilize and hold the proximal end. The invention further comprises a control device for controlling the stimulation device to stimulate the cardia sphincter. The distal end can be further adapted to treat obesity, for example by stretching the wall of the stomach or filling out a volume of the stomach.

10 Claims, 93 Drawing Sheets

(51) Int. Cl.
  *A61B 17/00* (2006.01)
  *A61B 17/04* (2006.01)
  *A61B 17/068* (2006.01)
  *A61N 1/36* (2006.01)
  *A61F 2/04* (2013.01)
  *A61B 17/08* (2006.01)
  *A61B 1/273* (2006.01)
  *A61B 1/04* (2006.01)
  *A61B 1/313* (2006.01)
  *A61B 17/064* (2006.01)
  *A61B 17/32* (2006.01)
  *A61B 17/34* (2006.01)
  *A61B 17/30* (2006.01)

(52) U.S. Cl.
  CPC ............ *A61B 1/3132* (2013.01); *A61B 17/00* (2013.01); *A61B 17/00234* (2013.01); *A61B 17/0469* (2013.01); *A61B 17/064* (2013.01); *A61B 17/068* (2013.01); *A61B 17/08* (2013.01); *A61B 17/30* (2013.01); *A61B 17/320016* (2013.01); *A61B 17/3423* (2013.01); *A61B 17/3474* (2013.01); *A61F 2/04* (2013.01); *A61F 5/0003* (2013.01); *A61F 5/004* (2013.01); *A61F 5/005* (2013.01); *A61F 5/0013* (2013.01); *A61F 5/0026* (2013.01); *A61F 5/0033* (2013.01); *A61F 5/0036* (2013.01); *A61F 5/0043* (2013.01); *A61F 5/0046* (2013.01); *A61F 5/0069* (2013.01); *A61F 5/0073* (2013.01); *A61F 5/0079* (2013.01); *A61F 5/0086* (2013.01); *A61F 5/0089* (2013.01); *A61N 1/36007* (2013.01); *A61B 17/0682* (2013.01); *A61B 2017/00278* (2013.01); *A61B 2017/00561* (2013.01); *A61B 2017/00818* (2013.01); *A61B 2017/00827* (2013.01); *A61B 2017/081* (2013.01); *A61B 2017/306* (2013.01); *A61B 2017/308* (2013.01); *A61F 5/0076* (2013.01); *A61F 2002/044* (2013.01); *A61F 2002/045* (2013.01); *A61F 2005/002* (2013.01); *A61F 2005/0016* (2013.01); *A61F 2005/0023* (2013.01); *A61F 2250/0001* (2013.01); *A61F 2250/0004* (2013.01)

(58) Field of Classification Search
  CPC .... A61B 2017/081; A61B 2017/00827; A61B 2017/306; A61B 2017/00561; A61B 2017/308; A61B 2017/00278; A61B 2017/00818; A61B 17/068; A61M 29/00; A61F 5/0089; A61F 5/0046; A61F 2/04; A61F 5/0069; A61F 5/0073; A61F 5/0033; A61F 5/0036; A61F 5/004; A61F 2005/0023; A61F 2250/0001; A61F 2250/0004; A61F 2005/0016
  See application file for complete search history.

(56) References Cited

U.S. PATENT DOCUMENTS

| | | | | |
|---|---|---|---|---|
| 1,471,943 A * | 10/1923 | Chambers | A63F 9/12 273/157 R |
| 2,041,030 A * | 5/1936 | Strutton | A63F 9/12 273/157 R |
| 2,201,724 A * | 5/1940 | Gable | A63F 9/12 273/157 R |
| D138,214 S * | 7/1944 | Miller | A63F 9/12 273/157 R |
| 2,574,158 A * | 11/1951 | Sullivan | A63F 9/12 273/160 |
| 3,303,604 A * | 2/1967 | Mote | A63H 33/06 273/160 |
| 3,372,936 A * | 3/1968 | Sanson | A63F 9/12 273/160 |
| 3,461,574 A * | 8/1969 | Larsen | A63F 9/06 273/156 |
| 3,546,792 A * | 12/1970 | Sherman | A63H 33/088 273/160 |
| 3,565,442 A * | 2/1971 | Burton | A63F 9/12 273/157 R |
| 3,659,360 A * | 5/1972 | Zeischegg | G09B 23/04 273/155 |
| 3,721,448 A * | 3/1973 | Coffin | A63F 9/12 273/160 |
| 3,840,234 A * | 10/1974 | Felsten | A63F 9/06 273/113 |
| 3,885,794 A * | 5/1975 | Coffin | A63F 9/12 273/160 |
| 4,113,256 A * | 9/1978 | Hutchings | A63F 9/06 273/160 |
| 4,121,831 A * | 10/1978 | Greene | A63F 9/12 273/160 |
| 4,133,538 A * | 1/1979 | Ambrose | A63F 3/00 273/157 R |
| 4,153,254 A * | 5/1979 | Marc | A63F 9/12 273/160 |
| 4,258,479 A * | 3/1981 | Roane | A63H 33/046 434/211 |
| 4,323,245 A * | 4/1982 | Beaman | A63F 9/1288 273/157 R |
| 4,597,579 A * | 7/1986 | Walton | A63F 9/12 273/156 |
| 4,676,507 A * | 6/1987 | Patterson | A63F 9/12 273/160 |
| 4,711,241 A * | 12/1987 | Lehmann | A61L 17/145 427/2.31 |
| 5,118,111 A * | 6/1992 | Suitor | A63F 9/12 273/160 |
| 5,230,508 A * | 7/1993 | Tabler | A63F 9/10 273/157 R |
| 5,593,337 A * | 1/1997 | Lapointe | A63H 33/084 446/125 |
| 5,826,873 A * | 10/1998 | Lavermicocca | A63F 9/12 273/157 R |
| 5,846,114 A * | 12/1998 | Frandsen, II | E04H 17/1404 446/106 |
| 6,095,521 A * | 8/2000 | Patel | A63F 9/12 273/156 |
| 6,601,849 B1 * | 8/2003 | Konkle | A63F 9/12 273/156 |
| D490,482 S * | 5/2004 | Chuang | D21/479 |
| D497,398 S * | 10/2004 | Chuang | D21/479 |
| D511,798 S * | 11/2005 | Chuang | D21/479 |
| 7,502,649 B2 * | 3/2009 | Ben-Haim et al. | 607/40 |
| D616,624 S * | 5/2010 | Steuer | D99/5 |
| D645,911 S * | 9/2011 | Kock | D21/479 |
| 8,100,931 B2 * | 1/2012 | Baker et al. | 606/191 |
| 8,657,288 B2 * | 2/2014 | Fletcher | A47G 19/2227 273/157 R |
| 9,458,872 B2 * | 10/2016 | Nelson | F16B 7/0446 |
| 2003/0021822 A1 * | 1/2003 | Lloyd | A61F 2/00 424/423 |
| 2003/0163029 A1 | 8/2003 | Sonnenschein et al. | |
| 2004/0044353 A1 * | 3/2004 | Gannoe | A61B 17/00234 606/153 |
| 2004/0260316 A1 | 12/2004 | Knudson et al. | |
| 2005/0236277 A9 * | 10/2005 | Imran et al. | 205/317 |
| 2005/0245957 A1 | 11/2005 | Starkebaum et al. | |
| 2005/0261712 A1 | 11/2005 | Balbierz et al. | |
| 2005/0267596 A1 | 12/2005 | Chen et al. | |
| 2005/0273060 A1 * | 12/2005 | Levy et al. | 604/192 |
| 2006/0089571 A1 * | 4/2006 | Gertner | 600/593 |
| 2006/0142635 A1 * | 6/2006 | Forsell | 600/29 |
| 2006/0149124 A1 * | 7/2006 | Forsell | 600/40 |
| 2006/0195139 A1 * | 8/2006 | Gertner | 606/201 |

(56) References Cited

U.S. PATENT DOCUMENTS

| | | | |
|---|---|---|---|
| 2006/0235448 A1* | 10/2006 | Roslin et al. | 606/157 |
| 2006/0286284 A1* | 12/2006 | Mistry | A23G 3/42 |
| | | | 426/660 |
| 2007/0100369 A1* | 5/2007 | Cragg et al. | 606/192 |
| 2007/0104755 A1 | 5/2007 | Sterling et al. | |
| 2007/0156248 A1* | 7/2007 | Marco et al. | 623/23.7 |
| 2007/0178160 A1* | 8/2007 | Burnett | 424/484 |
| 2007/0179556 A1* | 8/2007 | Ben Haim et al. | 607/40 |
| 2007/0233170 A1* | 10/2007 | Gertner | 606/192 |
| 2007/0250132 A1* | 10/2007 | Burnett | 607/40 |
| 2007/0276428 A1* | 11/2007 | Haller | A61F 5/0003 |
| | | | 606/192 |
| 2008/0027473 A1* | 1/2008 | Bjerken | 606/157 |
| 2008/0086179 A1 | 4/2008 | Sharma | |
| 2008/0147002 A1* | 6/2008 | Gertner | 604/104 |
| 2008/0154289 A1* | 6/2008 | Roslin | 606/153 |
| 2008/0161717 A1* | 7/2008 | Gertner | 600/561 |
| 2008/0249635 A1* | 10/2008 | Weitzner | A61F 5/0003 |
| | | | 623/23.65 |
| 2008/0275296 A1* | 11/2008 | Forsell | 600/41 |
| 2008/0275484 A1* | 11/2008 | Gertner | 606/192 |
| 2008/0300618 A1* | 12/2008 | Gertner | 606/192 |
| 2009/0157107 A1* | 6/2009 | Kierath et al. | 606/157 |
| 2009/0192404 A1* | 7/2009 | Ortiz et al. | 600/547 |
| 2009/0275962 A1* | 11/2009 | Zeiner et al. | 606/151 |
| 2010/0100079 A1* | 4/2010 | Berkcan et al. | 604/891.1 |
| 2010/0114144 A1* | 5/2010 | Albrecht et al. | 606/191 |
| 2010/0114146 A1* | 5/2010 | Albrecht et al. | 606/191 |
| 2010/0145139 A1* | 6/2010 | Forsell | 600/30 |
| 2010/0145301 A1* | 6/2010 | Magal | 604/503 |
| 2010/0185225 A1* | 7/2010 | Albrecht et al. | 606/191 |
| 2010/0191270 A1* | 7/2010 | Garza Alvarez | 606/192 |
| 2010/0211085 A1* | 8/2010 | Uth et al. | 606/151 |
| 2010/0305468 A1* | 12/2010 | Policker et al. | 600/547 |
| 2010/0312047 A1* | 12/2010 | Forsell | 600/37 |
| 2010/0331616 A1* | 12/2010 | Forsell | 600/37 |
| 2011/0009895 A1* | 1/2011 | Gertner | 606/191 |
| 2011/0068143 A1* | 3/2011 | Laufer et al. | 227/175.1 |
| 2011/0130625 A1* | 6/2011 | Lior et al. | 600/37 |
| 2011/0184230 A1* | 7/2011 | Forsell | 600/41 |
| 2011/0192402 A1* | 8/2011 | Forsell | 128/843 |
| 2011/0196194 A1* | 8/2011 | Forsell | 600/31 |
| 2011/0196411 A1* | 8/2011 | Forsell | 606/191 |
| 2011/0201873 A1* | 8/2011 | Forsell | 600/30 |
| 2011/0207994 A1* | 8/2011 | Burrell et al. | 600/37 |
| 2011/0208231 A1* | 8/2011 | Forsell | 606/193 |
| 2012/0041463 A1* | 2/2012 | Forsell | 606/191 |
| 2012/0095492 A1* | 4/2012 | Babkes et al. | 606/192 |
| 2012/0116182 A1* | 5/2012 | Wong et al. | 600/301 |
| 2012/0245412 A1* | 9/2012 | Lau et al. | 600/37 |
| 2012/0245553 A1* | 9/2012 | Raven et al. | 604/500 |
| 2013/0190557 A1* | 7/2013 | Hoover et al. | 600/37 |
| 2013/0218190 A1* | 8/2013 | Gaur et al. | 606/192 |
| 2014/0276546 A1* | 9/2014 | Connor | 604/503 |
| 2014/0277249 A1* | 9/2014 | Connor | 607/40 |

FOREIGN PATENT DOCUMENTS

| | | |
|---|---|---|
| WO | 2004112563 A1 | 12/2004 |
| WO | 2005018468 A1 | 3/2005 |
| WO | 2006044640 A1 | 4/2006 |
| WO | WO 2008/016776 | 2/2008 |
| WO | WO 2009096868 | 8/2009 |

* cited by examiner

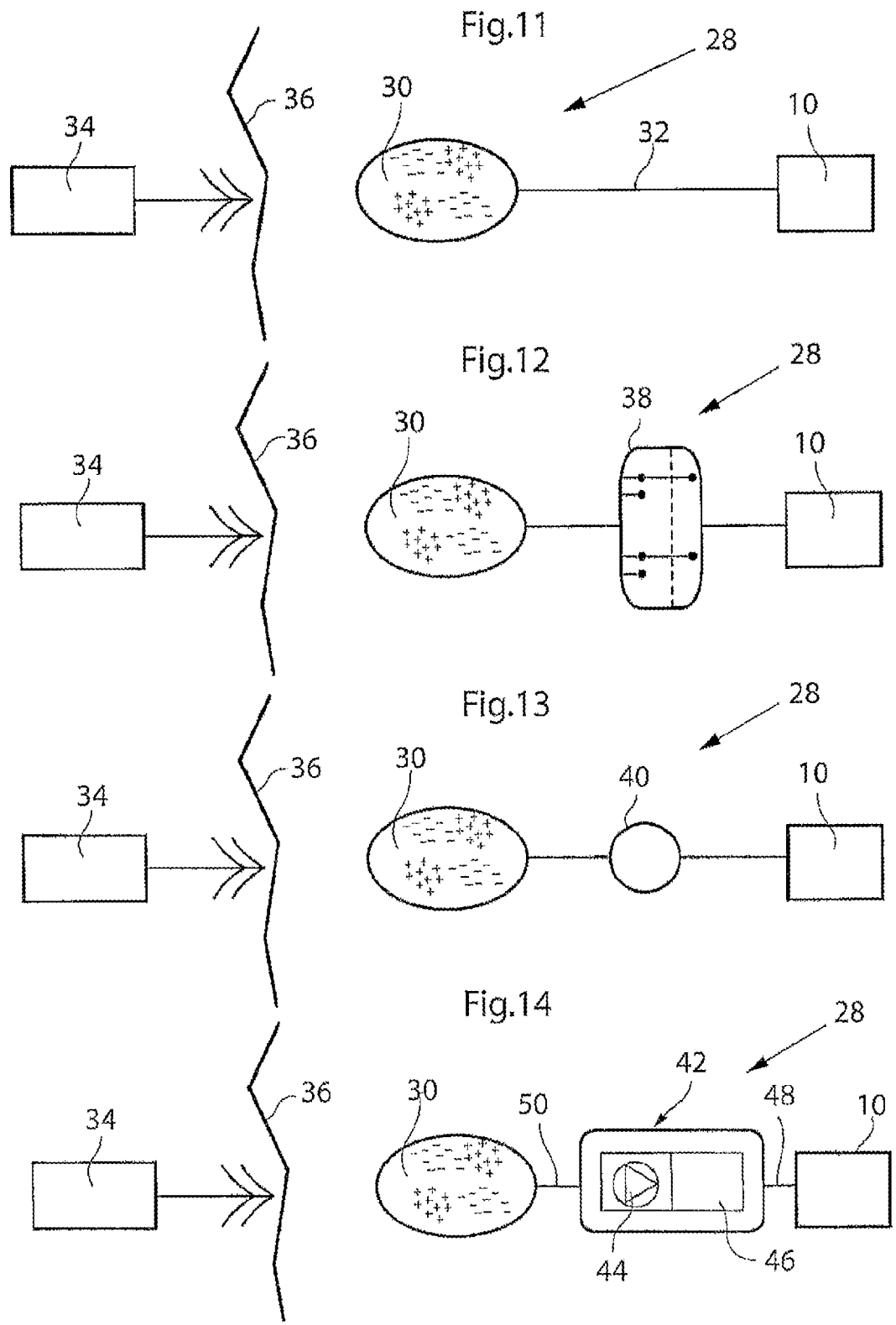

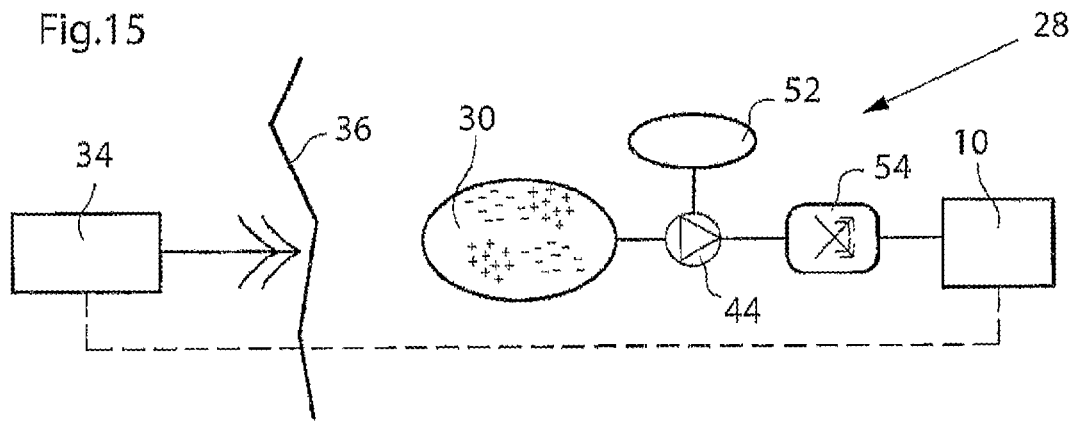
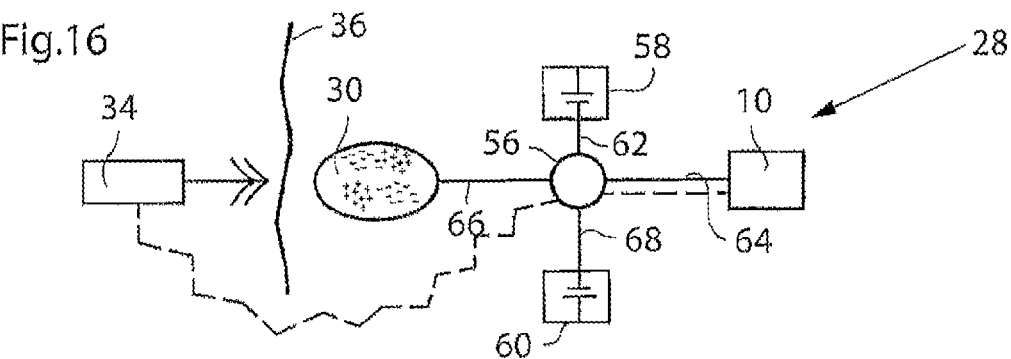
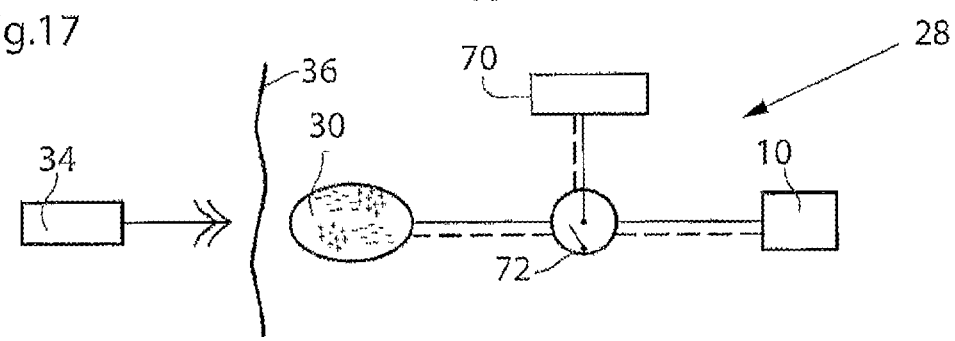
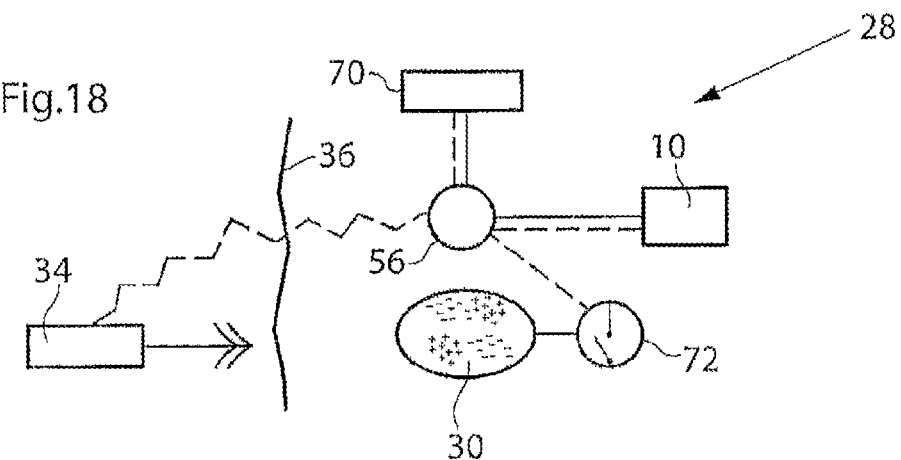

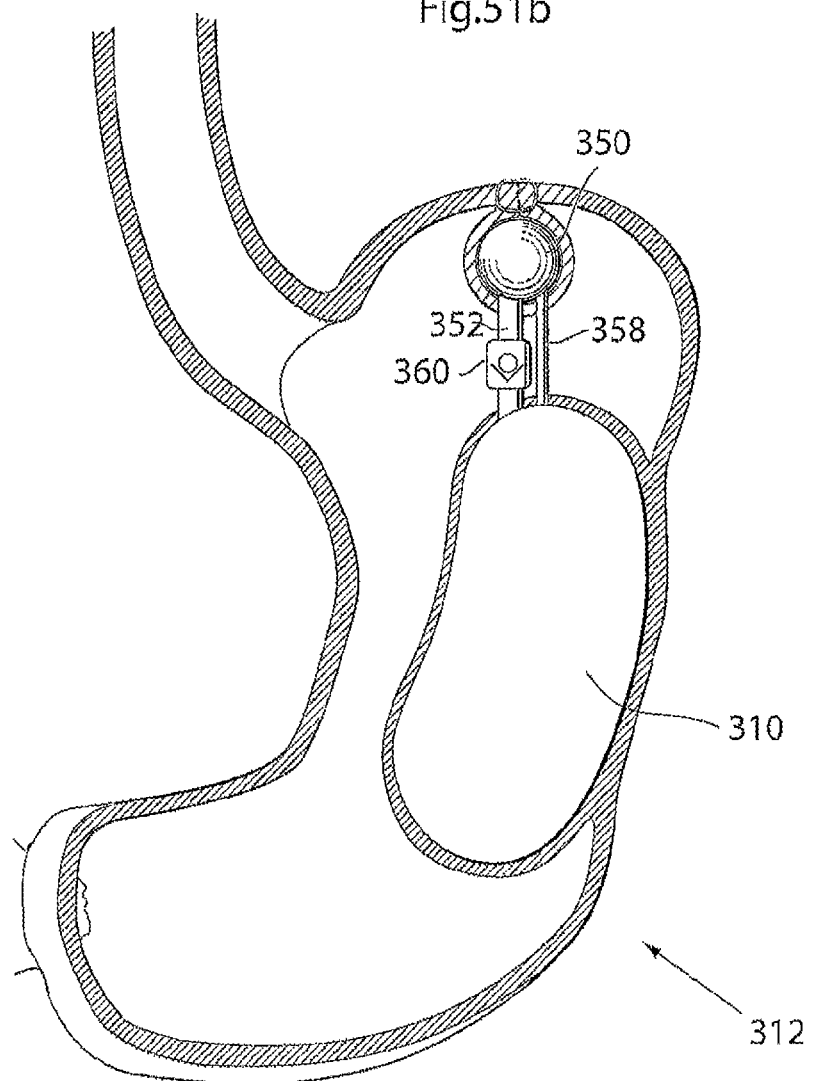

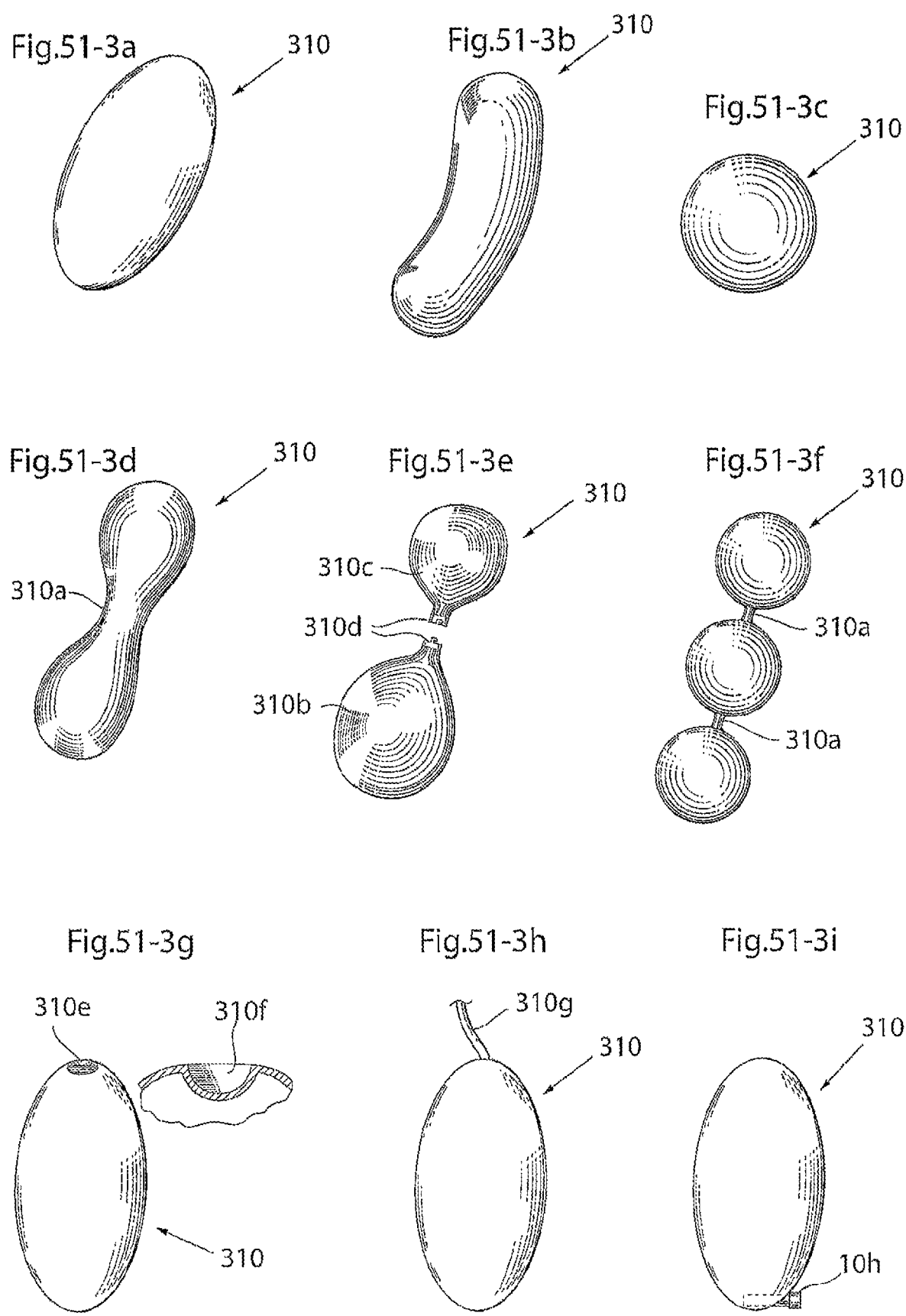

Fig.73a
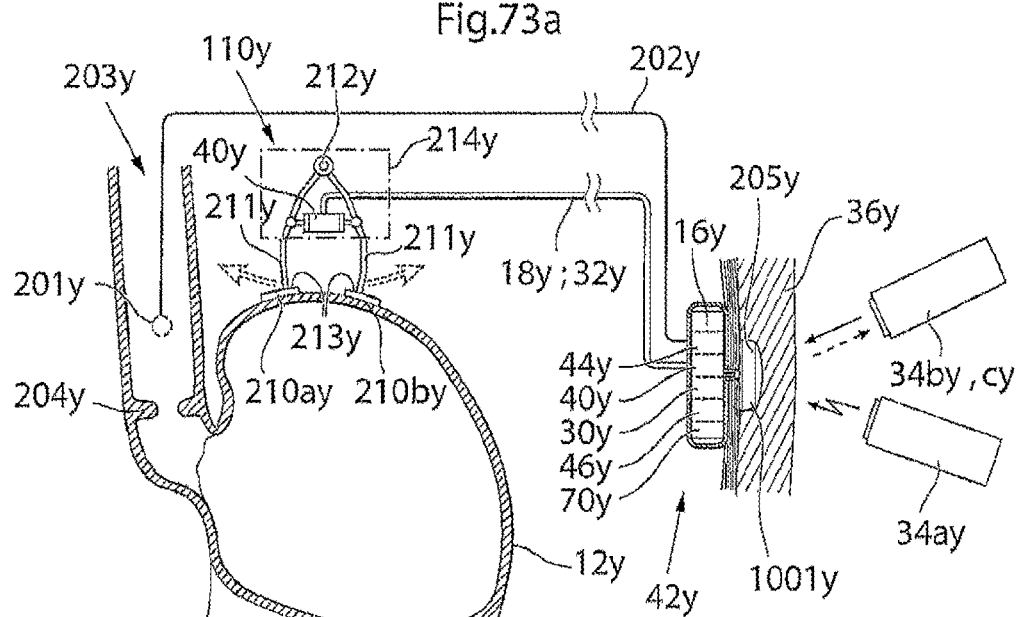
Fig.73b "Net to put over the feet"
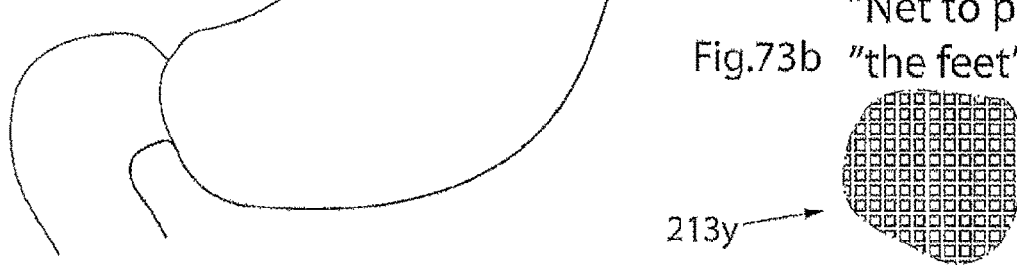
Fig.73c
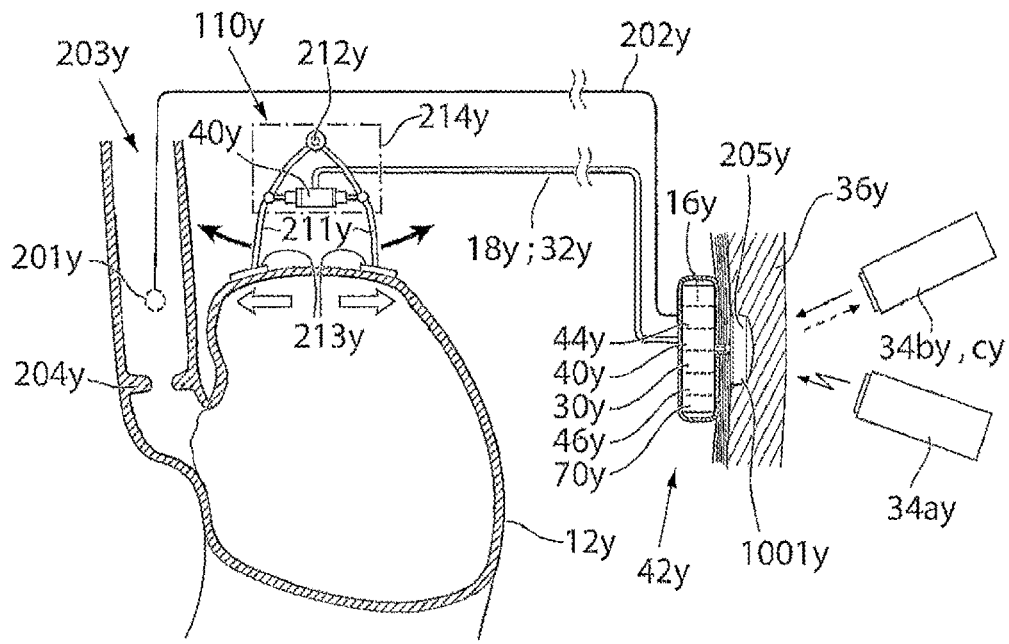

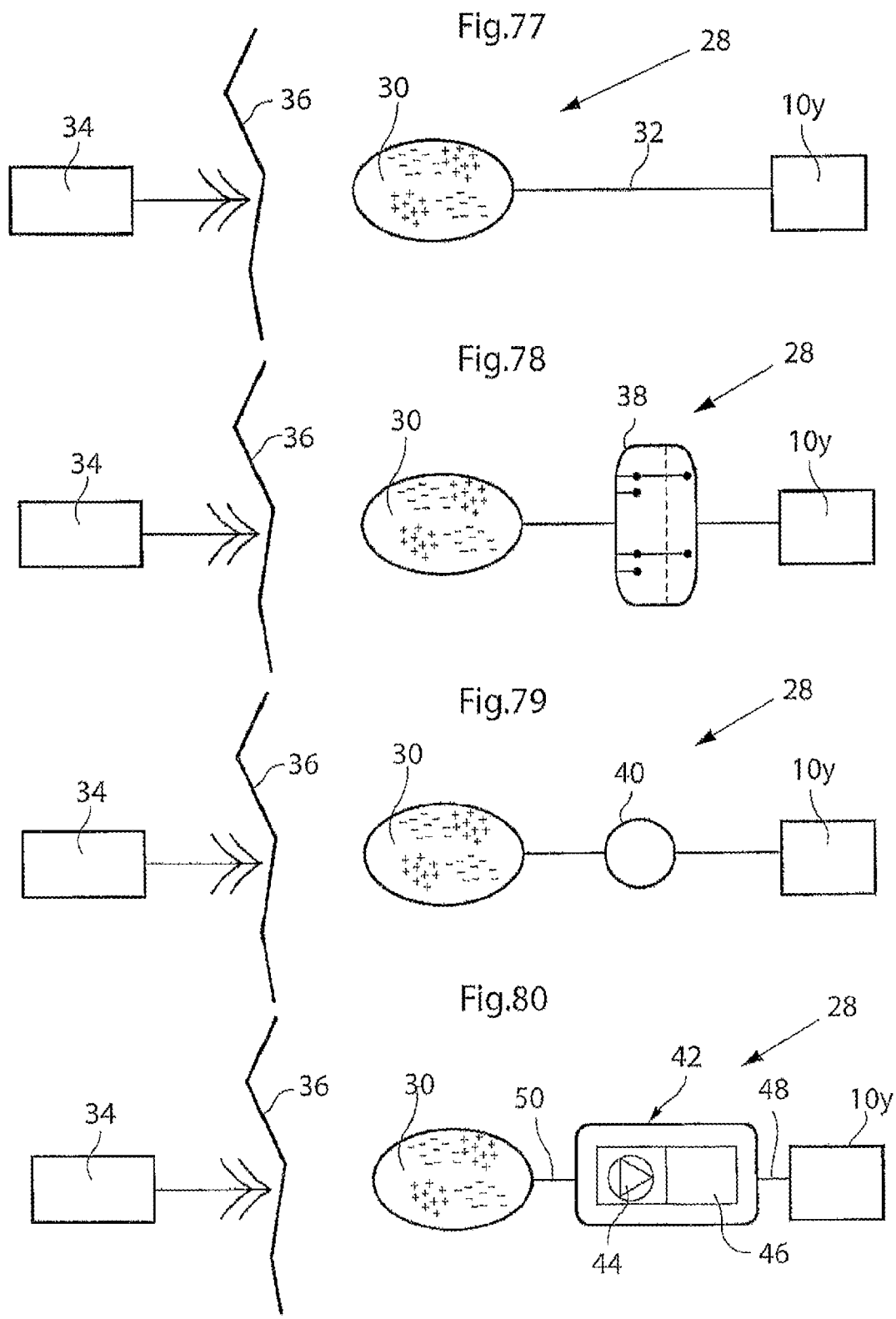

US 10,653,543 B2

APPARATUS FOR TREATING GERD

This application is the U.S. national phase of International Application No. PCT/SE20101050100, filed 29 Jan. 2010, which designated the U.S. and claims priority to International Application Nos. PCT/SE2009/000051, filed 29 Jan. 2009 and PCT/SE2009/051155, filed 12 Oct. 2009, and to Swedish application No. 0900997-8 filed 17 Jul. 2009; and claims the benefit of U.S. Provisional Application No. 61/213,813, filed 17 Jul. 2009, the entire contents of each of which are hereby incorporated by reference.

TECHNICAL FIELD

The present invention relates to an apparatus for treating Gastro Esophageal Reflux Disease (GERD).

The present invention relates to a reflux disease treatment apparatus, comprising an implantable elongated movement restriction device having a proximal part that maintains the cardia in the correct position and a distal part that stabilizes the proximal part and is adaptable to additional treat obesity. The apparatus may further comprise an implantable stimulation device adapted to engage with the cardia sphincter of a patient and a control device for controlling the stimulation device to stimulate the cardia sphincter. The invention can be further combined with various methods for treating obesity, in particular methods that creates satiety by stretching the wall of the stomach or fills out a volume of the stomach.

BACKGROUND ART

Gastro Esophageal Reflux Disease (GERD), or acid reflux disease, is a chronic condition resulting in mucosal damage in the esophagus produced by the recurring occurrence of acid reflux in the esophagus. This is commonly due to transient or permanent changes in the barrier between the esophagus and the stomach. This can be due to incompetence of the lower esophageal sphincter (IES), transient IES relaxation, impaired expulsion of gastric reflux from the esophagus, or a hiatal hernia.

Gastro Esophageal Reflux Disease can be treated in a number of different ways. Treatment include, but are not limited to, both medical and surgical treatment. A standard surgical treatment, which sometimes is preferred over long-time use of medication, is Nissen fundoplication surgery, in which the upper curve of the stomach (the fundus) is wrapped around the IES to strengthen the sphincter and prevent acid reflux and to repair a hiatal hernia. The procedure is often done laparoscopically.

Another surgical treatment which has been used is the Anglechik prosthesis, in which a device formed like a horseshoe is placed around the esophagus above the cardia. The intended effect is to prevent the cardia from slipping up into the thorax cavity. However, this device has a number of complications, including migrating through and damaging the esophagus.

From experience with implantation of medical devices, it is known that sutures between an implanted device and human tissue will not hold over the long term. For long term implantation of a device, there are two possibilities to keep the device in place. A first solution has been to suture human tissue to human tissue, to thereby keep the device in place. A second approach has been to provide sutures holding a device in place in the short term and to allow in-growth of human tissue into the device for holding the device in place over the long term.

A problem with providing an implantable device associated with the esophagus is that the outer surface of the esophagus is only comprised of esophagus muscle tissue, which is very easy to damage or migrate through. This is probably one reason why the Anglechik prosthesis described above has resulted in many complications, such as migration.

The stomach, on the other hand, has a serosa on its outside, thereby providing a much stronger membrane for suturing. Thus, suturing a device directly to the stomach wall provides a better result than suturing an implanted device to the esophagus.

Today, there exists a need for a long term treatment of GERD that is more effective than prior treatments and which does not result in any severe complications.

SUMMARY OF INVENTION

It is an object of the present invention to overcome, or at least reduce, some of the problems associated with existing surgical treatments of Gastro Esophageal Reflux Disease (GERD). It is another object of the present invention to provide an apparatus for treating Gastro Esophageal Reflux Disease. These objects and others are obtained by the apparatus described in the appended claims.

An object of the present invention is to provide reflux disease treatment apparatus with improved long term properties which also can be additionally provided with obesity treatment functions.

This object and others are obtained by an apparatus described in the appended claims. In general terms, the present invention relates to an apparatus for treating reflux disease in a human or animal mammal patient comprising two or more movement restriction device segments to form an implantable movement restriction device having an outer surface with an elongated shape adapted to be at least partly be invaginated by a stomach wall portion of a patient. The movement restriction device has, when implanted in a patient, a proximal part and a distal part, and the device is adapted to rest at least partially with the outer surface of its proximal part against the patient's stomach fundus wall, in a position between the patient's diaphragm and the fundus wall, such that movement of the cardiac notch of the patient's stomach towards the patient's diaphragm is restricted, when the movement restriction device is implanted in the patient, to thereby prevent the cardia from sliding through the patient's diaphragm opening into the patient's thorax, so as to maintain the supporting pressure against the patient's cardia sphincter muscle exerted from the patient's abdomen. The device is also adapted to stabilize and hold the proximal part by the distal part adapted to be substantially invaginated in the stomach wall in order to prevent the cardia from sliding through the patient's diaphragm opening into the patient's thorax. The terms "proximal" and "distal" have the usual anatomical meaning. Accordingly, proximal as an anatomical position means nearest the center of the body, or at the beginning of a structure. In the present context proximal and distal refer to parts of the movement restriction in its implanted position. The length of the distal invaginated part of the elongated movement restriction device is sufficiently long to stabilize the proximal part of the elongated movement restriction device to prevent the cardia from sliding through the patient's diaphragm opening into the patient's thorax. The circumference of the distal invaginated part of the elongated movement restriction device is such that it is stabilizing the proximal part of the elongated movement restriction device to prevent the cardia from sliding through the patient's diaphragm opening into the patient's thorax. The proximal part of the movement restriction device has a size of at least 125 mm3 and a circumference of at least 15 mm.

Preferably, the apparatus comprises an implantable first fixation device that secures the proximal part of the movement restriction device in a position that restrict the movement of the cardiac notch of the stomach towards the patient's diaphragm, with the outer surface of the movement restriction device substantially contacting the patient's stomach fundus wall. The first fixation device may include sutures or staples that attach together portions of the fundus stomach wall that enclose the proximal part of the movement restriction device to secure the movement restriction device in said position, i.e., the movement restriction device is at least partly placed in an invaginated space. Thus, by affixing the proximal part of the implantable movement restriction device indirectly in this manner, no suturing between the movement restriction device and tissue is required, which, in turn, further reduces the risk for complications. Keeping the proximal part of the movement restriction device in place in this manner has resulted in an elastic suspension with improved long term properties.

The first fixation device, such as sutures or staples, attach together portions of the fundus stomach wall so at to invaginate the proximal part of the movement restriction device from either inside or outside of the patient's stomach wall.

Alternatively, a tissue growth promoting structure may be sutured to the stomach wall with a relatively large contact surface towards the stomach. The relatively large surface of the structure, such as a net, will allow for in-growth of human tissue for holding the proximal part of the movement restriction device in place over the long term. The tissue growth promoting structure may comprise sutures or staples that attach the netlike structure to the fundus stomach wall.

In addition to affixing the proximal part of the movement restriction device to the stomach wall a second fixation device may be employed. The second fixation device can be used to affix the proximal part of movement restriction device in relation to the cardia. For example, the proximal part of the movement restriction device can be affixed in a position above the cardia, between the cardia and the diaphragm muscle, by a second direct or indirect affixation of the proximal part of the movement restriction device via the fundus stomach wall. The second fixation device may secure, indirectly or directly, the proximal part of the movement restriction device to the esophagus close to the patient's angle of His. The second fixation device suitably includes a plurality of sutures or staples that attach the fundus wall and a wall of the patient's esophagus to hold the movement restriction device in said position.

The apparatus may also comprise a third fixation device that secures, indirectly or directly, the proximal part of the movement restriction device to the patient's diaphragm muscle or other muscle tissue. The third fixation device suitably comprises a plurality of sutures or staples that attach the fundus wall and the diaphragm muscle or other muscle tissue to hold the movement restriction device in said position.

The proximal part of the movement restriction device may be adapted to be substantially or completely invaginated by the patient's stomach fundus wall, and be placed either on the inside or outside of the stomach fundus wall.

The proximal part of the movement restriction device may be adapted to be placed on the outside of the patient's stomach wall, such that the stomach cavity is substantially reduced, by a volume substantially exceeding the volume of the movement restriction device.

At least a part of the proximal part of the movement restriction device may be made of a material which is destructible or not destructible by stomach acid.

In an embodiment, the proximal part of the movement restriction device is inflatable and adapted to be inflated with a gel or fluid. A fluid or gel receiving member for receiving fluid to inflate the movement restriction device may be provided.

The proximal part of the movement restriction device may include a homogenous material and may be a solid body.

The proximal part of the movement restriction device may include an enclosure wall defining a chamber.

The proximal part of the movement restriction device may have a rigid, elastic or flexible outer wall. Where the outer wall is rigid, it is rigid enough to maintain non-deformed when subject to forces created by stomach movements.

In accordance with a preferred embodiment of the apparatus, the proximal part of the movement restriction device comprises a body adapted to be at least partly invaginated by the patient's stomach fundus wall and having an outer surface that includes a biocompatible material. A substantial part of the outer surface of the body is adapted to rest against the stomach wall in said position between the patient's diaphragm and the portion of the lower part of the invaginated stomach fundus wall. Suitably, the body is made of a material softer than 25 or 15 Shore.

In accordance with a first general design of the body, the body has a maximum circumference as seen in a plane perpendicular to an axis through the body. The circumferences of the body as seen in other planes perpendicular to said axis are equal to the maximum circumference or decrease as seen along said axis in the direction from the maximum circumference. For example, the body may be substantially egg shaped, spherically shaped, or substantially shaped like an egg with an indented middle section or like a bent egg.

In accordance with a second general design of the body, the circumference of the body as seen in a plane perpendicular to an axis through the body increases and decreases at least two times as the plane is displaced along said axis, or decreases and increases at least one time as the plane is displaced along said axis. For example, the body may be substantially shaped like a kidney.

Preferably, the body is dimensioned with a size larger than the intestinal outlet from the stomach. The body may have a smallest outer diameter of 30 or 40 mm or larger and may have a smallest outer circumference of 150, 110, 90, 70, 50 or 30 mm.

Suitably, the body has rounded contours without too sharp edges that would be damaging to the patient's stomach wall, and has a generally smooth outer surface for resting against the fundus wall.

The body is implantable either inside or outside of the patient's stomach and is adapted to be attached to the patient's stomach wall by surgery. The body may be changeable to assume a slender form having a smaller diameter than that of a trocar for laparoscopic use, whereby the body when changed to said slender form can be pushed or pulled through the trocar. The body may include a flexible outer wall defining a chamber filled with a fluid, such as a gel, allowing the body to pass through such a trocar. Alternatively, the body may include an elastic compressible material, allowing the body to pass through a trocar.

The body may be hollow and include at least two separate pieces adapted to be inserted into the hollow body, and further adapted to be put together to one unitary piece inside the body, thereby allowing the body to pass through a trocar for laparoscopic use. Alternatively, the body may include an outer wall and a hollow compressed inner part, for being filled with a fluid or gel after insertion into the patient's body.

The body may include a chamber with an injection port, wherein the chamber of the body is filled with a fluid through the injection port.

The body may include at least one holding device adapted to be used for pushing or pulling the body through a trocar for laparoscopic use. The holding device is adapted to hold a prolongation of the body that is adapted to be held by a surgical instrument. More specifically, the holding device is adapted to hold a thread or band inserted through the holding device. Where the body comprises an outer wall the holding device is at least partly placed inside the outer wall of the body.

In one embodiment the apparatus according to the invention further comprise an adjustment device for adjusting at least the proximal part of the movement restriction device. For this purpose, the movement restriction device can comprise a body, the size of which is hydraulically adjustable, and the adjustment device can comprise a hydraulic fluid reservoir that when implanted in the patient, is connected to the body, and wherein the body's size is non-invasively regulated by manually pressing the hydraulic fluid reservoir so as to adjust the amount of hydraulic fluid supplied to the body and thereby the body's size. The apparatus can further comprise a hydraulic regulation device comprising at least one chamber that when implanted in the patient, is invaginated in the patient's stomach wall with the body and connected to the body, and wherein the amount of hydraulic fluid contained in the body is non-invasively regulated by distributing fluid between the hydraulic reservoir and the at least one chamber. Preferably, the at least one chamber is, when implanted in the patient, filled with the hydraulic fluid using a pump in the reservoir so as to stretch the fundus wall to create satiety in the patient. Further, the adjustment device further can comprise a reverse servo, wherein a small volume of fluid in the reservoir is compressed with a higher force and the chamber creates a movement of a larger total volume with less force per unit of volume. In one embodiment, the body forms a first chamber, further comprising at least one additional body forming a second chamber smaller than the first chamber, the first and second chambers being in contact with each other, preferably in fluid communication with each other. The hydraulic reservoir is preferably adapted to be placed subcutaneously in the patient and the hydraulic reservoir is preferably adapted to be placed in the patient's abdomen. The hydraulic reservoir may have a wall defining the volume thereof, and the volume of the hydraulic reservoir is regulated by moving a wall portion of the wall of the hydraulic reservoir. The apparatus can comprise a motor for moving the wall portion. The hydraulic regulation device can comprise a pump, and the hydraulic reservoir is regulated by the pump pumping fluid between the hydraulic reservoir and said at least one chamber. A mechanical device can operatively connected to the hydraulic regulation device to be moved as the hydraulic regulation device is operated. In one embodiment, at least the proximal part of the movement restriction device is mechanically regulated. The apparatus can further comprise a motor for mechanically regulating the movement restriction device.

In one embodiment, the apparatus according further comprises a second body that when implanted in the patient with the body, fills two volumes, respectively, at two different park of the patient's the stomach, thereby affecting the patient's reflux. The reflux disease treatment device is adapted to be postoperatively and non-invasively regulated, and adapted to be regulated from time to time such that at a first time one of the filling bodies fills the volume at one of the parts of the stomach and at a second time the other of the filling bodies fills the volume at the other part of the stomach.

In one embodiment, the apparatus according to the invention comprises an adjustment device for adjusting the size and/or shape of the movement restriction device. The size of the movement restriction device can be hydraulically adjustable, and the adjustment device can comprises a hydraulic fluid reservoir that when implanted in the patient, is connected to the movement restriction device, and the size of the movement restriction device can be non-invasively regulated by moving hydraulic fluid between the hydraulic fluid reservoir and the movement restriction device. The movement restriction device may be seen as a body. The apparatus can further comprise a hydraulic regulation device comprising at least one chamber that when implanted in the patient, is invaginated in the patient's stomach wall with the body and connected to the body, and wherein the amount of hydraulic fluid contained in the body is non-invasively regulated by distributing fluid between the hydraulic reservoir and the at least one chamber. The at least one chamber can, when implanted in the patient, be filled with the hydraulic fluid using a pump in the reservoir so as to stretch the fundus wall to create satiety in the patient. Further, the adjustment device can comprise a reverse servo comprising three adjustable reservoirs with hydraulic fluid, wherein a small volume of fluid in a first reservoir placed subcutaneously, being part of a first closed system including a second reservoir, is compressed with a high force per area unit for moving a small volume of hydraulic fluid, and wherein the second reservoir affects a larger volume of hydraulic fluid in a third reservoir, the third reservoir being part of a second closed system having larger volume than said first reservoir, thereby creating a movement of a larger total volume of hydraulic fluid with less force per area unit.

In a special embodiment, the movement restoration device as outlined in the previous sections comprises two or more movement restriction device segments, preferably comprising more than three segments, adapted to be assembled to an implantable assembled movement restriction device of a controlled size involving at least the proximal part of the movement restriction device. The assembled movement restriction device is adapted to rest with at least a part of its outer surface against the patient's stomach fundus wall, in a position between the patient's diaphragm and the fundus wall, such that movement of the cardiac notch of the patient's stomach towards the patient's diaphragm is restricted, when the movement restriction device is implanted in the patient, to thereby prevent the cardia from sliding through the patient's diaphragm opening into the patient's thorax, so as to maintain the supporting pressure against the patient's cardia sphincter muscle exerted from the patient's abdomen. The assembled movement restriction device preferably is adapted to disassemble into its segments if it leaves its implanted position of at least partially contacting the stomach fundus wall in a position between the diaphragm and the fundus wall. Preferably, the assembled movement restriction device is adapted to be invaginated in the stomach wall, and to disassemble into its segments if it leaves its implanted stomach position including penetrating the stomach wall to retain a position inside the stomach. The segments are preferably adapted to separately pass through the food passage way, thereby reducing risk of causing obstruction/ileus in the patient's intestine. The movement restriction device segments can be adapted to pass through a trocar, for assembly and implantation of said movement restriction device into the abdominal cavity. The movement restriction device segments can have a flexible outer shape adapted to pass through a trocar. The movement restriction device segments can be adapted to have a shape allowing them to be assembled into said movement restriction device, when implanted. In one embodiment, the movement restriction device segments are hollow with a flexible outer surface. The movement restriction device segments can be adapted to be filled with at least one of a fluid a foam, a gel or a fluid that hardens to a solid material. In one embodiment the movement restriction device segments are solid. It is preferred that the movement restriction device segments are adapted to temporary be holding their assembled position, preferably by the invaginated stomach wall, or alternatively by an adhesive.

For its assembly, the movement restriction device is provided with at least one assembly element that sufficiently fits with at least one assembly element of another segment, so the segments by fitting assembly elements can be assembled into the implantable movement restriction device. Preferably, the segments for this purpose comprise a core part and a plurality of outer parts, and preferably, the at least one assembly element is selected among sufficiently fitting flanges and slits. The core part is adapted to receive and assemble the outer elements into an implantable movement restriction device, and preferably the core part has assembly slits adapted to receive corresponding assembly flanges of the outer parts when assembling the movement restriction device. In one embodiment the slits are distributed around the outer peripheral area of the core part. The outer parts are then provided with flanges sufficiently matching the slits to assemble the device. In another embodiment, the at least one assembly element immobilizes each of the movement restriction device segments to a core part along a first plane, and wherein movement, and wherein the movement restriction device segments and the core part further comprises a second assembly element, which following the assembly of said segments and core part, immobilize each segment and core part along a second plane in an angle to said first plane. For example, the first plane and the second plane can be substantially perpendicular. The second assembly element comprises mating elements, preferably with matching protrusions and recesses provided on the movement restriction device segments and the core part, while the at least one assembly element further comprises protrusions and recesses. Preferably, the at least one assembly element comprises an assembly slit in the core part and an assembly flange in a segment, and wherein a mating element comprises a protrusion in said slit and a recess in said flange; or alternatively, the at least one assembly element comprises an assembly flange in the core part and an assembly slit in a segment, and wherein the a mating element comprises a protrusion in said slit and a recess in said flange.

In one particular embodiment, the apparatus preferably further comprises a guiding device, operable for assembling the movement restriction device segments to an implantable movement restriction device. Preferably, the guiding device is an operation wire operably connected to the segments.

The operation wire can be made of a material that is biodegradable in contact with the body fluid in the abdominal cavity so as to facilitate disassembly of the movement restriction device into its segments. In order to assist with assembly procedure, each segment can be provided with at least one assembly element that sufficiently fits with at least one assembly element of another segment, so the segments by fitting assembly elements can be assembled into the implantable movement restriction device. In one embodiment the segments comprise a core part and a plurality of outer parts and in one embodiment wherein the assembly elements are selected among sufficiently fitting flanges and slits.

The core part preferably is adapted to receive and assemble the outer elements into an implantable movement restriction device. In one embodiment the core part has assembly slits adapted to receive corresponding assembly flanges of the outer parts when assembling the movement restriction device. Preferably the slits are distributed around the outer peripheral area of the core part. The slits and flanges may be designed to have loose fit adapted keep the segments together as a movement restriction device at it implanted located, but assist with disassemble the device if it inadvertently leaves such a position, for example to the stomach cavity. In such event the degradation of the guiding device will also assist with disassembling the movement restriction device into segments which are designed not cause any obstructions or in any other form damage the patient.

In order to assemble the segments, the operation wire is connected to the core part and to the outer parts so the outer parts can be sequentially assembled to the core part so as to assemble the movement restriction device. For this purpose, the operation wire preferably is connected to the assembly flanges of the outer part and preferably, the core part is provided with at least one operation channel for receiving the operation wire. Preferably, each outer part is connected to two operation channels by the operation wire. In one embodiment, a first operation channel has a first orifice in an end surface of the core part and second orifice in a first slit of the core part, so when displacing the operation wire received in said first operation channel in a direction from said end surface, a first outer part is assembled to said core part. A second operation channel has two orifices in a second slit of the core part, so when displacing the operation wire connected to the first operation cannel in a directed from the end surface, a second outer part is assembled to said core part. Preferably, the guiding wire protrudes from the first channel orifice so it can be operated on with an instrument to displace the guiding wire and a first outer element so its assembly flange fits with its designated first assembly slit on the core element, and in a predetermined sequence in the same manner displacing the remaining outer elements so as to assemble the implantable movement restriction device. The segments can comprise three or more outer parts assembled to designated slits of the core part with the guiding wire through operation channels having orifices in each designated slit of said core part. In one embodiment the movement restriction device comprises one core part and four outer parts. However other ways of designing the segments within the present concept is feasible according to the skilled person. The so assembled movement restriction device can retain a generally spherical form, but as will be described later other shapes and additional function elements are made part of the present invention.

Other features of the proximal part of the movement restriction device will be described in the following part of description. These features can be combined with any of the following features related to the distal part of the movement restriction device.

In an advantageous embodiment of the apparatus now adapted to also treat obesity, the body is adjustable in size and invaginated in the patient's fundus stomach wall. As a result, the body stretches the patient's stomach fundus wall when the size thereof is increased, thereby creating satiety in a patient also suffering from obesity. At least two implantable adjustable stretching devices may be provided to stretch different parts of the patient's stomach wall, to thereby treat obesity by efficiently affecting the patient's appetite. The two stretching devices are suitably regulated from outside of the patient's body, whereby a first of the stretching devices is regulated at a first time to stretch a first part of the patient's stomach wall and a second of the stretching devices is regulated at a second time to stretch a second part of the patient's stomach wall.

The apparatus of the present invention in any form outlined in the previous sections can be further adapted to treat obesity together with reflux disease as it is common that a patient suffers from both complications. For this purpose the distal part of the movement restriction device is further adapted for obesity treatment. The distal part will have the functionality of a volume filling device In accordance with a first option, the distal part of the movement restriction device is adapted to be placed inside the stomach with the outer surface of the distal part of resting against the inside of the stomach wall.

In accordance with a second option, the distal part of the movement restriction device is adapted to be placed outside the stomach with the outer surface of the volume filling device resting against the outside of the stomach wall.

Preferably, the distal part of the movement restriction device is adapted to be completely invaginated by the stomach wall of the patient and to be placed inside or outside the stomach wall via a gastroscopic instrument. To this end the distal part of the movement restriction device may comprise an attachment device adapted to co-operate with a gripping instrument. Suitably, the distal part of the movement restriction device is adapted to be non-invasively adjustable postoperatively.

The apparatus may comprise a fixation device, suitably two or more fixation devices, adapted to be involved in the fixation of the distal part of the movement restriction device to the stomach wall. The distal part of the movement restriction device may comprise a holding device adapted to be held by an instrument, suitably two or more holding devices, to simplify the implantation of the device.

At least a part of the distal part of the movement restriction device may be made of a material which is not destructible by stomach acid. The distal part of the movement restriction device may be destructible by acids, for example hydrochloric acid.

In an embodiment, the distal part of the movement restriction device is inflatable to an expanded state and comprises an enclosure wall defining a chamber, the distal part of the movement restriction device is inflated with a gel or fluid supplied into the chamber. At least one tube may be connected to the distal part of the movement restriction device for supplying gel or fluid to the chamber. An injection port connectable with the tube may be provided. Alternatively, the distal part of the movement restriction device may be provided with an inlet port for a fluid or a gel connectable to a gastroscopic instrument, wherein the inlet port comprises a fluid connection adapted to interconnect the inflatable device and the gastroscopic instrument.

The distal part of the movement restriction device may include a homogenous material, such as gel having a Shore value of less than 15. The device may also be a solid body.

At least one of the distal and proximal parts of the movement restriction device may at least to a part comprise a rigid, elastic or flexible outer surface. Where the outer surface is rigid, it is rigid enough to maintain non-deformed when subject to forces created by stomach movements. The distal part of the movement restriction device may comprise a flexible non-elastic material.

In accordance with a first general design of the distal part of the movement restriction device, the device has a maximum circumference as seen in a plane perpendicular to an axis through the device. The circumferences of the device as seen in other planes perpendicular to said axis are equal to the maximum circumference or decrease as seen along said axis in the direction from the maximum circumference. For example, the device may be substantially egg shaped, spherically shaped, or substantially shaped like an egg with an indented middle section or like a bent egg.

In accordance with a second general design of the device, the circumference of the device as seen in a plane perpendicular to an axis through the device increases and decreases at least two times as the plane is displaced along said axis, or decreases and increases at least one time as the plane is displaced along said axis. For example, the device may be substantially shaped like a kidney.

The distal part of the movement restriction device has an elongated, rounded, bent and/or curved shape.

The distal part of the movement restriction device has a circumference of at least 30, 50, 80, 120, 150, 180 or 220 mm.

The distal part of the movement restriction device has a volume in the range of 0.0001 to 0.001 m3, or 0.00001 to 0.001 m3, or 0.00001 to 0.0002 m3. The volume of the volume filling device has a volume of less than 0.0002 m3.

The distal part of the movement restriction device may comprise at least two interconnectable portions adapted to be placed inside or outside the stomach as separate portions.

The distal part of the movement restriction device may comprise an elastic material, a bio-compatible material and/or silicone. Suitably, at least one of the distal and proximal park of the movement restriction device is provided with at least one layer. For example, a metal layer, a Parylene layer, a polytetrafluoroethylene layer or a polyurethane layer. The layers may comprise multiple layers in any order. Suitably, one of the layers may be made of made of metal, silicon or PTFE. The volume filling device may comprise an outer surface layer of silicone, polyurethane, Teflon®, or polytetrafluoroethylene, metal, Parylene, PTFE or a combination thereof. The volume filling device may comprise an inner surface layer of silicone, polyurethane, Teflon®, or polytetrafluoroethylene, metal, Parylene, FIFE or a combination thereof. Other combinations of layers include an inner surface layer of polytetrafluoroethylene and an outer layer of silicone, an inner surface layer of polytetrafluoroethylene, an intermediate layer of silicone, and an outer layer of Parylene, an inner surface layer of polyurethane and an outer layer of silicone, and an inner surface layer of polyurethane, an intermediate layer of silicone, and an outer layer of Parylene.

The distal part of the movement restriction device may comprise a fluid adapted to be transformed into solid state or fixed form. Such a fluid may be liquid polyurethane or isotonic. The fluid may comprises large molecules, such as iodine molecules, to prevent diffusion.

The distal part of the movement restriction device may have a maximum circumference of at least 50 millimeters, preferably at least 80 millimeters. Suitably, the distal part of the movement restriction device is deformable to a maximum diameter, so as to be insertable into a laparoscopic trocar.

Preferably the distal part of the movement restriction device is adapted to be kept in place by stomach-to-stomach sutures or staples to invaginate the device in the stomach wall. Advantageously, the distal part of the movement restriction device has varying circumference to better be kept in place invaginated in the stomach wall of the patient. The stomach-to-stomach sutures or staples may be provided with fixation portions exhibiting a structure adapted to be in contact with the stomach wall to promote growth in of human tissue to secure long term placement of the volume filling device attached to the stomach wall. The structure may comprise a net like structure.

In embodiment of the invention, the apparatus comprises a stretching device placed outside the stomach wall and adapted to stretch a portion of the stomach wall, thereby affecting the patient's appetite. Where the volume filling device is inflatable, the apparatus may comprise a fluid connection interconnecting the stretching device and the volume filling device.

The stretching device may be hydraulically regulated. In this case, a subcutaneously implantable hydraulic reservoir connected to the hydraulic regulated stretching device may be provided, whereby the hydraulic regulated stretching device, when implanted in the patient, is adapted to be non-invasively regulated using fluid from the hydraulic reservoir. In one embodiment the hydraulic regulated stretching device is non-invasively regulated by manually pressing the hydraulic reservoir. Further, the movement restriction device suitably includes an inflatable body, and a pump and a chamber in fluid contact with the body are provided, wherein the pump regulates the hydraulic reservoir by pumping fluid or air from the body to the chamber.

The apparatus may include an implantable stimulation device that sends out stimulation pulses to the cardia muscle, especially the cardia sphincter muscle to stimulate the cardia muscle and thereby further close the cardia to additionally prevent reflux disease. The stimulation device is comprised of at least one conductor and at least one electrode that receives the stimulation pulses and applies them to the cardia sphincter muscle to thereby stimulate the cardia sphincter muscle. The at least one electrode may also be kept in place by the stomach-oesophagal sutures or invagination in the stomach wall. The stimulation pulses may be sent as a train of pulses, wherein the pulse train is repeated with a time break in between, the break extending the break between each pulse in the pulse train. Preferably, the stimulation device sends out a number of pulse trains in a row followed by a break longer than that between the pulse trains to let the muscle rest still keeping the cardia sphincter closed The stimulation device may include an electronic circuit and an energy source preferably adapted to incorporate the electronic circuit and energy source.

The stimulation device preferably comprises at least one sensor for sensing a physical parameter of the patient or a functional parameter of the movement restriction device and an internal control unit for controlling the stimulation device.

Normally, the internal control unit controls the stimulation device in response to information from the sensor.

A sensor sensing a contraction wave of the esophagus, or any other parameter correlated to food intake, sends the information to the internal control unit and the internal control unit then ceases the stimulation in response to such information from the sensor.

The stimulation device may, at any time, be controlled by the patient.

This object is also obtained by providing an apparatus, the apparatus comprising an implantable movement restriction device having an elongated shape and having, when implanted in a patient, a proximal and a distal part, wherein the proximal part is adapted to be at least partly invaginated by the patient's stomach fundus wall and having an outer surface that preferably includes a bio compatible material, wherein a substantial part of the outer surface of the proximal part of the movement restriction device is adapted to rest against the stomach wall without injuring the latter in a position between the patient's diaphragm and at least a portion of the lower part of the invaginated stomach fundus wall, such that movement of the cardiac notch of the patient's stomach towards the patient's diaphragm is restricted, when the movement restriction device is invaginated, to thereby prevent the cardia from sliding through the patient's diaphragm opening into the patient's thorax, so as to maintain the supporting pressure against the patient's cardia sphincter muscle exerted from the patient's abdomen. The distal part of the movement restriction device stabilizes and holds the proximal part and is adapted by substantially invaginated in the stomach wall. The fundus stomach wall is more easily movable and thereby stabilized by the distal part being invaginated in the stomach wall at least partly below the fundus stomach wall. The proximal part of the movement restriction device has a size of at least 125 mm3 and a circumference of at least 15 mm, further comprises an implantable stimulation device adapted to engage with the cardia sphincter of a patient, and a control device for controlling the stimulation device to stimulate the cardia sphincter, wherein the stimulation of the cardia sphincter is made with energy pulses to increase sphincter tonus so that the cardia closes and said control device is operable by the patient in that it can be set out of operation, wherein the control device is further operable by the patient to set the stimulation device into operation, in which operational state the stimulation device continuously alternates at a time when the patient does not swallow between an operation mode, in which the cardia sphincter is stimulated with said energy pulses, and a rest mode, in which the cardia sphincter is not stimulated.

Movement Restriction Device

The movement restriction device of the apparatus will be described. It is to be understood that in the present context all features, functionalities or adaptations described with the movement restriction device in this section are related to its proximal part, even if this is not explicitly mentioned. However, all features, embodiments, or part of embodiments as well as any method described in this application may, where applicable, be used for both the proximal or distal part of the device.

The apparatus comprises an implantable movement restriction device having an outer surface that includes a biocompatible material, wherein the movement restriction device is adapted to rest with at least a part of its outer surface against the patient's stomach fundus wall, in a position between the patient's diaphragm and the fundus wall, such that movement of the cardiac notch of the patient's stomach towards the patient's diaphragm is restricted, an apparatus for treating Gastro Esophageal Reflux Disease is obtained. The movement restriction device has a size of at least 125 mm3 and a circumference of at least 15 mm and restricts movement of the cardiac notch of the patient's stomach towards the patient's diaphragm thereby preventing the cardia from sliding through the patient's diaphragm opening into the patient's thorax, maintaining the supporting pressure against the patient's cardia sphincter muscle exerted from the patient's abdomen. Fixation device are adapted to secure the movement restriction device in said position.

By adapting the outer surface of the implanted movement restriction device to rest against the wall of the fundus, there is a minimal risk of complications, such as migration of damage to tissue, because the fundus is less fragile than the esophagus.

In a first embodiment of the invention, the fixation device comprises sutures or staples that attach together portions of the fundus stomach wall that enclose the movement restriction device to secure the movement restriction device in said position. I.e., the movement restriction device is at least partly placed in an invaginated space. Thus, by affixing the implantable movement restriction device indirectly in this manner, no suturing between the movement restriction device and tissue is required, which, in turn, further reduces the risk for complications. Keeping the movement restriction device in place in this manner has resulted in an elastic suspension with improved long term properties.

The fixation device, such as sutures or staples, may attach together portions of the fundus stomach wall so at to substantially or completely invaginate the movement restriction device from either inside or outside of the patient's stomach wall. Where the movement restriction device is placed on the outside of the patient's stomach wall, the movement restriction device is invaginated by the fundus stomach wall such that the stomach cavity is substantially reduced, by a volume substantially exceeding the volume of the movement restriction device.

In a another embodiment of the invention, the fixation device comprises an implantable first fixation device that attach the movement restriction device in said position to the fundus wall, a second fixation device that secures, indirectly or directly, the movement restriction device to the esophagus close to the patient's angle of His, and a third fixation device that secures, indirectly or directly, the movement restriction device to the patient's diaphragm muscle or associated muscles. Any of the first, second and third fixation devices may be comprised of a plurality of sutures or staples. The first fixation device may comprise a tissue growth promoting structure for long term attachment of the movement restriction device to the stomach wall. The tissue growth promoting structure may be sutured to the stomach wall with a relatively large contact surface towards the stomach. The relatively large surface of the structure, such as a net, will allow for in-growth of human tissue for holding the movement restriction device in place over the long term. The tissue growth promoting structure may comprise sutures or staples that attach the net like structure to the fundus stomach wall.

In addition to invaginating the movement restriction device in accordance with the first embodiment of the invention, the second fixation device can be used to secure, indirectly or directly, the movement restriction device to the esophagus close to the patient's angle of His, and the third fixation device may be used to secure, indirectly or directly, the movement restriction device to the patient's diaphragm muscle or other muscle tissue.

At least a part of the movement restriction device may be made of a material which is destructible or not destructible by stomach acid.

The movement restriction device may be inflatable and adapted to be inflated with a gel or fluid. A fluid or gel receiving member for receiving fluid to inflate the movement restriction device may be provided.

The movement restriction device may include a homogenous material and may be a solid body.

The movement restriction device may include an enclosure wall defining a chamber.

The movement restriction device may have a rigid, elastic or flexible outer wall. Where the outer wall is rigid, it is rigid enough to maintain non-deformed when subject to forces created by stomach movements. Where the movement restriction device is invaginated, in accordance with the first embodiment described above, the movement restriction device preferably comprises a body adapted to be at least partly invaginated by the patient's stomach fundus wall and having an outer surface that includes a biocompatible material. A substantial part of the outer surface of the body is adapted to rest against the stomach wall in said position between the patient's diaphragm and the portion of the lower part of the invaginated stomach fundus wall. Suitably, the body is made of a material softer than 25 or 15 shore.

In accordance with a first general design of the body, the body has a maximum circumference as seen in a plane perpendicular to an axis through the body. The circumferences of the body as seen in other planes perpendicular to said axis are equal to the maximum circumference or decrease as seen along said axis in the direction from the maximum circumference. For example, the body may be substantially egg shaped, spherically shaped, or substantially shaped like an egg with an indented middle section or like a bent egg.

In accordance with a second general design of the body, the circumference of the body as seen in a plane perpendicular to an axis through the body increases and decreases at least two times as the plane is displaced along said axis, or decreases and increases at least one time as the plane is displaced along said axis. For example, the body may be substantially shaped like a kidney.

Preferably, the body is dimensioned with a size larger than the intestinal outlet from the stomach. The body may have a smallest outer diameter of 30 or 40 mm or larger and may have a smallest outer circumference of 150, 110, 90, 70, 50 or 30 mm.

Suitably, the body has rounded contours without too sharp edges that would be damaging to the patient's stomach wall, and has a generally smooth outer surface for resting against the fundus wall.

The body is implantable either inside or outside of the patient's stomach and is adapted to be attached to the patient's stomach wall by surgery. The body may be changeable to assume a slender form having a smaller diameter than that of a trocar for laparoscopic use, whereby the body when changed to said slender form can be pushed or pulled through the trocar. The body may include a flexible outer wall defining a chamber filled with a fluid, such as a gel, allowing the body to pass through such a trocar. Alternatively, the body may include an elastic compressible material, allowing the body to pass through a trocar.

The body may be hollow and include at least two separate pieces adapted to be inserted into the hollow body, and further adapted to be put together to one unitary piece inside the body, thereby allowing the body to pass through a trocar for laparoscopic use. Alternatively, the body may include an outer wall and a hollow compressed inner part, for being filled with a fluid or gel after insertion into the patient's body.

The body may include a chamber with an injection port, wherein the chamber of the body is filled with a fluid through the injection port.

The body may include at least one holding device adapted to be used for pushing or pulling the body through a trocar for laparoscopic use. The holding device is adapted to hold a prolongation of the body that is adapted to be held by a surgical instrument. More specifically, the holding device is adapted to hold a thread or band inserted through the holding device. Where the body comprises an outer wall the holding device is at least partly placed inside the outer wall of the body.

In an advantageous embodiment, the body is adjustable in size and invaginated in the patient's fundus stomach wall. As a result, the body stretches the patient's stomach fundus wall when the size thereof is increased, thereby creating satiety in a patient also suffering from obesity. At least two implantable adjustable stretching devices may be provided to stretch different park of the patient's stomach wall, to thereby treat obesity by efficiently affecting the patient's appetite. The two stretching devices are suitably regulated from outside of the patient's body, whereby a first of the stretching devices is regulated at a first time to stretch a first part of the patient's stomach wall and a second of the stretching devices is regulated at a second time to stretch a second part of the patient's stomach wall.

The stretching device may be hydraulically regulated. In this case, a subcutaneously implantable hydraulic reservoir connected to the hydraulic regulated stretching device may be provided, whereby the hydraulic regulated stretching device is non-invasively regulated by manually pressing the hydraulic reservoir. Further, the movement restriction device suitably includes an inflatable body, and a pump and a chamber in fluid contact with the body are provided, wherein the pump regulates the hydraulic reservoir by pumping fluid or air from the body to the chamber.

The apparatus may include an implantable stimulation device that sends out stimulation pulses to the cardia muscle to stimulate the cardia muscle and thereby further close the cardia to additionally prevent reflux disease. The stimulation device is comprised of at least one conductor and at least one electrode that receives the stimulation pulses and applies them to the cardia muscle to thereby stimulate the cardia muscle. The at least one electrode may also be kept in place by the stomach-oesophagal sutures or invagination in the stomach wall. The stimulation pulses may be sent as a train of pulses, wherein the pulse train is repeated with a time break in between, the break extending the break between each pulse in the pulse train. The stimulation device may include an electronic circuit and an energy source preferably adapted to incorporate the electronic circuit and energy source.

The stimulation device preferably comprises at least one sensor for sensing a physical parameter of the patient or a functional parameter of the movement restriction device and an internal control unit for controlling the stimulation device.

Normally, the internal control unit controls the stimulation device in response to information from the sensor.

A sensor sensing a contraction wave of the esophagus, or any other parameter correlated to food intake, sends the information to the internal control unit and the internal control unit then ceases the stimulation in response to such information from the sensor.

The stimulation device may, at any time, be controlled by the patient

Stimulation Device

The stimulation device of the apparatus will now be described.

The control device is operable by the patient to control the stimulation device to continuously alternate between an operation mode, in which the cardia sphincter is stimulated with energy pulses, and a rest mode, in which the cardia sphincter is not stimulated. (The term "patient" includes an animal or a human being.) The continuous alternation between the operation and rest modes gives the advantage that the cardia sphincter is able to "recover" during the rest modes and as a result be more sensitive during the operation modes. Another advantage is that the energy consumption of the new apparatus will be considerably lower as compared with the above-discussed prior continuous stimulation system. In addition, since the control device is operable by the patient he or she may choose when the apparatus should be in operation. For example, for some patient's it may be sufficient to keep the apparatus temporarily "on" when the patient feels reflux troubles, such as at night when the patient is lying, others may need to have the apparatus all the time "on", except when the patient eats.

In accordance with a preferred embodiment of the invention, the apparatus comprises a source of energy, wherein the control device controls the source of energy to release energy for use in connection with the power of the stimulation device, when the stimulation device is implanted. As a result, the apparatus of the invention provides a simple and effective control of the energy supplied to implanted components of the apparatus, which ensures an extended and reliable functionality of the apparatus, possibly for the rest of the patient's life and at least many years.

In the preferred embodiment, the control device may be controllable from outside the patient's body to control the stimulation device to vary the intensity of the stimulation of the cardia sphincter over time. More specifically, the control device may be adapted to control the stimulation device to change the intensity of the stimulation of the cardia sphincter so that the cardia sphincter tonus is changed.

Preferably, the source of energy comprises an electric source of energy and the control device is adapted to control the electric source of energy to deliver electric pulses to the stimulation device. An implantable switch for switching the delivery of electric pulses from the electric source of energy may be provided. The switch may be manually operable by the patient, or, alternatively, the control device may comprise a wireless remote control operable by the patient to control the switch.

Where the stimulation device stimulates the cardia sphincter with electric pulses there may be a problem of providing a voltage intensity strong enough to achieve the desired electric stimulation of the cardia sphincter. This is so because the intensity of the electric stimulation might fade over time, due to increasing electric resistance caused by the formation of fibrosis where electric conductors engage the cardia sphincter. This problem is solved by a main embodiment of the present invention, in which the stimulation device comprises electric conductors for engaging the cardia sphincter, the electric source of energy is adapted to provide a current through the electric conductors, and the control device is adapted to control the electric source of energy to release electric energy such that the intensity of the current through the electric conductors amounts to a predetermined value. As a result, decreasing current intensity caused by the formation of fibrosis where the conductors engage the cardia sphincter can be compensated for. Thus, if the current through the conductors decreases the control device automatically controls the electric source of energy to release more electric energy to restore the desired current intensity.

Advantageously, the control device is adapted to control the electric source of energy to release energy in the form of an alternating current. The inventor has found that unlike an alternating current a direct current could cause electrolysis in the cardia sphincter. Such electrolysis could injure the cardia sphincter.

All of the above embodiments may be combined with at least one implantable sensor for sensing at least one physical parameter of the patient, wherein the control device may control the stimulation device in response to signals from the sensor. In particular, the sensor may sense as the physical parameter the contraction wave in the esophagus caused by the patient swallowing food. In this case the stimulation device is adapted to cease the stimulation of the cardia sphincter in response to the sensor sensing the contraction wave in the patient's esophagus.

As an alternative, the sensor may comprise a pressure sensor for directly or indirectly sensing the pressure in the esophagus. The expression "indirectly sensing the pressure in the esophagus" should be understood to encompass the cases where the sensor senses the pressure against the stimulation device or human tissue of the patient.

The control device may comprise an internal control unit, preferably including a microprocessor, to be implanted in the patient for controlling the stimulation device. The internal control unit may suitably directly control the stimulation device in response to signals from the sensor. In response to signals from the sensor, for example pressure, the patient's position, the contraction wave in the patient's esophagus or any other important physical parameter, the internal control unit may send information thereon to outside the patient's body. The control unit may also automatically control the stimulation device in response to signals from the sensor. For example, the control unit may control the stimulation device to efficiently stimulate the cardia sphincter, such that the cardia for certain is completely closed in response to the sensor sensing that the patient is lying.

The control device may also, or alternatively, comprise an external control unit outside the patient's body, wherein the internal control unit is programmable by the external control unit, for example for controlling the stimulation device over time. Alternatively, the internal control unit may control the stimulation device over time in accordance with an activity schedule program, which may be adapted to the patient's needs.

The external control unit may also, suitably directly, control the stimulation device in response to signals from the sensor. The external control unit may store information on the physical parameter sensed by the sensor and may be manually operated to control the stimulation device based on the stored information. In addition, there may be at least one implantable sender for sending information on the physical parameter sensed by the sensor.

A great advantage is that the patient is enabled to keep the cardia completely closed by means of the stimulation device by using the control device whenever he likes during the day. This advantage should not be underestimated, because in case the patient would need to vomit it would be very difficult for him to do so if he were unable to immediately stop the stimulation of the cardia.

Conveniently, the external control unit may load the internal control unit with data in accordance with a loading mode only authorised for a doctor. For specialised controls of the stimulation device, such as electric power, electric pulse frequency etc, the external control unit may control the internal control unit in accordance with a doctor mode only authorised for the doctor. For simple controls of the stimulation device, such as "on" and "off", the external control unit may control the internal control unit in accordance with a patient mode permitted for the patient. Thus, by using the external control unit in accordance with different modes it is possible to have certain functions of the stimulation device controlled by the patient and other more advanced functions controlled by the doctor, which enables a flexible post-operation treatment of the patient.

The control device may be adapted to control the source of energy to release energy, for instance to intermittently release energy in the form of a train of energy pulses, for direct use in connection with the power of the stimulation device. In accordance with a suitable embodiment the control device controls the source of energy to release electric energy, and the apparatus further comprises an implantable capacitor for producing the train of energy pulses from the released energy. In this case the term "direct" is used to mean, on one hand, that the released energy is used while it is being released by the control device, on the other hand, that the released energy may be somewhat delayed, in the order of seconds, by for instance an energy stabilizer before being used in connection with the power of the stimulation device.

Further below is described further embodiments related to energy supply and control. All these embodiments may be used for all the different applicable embodiments in this application not only for the stimulation device.

In accordance with an embodiment of the invention, the apparatus comprises implantable electrical component including at least one, or only one single voltage level guard and a capacitor or accumulator, wherein the charge and discharge of the capacitor or accumulator is controlled by use of the voltage level guard.

In one embodiment, the source of energy is external to the patient's body and the control device controls the source of energy to release wireless energy. An energy storage device, preferably an electric accumulator, may be implanted in the patient for storing the wireless energy released from the external source of energy. The electric accumulator may comprise at least one capacitor or at least one rechargeable battery, or a combination of at least one capacitor and at least one rechargeable battery. Alternatively, a battery may be implanted in the patient for supplying electric energy to implanted electric energy consuming component of the apparatus, in addition to the supply of wireless energy. Where the control device comprises an implantable control unit the electronic circuit thereof and the stimulation device may be directly powered with transformed wireless energy, or energy from either the implanted energy storage device or battery.

In one embodiment the wireless energy is directly used for the power of the stimulation device, i.e. the stimulation device is powered as the wireless energy is released from the external source of energy by the control device. In this case the term "directly" is used to mean, on one hand, that the stimulation device is promptly powered by using the released energy whiteout first storing the latter, on the other hand, that the released energy may be somewhat delayed, in the order of seconds, by for instance an energy stabilizer before being used for the power of the stimulation device. Both the wireless energy may be used to create direct kinetic energy the wireless field affecting an the apparatus directly or by using an energy transforming device, transforming the wireless energy to electric energy which may be used to power any energy consuming parts of the apparatus directly during wireless energy transmission or indirect after charging an accumulator. As a result, a very simple control of the stimulation device is achieved and there are only a few implanted components of the apparatus. For example, there is no implanted source of energy, such as a battery, nor any implanted complicated signal control system. This gives the advantage that the apparatus will be extremely reliable.

In one embodiment, the source of energy comprises an implantable internal source of energy. Thus, when the internal source of energy is implanted in a patient the control device controls it from outside the patient's body to release energy. This solution is advantageous for sophisticated embodiments of the apparatus that have a relatively high consumption of energy that cannot be satisfied by direct supply of wireless energy. The internal source of energy preferably comprises an electric source of energy, such as an accumulator or a battery. Alternatively, the control device may be adapted to release wireless energy from the internal source of energy and to control the stimulation device to stimulate the patient's cardia sphincter with the released wireless energy. The wireless energy may comprise radiant energy or sound energy, such as ultrasound energy.

In one embodiment of the invention, the apparatus comprises a switch implanted in the patient for directly or indirectly switching the power of the stimulation device and an internal electric source of energy, such as a battery, implanted in the patient for supplying electric energy for the power of the stimulation device, wherein the switch directly or indirectly affects the supply of electric energy from the internal electric source of energy. This solution is advantageous for embodiments of the apparatus that have a relatively high consumption of energy that cannot be met by direct supply of wireless energy.

In one embodiment of the invention, the switch switches between an "off" mode, in which the internal electric source of energy is not in use, and an "on" mode, in which the internal electric source of energy supplies electric energy for the power of the stimulation device. In this case, the switch is conveniently operated by the wireless energy released from the external source of energy to switch between the "on" and "off" modes. The control device, preferably comprising a wireless remote control, may control the external source of energy to release the wireless energy. The advantage of this embodiment is that the lifetime of the implanted electric source of energy, such as a battery, can be significantly prolonged, since the implanted source of energy does not supply energy when the switch is in its off mode.

In one embodiment, the control device comprises a wireless remote control for controlling the internal electric source of energy. In this case, the switch is operable by the wireless energy from the external source of energy to switch between an "off" mode, in which the internal electric source of energy and remote control are not in use, and a "standby" mode, in which the remote control is permitted to control the internal electric source of energy to supply electric energy for the power of the stimulation device.

In one embodiment, the apparatus further comprises an energy transforming device to be implanted in the patient for transforming the wireless energy into storable energy, and an implantable energy storage device for storing the storable energy, wherein the switch is operable by energy from the implanted energy storage device to switch between an "off" mode, in which the internal electric source of energy is not in use, and an "on" mode, in which the internal electric source of energy supplies electric energy for the power of the stimulation device. In this case, the control device suitably comprises a wireless remote control for controlling the energy storage device to operate the switch.

An external data communicator may be provided outside the patient's body and an internal data communicator to be implanted in the patient may be provided for communicating with the external data communicator. The internal data communicator may feed data related to the patient, or related to the stimulation device, back to the external data communicator. Alternatively or in combination, the external data communicator may feed data to the internal data communicator. The internal data communicator may suitably feed data related to at least one physical signal of the patient.

Suitably, an implantable stabilizer, such as a capacitor, a rechargeable accumulator or the like, may be provided for stabilizing the electric energy released by the control device. In addition, the control device may control the source of energy to release energy for a determined time period or in a determined number of energy pulses.

All of the above embodiments are preferably remote controlled. Thus, the control device advantageously comprises a wireless remote control transmitting at least one wireless control signal for controlling the stimulation device. With such a remote control it will be possible to adapt the function of the apparatus to the patient's need in a daily basis, which is beneficial with respect to the treatment of the patient.

The wireless remote control may be capable of obtaining information on the condition of the stimulation device and of controlling the stimulation device in response to the information. Also, the remote control may be capable of sending information related to the stimulation device from inside the patient's body to the outside thereof.

In a particular embodiment of the invention, the wireless remote control comprises at least one external signal transmitter or transceiver and at least one internal signal receiver or transceiver implantable in the patient. In another particular embodiment of the invention, the wireless remote control comprises at least one external signal receiver or transceiver and at least one internal signal transmitter or transceiver implantable in the patient.

The remote control may transmit a carrier signal for carrying the control signal, wherein the carrier signal is frequency, amplitude or frequency and amplitude modulated and is digital, analogue or digital and analogue. Also the control signal used with the carrier signal may be frequency, amplitude or frequency and amplitude modulated.

The control signal may comprise a wave signal, for example, a sound wave signal, such as an ultrasound wave signal, an electromagnetic wave signal, such as an infrared light signal, a visible light signal, an ultra violet light signal, a laser signal, a micro wave signal, a radio wave signal, an x-ray radiation signal, or a gamma radiation signal. Where applicable, two or more of the above signals may be combined.

The control signal may be digital or analogue, and may comprise an electric or magnetic field. Suitably, the wireless remote control may transmit an electromagnetic carrier wave signal for carrying the digital or analogue control signal. For example, use of an analogue carrier wave signal carrying a digital control signal would give safe communication. The control signal may be transmitted in pulses by the wireless remote control.

The control device may be activated in a manual or non-manual manner to control the source of energy to release energy.

In the above-presented embodiments of the invention the released energy may comprise electric energy and an implantable capacitor having a capacity less than 0.1 µF may be provided for producing the above-mentioned train of energy pulses.

Generally, the wireless energy comprises a signal.

The apparatus may further comprise an implantable energy transforming device for transforming wireless energy, for example in the form of sound waves, directly or indirectly into electric energy, for the power of the stimulation device. More specifically, the energy transforming device may comprise a capacitor adapted to produce electric pulses from the transformed electric energy.

Generally, the stimulation device advantageously is embedded in a soft or gel-like material, such as a silicone material having hardness less than 20 Shore.

The stimulation device may comprise a band for application around the cardia, wherein the band has electric conductors for contacting the cardia sphincter. The electric conductors may comprise hooks to secure the conductors on the cardia.

The present invention also provides a system for treating heartburn and reflux disease, comprising an implantable stimulation device adapted to stimulate the cardia sphincter of a patient to increase the sphincter tonus, and a control device that controls the stimulation device to continuously alternate between an operation mode, in which the cardia sphincter is stimulated with energy pulses, and a rest mode, in which the cardia sphincter is not stimulated. The energy pulses may comprise electric pulses. The stimulation device may comprise electric conductors for engaging the cardia sphincter, and an electric source of energy may be adapted to provide a current through the electric conductors to form the electric pulses. Advantageously, the control device may control the electric source of energy to release the electric energy such that the current through the electric conductors amounts to a predetermined value.

All the above described various components may be combined in the different embodiments where applicable. Also the various functions described in connection with the above embodiments of the invention may be used in different applications, where applicable.

All the various ways of transferring energy and controlling the energy presented in the present specification may be practiced by using all of the various components and solutions described.

The present invention also provides methods for treating heartburn and reflux disease.

Accordingly, in accordance with a first alternative method, there is provided a method of treating heartburn and reflux disease, comprising the steps of:

implanting an stimulation device in a patient, so that the stimulation device engages the cardia, and controlling the stimulation device to continuously alternate between an operation mode, in which the cardia sphincter is stimulated with energy pulses to increase the sphincter tonus, so that the cardia completely closes, and a rest mode, in which the cardia sphincter is not stimulated.

The first alternative method may also be performed laparoscopically. Thus, there may be provided a laparoscopic method of treating heartburn and reflux disease, comprising the steps of laparoscopically implanting an stimulation device in a patient, so that the stimulation device engages the cardia, and controlling the stimulation device to continuously alternate between an operation mode, in which the cardia sphincter is stimulated with energy pulses to increase the sphincter tonus, so that the cardia completely closes, and a rest mode, in which the cardia sphincter is not stimulated.

In accordance with a second alternative method, there is provided a method of treating a patient having heartburn and reflux disease, comprising:

(a) Surgically implanting in the patient an electric stimulation device engaging the cardia.

(b) Providing a source of energy external to the patient's body.

(c) Controlling the external source of energy from outside the patient's body to release wireless energy. And (d) using the released wireless energy in connection with the powering of the stimulation device.

The second alternative method may further comprise implanting an energy transforming device, controlling the external source of energy to release wireless energy, and transforming the wireless energy by the energy transforming device into energy different from the wireless energy for use in connection with the power of the stimulation device. This method may further comprise implanting a stabilizer in the patient for stabilizing the energy transformed by the energy-transforming device.

There is also provided a method of treating heartburn and reflux disease, comprising the steps of implanting a stimulation device in a patient to engage the cardia sphincter, providing a control device for controlling the stimulation device to stimulate the cardia sphincter to increase the sphincter tonus, so that the cardia completely closes, and permitting the patient to operate the control device to vary the intensity of In one embodiment there is provided an apparatus where the stimulation of the cardia sphincter is made with energy pulses to increase the sphincter tonus so that the cardia completely closes and said control device is operable by the patient in that it can be set out of operation, wherein the control device is further operable by the patient to set the stimulation device into operation, in which operational state the stimulation device continuously alternates between an operation mode, in which the cardia sphincter is stimulated with said energy pulses, and a rest mode, in which the cardia sphincter is not stimulated, wherein the apparatus further comprises at least one implantable sensor for sensing at least one physical parameter of the patient, wherein the control device is adapted to control the stimulation device to cease the continuous alternation between the operation mode and the rest mode and to put the stimulation device in the rest mode in response to the sensor sensing the physical parameter of the patient.

In one embodiment there is provided an apparatus where the stimulation of the cardia sphincter is made with energy pulses to increase the sphincter tonus so that the cardia completely closes and said control device is operable by the patient in that it can be set out of operation, wherein the control device is further operable by the patient to set the stimulation device into operation, in which operational state the stimulation device continuously alternates between an operation mode, in which the cardia sphincter is stimulated with said energy pulses, and a rest mode, in which the cardia sphincter is not stimulated, wherein the apparatus further comprises at least one implantable sensor for sensing as a physical parameter of the patient at least the contraction wave in the esophagus caused by the patient swallowing food, wherein the control device is adapted to control the stimulation device to cease the continuous alternation between the operation mode and the rest mode and to put the stimulation device in the rest mode in response to the sensor sensing the contraction wave in the patient's esophagus.

Surface Structure

The surface structure of the various implants of the invention will now be described.

The present invention concerns an implant, adapted to post-operatively be adjustable and comprising at least one expandable section, wherein the implant is adapted to be adjustable between a first collapsed state and a second expanded state. In the first collapsed state the expandable section is collapsed, and in the second expanded state, the expandable section is expanded. The outer surface of said expandable section does at least partly comprise a surface structure having elevated areas alternating with lowered areas. The expandable section is adapted to have, in at least one of said first collapsed and second expanded states a first distance between adjacent elevated areas sufficiently extended to prevent growth of fibrotic tissue from directly interconnecting adjacent elevated areas to an extent that compromises the adjustability between a first collapsed and a second expanded state of said implant. The expandable section further comprising connecting areas between adjacent elevated and lowered areas, further adapted to have, in at least one of said first collapsed and second expanded states, a second distance between adjacent connecting areas sufficiently extended to prevent growth of fibrotic tissue from directly interconnecting adjacent connecting areas to an extent that compromises the adjustability between a first collapsed and a second expanded state of said implant.

According to one embodiment the expandable section is hollow or comprises a hollow body.

According to another embodiment the implant is substantially completely hollow or comprises a hollow body extending along substantially the complete length and/or complete volume of said implant.

Fibrotic tissue can ohm have an extension or thickness of about 0.5 mm to about 1.5 mm and hence the distances between relevant surfaces of the elements of the surface structure are suitably greater than about 3 mm, hence greater than about 2×1.5 mm. But depending on the circumstances also distances greater than about 1.0 mm to about 3 mm may be sufficient. In cases where the fibrotic tissue can be expected to have an extension or thickness greater than about 1.5 mm the distances between relevant surfaces of the elements of the surface structure are adapted in a suitable manner.

The surface structure may comprise elevated and lowered areas and it may be suitable that also a distance between the different planes of the elevated and lowered areas is bigger than a certain threshold to facilitate the collapsible and/or expandable functionality of the implant. If said distance is too small, the collapsible and/or expandable functionality of the implant may be limited. A suitable interval for said distance is around 0.5 to 10 mm, more suitable around 2-8 mm and most suitable around 3-7 mm The surface structure may comprise different geometrical elements or shapes and any combination of such elements or shapes as long as the above mentioned conditions for the distances can be met. The surface structure may e.g. comprise ridges and grooves of different shapes. The ridges and grooves may each have a cross-section that is e.g. wedge-shaped, polygonal, square-formed, pyramidal-shaped, truncated pyramidal-shaped or. Further may the ridges and grooves have cross-sections of different shapes. The surface structure may as well in general comprise a bellows-shaped structure or a surface structure where geometrical objects of the same or different kind(s) are placed on a surface. The geometrical objects may be practically randomly placed on the surface or according to some scheme.

One type of implants where this type of surface structure may be suitable is implants where the implant should have the ability to change shape and/or size substantially. Hence, this is a case where the presence of fibrotic tissue substantially could hinder or impede the function of the implant. But the surface structure may be used by any implant where the characteristics of the surface structure would be advantageous for the implant.

Combination with Obesity Treatment

The various embodiments can be combined with various methods for treating obesity. In particular two embodiments, one comprising a stretching device and one comprising a volume filling device, will be described below.

Stretching Device for Treating Obesity

Please note that all embodiment or part of embodiments or methods may be used where applicable for all the different embodiments in this application.

In addition the various embodiments the apparatus for treating reflux can be combined with a device for the treatment of obesity that that is based on the realization that by creating a stretching effect of the stomach wall a feeling of satiety is created. By means of providing an apparatus with a stretching device stretching part of the stomach wall, a simpler, safer and long term working apparatus is provided.

The expression "powered" should be understood as energized with everything without manual force, preferably electric energy. In other words, the adjustment device is operated in a non-manual manner. The expression "non-manual manner" should be understood to mean that the adjustment device is not operated by manually touching subcutaneously implanted components of the apparatus or not manipulated by touching the skin of the patient. Thus, as opposed to prior practice when treating anal incontinence, the adjustment device of the invention is not operated by manual forces, such as by manually compressing a fluid containing balloon implanted in the scrotum or in the region of labia major. Of course, manual manipulation of an implanted reservoir or other mechanical or hydraulic solutions may also be used as well as manual manipulation of a subcutaneous start button or the like for activating the powered operation device everything is permitted within the scope of the present invention.

Alternatively, or preferably in combination with a powered operation device, the servo means may be used, which enables for example a motor to run with high speed and low force and with for example a gear box to decrease the speed and increase the force or torque. The servo means may comprise hydraulic means, electric control means, magnetic means, or mechanical means, which may be activated by manual manipulating means and/or remote control. Using a servo system will save the use of force when adjusting the adjustment device, which may be of importance in many applications.

The term "servo means" encompasses the normal definition of a servo mechanism, i.e. an automatic device that controls large amounts of power by means of very small amounts of power, but may alternatively or additionally encompass the definition of a mechanism that transfers a weak force acting on a moving element having a long stroke into a strong force acting on another moving element having a short stroke. The servo means may comprise a motor, preferably an electric motor, which may be reversible.

Alternatively, or preferably in combination with a manual manipulation, a reversed servo means may be used, which enables for example a the patient's hand to use a higher force to with for example manipulate a hydraulic reservoir to move a small amount of fluid with strong force to control a larger movement of fluid. The reversed servo means may comprise hydraulic means, electric control means, magnetic means, or mechanical means, which may be activated by manual manipulating means and/or remote controlled. Using a reversed servo system will save the use of stroke when adjusting the adjustment device, which may be of importance in many applications.

The term "reversed servo means" encompasses the definition of an device that is controlled with a higher force and a small stroke i.e. for example movement of a small amount of fluid with a high force controls a larger amount of fluid moving by means of very smaller force, but may alternatively or additionally encompass the definition of a mechanism that transfers a strong force acting on a moving element having a short stroke into a small force acting on another moving element having a long stroke. The reversed servo means is preferably used when manual control of the device through intact skin is possible.

In general, two points on the stomach wall should be moved in relation to each other and away from each other to cause distension of a small part of the stomach wall, thereby causing satiety. This could be done in many different ways. One way is to expand an invaginated device invaginated in the stomach wall. Another way is to move two fixation points on the stomach wall. Of course first and second positions may be sutured or fixated to the stomach wall in many possible ways and the invention covers all possibilities to distend the stomach wall by moving two portions of the stomach wall away from each other and thereby a first fixation of the device being moved in relation to a second fixation, at least two positions on the stomach wall. However, the soft suspended connection to the stomach wall achieved by invaginating at least one adapted part of the device is preferred, where fibrotic stomach to stomach tissue helps to give a long term stable position.

Any kind of mechanical construction may be used. Any mechanical construction driven mechanically or hydraulically or any pneumatic construction may be used. Any motor or any pump or moving material changing form when powered may be used to achieve the simple goal of stretching a part of the stomach wall by moving at least two portions of the stomach wall away from each other.

Any kind of hydraulic operation may be used. It will be appreciated that instead of hydraulic operation, pneumatic operation can be used, wherein air instead of hydraulic fluid is moved between a reservoir and a chamber formed by the stretching device. Preferably the reservoir has a locking position to keep it in the desired position if it is handled by the patient. To compress the reservoir it preferably stays compressed and releases after pressing again.

Any kind of hydraulic solution may be used for the stretching device. The hydraulic solution may be driven by both mechanically and powered with any motor or pump as well as manual.

Of course just expanding an invaginated part of the stomach also stretches away the stomach wall which also may be achieved both mechanically, hydraulically, pneumatically and both being powered with a motor or pump or by manual force.

Volume Filling Device for Treating Obesity

In addition the various embodiments the apparatus for treating reflux can be adapted to additionally treat obesity that is based on volume filling capacity of the distal part of elongated movement restriction device in the stomach that creates satiety. In the present context, when volume filling device and its features, functionality and adaptations are discussed, it refers to the distal part of the elongated movement restriction device. Please note that any feature, embodiment, part of embodiment or method described herein may where applicable be used for both the distal or proximal part of the movement restriction device.

The following embodiment is based on the realization that by invaginating a volume filling device (here represented by the distal part of the movement restriction device) by the stomach wall of the patient, this inflatable object is protected from the stomach acids and will thus remain functioning for a very long time.

According to one embodiment of the invention, an apparatus to treat obesity and reflux of a patient having a stomach with a food cavity is provided, the apparatus comprising at least one volume filling device adapted to be at least substantially invaginated by a stomach wall portion of the patient, wherein the volume filling device is adapted to be placed on the outside of the stomach wall, so that the volume of the food cavity is reduced in size by a volume substantially exceeding the volume of the volume filling device, wherein the surface of the volume filling device comprises a biocompatible material, wherein a substantial part of the surface of the volume filling device is adapted to rest against the outside of the stomach wall, and wherein the volume filling device has a maximum circumference of at least 30 mm.

By invaginating the volume filling device by a stomach wall portion of the patient on the outside of the stomach wall, the volume filling device is protected from the stomach acids, thereby providing a device that will last for a long time.

The volume filling device is adapted to be placed with the outer surface of the volume filling device resting against the stomach wall, such that the volume of the food cavity is reduced in size by a volume substantially exceeding the volume of the volume filling device. The volume filling device has a maximum circumference of at least 30 millimeters. Accordingly, the apparatus of the present invention is well suited for treating obesity of an obese patient, as well as reflux disease of the same patient. This is advantageous, because reflux disease is a very common condition among human beings suffering from obesity.

In accordance with a first option, the volume filling device is adapted to be placed inside the stomach with the outer surface of the volume filling device resting against the inside of the stomach wall.

In accordance with a second option, the volume filling device is adapted to be placed outside the stomach with the outer surface of the volume filling device resting against the outside of the stomach wall.

Preferably, the volume filling device is adapted to be completely invaginated by the stomach wall of the patient and to be placed inside or outside the stomach wall via a gastroscopic instrument. To this end the volume filling device may comprise an attachment device adapted to co-operate with a gripping instrument. Suitably, the volume filling device is adapted to be non-invasively adjustable postoperatively.

The apparatus may comprise a fixation device, suitably two or more fixation devices, adapted to be involved in the fixation of the volume filling device to the stomach wall. The volume filling device may comprise a holding device adapted to be held by an instrument, suitably two or more holding devices, to simplify the implantation of the device.

At least a part of the volume filling device may be made of a material which is not destructible by stomach acid. The volume filling device may be destructible by acids, for example hydrochloric acid.

In an embodiment, the volume filling device is inflatable to an expanded state and comprises an enclosure wall defining a chamber, wherein the volume filling device is inflated with a gel or fluid supplied into the chamber. At least one tube may be connected to the volume filling device for supplying gel or fluid to the chamber. An injection port connectable with the tube may be provided. Alternatively, the volume filling member may be provided with an inlet port for a fluid or a gel connectable to a gastroscopic instrument, wherein the inlet port comprises a fluid connection adapted to interconnect the inflatable device and the gastroscopic instrument.

The volume filling device may include a homogenous material, such as gel having a Shore value of less than 15. The device may also be a solid body.

The volume filling device may comprise a rigid, elastic or flexible outer surface. Where the outer surface is rigid, it is rigid enough to maintain non-deformed when subject to forces created by stomach movements. The volume filling device may comprise a flexible non-elastic material.

In accordance with a first general design of the volume filling device, the device has a maximum circumference as seen in a plane perpendicular to an axis through the device. The circumferences of the device as seen in other planes perpendicular to said axis are equal to the maximum circumference or decrease as seen along said axis in the direction from the maximum circumference. For example, the device may be substantially egg shaped, spherically shaped, or substantially shaped like an egg with an indented middle section or like a bent egg.

In accordance with a second general design of the device, the circumference of the device as seen in a plane perpendicular to an axis through the device increases and decreases at least two times as the plane is displaced along said axis, or decreases and increases at least one time as the plane is displaced along said axis. For example, the device may be substantially shaped like a kidney.

The volume filling device has an elongated, rounded, bent and/or curved shape.

The volume filling device has a circumference of at least 120, 150, 180 or 220 mm.

The volume filling device has a volume in the range of 0.0001 to 0.001 m3, or 0.00001 to 0.001 m3, or 0.00001 to 0.0002 m3. The volume of the volume filling device has a volume of less than 0.0002 m3.

The volume filling device may comprise at least two interconnectable portions adapted to be placed inside or outside the stomach as separate portions.

The volume filling device may comprise an elastic material, a bio-compatible material and/or silicone.

Suitably, the volume filling device is provided with a coating. For example, a Parylene coating, a polytetrafluoroethylene coating or a polyurethane coating. The coating may be a multi-layer coating. The volume filling device may comprise an outer surface layer of polyurethane, Teflon®, or PTFE, or a combination thereof.

The volume filling device may comprise a fluid adapted to be transformed into solid state or fixed form. Such a fluid may be liquid polyurethane or iso-tonic. The fluid may comprises large molecules, such as iodine molecules, to prevent diffusion.

The volume filling device may have a maximum circumference of at least 50 millimeters, preferably at least 80 millimeters. Suitably, the volume filling device is deformable to a maximum diameter, so as to be insertable into a laparoscopic trocar.

Preferably, the volume filling device is adapted to be kept in place by stomach-to-stomach sutures or staples to invaginate the device in the stomach wall. Advantageously, the volume filling device has varying circumference to better be kept in place invaginated in the stomach wall of the patient. The stomach-to-stomach sutures or staples may be provided with fixation portions exhibiting a structure adapted to be in contact with the stomach wall to promote growth in of human tissue to secure long term placement of the volume filling device attached to the stomach wall. The structure may comprise a netlike structure.

In embodiment of the invention, the apparatus also comprises a stretching device placed outside the stomach wall and adapted to stretch a portion of the stomach wall, thereby affecting the patient's appetite. When the volume filling device is inflatable, the apparatus may comprise a fluid connection interconnecting the stretching device and the volume filling device.

In an embodiment, the apparatus comprises a stretching device comprising at least one operable stretching device implantable in an obese patient and adapted to stretch a portion of the patient's stomach wall and an operation device for operating the stretching device when implanted to stretch the stomach wall portion such that satiety is created.

In an embodiment, the apparatus comprises at least one operable stretching device implantable in the patient and adapted to stretch a portion of the patient's stomach wall, and an implantable control unit for automatically controlling the operable stretching device, when the control unit and stretching device are implanted, to stretch the stomach wall portion in connection with the patient eating such that satiety is created.

In an embodiment, the apparatus comprises a stretching device comprising at least one operable stretching device implantable in an obese patient and adapted to stretch a portion of the patient's stomach wall, wherein said stretching device comprising an expandable stretching reservoir and an operation device for operating the stretching device when implanted to stretch the stomach wall portion, wherein the at least the distal part of the movement restriction device is inflatable and in fluid connection with said stretching reservoir, wherein said operation device comprises a pump for pumping fluid between said main reservoir and said stretching reservoir to stretch said stomach wall portion such that satiety is created. A control device may be provided for controlling said stretching device including said pump. The control device may comprise a wireless remote control adapted to control the stretching device from the outside of the patient's body, or an implantable control unit for controlling said stretching device. Alternatively, the control device may comprise a subcutaneously placed switch or reservoir adapted to control the stretching device from the outside of the patient's body. A sensor or sensing device to be implanted in the patient body may be provided, wherein the implantable control unit is adapted to control the stretching device from the inside of the patient's body using information from said a sensor or sensing device, adapted to sense, direct or indirect, the food intake of the patient.

In an embodiment, the distal part of the movement restriction device comprises a main volume filling reservoir, a stretching device comprising at least one operable stretching device implantable in an obese patient and adapted to stretch a portion of the patient's stomach wall, wherein said stretching device comprising an expandable reservoir, adapted to be invaginated in the stomach wall at the upper part of the stomach, higher up than the inflatable main volume filling device when the patient is standing, wherein the volume filling device is inflatable and in fluid connection with said stretching reservoir, wherein normal contractions of the stomach wall, related to food intake, cause fluid to flow from said invaginated main volume filling reservoir lower placed onto the stomach wall adapted to cause said stretching reservoir to stretch said stomach wall portion such that satiety is created. The fluid connection between the main volume filling reservoir and the stretching reservoir comprises a non-return valve. The fluid connection between the main volume filling reservoir and the stretching reservoir comprises a release function adapted to release the volume in the stretching reservoir back to the main volume filling reservoir. Said release function may comprise a fluid return connection of a substantially smaller area than said fluid connection, to slowly release back fluid to said main volume filling device reservoir from the stretching reservoir to release said stretching of the stomach wall portion. A further manual control device comprising a subcutaneously placed reservoir adapted to control the stretching device from the outside of the patient's body may be provided to further affect the stretching device to stretch the stomach wall portion.

In an embodiment, the a main volume filling reservoir adapted to be inflatable may be provided, wherein the distal part of the movement restriction device further comprises an expandable structure, adapted to expand, when the device is invaginated in the stomach wall, wherein said structure comprising a bellow adapted to take into account the fibrosis surrounding the device when implanted, such that the movement of the bellow is substantially unaffected of fibrosis.

In an embodiment, the apparatus comprises a stretching device comprising at least one operable stretching device implantable in an obese patient and adapted to stretch a portion of the patient's stomach wall and wherein the stretching device comprising a expandable structure, adapted to expand and stretch the stomach wall portion, when the device is invaginated in the stomach wall, wherein said structure comprising a special bellow adapted to take into account the fibrosis surrounding the device when implanted, such that the movement of the bellow is substantially unaffected of said fibrosis. An operation device for operating the stretching device may be provided to stretch the stomach wall portion such that satiety is created. The apparatus may comprise an implantable control unit for automatically controlling the operable stretching device, when the control unit and stretching device are implanted, to stretch the stomach wall portion in connection with the patient eating such that satiety is created.

In an embodiment, the apparatus comprises a stretching device comprising at least one operable stretching device implantable in an obese patient and adapted to stretch a portion of the patient's stomach wall such that satiety is created. The control device may comprise a wireless remote control adapted to control the stretching device from the outside of the patient's body or an implantable control unit for controlling said stretching device. Alternatively, said control device may comprise a subcutaneously placed switch or reservoir adapted to control the stretching device from the outside of the patient's body. A sensor or sensing device adapted to be implanted in the patient body may be provided, wherein the implantable control unit is adapted to control the stretching device from the inside of the patient's body using information from said sensor or sensing device, adapted to sense, direct or indirect, the food intake of the patient.

In an embodiment, the apparatus is adapted to treat reflux disease. To this end, it further comprises an implantable movement restriction device having an elongated shape with a proximal part and a distal part, the proximal part being adapted to be at least partly invaginated by the patient's stomach fundus wall and having an outer surface that includes a biocompatible material. A substantial part of the outer surface of the proximal part of the movement restriction device is adapted to rest against the stomach wall without injuring the latter in a position between the patient's diaphragm and at least a portion of the lower part of the invaginated stomach fundus wall, such that movement of the cardiac notch of the patient's stomach towards the patient s diaphragm is restricted, when the proximal part of the movement restriction device is invaginated, to thereby prevent the cardia from sliding through the patient's diaphragm opening into the patient's thorax, so as to maintain the supporting pressure against the patient's cardia sphincter muscle exerted from the patient's abdomen. The proximal part of the movement restriction device has a size of at least 125 mm3 and a circumference of at least 15 mm. The distal part stabilizes and holds the proximal part and is adapted to be substantially invaginated in the stomach wall.

In another embodiment, the apparatus is adapted to treat reflux disease. To this end, it further comprises an implantable movement restriction device having an elongated shape with a proximal part and a distal part and having an outer surface including a biocompatible material. The proximal part of the movement restriction device is adapted to rest with at least a part of its outer surface against the patient's stomach fundus wall, in a position between the patient's diaphragm and the fundus wall, such that movement of the cardiac notch of the patient's stomach towards the patient's diaphragm is restricted, when the movement restriction device is implanted in the patient, to thereby prevent the cardia from sliding through the patient's diaphragm opening into the patient's thorax, so as to maintain the supporting pressure against the patient's cardia sphincter muscle exerted from the patient's abdomen, wherein the proximal part of the movement restriction device having a size of at least 125 mm3 and a circumference of at least 15 mm. An affixation device adapted to secure the proximal part of the movement restriction device in said position, when the movement restriction device is implanted. The distal part stabilizes and holds the proximal part and is adapted to be substantially invaginated in the stomach wall In another embodiment, the apparatus is adapted to treat reflux disease. To this end, it further comprises an implantable movement restriction device having an elongated shape with a proximal part and a distal part and having an outer surface that includes a biocompatible material, the proximal part being adapted to be at least partly invaginated by the patient's stomach fundus wall. A substantial part of the outer surface of the proximal part of the movement restriction device is adapted to rest against the stomach wall without injuring the latter in a position between the patient's diaphragm and at least a portion of the lower part of the invaginated stomach fundus wall, such that movement of the cardiac notch of the patient's stomach towards the patient's diaphragm is restricted, when the movement restriction device is invaginated, to thereby prevent the cardia from sliding through the patient's diaphragm opening into the patient's thorax, so as to maintain the supporting pressure against the patient's cardia sphincter muscle exerted from the patient's abdomen, the movement restriction device having a size of at least 125 mm3 and a circumference of at least 15 mm, further comprising a stretching device comprising at least one operable stretching device implantable in the obese patient and adapted to stretch a portion of the patient's stomach wall such that satiety is created. The distal part stabilizes and holds the proximal part and is adapted to be substantially invaginated in the stomach wall.

In another embodiment, the apparatus is adapted to treat reflux disease. To this end, it further comprises an implantable movement restriction device having an elongated shape with a proximal part and a distal part and having an outer surface including a biocompatible material. The proximal part of the movement restriction device is adapted to rest with at least a part of its outer surface against the patient's stomach fundus wall, in a position between the patient's diaphragm and the fundus wall, such that movement of the cardiac notch of the patient's stomach towards the patient's diaphragm is restricted, when the movement restriction device is implanted in the patient, to thereby prevent the cardia from sliding through the patient's diaphragm opening into the patient's thorax, so as to maintain the supporting pressure against the patient's cardia sphincter muscle exerted from the patient's abdomen, wherein the movement restriction device having a size of at least 125 mm3 and a circumference of at least 15 mm, and a fixation device adapted to secure the movement restriction device in said position, when the movement restriction device is implanted. The distal part stabilizes and holds the proximal part and is adapted to be substantially invaginated in the stomach wall. The apparatus further comprises a stretching device comprising at least one operable stretching device implantable in the obese patient and adapted to stretch a portion of the patient's stomach wall such that satiety is created.

In an embodiment, the apparatus further comprises a stretching device comprising three or more mechanical park engaged with different park of the stomach wall, one part each, wherein said engagement includes suturing or stapling to the stomach wall or invaginating the mechanical park in the stomach wall part with stomach to stomach sutures, wherein the three or more mechanical park are adapted to move in relation to each other adapted to stretch three different wall portions, the stretching device further adapted to having said wall portions stretched independently from each other both regarding force used for stretching the stomach wall portion as well as, time periods the stretching is applied, and when the stretching is applied.

In an embodiment, the apparatus further comprises a stretching device comprising two or more hydraulic park engaged with different park of the stomach wall, one part each, wherein said engagement includes suturing or stapling to hydraulic part to the stomach wall or invaginating the hydraulic park in the stomach wall part, with stomach to stomach sutures, wherein the two or more hydraulic park are adapted to move in relation to each other adapted to stretch three different wall portions, the stretching device further adapted to having said wall portions stretched independently from each other both regarding force used for stretching the stomach wall portion as well as, time periods the stretching is applied, and when the stretching is applied.

In an embodiment, the apparatus further comprises a stretching device is engaged with a part of the stomach wall, including suturing or stapling the stretching device to the stomach wall or invaginating the stretching device in the stomach wall part, with stomach to stomach sutures, wherein the stretching device is further adapted to stretch a stomach wall portion controlling force used for stretching the stomach wall portion as well as, time periods the stretching is applied, and when the stretching is applied.

In an embodiment, the apparatus further comprises a stretching device comprising two parts engaged with different park of the stomach wall, one part each, wherein said engagement includes suturing or stapling the park to the stomach wall or invaginating the park in the stomach wall part, with stomach to stomach sutures, wherein the stretching device further adapted to have different wall portions stretched independently from each other controlling force used for stretching the stomach wall portion as well as, time periods the stretching is applied, and when the stretching is applied.

In an embodiment, the apparatus further comprises an external control unit for controlling the distal part of the movement restriction device from the outside of the patient's body. The external control unit may comprise a wireless remote control adapted to control the device from the outside of the patient's body. Alternatively, the external control unit may comprise a subcutaneously placed switch or reservoir adapted to control the device from the outside of the patient's body.

In an embodiment, the apparatus further comprises a sensor or sensing device adapted to be implanted in the patient body, wherein the implantable control unit is adapted to control the device from the inside of the patient's body using information from said a sensor or sensing device, adapted to sense, direct or indirect, the food intake of the patient.

In accordance with another aspect of the present invention, there is provided an apparatus for treating a reflux disease and obesity of an obese patient having a stomach with a food cavity, the apparatus comprises an implantable movement restriction device having a proximal part and a distal part, wherein the distal part is adapted to be at least substantially invaginated by a stomach wall portion of the patient and having an outer surface that includes a biocompatible material, wherein the distal part of the movement restriction device is adapted to be placed inside the stomach with the outer surface of the volume filling device resting against the inside of the stomach wall, such that the volume of the food cavity is reduced in size by a volume substantially exceeding the volume of the volume filling device. The distal part of the movement restriction device has a maximum circumference of at least 30 millimeters.

In one embodiment of the apparatus, at least one of the movement restriction device segments has at least one flat surface. Preferably, at least one of the movement restriction device segments has the shape of a polyhedron, preferably one of the following shapes: tetrahedron, hexahedron, octahedron, dodecahedron and icosahedrons.

In one embodiment of the apparatus, a friction enhancing material is provided. This increases the friction between adjacent movement restriction device segments, thereby stabilizing the movement restriction device. This friction enhancing material is preferably a glue or an adhesive. Alternatively, at least one of the movement restriction device segments has a surface with a rugged texture.

In one embodiment of the apparatus, at least one of the movement restriction device segments has spherical shape. Alternatively, it has at least one flat surface.

In an alternative embodiment, the apparatus comprises a fluid for reducing the friction between adjacent movement restriction device segments. The movement restriction device can thereby more easily adapt its shape to the movements of the patient's body.

The apparatus may in one embodiment comprise a friction reducing material on the outer surface of the volume filing device segments. This friction reducing material may be a fluid reducing the friction between adjacent movement restriction device segments.

The apparatus may comprise an expandable second movement restriction device segment for enclosing two or more first movement restriction device segments different from the second movement restriction device segment, wherein the second movement restriction device segment and the first movement restriction device segments together form the movement restriction device. In one alternative, the second movement restriction device segment comprises a friction reducing material on an inner surface thereof, the friction reducing material being in contact with the first movement restriction device segments, when implanted.

The second movement restriction device segment may be adapted to be filled with a fluid to allow mutual movement between adjacent first movement restriction device segments so that the shape of the movement restriction device adapts to stomach wall movements, when said movement restriction device is invaginated in a stomach wall. It is then preferred that at least a wall portion of the second movement restriction device segment is flexible or stretchable.

The fluid provided in the movement restriction device may be isotonic or hypertonic.

The movement restriction device segments may be adapted to be inserted into a pouch formed by part of a stomach wall of the patient. The movement restriction device segments may be adapted to be filled, directly or indirectly, into the pouch formed by part of a stomach wall of the patient via a tubular instrument.

In one embodiment, the movement restriction device comprises a solidifying liquid.

This liquid or fluid may be supplied to the pouch by means of a conduit.

In one embodiment, the plurality of movement restriction device segments are adapted to be interconnected to form the movement restriction device, after said plurality of movement restriction device segments have been inserted into a human or artificial pouch.

In one embodiment, the movement restriction device segments are adapted to be assembled to an implantable movement restriction device.

The movement restriction device segments are preferably adapted to form an implantable movement restriction device of a controlled size.

An operational method to be combined in any way using any apparatus, part of apparatus or system or part of system or any claimed embodiment described anywhere in this document.

A method or part of method to be used in any combination and using any apparatus or part of apparatus or any feature in any combination where the following method steps is applicable, wherein said method may comprise one or more of the following operational method steps:
 introducing an instrument into the throat
 passing down the esophagus,
 placing an anvil or unit for delivery of fixating members in the esophagus between the cardia and the diaphragm level, for engaging in the fixation of the esophagus to the stomach tissue,
 passing down the esophagus and additionally further down into the stomach,
 filling the stomach with gas to expand the stomach,
 sucking fluid from the stomach,
 looking at a guiding vision when said instrument comprising a camera,
 engaging the instrument with the stomach,
 creating and suturing at least one pouch of the stomach wall,
 filling said at least one pouch with a fluid and/or volume filling device or two or more volume filling devices,
 deliver a plurality of volume filling devices into said pouch created in the stomach tissue through a tubular member,
 passing through the stomach wall with said instrument,
 passing through the stomach wall with said instrument for the placement of a volume filling device on the outside of the stomach wall,
 passing through the stomach wall with said instrument for the placement of a tube allowing placement of a subcutaneous injection port,
 placing an subcutaneous injection port,
 suturing or stapling the stomach wall from the inside thereof to the esophagus,
 suturing or stapling the stomach wall to stomach wall from the inside of the stomach,
 engaging the instrument with the esophagus,
 suturing or stapling one layer of stomach tissue to one layer of esophageal tissue,
 suturing or stapling two layers of stomach tissue to one layer of esophageal tissue,
 suturing or stapling three layers of stomach tissue to one layer of esophageal tissue,
 suturing or stapling four layers of stomach tissue to one layer of esophageal tissue,
 suturing or stapling one or more layers of stomach tissue to two or more positions on the esophageal tissue, the esophagus having an esophagus center axis, the esophagus further having an inner and outer substantially cylindrical surface extending radially in relation to the esophagus center axis and wherein the stomach tissue is attached to esophageal tissue both at a first point along a first esophagus surface length axis, substantially parallel to said esophagus center axis and at a second point along a second esophagus surface length axis, substantially parallel to said esophagus center axis, at a distance from said first esophagus surface length axis, radially in relation to said esophagus center axis,
 delivering fixating members by a unit placed on said instrument,
 penetrating at least one layer of stomach tissue and one layer of esophagus tissue with said fixating members,
 placing said fixating members above the gastro-esophageal junction for creating a tunnel between the esophagus and stomach above said junction,
 placing an esophagus part in the esophagus and a stomach part in the stomach,
 placing the fixating member substantially between the stomach and esophagus part,
 inserting said instrument into the main stomach cavity through the cardia and adapted to direct the instrument in cranial direction to reach a position of said unit above said junction,
 allowing the tunnel a substantially unrestricted contraction and release of the cardia closing sphincter muscle placed in said junction, when such a tunnel has been created.

A method or part of method to be used in any combination and using any apparatus or part of apparatus or any feature in any combination where the following method steps is applicable, wherein said method comprises one or more of the following operational method steps:
  cutting the skin of a patient
  creating an opening in the abdominal wall of the patient
  Introducing said instrument into the abdominal cavity through said opening in the abdominal wall,
  engaging the instrument with the stomach,
  pulling down into the stomach wall for creating at least one pre-shaped pouch of the stomach wall,
  clamping the stomach wall for creating at least one pre-shaped pouch of the stomach wall,
  suturing or stapling at least one pouch in the stomach wall,
  filling said at least one pouch with a fluid and/or volume filling device or two or more volume filling devices,
  deliver a plurality of volume filling devices into said pouch created in the stomach tissue through a tubular member,
  passing through the stomach wall into the stomach with said instrument,
  passing through the stomach wall with said instrument for the placement of a volume filling device on the inside of the stomach wall,
  passing through the stomach wall with said instrument for suturing the stomach wall to the esophagus wall,
  placing a volume filling device on the outside of the stomach wall,
  invaginating said volume filling device in the stomach wall
  placing a subcutaneous injection port,
  suturing or stapling the stomach wall to stomach wall from the outside of the stomach,
  suturing or stapling the stomach wall to stomach wall from the outside of the stomach without penetrating the mucosa,
  suturing or stapling two layers of stomach wall to one or two layers of stomach wall,
  engaging the instrument with the esophagus,
  clamping the on both sides of the esophagus for fixating one layer of esophageal wall to stomach tissue,
  clamping the on both sides of the esophagus and the stomach fundus wall for fixating one layer of esophageal wall to one or two layers of stomach tissue,
  introducing a tube or a gastroscopic instrument into the esophagus comprising an anvil member or a fixating delivery member involving in the fixation of the esophagus to the stomach,
  coordinating the position of the anvil member or a fixating delivery member inside the esophagus to said instrument clamping around the esophagus,
  suturing or stapling one layer of stomach tissue to one layer of esophageal tissue,
  suturing or stapling two layers of stomach tissue to one layer of esophageal tissue,
  suturing or stapling three layers of stomach tissue to one layer of esophageal tissue,
  suturing or stapling four layers of stomach tissue to one layer of esophageal tissue,
  stapling using staplers of different stapling depths at different positions in a stapler row,
  stapling stomach to esophagus with one first stapler depth and stapling stomach to stomach with a second smaller stapler depth,
  stapling a pouch with stomach to stomach sutures in a stapler row, further comprising stapling the esophagus with staplers of a larger depth included as a part of said stapler row,
  suturing or stapling one or more layers of stomach tissue to two or more positions on the esophageal tissue, the esophagus having an esophagus center axis, the esophagus further having an inner and outer substantially cylindrical surface extending radially in relation to the esophagus center axis and wherein the stomach tissue is attached to esophageal tissue both at a first point along a first esophagus surface length axis, substantially parallel to said esophagus center axis and at a second point along a second esophagus surface length axis, substantially parallel to said esophagus center axis, at a distance from said first esophagus surface length axis, radially in relation to said esophagus center axis,
  delivering fixating members by a unit placed on said instrument,
  penetrating at least one layer of stomach tissue and one layer of esophagus tissue with said fixating members,
  placing said fixating members above the gastro-esophageal junction for creating a tunnel between the esophagus and stomach above said junction,
  allowing the tunnel a substantially unrestricted contraction and release of the cardia closing sphincter muscle placed in said junction, when such a tunnel has been created,
  placing an esophagus part in the esophagus and a stomach part in the stomach via an introduction into the stomach cavity,
  placing the fixating member substantially between the stomach and esophagus part,
  inserting said instrument into the main stomach cavity below said junction and adapted to direct the instrument in cranial direction to reach a position of said unit above said junction,
  operating a joint comprised in said instrument, for enabling said instrument to be inserted into the main stomach cavity bending said joint in a direction to reach a position of said part of the unit in the esophagus above said junction.

A method or part of method to be used in any combination and using any apparatus or part of apparatus or any feature in any combination where the following method steps is applicable, wherein said method comprises one or more of the following laparoscopic operational method steps:
  cutting the skin of a patient
  introducing a tube through the abdominal wall,
  filling a fluid or gas into the abdominal cavity,
  introducing two or more trocars into the abdominal cavity,
  introducing a camera into the abdominal cavity through one of the trocars,
  introducing said instrument into the abdominal cavity through a trocar,
  engaging the instrument with the stomach,
  pulling down into the stomach wall for creating at least one pre-shaped pouch of the stomach wall,
  clamping the stomach wall for creating at least one pre-shaped pouch of the stomach wall,
  suturing or stapling at least one pouch in the stomach wall,
  filling said at least one pouch with a fluid and/or a volume filling device or two or more volume filling devices,
  deliver a plurality of volume filling devices into said pouch created in the stomach tissue through a tubular member,
  passing through the stomach wall into the stomach with said instrument, passing through the stomach wall with said instrument for the placement of a volume filling device on the inside of the stomach wall, passing through the stomach wall with said instrument for suturing the stomach wall to the esophagus wall, placing a volume filling device on the outside of the stomach wall, invaginating said volume filling device in the stomach wall placing a subcutaneous injection port, suturing or stapling the stomach wall to stomach wall from the outside of the stomach, suturing or stapling two layers of stomach wall to one or two layers of stomach wall, suturing or stapling the stomach wall to stomach wall from the outside of the stomach without penetrating the mucosa, engaging the instrument with the esophagus, clamping the on both sides of the esophagus for fixating one layer of esophageal wall to stomach tissue, clamping the on both sides of the esophagus and the stomach fundus wall for fixating one layer of esophageal wall to one or two layers of stomach tissue, introducing a tube or a gastroscopic instrument into the esophagus comprising an anvil member or a fixating delivery member involving in the fixation of the esophagus to the stomach, coordinating the position of the anvil member or a fixating delivery member inside the esophagus to said instrument clamping around the esophagus, suturing or stapling one layer of stomach tissue to one layer of esophageal tissue, suturing or stapling two layers of stomach tissue to one layer of esophageal tissue, suturing or stapling three layers of stomach tissue to one layer of esophageal tissue, suturing or stapling four layers of stomach tissue to one layer of esophageal tissue, stapling using staplers of different stapling depths at different positions in a stapler row, stapling stomach to esophagus with one first stapler depth and stapling stomach to stomach with a second smaller stapler depth, stapling a pouch with stomach to stomach sutures in a stapler row, further comprising stapling the esophagus with staplers of a larger depth included as a part of said stapler row, suturing or stapling one or more layers of stomach tissue to two or more positions on the esophageal tissue, the esophagus having an esophagus center axis, the esophagus further having an inner and outer substantially cylindrical surface extending radially in relation to the esophagus center axis and wherein the stomach tissue is attached to esophageal tissue both at a first point along a first esophagus surface length axis, substantially parallel to said esophagus center axis and at a second point along a second esophagus surface length axis, substantially parallel to said esophagus center axis, at a distance from said first esophagus surface length axis, radially in relation to said esophagus center axis, delivering fixating members by a unit placed on said instrument, penetrating at least one layer of stomach tissue and one layer of esophagus tissue with said fixating members, placing said fixating members above the gastro-esophageal junction for creating a tunnel between the esophagus and stomach above said junction, allowing the tunnel a substantially unrestricted contraction and release of the cardia closing sphincter muscle placed in said junction, when such a tunnel has been created, placing an esophagus part in the esophagus and a stomach part in the stomach via an introduction into the stomach cavity, placing the fixating member substantially between the stomach and esophagus part, inserting said instrument into the main stomach cavity below said junction and adapted to direct the instrument in cranial direction to reach a position of said unit above said junction, operating a joint comprised in said instrument, for enabling said instrument to be inserted into the main stomach cavity bending said joint in a direction to reach a position of said part of the unit in the esophagus above said junction.

Please note that any embodiment or part of embodiment as well as any method or part of method or any apparatus or part of apparatus or any feature or part of feature or any system or part of system or any figure or part of figure could be combined in any applicable way. All examples herein should be seen as part of the general description and therefore possible to combine in any way in general terms.

It should be noted that any embodiment or part of embodiment or feature or method or associated system or part of system described herein may be combined in any combination.

BRIEF DESCRIPTION OF DRAWINGS

The present invention will now be described in more detail by way of non-limiting examples, and with reference to the accompanying drawings, in which

FIGS. 11-27 are schematic views of various ways of powering an apparatus for treating Gastro Esophageal Reflux Disease.

FIG. 70-76 are views of various embodiments of an apparatus for treating obesity that can be combined with the reflux treatment apparatus implanted in a human patient.

FIGS. 77-93 show various ways of powering an apparatus for treating obesity that can be combined with an apparatus for treating reflux implanted in a human patient.

DESCRIPTION OF EMBODIMENTS

As used herein, the term "segment" should be construed broadly to define any of the parts into which something can be divided.

Movement Restriction Device

Figure 1A:
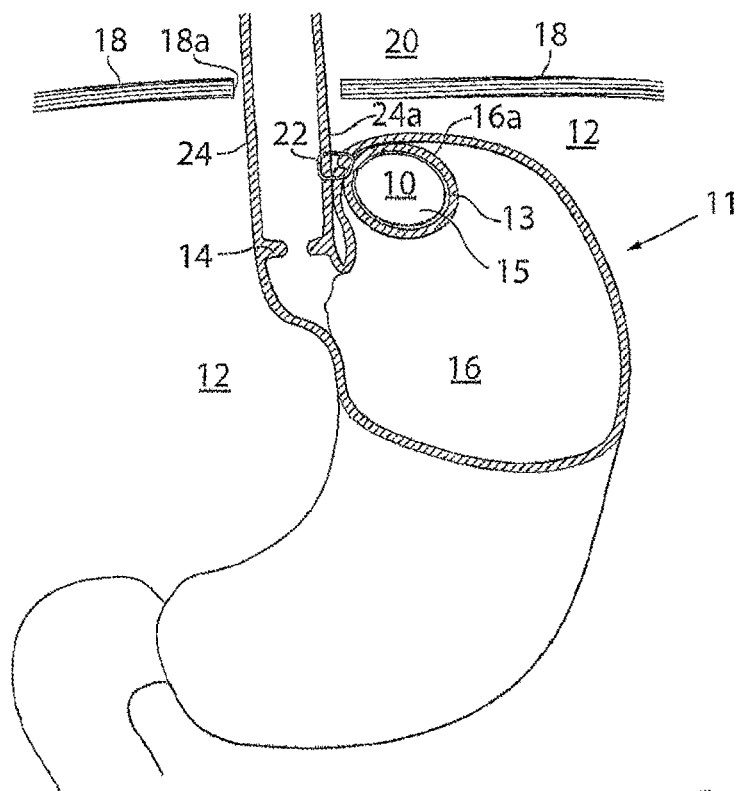
FIGS. 1A-C are schematic views of various embodiments of an apparatus for treating Gastro Esophageal Reflux Disease implanted in a human patient.

FIG. 1A is a schematic view depicting an apparatus 11, including a movement restriction device 10 of a biocompatible material, for treating reflux disease, in accordance with the invention, implanted in a human patient In FIG. 1A, the device 10 is invaginated in the fundus. The device 10 comprises a body 13 having an outer surface 15 suitable for resting against a portion of the outside wall 16a of the stomach fundus wall 16 in a position between the patient's diaphragm 18 and at least a portion of the lower part of the invaginated stomach fundus wall 16. Thus, with the device 10 invaginated in this fashion, movement of the cardiac notch of the patient's stomach towards the patient's diaphragm is restricted, thereby the cardia is prevented from sliding through the patient's diaphragm opening into the patient's thorax 20 and the supporting pressure against the patient's cardia sphincter muscle exerted from the patient's abdomen is maintained The body 13 is inflatable and adapted to be inflated with a gel or fluid. A fluid or gel receiving member for receiving fluid to inflate said movement restriction device may be provided. Alternatively, the body 13 includes a homogenous material and be a solid body. Alternatively, the body 13 includes an outer wall in the form of an enclosure wall defining a chamber. The outer wall may be rigid, elastic or flexible. When the outer wall is rigid, it is rigid enough to maintain non-deformed when subject to forces created by stomach movements.

The body 13 of the movement restriction device 10 can be affixed to the wall 16a of the fundus 16 in a number of different ways. In the embodiment shown in FIG. 1A, the device 10 is invaginated in the fundus stomach wall from outside the stomach. After invagination, a first fixation device consisting of a number of stomach-to-stomach sutures or staples 22a is applied to keep the invagination in tact in the short term. This allows the growth of human tissue to keep the invagination in tact over the long term.

There may optionally be a second fixation device consisting of a number of sutures or staples 22b that are provided between the wall 16a of the fundus 16 and the wall 24a of the esophagus 24 to hold the device 10 in said position between the patient's diaphragm 18 and at least a portion of the lower part of the invaginated stomach fundus wall 16. Thus, the device 10 is affixed in this position by this second fixation apparatus. A direct or indirect affixation of the device 10 to the diaphragm muscle 18 or other muscle tissue may be provided. As an alternative, a direct or indirect affixation of the device 10 to the esophagus His can be provided. Alternatively, or additionally, there may be a third fixation device in the form of sutures or staples 22c provided between the wall 16a of the fundus 16 and the diaphragm 18 to hold the device 10 in said position.

Figure 1B:
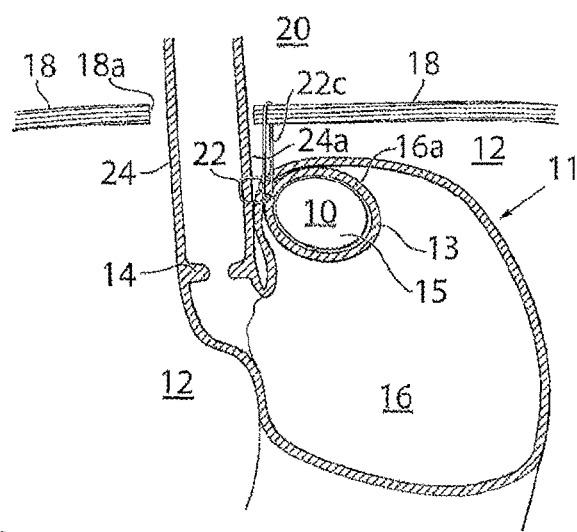

FIG. 1B shows an embodiment substantially similar to the one shown in FIG. 1A. In FIG. 1B the body 13 and invagination are, in addition to the affixation 22, fixed by means of sutures and/or staples 22c between the reflux body 13 and the diaphragm 18, to hold the device in position above the cardia 14.

Figure 1C:
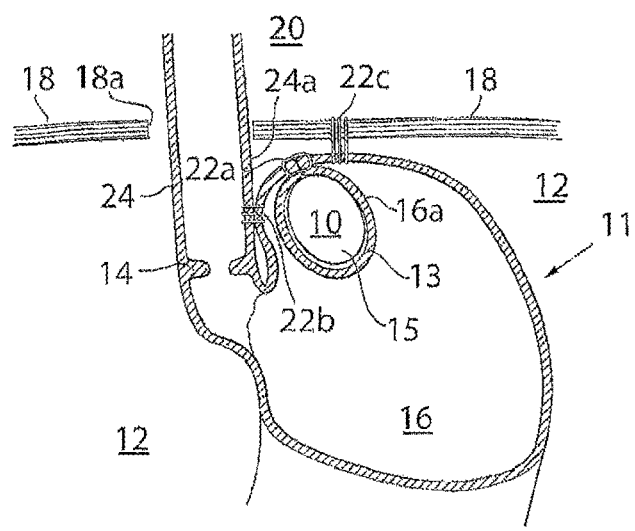

FIG. 1C shows another embodiment substantially similar to the one shown in FIG. 1A. In FIG. 1C the reflux treatment device is held in place by stomach-to-stomach sutures or staples 22a that connect the wall 16a of the fundus 16 to the wall 16a of the fundus 16. In addition the reflux treatment device 10 is held in place by sutures 22b or staples from the wall 16 of the fundus 16a to the wall of the esophagus 24a, and by sutures or staples from the wall of the fundus 16a to the diaphragm.

Figure 2A:
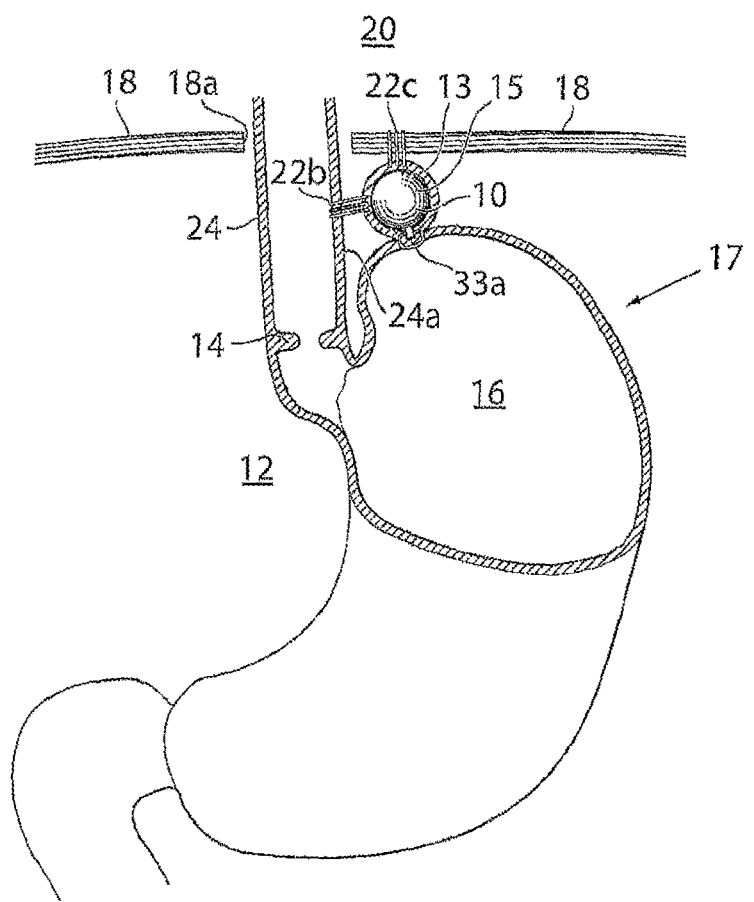
FIGS. 2A-B are schematic views of various embodiments of an apparatus for treating Gastro Esophageal Reflux Disease implanted in a human patient.

An alternative embodiment of an apparatus 17 for the treatment of reflux disease in accordance with the invention is depicted in FIG. 2A. This embodiment is, in many aspects, similar to the one described above with reference to FIG. 1A-C. Thus, a movement restriction device 10 is shown implanted in a human patient and invaginated in the fundus. However, in the embodiment shown in FIG. 2A, the device 10 is invaginated from the inside of the stomach, instead of from outside of the stomach, as in FIG. 1A-C. The movement restriction device 10 comprises a body 13 adapted to rest against a portion of the inside wall of the stomach fundus wall 16 in a position between the patient's diaphragm 18 and at least a portion of the lower part of the invaginated stomach fundus wall 16. In this embodiment, the body 13 is situated above the cardia area 14 of a standing human or animal mammal patient. The body 13 of the device 10 is shaped to rest against the wall 16a of the fundus 16, and further, has an outer surface 15 suitable to rest against this fundus wall. Thus, with the device 10 invaginated in this fashion as described above in connection with FIG. 1A, movement of the cardiac notch of the patient's stomach towards the patient's diaphragm is restricted, thereby the cardia is prevented from sliding through the patient's diaphragm opening into the patient's thorax 20 and the supporting pressure against the patient's cardia sphincter muscle exerted from the patient's abdomen is maintained.

After invagination, a number of stomach-to-stomach sutures or staples 33a comprising a first fixation device are applied from inside the stomach 16 to keep the invagination in tact in the short term. This allows the growth of human tissue, keeping the invagination in tact over the long term. Additional sutures or staples 22b comprising a second fixation device can be provided between a wall portion 16b of the fundus 16 forming part of the invagination of the device 10 and the wall 24a of the esophagus 24 to hold the device 10 in said position. Similarly, a third fixation device in the form of sutures or staples 22c can be provided between another wall portion 16c of the fundus 16 forming part of the invagination of the device 10 and the diaphragm 18 to hold the device 10 in said position.

Figure 2B:
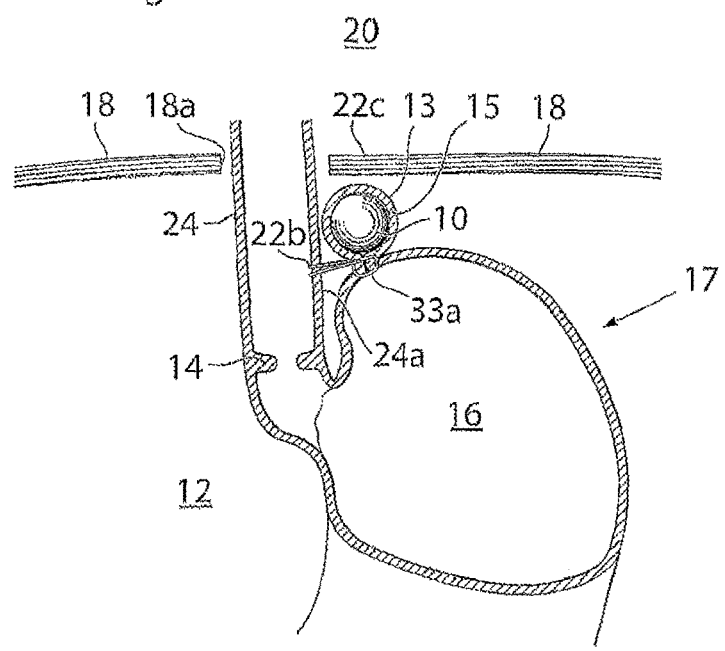

An alternative embodiment is shown in FIG. 2B. This embodiment is in many aspects similar to the one described with reference to FIG. 2A. However, here the sutures and staples 22b and 33a are all connected to the fixator of the reflux treatment device 10. This embodiment lacks stomach-to-diaphragm sutures or staples.

Figure 3A:
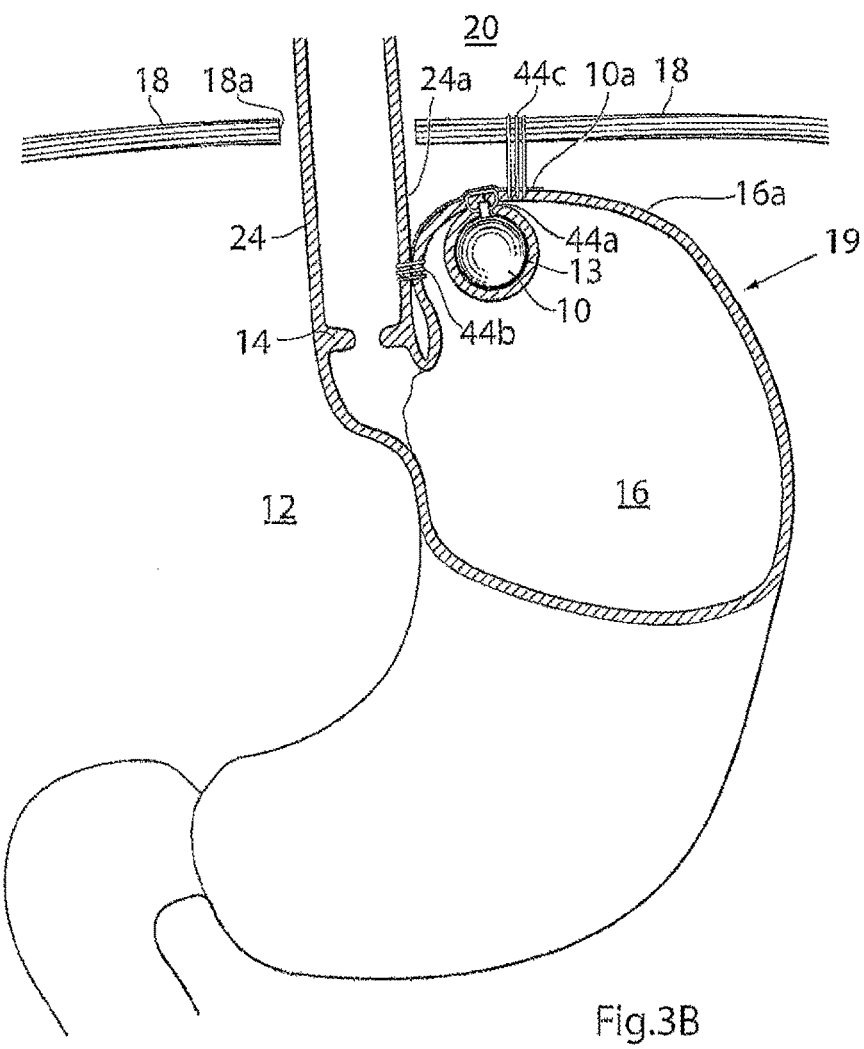
FIGS. 3A-B are schematic views of various embodiment of an apparatus for treating Gastro Esophageal Reflux Disease implanted in a human patient.

An alternative an apparatus 19 for the treatment of reflux disease is depicted in FIG. 3A. This alternative is in many aspects similar to the ones described above with reference to FIGS. 1A-C and 2A-B. Thus, a movement restriction device 10 is shown implanted in a human patient. The device 10 comprises a body 13 adapted to rest against a portion of the stomach fundus wall 16 in a position between the patient's diaphragm 18 and stomach fundus wall 16. However, in this alternative, the device 10 is not invaginated in the stomach 16. Instead, the affixation of the device 10 comprises an attachment structure 10a, preferably a netlike-structure that is adapted to be in contact with the fundus stomach wall 16a to promote the growth of human tissue to secure long term placement of the reflux disease treatment device attached to the stomach wall. In the short term, a first fixation device in the form of sutures or staples 44a may be provided between the attachment structure 10a and the fundus wall 16a to keep the attachment structure 10a in place.

The attachment structure 10a may be adapted for a second fixation device in the form of sutures or staples 44b that are provided between the wall 16a of the fundus 16 and the wall 24a of the esophagus 24 to hold the device 10 in said position between the patient's diaphragm 18 and stomach fundus wall 16. Similarly, the attachment structure 10a may also be adapted for a third fixation device in the form of sutures or staples 44c that are provided between the wall 16a of the fundus 16 and the diaphragm 18, again, to hold the device 10 in said position.

Figure 3B:
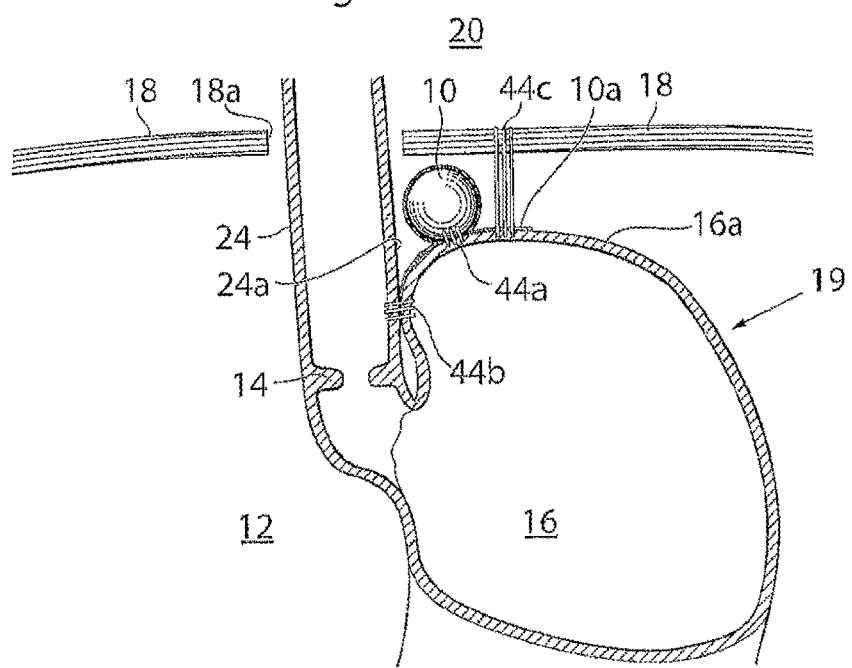

An alternative embodiment is shown in FIG. 3B. This embodiment is in many aspects similar to the one described with reference to FIG. 3A. In this embodiment, the reflux treatment device 10 is, like in FIG. 2A-B invaginated from the inside of the stomach. The attachment structure 10a is positioned on the wall 16a of the fundus 16 above and around the invagination created by the reflux treatment device 10.

Figure 4A:
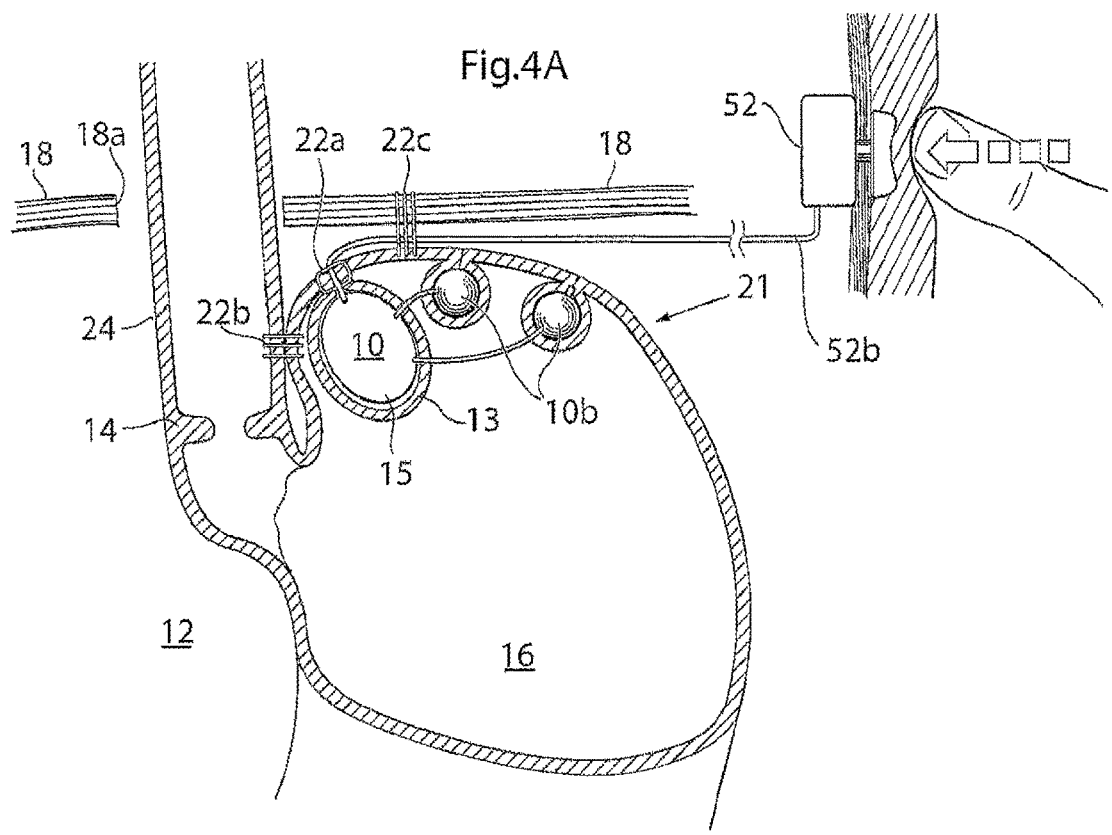
FIGS. 4D-B are schematic views of embodiments of an apparatus for treating Gastro-esophageal Reflux Disease and obesity implanted in a human patient

A alternative embodiment of an apparatus 21 for treatment of reflux disease in accordance with the invention is depicted in FIG. 4A. This embodiment is in many aspects similar to the one described above with reference to FIG. 1A-C. In FIG. 4A, a view of a device 10 for treatment of reflux disease in accordance with the invention is shown implanted in a human patient. In FIG. 4A, the movement restriction device 10 is again invaginated in the fundus 16. The device 10 comprises a body 13 having an outer surface 15 suitable for resting against a portion of the outside wall 16a of the stomach fundus wall 16 in a position between the patient's diaphragm 18 and at least a portion of the lower part of the invaginated stomach fundus wall 16. The body 13 is shaped to rest against the outside wall 16a of the fundus 16. Thus, with the device 10 invaginated in this fashion, movement of the cardiac notch of the patient's stomach towards the patient's diaphragm is restricted, thereby the cardia is prevented from sliding through the patient's diaphragm opening into the patient's thorax 20 and the supporting pressure against the patient's cardia sphincter muscle exerted from the patient's abdomen is maintained.

In the embodiment of FIG. 4A, as in the embodiment of FIG. 1A, after invagination of the device 10 in the fundus 16, a first fixation device consisting of a number of stomach-to-stomach sutures or staples 22a is applied to keep the invagination in tact in the short term. A second fixation device consisting of a number of sutures or staples 22b is provided to hold the device 10 in said position between the patient's diaphragm 18 and at least a portion of the lower part of the invaginated stomach fundus wall 16. Additionally, a third fixation device in the form of sutures or staples 22c may be provided between the wall 16a of the fundus 16 and the diaphragm 18, again, to hold the device 10 in said position.

In the embodiment depicted in FIG. 4A, the size of the movement restriction device 10 can be regulated while being implanted. The device 10 is associated with a hydraulic reservoir 52 connected to the device 10 by a lead 52b, whereby a non-invasive regulation can be performed by manually pressing the reservoir 52. The device 10 is, in turn, connected to one or more smaller chambers 10b.

Furthermore, the embodiment above may alternatively be used to also treat obesity. The apparatus may, in this embodiment, be adapted to treat obesity by using the volume of the movement restriction body 13 to contain a fluid, and further using one or more smaller chambers 10b connected to the body 13 with a pump to be filled with fluid to stretch the fundus wall to create satiety. The small chambers 10b are also adapted to be invaginated to in the fundus stomach wall, and when filled with fluid, an expansion occurs that results in human sensor feedback creating satiety. By placing the small hydraulic reservoir/pump subcutaneously in the patient, the patient is able to pump hydraulic fluid to fill the small chambers to feel full on request.

Figure 4B:
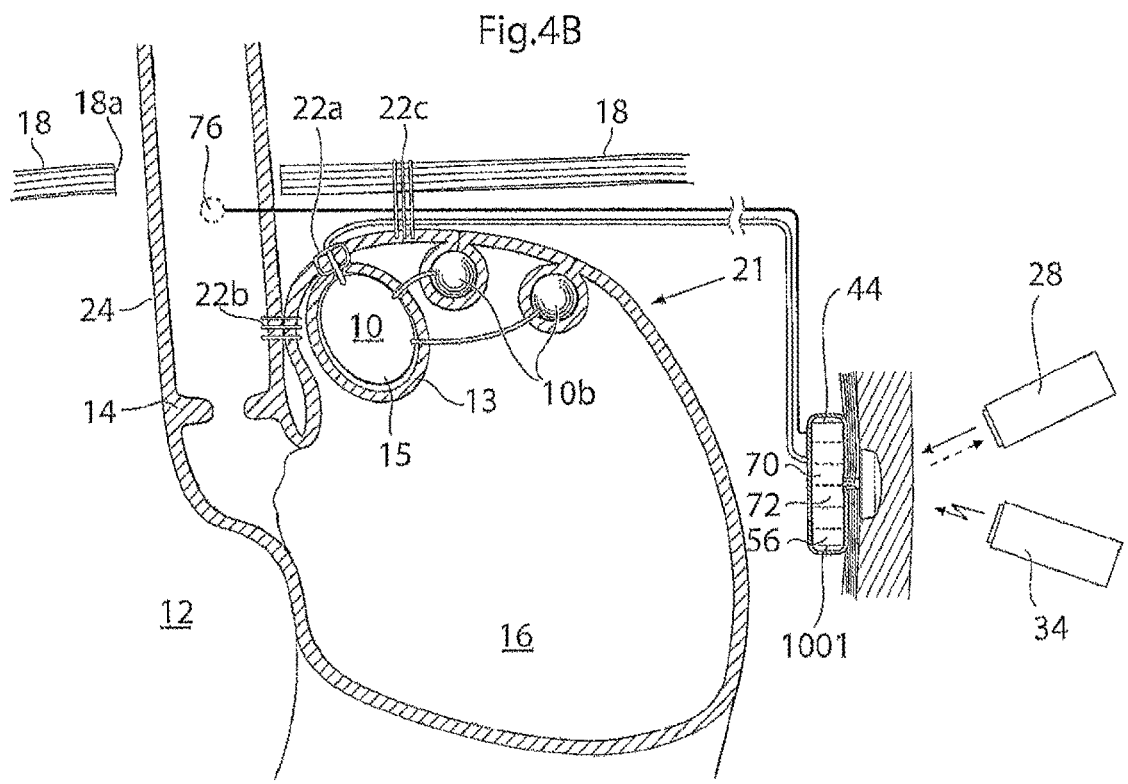

An alternative embodiment is shown in FIG. 4B. This embodiment is substantially similar to the one shown in FIG. 4A but differs in how the reflux treatment device 10 and chambers 10b are controlled. Here, the chambers 10b are not controlled by a subcutaneous pump but a powered internal control unit 56. The internal control unit 56 comprises means for the patient to control the device 10 in how it shall be used regarding treatment of reflux and/or obesity. It may also comprise means of supplying power to the device.

The internal control unit 56 may comprise a battery 70, an electric switch 72, a motor/pump 44, a reservoir 52, and an injection port 1001. An energy transmission device 34 with a remote control is adapted for controlling and powering the device. The items being selected depending on the circumstances, e.g. if the device is electrically, hydraulically, pneumatically or mechanically operated.

The control unit may receive input from any sensor 76, specially a pressure sensor. Any type of sensor may be supplied. The internal control unit 56 preferable includes intelligence in forms of a FPGA or MCU or ASIC or any other circuit, component or memory (For a more extensive description see below under "system").

Figure 4C:
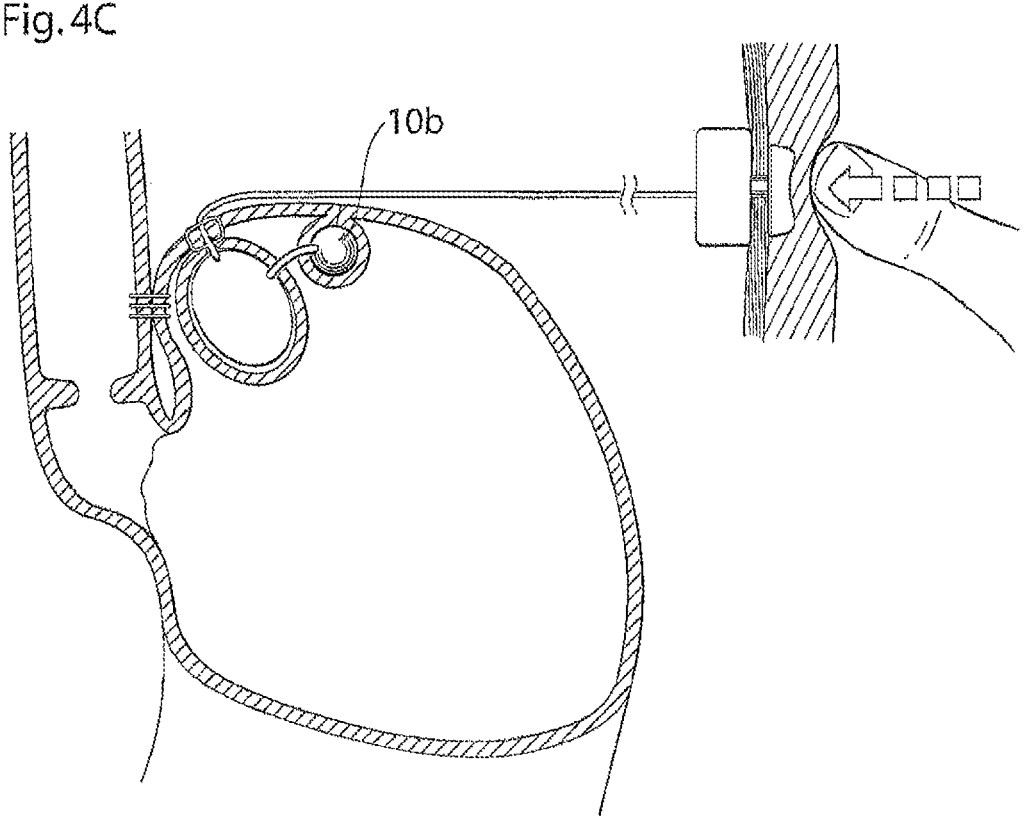
Figure 4D:
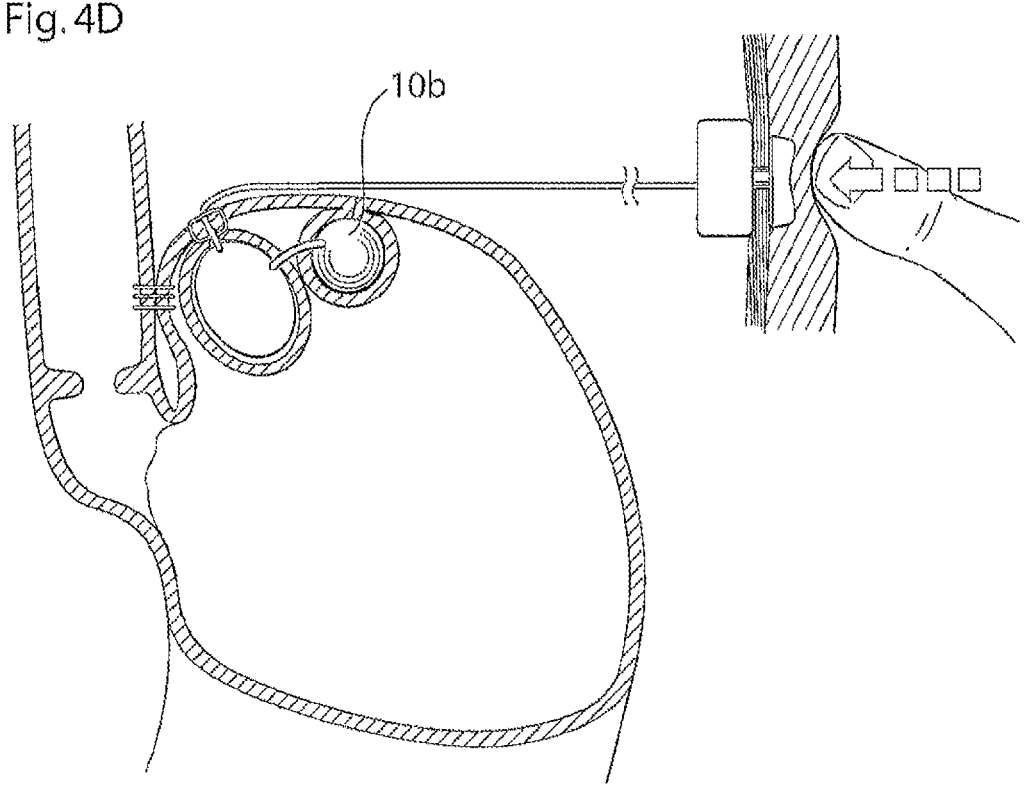

FIG. 4C shows essentially the same as FIG. 4A with the difference that there is one small chamber 10b instead of two small chambers as in 4A. FIG. 4C shows the small chamber 10b in its empty state whereas FIG. 4D shows the small chambers 10b when it has been filled and enlarged to create satiety.

Figure 5A:
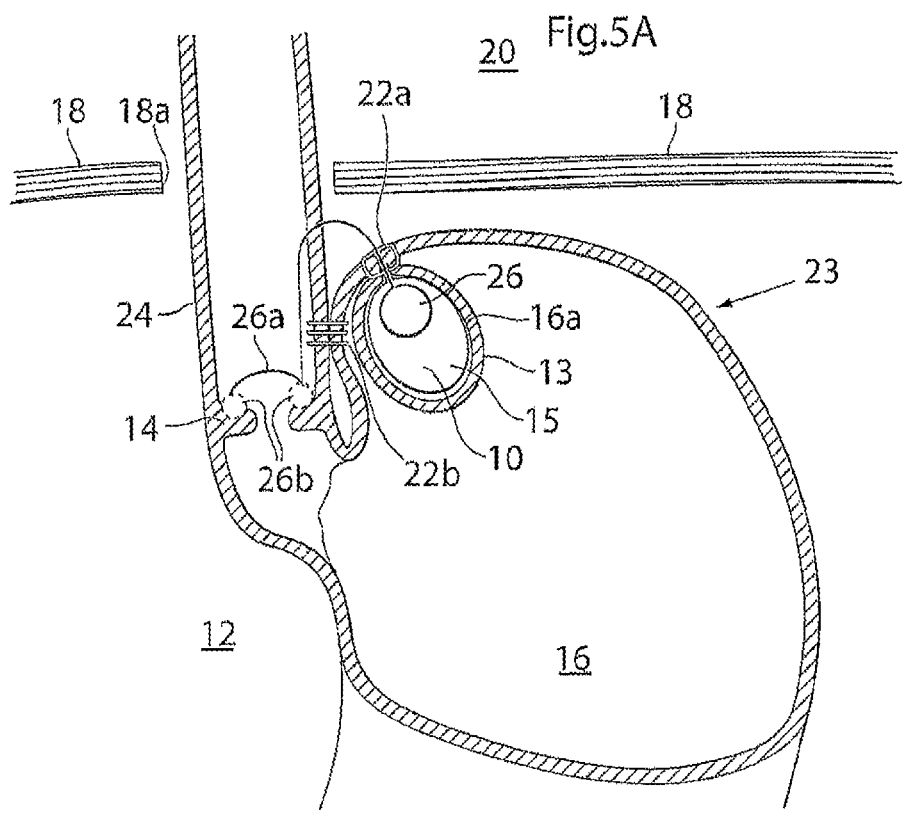
FIG. 5 is a schematic view of an embodiment of an apparatus for treating Gastro-esophageal Reflux Disease implanted in a human patient

Yet an alternative embodiment of an apparatus 23 for the treatment of reflux disease in accordance with the invention is depicted in FIG. 5A. This embodiment is, again, in many aspects similar to the one described above with reference to FIG. 1A-C. Thus, as in the embodiment of FIG. 1A, a movement restriction device 10, which is invaginated in the fundus, is comprised of a body 13 having an outer surface 15 suitable for resting against a portion of the outside wall 16a of the stomach fundus wall 16 in a position between the patient's diaphragm 18 and at least a portion of the lower part of the invaginated stomach fundus wall 16. The body 13 of the device 10 is shaped to rest against the outside wall 16a of the fundus 16 and has a generally smooth outer surface 15 suitable for resting against this fundus wall. And, again, after invagination of the device 10 in the fundus 16, a first fixation device consisting of a number of stomach-to-stomach sutures or staples 22a is applied to keep the invagination in tact in the short term. A second fixation device consisting of a number of sutures or staples 22b applied between the wall 16a of the fundus 16 and the wall 24a of the esophagus 24 is provided to hold the device 10 in said position.

In the alternative embodiment shown in FIG. 5A, the apparatus 23 further comprises a stimulation device 26 for sending out stimulation pulses adapted to stimulate the cardia muscle to further close the cardia to additionally prevent reflux disease. The apparatus 23 comprises at least one conductor 26a and at least one electrode 26b adapted to receive the stimulation pulses.

The stimulation device 26 preferably comprises an electronic circuit and an energy source, which in the preferred embodiment is provided in the device 10.

The stimulation device 26 preferably sends stimulation pulses as a train of pulses, wherein the pulse train is adapted to be repeated with a time break in between, the break extending the break between each pulse in the pulse train.

Figure 5B:
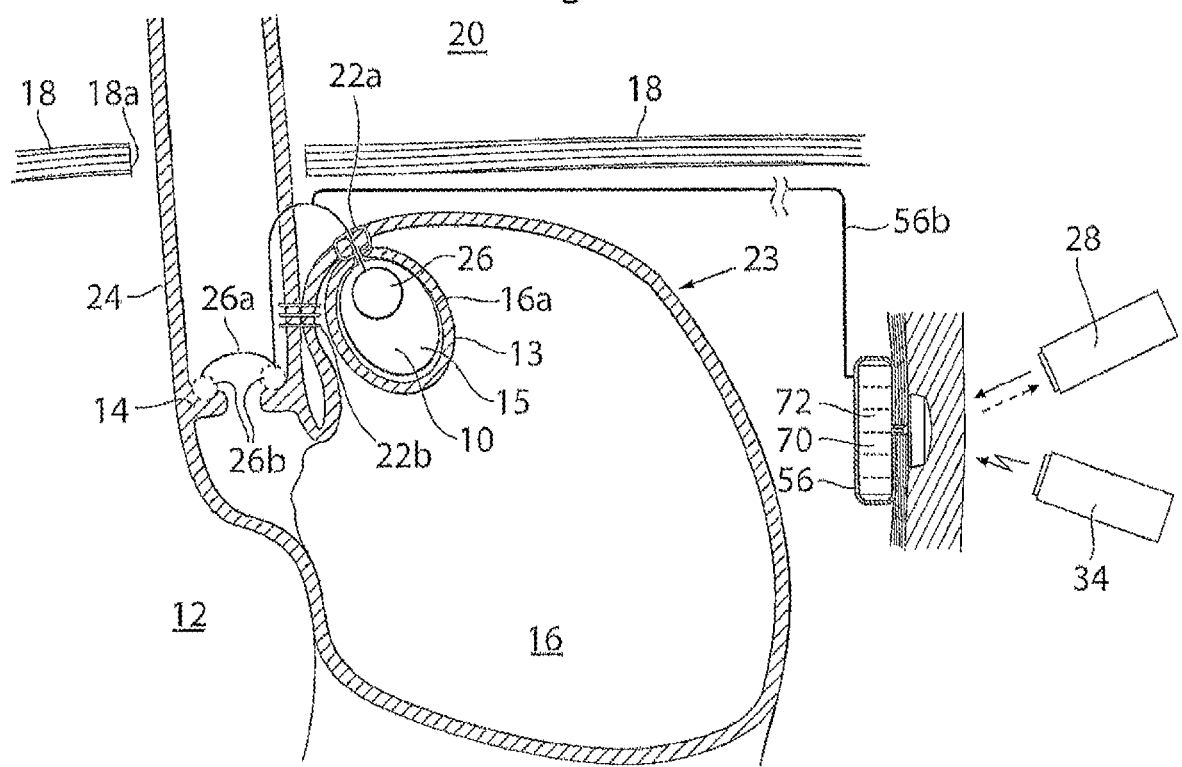

FIG. 5B shows essentially the same embodiment as in FIG. 5A, with the addition of an internal control unit 56, a remote control 28 and an external energy transmission device 34. The internal control unit 56 is connected to the stimulation device with a power lead 56b. The internal control unit 57 may comprise a battery 70 and an electric switch 72 and other component described below under "system".

Figure 6A:
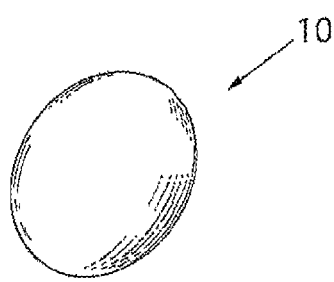
FIGS. 6A-D and 7-9 show alternative shapes of a movement restriction device for treating Gastro Esophageal Reflux Disease adapted to be implanted in a human patient
Figure 6B:
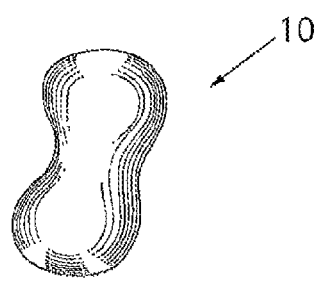
Figure 6C:
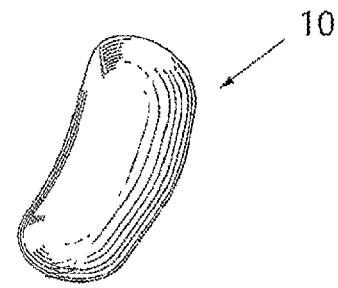

The reflux disease treatment device 10 can, in accordance with one embodiment of the present invention, be formed as a generally egg shaped body, as is shown in FIG. 6A. The reflux disease treatment device 10 can, in accordance with another embodiment of the present invention, also be formed as an egg or sphere shaped body with an indent in its middle, as is shown in FIG. 6B. The reflux disease treatment device 10 can, in accordance with yet another embodiment of the present invention, further be formed as a slightly bent egg shaped body as shown in FIG. 6C.

Figure 6D:
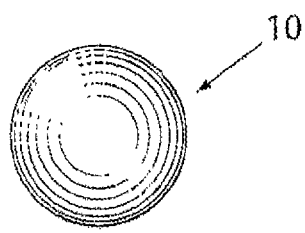

The reflux disease treatment device 10 can, in accordance with a further embodiment of the present invention, be formed as a generally spherically-shaped body, as shown in FIG. 6D.

Figure 7:
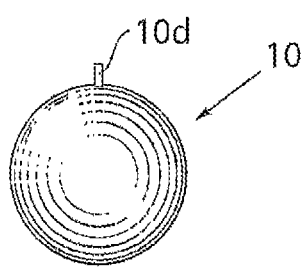

As discussed above, the reflux treatment device 10 is fixed in a position which is above the esophagus in a standing patient. To enable this, one embodiment of the reflux treatment shown in FIG. 7 comprises a fixator 10d that may, for example, serve as an attachment point for sutures or staples. The fixator may be a loop or a ridge with or without holes or have any other shape that makes it suitable for fixating the reflux treatment device 10.

Figure 8:
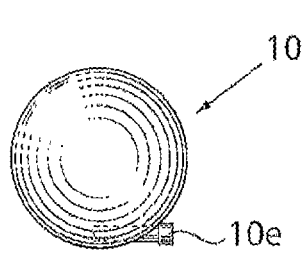

FIG. 8 show an embodiment of the reflux treatment device 10 where it is adjustable by a hydraulic mean, and 10e is an injection port where hydraulic fluid can be in order to expand the device. Alternatively, in one embodiment the reflux treatment device 10 can be inflated from a small size to a larger size during a surgical procedure where it is advantageous that the device is initially of small size, for example during a laparoscopic procedure. In such an embodiment, any filling material, solid, liquid or gas many injected trough the injection port 10e in order for the reflux treatment device 10 to achieve its final shape.

Figure 9:
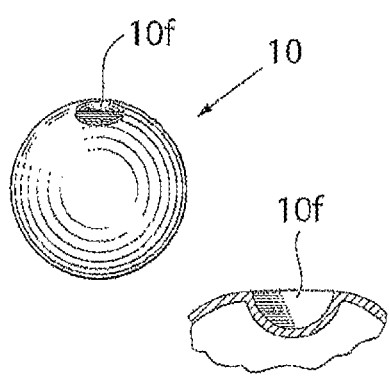

FIG. 9 shows an embodiment where the reflux treatment device 10 has a sunken ridge 10f adapted to being held with a surgical tool. This is to be used, for example, during a surgical procedure when the reflux treatment device is implanted.

When the reflux disease treatment device 10 is generally spherical, whereby it can be made to wholly or partly encompass the esophagus, the inner diameter D of the reflux disease treatment device 10, is preferably such that it can encompass the esophagus and at least a part of the fundus so that the device does not rest directly against the wall of the esophagus when implanted.

The movement restriction device 10 may take any form that enables the device 10 to rest in a position in which movement of the cardiac notch of the patient's stomach towards the patient's diaphragm is restricted, thereby the cardia is prevented from sliding through the patient's diaphragm opening into the patient's thorax and the supporting pressure against the patient's cardia sphincter muscle exerted from the patient's abdomen is maintained.

System

An energy and operation system, generally designated 28, to be incorporated in the apparatus according to the invention, will now be described with reference to FIGS. 10-27.

Figure 10:
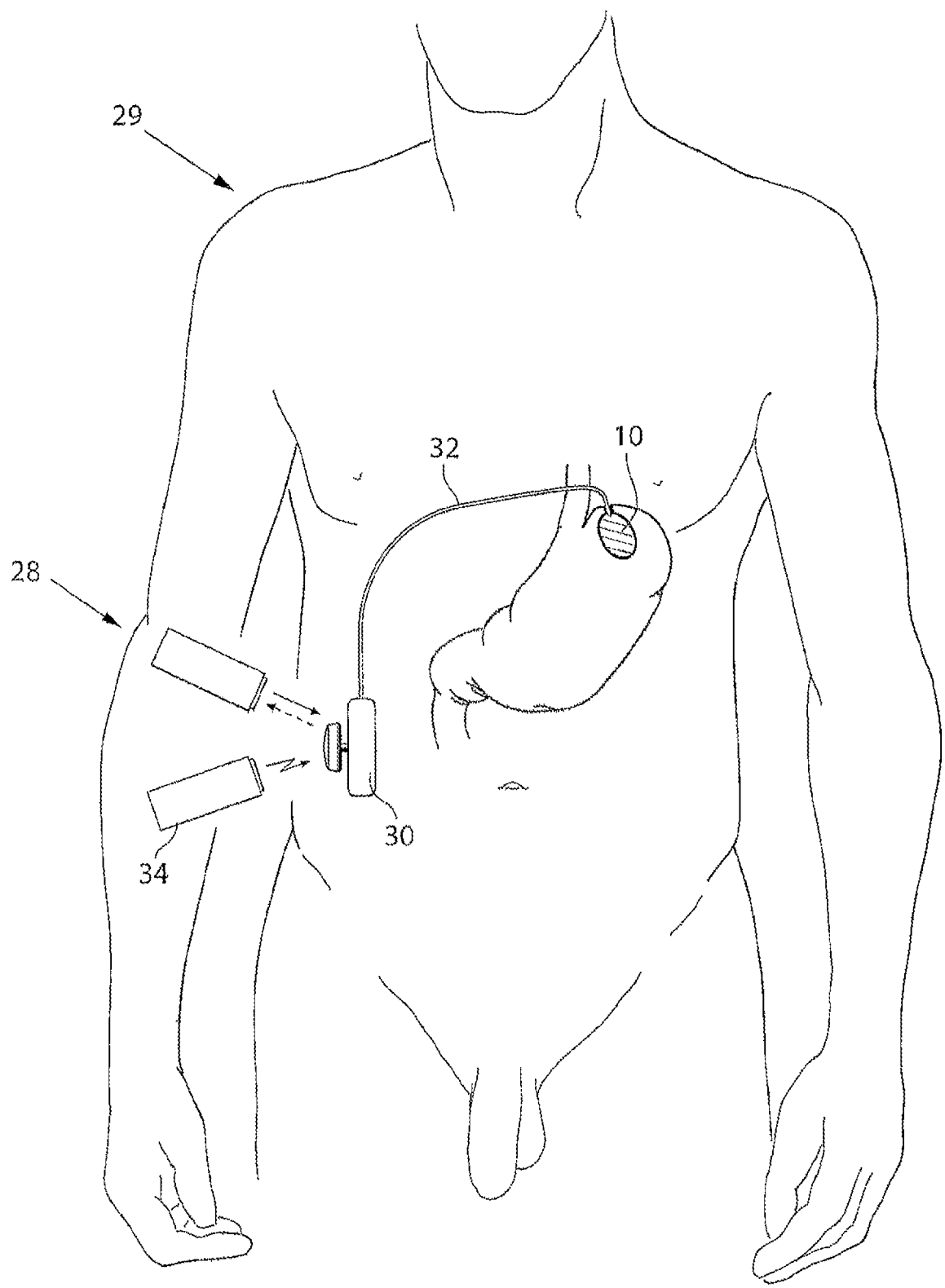
FIG. 10 is an overall view of a patient with an implanted movement restriction device for treating Gastro Esophageal Reflux Disease.

The system 28 shown in FIG. 10 comprises an internal energy source in the form of an implanted energy transforming device 30 adapted to supply energy consuming component of the reflux disease treatment apparatus with energy via a power supply line 32. An external energy transmission device 34 includes a wireless remote control transmitting a wireless signal, which is received by a signal receiver which may be incorporated in the implanted energy transforming device 30, or be separate. The implanted energy transforming device 30 transforms energy from the signal into electric energy which is supplied via the power supply line 32.

The system 28 of FIG. 10 is shown in a more generalized block diagram form in FIG. 11, wherein the patient's skin 36, generally shown by a vertical line, separates the interior of the patient 29 to the right of the line from the exterior to the left of the line.

FIG. 11 shows a simplified block diagram showing the movement restriction device 10, the energy transforming device 30 powering the device 10 via power supply line 32, and the external energy transmission device 34.

FIG. 12 shows an embodiment of the invention identical to that of FIG. 11, except that a reversing device in the form of an electric switch 38 operable by polarized energy also is implanted in the patient 29 for reversing the device 10. The wireless remote control of the external energy transmission device 34 transmit a wireless signal that carries polarized energy and the implanted energy transforming device 30 transforms the wireless polarized energy into a polarized current for operating the electric switch 38. When the polarity of the current is shifted by the implanted energy transforming device 30 the electric switch 38 reverses the function performed by the device 10.

FIG. 13 shows an embodiment of the invention identical to that of FIG. 11, except that an operation device 40 implanted in the patient for regulating the reflux disease treatment device 10 is provided between the implanted energy transforming device 30 and the device 10. This operation device can be in the form of a motor 40, such as an electric servomotor. The motor 40 is powered with energy from the implanted energy transforming device 30, as the remote control of the external energy transmission device 34 transmit a wireless signal to the receiver of the implanted energy transforming device 30.

FIG. 14 shows an embodiment of the invention identical to that of FIG. 11, except that it also comprises an operation device is in the form of an assembly 42 including a motor/pump unit 78 and a fluid reservoir 46 is implanted in the patient. In this case the device 10 is hydraulically operated, i.e. hydraulic fluid is pumped by the motor/pump unit 44 from the fluid reservoir 46 through a conduit 48 to the device 10 to operate the device, and hydraulic fluid is pumped by the motor/pump unit 44 back from the device 10 to the fluid reservoir 46 to return the device 10 to a starting position. The implanted energy transforming device 30 transforms wireless energy into a current, for example a polarized current, for powering the motor/pump unit 44 via an electric power supply line 50.

Instead of a hydraulically operated movement restriction device 10, it is also envisaged that the operation device comprises a pneumatic operation device. In this case, pressurized air can be used for regulation and the fluid reservoir is replaced by an air chamber and the fluid is replaced by air.

In all of these embodiments the energy transforming device 30 may include a rechargeable accumulator like a battery or a capacitor to be charged by the wireless energy and supplies energy for any energy consuming part of the apparatus.

The external energy transmission device 34 is preferably wireless and may include a remotely controlled control device for controlling the device 10 from outside the human body.

Such a control device may include a wireless remote control as well as a manual control of any implanted part to make contact with by the patient's hand most likely indirect for example a button to press placed under the skin FIG. 15 shows an embodiment of the invention comprising the external energy transmission device 34 with its wireless remote control, the device 10, in this case hydraulically operated, and the implanted energy transforming device 30, and further comprising a hydraulic fluid reservoir 52, a motor/pump unit 44 and an reversing device in the form of a hydraulic valve shilling device 54, all implanted in the patient. Of course the hydraulic operation could easily be performed by just changing the pumping direction and the hydraulic valve may therefore be omitted. The remote control may be a device separated from the external energy transmission or included in the same. The motor of the motor/pump unit 44 is an electric motor. In response to a control signal from the wireless remote control of the external energy transmission device 34, the implanted energy transforming device 30 powers the motor/pump unit 44 with energy from the energy carried by the control signal, whereby the motor/pump unit 44 distributes hydraulic fluid between the hydraulic fluid reservoir 52 and the device 10. The remote control of the external energy transmission device 34 controls the hydraulic valve shilling device 54 to shift the hydraulic fluid flow direction between one direction in which the fluid is pumped by the motor/pump unit 44 from the hydraulic fluid reservoir 52 to the device 10 to operate the device 10, and another opposite direction in which the fluid is pumped by the motor/pump unit 44 back from the device 10 to the hydraulic fluid reservoir 52 to return the device 10 to a starting position.

FIG. 16 shows an embodiment of the invention identical to that of FIG. 15, except that an internal control unit 56 controlled by the wireless remote control of the external energy transmission device 34, an accumulator 58 and a capacitor 60 also are implanted in the patient. The internal control unit 56 arranges storage of electric energy received from the implanted energy transforming device 30 in the accumulator 58, which supplies energy to the device 10. In response to a control signal from the wireless remote control of the external energy transmission device 34, the internal control unit 56 either releases electric energy from the accumulator 58 and transforms the released energy via power lines 62 and 64, or directly transforms electric energy from the implanted energy transforming device 30 via a power line 66, the capacitor 60, which stabilizes the electric current, a power line 68 and the power line 64, for the operation of the device 10.

The internal control unit is preferably programmable from outside the patient's body. In a preferred embodiment, the internal control unit is programmed to regulate the device 10 to stretch the stomach according to a pre-programmed time-schedule or to input from any sensor sensing any possible physical parameter of the patient or any functional parameter of the device.

In accordance with an alternative, the capacitor 60 in the embodiment of FIG. 16 may be omitted. In accordance with another alternative, the accumulator 58 in this embodiment may be omitted.

FIG. 17 shows an embodiment of the invention identical to that of FIG. 10, except that a battery 70 for supplying energy for the operation of the device 10 and an electric switch 72 for switching the operation of the device 10 also are implanted in the patient. The electric switch 72 is operated by the energy supplied by the implanted energy transforming device 30 to switch from an off mode, in which the battery 70 is not in use, to an on mode, in which the battery 70 supplies energy for the operation of the device 10.

FIG. 18 shows an embodiment of the invention identical to that of FIG. 16, except that an internal control unit 56 controllable by the wireless remote control of the external energy transmission device 34 also is implanted in the patient. In this case, the electric switch 72 is operated by the energy supplied by the implanted energy transforming device 30 to switch from an off mode, in which the wireless remote control is prevented from controlling the internal control unit 56 and the battery is not in use, to a standby mode, in which the remote control is permitted to control the internal control unit 56 to release electric energy from the battery 70 for the operation of the device 10.

Figure 19:
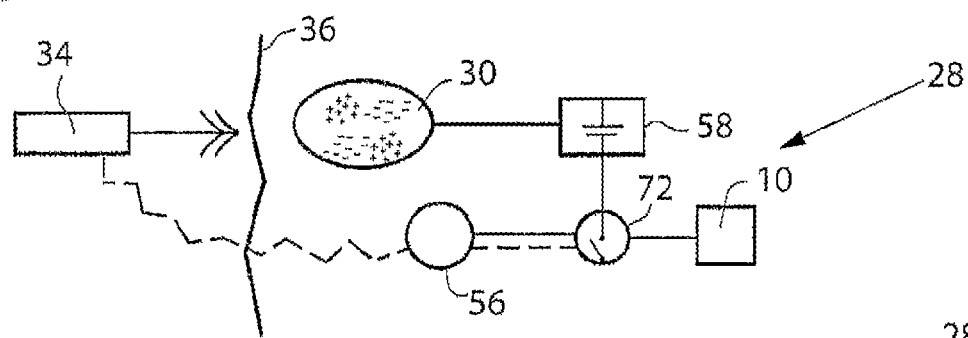

FIG. 19 shows an embodiment of the invention identical to that of FIG. 17, except that an accumulator 58 is substituted for the battery 70 and the implanted component are interconnected differently. In this case, the accumulator 58 stores energy from the implanted energy transforming device 30. In response to a control signal from the wireless remote control of the external energy transmission device 34, the internal control unit 56 controls the electric switch 72 to switch from an off mode, in which the accumulator 58 is not in use, to an on mode, in which the accumulator 58 supplies energy for the operation of the device 10.

Figure 20:
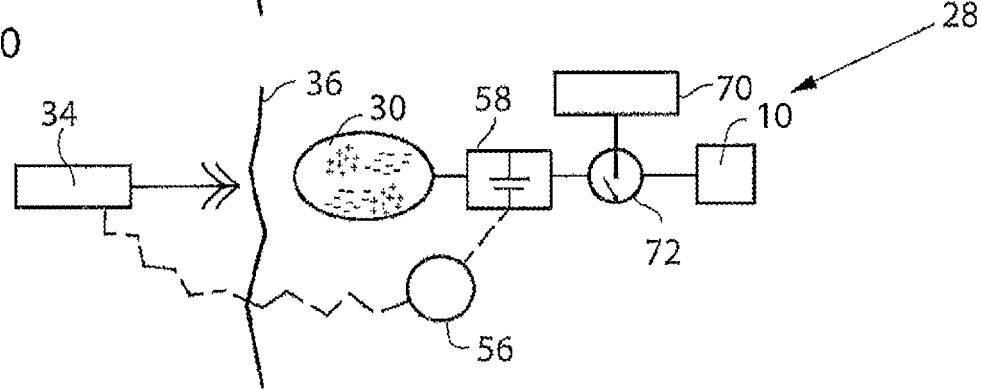

FIG. 20 shows an embodiment of the invention identical to that of FIG. 18, except that a battery 70 also is implanted in the patient and the implanted component are interconnected differently. In response to a control signal from the wireless remote control of the external energy transmission device 34, the internal control unit 56 controls the accumulator 58 to deliver energy for operating the electric switch 72 to switch from an off mode, in which the battery 70 is not in use, to an on mode, in which the battery 70 supplies electric energy for the operation of the device 10.

Alternatively, the electric switch 72 may be operated by energy supplied by the accumulator 58 to switch from an off mode, in which the wireless remote control is prevented from controlling the battery 70 to supply electric energy and is not in use, to a standby mode, in which the wireless remote control is permitted to control the battery 70 to supply electric energy for the operation of the device 10.

It should be understood that the switch should be interpreted in it broadest embodiment. This means an FPGA or a DA converter or any other electronic component or circuit may switch power on and off preferably being controlled from outside the patient's body or by an internal control unit.

Figure 21:
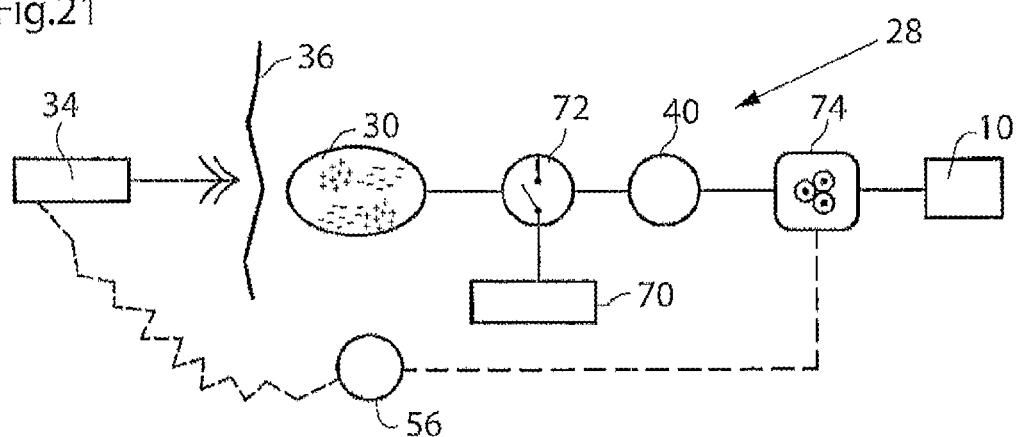

FIG. 21 shows an embodiment of the invention identical to that of FIG. 17, except that a motor 40, a mechanical reversing device in the form of a gear box 74, and an internal control unit 56 for controlling the gear box 74 also are implanted in the patient. The internal control unit 56 controls the gear box 74 to reverse the function performed by the device 10 (mechanically operated). Even simpler is to switch the direction of the motor electronically.

Figure 22:
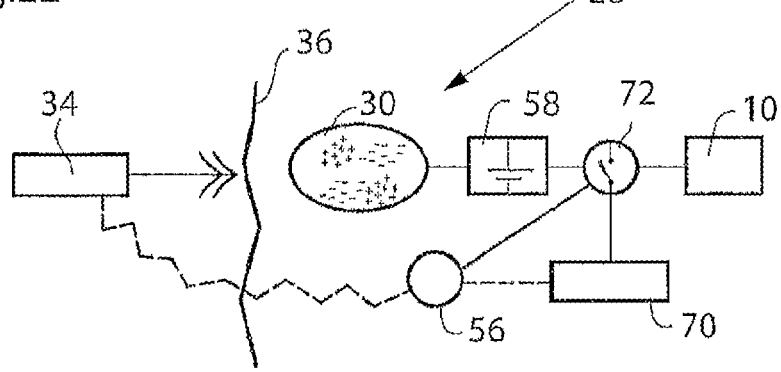

FIG. 22 shows an embodiment of the invention identical to that of FIG. 20 except that the implanted component are interconnected differently. Thus, in this case, the internal control unit 56 is powered by the battery 70 when the accumulator 58, suitably a capacitor, activates the electric switch 72 to switch to an on mode. When the electric switch 72 is in it on mode the internal control unit 56 is permitted to control the battery 70 to supply, or not supply, energy for the operation of the device 10.

Figure 23:
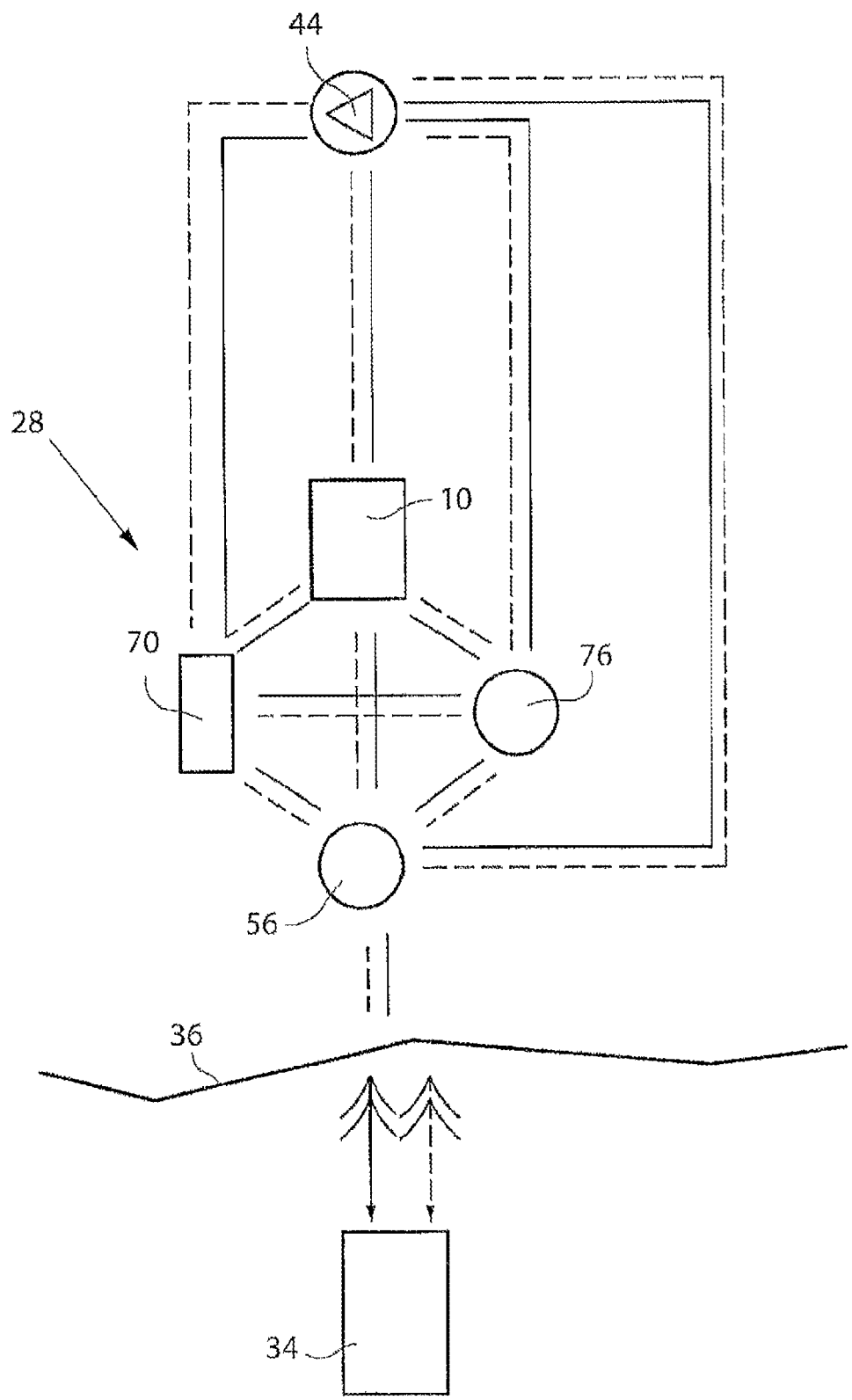

FIG. 23 schematically shows conceivable combinations of implanted component of the apparatus for achieving various communication options. Basically, there are the device 10, the internal control unit 56, motor or pump unit 44, and the external energy transmission device 34 including the external wireless remote control. As already described above the wireless remote control transmit a control signal which is received by the internal control unit 56, which in turn controls the various implanted component of the apparatus.

A feedback device, preferably in the form of a sensor 76, may be implanted in the patient for sensing a physical parameter of the patient, such as a contraction wave in the esophagus informing the patient is eating. The internal control unit 56, or alternatively the external wireless remote control of the external energy transmission device 34, may control the device 10 in response to signals from the sensor 76. A transceiver may be combined with the sensor 76 for sending information on the sensed physical parameter to the external wireless remote control. The wireless remote control may comprise a signal transmitter or transceiver and the internal control unit 56 may comprise a signal receiver or transceiver. Alternatively, the wireless remote control may comprise a signal receiver or transceiver and the internal control unit 56 may comprise a signal transmitter or transceiver. The above transceivers, transmitters and receivers may be used for sending information or data related to the device 10 from inside the patient's body to the outside thereof.

Alternatively, the sensor 76 may be arranged to sense a functional parameter of the device 10.

Where the motor/pump unit 44 and battery 70 for powering the motor/pump unit 44 are implanted, the battery 70 may be equipped with a transceiver for sending information on the condition of the battery 70. To be more precise, when charging a battery or accumulator with energy feedback information related to said charging process is sent and the energy supply is changed accordingly.

Figure 24:
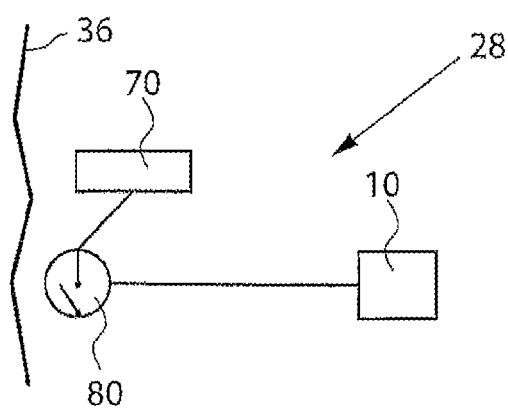

FIG. 24 shows an alternative embodiment wherein the device 10 is regulated from outside the patient's body. The system 28 comprises a movement restriction device 10 connected to a battery 70 via a subcutaneous switch 80. Thus, the regulation of the device 10 is performed non-invasively by manually pressing the subcutaneous switch, whereby the operation of the device 10 is switched on and off. It will be appreciated that the shown embodiment is a simplification and that additional component, such as an internal control unit or any other part disclosed in the present application can be added to the system.

Figure 25:
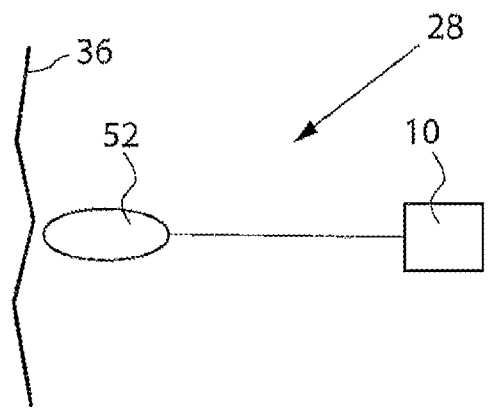

FIG. 25 shows an alternative embodiment, wherein the system 28 comprises a movement restriction device 10 in fluid connection with a hydraulic fluid reservoir 52. Non-invasive regulation is performed by manually pressing the hydraulic reservoir connected to the device 10.

A further embodiment of a system to be incorporated in the apparatus according to the invention comprises a feedback device for sending information from inside the patient's body to the outside thereof to give feedback information related to at least one functional parameter of the movement restriction device or apparatus or a physical parameter of the patient, thereby optimizing the performance of the apparatus.

One preferred functional parameter of the device is correlated to the transfer of energy for charging the internal energy source.

Figure 26:
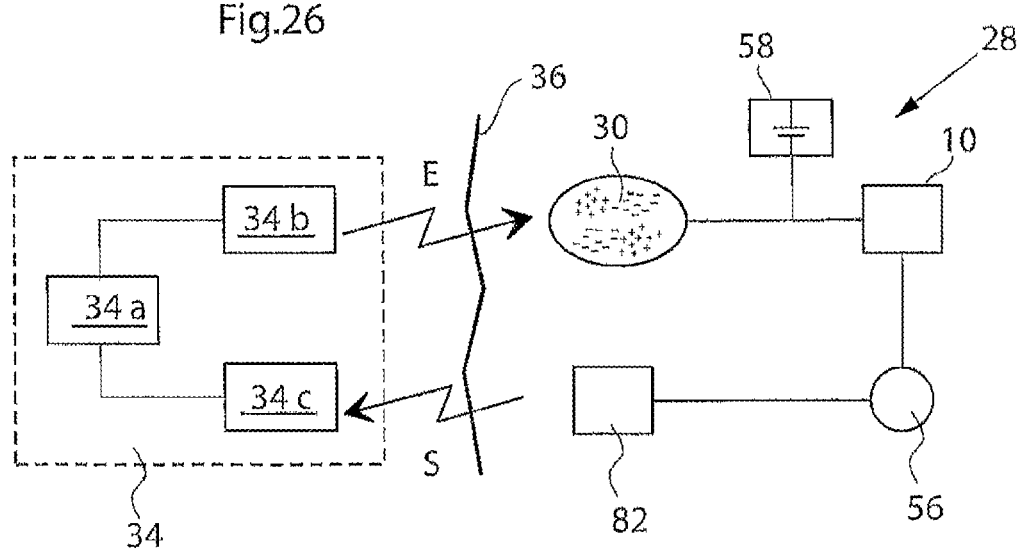
Figure 27:
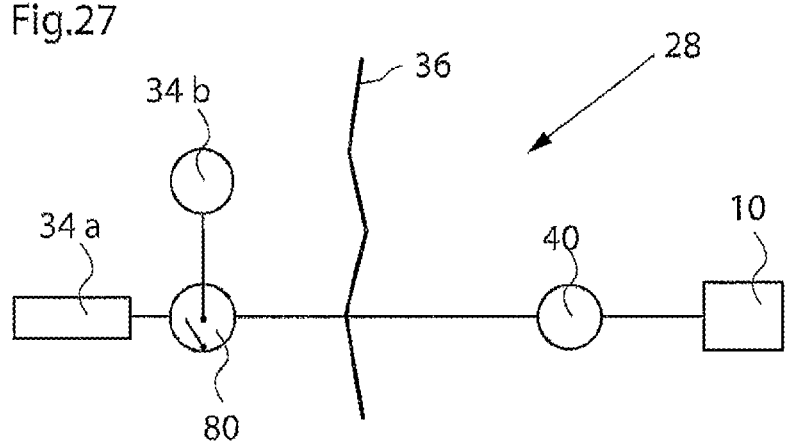

In FIG. 26, an arrangement is schematically illustrated for supplying an accurate amount of energy to a system 28 implanted in a patient, whose skin 36 is indicated by a vertical line. A movement restriction device 10 is connected to an implanted energy transforming device 30, likewise located inside the patient, preferably just beneath the patient's skin 36. Generally speaking, the implanted energy transforming device 30 may be placed in the abdomen, thorax, muscle fascia (e.g. in the abdominal wall), subcutaneously, or at any other suitable location. The implanted energy transforming device 30 is adapted to receive wireless energy E transmitted from an external energy source 34*a* provided in the external energy transmission device 34 located outside the patient's skin 36 in the vicinity of the implanted energy transforming device 30.

As is well known in the art, the wireless energy E may generally be transferred by means of any suitable Transcutaneous Energy Transfer (TET) device, such as a device including a primary coil arranged in the external energy source 34*a* and an adjacent secondary coil arranged in the implanted energy transforming device 30. When an electric current is fed through the primary coil, energy in the form of a voltage is induced in the secondary coil which can be used to operate a movement restriction device, e.g. after storing the incoming energy in an energy storing device or accumulator, such as a battery or a capacitor. However, the present invention is generally not limited to any particular energy transfer technique, TET devices or energy storing devices, and any kind of wireless energy may be used.

The amount of energy received inside the body to the device may be compared with the energy used by the device. The term used by the device is then understood to include also energy stored by the device. The amount of transferred energy can be regulated by means of an external control unit 34*b* controlling the external energy source 34*a* based on the determined energy balance, as described above. In order to transfer the correct amount of energy, the energy balance and the required amount of energy can be determined by means of an internal control unit 56 connected to the reflux disease treatment device 10. The internal control unit 56 may thus be arranged to receive various measurements obtained by suitable sensors or the like, not shown, measuring certain characteristics of the r10, somehow reflecting the required amount of energy needed for proper operation of the device 10. Moreover, the current condition of the patient may also be detected by means of suitable measuring devices or sensors, in order to provide parameters reflecting the patient's condition. Hence, such characteristics and/or parameters may be related to the current state of the device 10, such as power consumption, operational mode and temperature, as well as the patient's condition reflected by, e.g., body temperature, blood pressure, heartbeats and breathing.

Furthermore, an energy storing device or accumulator 58 may optionally be connected to the implanted energy transforming device 30 for accumulating received energy for later use by the device 10. Alternatively or additionally, characteristics of such an accumulator, also reflecting the required amount of energy, may be measured as well. The accumulator may be replaced by a battery, and the measured characteristics may be related to the current state of the battery, such as voltage, temperature, etc. In order to provide sufficient voltage and current to the device 10, and also to avoid excessive heating, it is clearly understood that the battery should be charged optimally by receiving a correct amount of energy from the implanted energy transforming device 30, i.e., not too little or too much. The accumulator may also be a capacitor with corresponding characteristics.

For example, battery characteristics may be measured on a regular basis to determine the current state of the battery, which then may be stored as state information in a suitable storage means in the internal control unit 56. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 56 is adapted to determine the energy balance and/or the currently required amount of energy, (either energy per time unit or accumulated energy)

based on measurements made by the above-mentioned sensors or measuring devices on the reflux disease treatment device 10, or the patient, or an energy storing device if used, or any combination thereof. The internal control unit 56 is further connected to an internal signal transmitter 82, arranged to transmit a control signal reflecting the determined required amount of energy, to an external signal receiver 34c connected to the external control unit 34b. The amount of energy transmitted from the external energy source 34a may then be regulated in response to the received control signal.

Alternatively, sensor measurements can be transmitted directly to the external control unit 34b wherein the energy balance and/or the currently required amount of energy can be determined by the external control unit 34b, thus integrating the above-described function of the internal control unit 56 in the external control unit 34b. In that case, the internal control unit 56 can be omitted and the sensor measurements are supplied directly to the internal signal transmitter 82 which sends the measurements over to the external signal receiver 34c and the external control unit 34b. The energy balance and the currently required amount of energy can then be determined by the external control unit 34b based on those sensor measurements.

Hence, the present solution employs the feedback of information indicating the required energy, which is more efficient than previous solutions because it is based on the actual use of energy that is compared to the received energy, e.g. with respect to the amount of energy, the energy difference, or the energy receiving rate as compared to the energy rate used by the device 10. The device 10 may use the received energy either for consuming or for storing the energy in an energy storage device or the like. The different parameters discussed above would thus be used if relevant and needed and then as a tool for determining the actual energy balance. However, such parameters may also be needed per se for any actions taken internally to specifically operate the device.

The internal signal transmitter 82 and the external signal receiver 34c may be implemented as separate unit using suitable signal transfer means, such as radio, IR (Infrared) or ultrasonic signals. Alternatively, the internal signal transmitter 82 and the external signal receiver 34c may be integrated in the implanted energy transforming device 30 and the external energy source 34a, respectively, so as to convey control signals in a reverse direction relative to the energy transfer, basically using the same transmission technique. The control signals may be modulated with respect to frequency, phase or amplitude.

To conclude, the energy supply arrangement illustrated in FIG. 26 may operate basically in the following manner. The energy balance is first determined by the internal control unit 56. A control signal reflecting the required amount of energy is also created by the internal control unit 56, and the control signal is transmitted from the internal signal transmitter 82 to the external signal receiver 34c. Alternatively, the energy balance can be determined by the external control unit 34b instead depending on the implementation, as mentioned above. In that case, the control signal may carry measurement results from various sensors. The amount of energy emitted from the external energy source 34a can then be regulated by the external control unit 34b, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 34a, such as voltage, current, amplitude, wave frequency and pulse characteristics.

A method is thus provided for controlling transmission of wireless energy supplied to an electrically operable reflux disease treatment device implanted in a patient. The wireless energy E is transmitted from an external energy source located outside the patient and is received by an internal energy receiver located inside the patient, the internal energy receiver being connected to the device 10 for directly or indirectly supplying received energy thereto. An energy balance is determined between the energy received by the internal energy receiver and the energy used for the device 10. The transmission of wireless energy E from the external energy source is then controlled based on the determined energy balance.

A system is also provided for controlling transmission of wireless energy supplied to an electrically operable movement restriction device 10 implanted in a patient. The system is adapted to transmit the wireless energy E from an external energy source located outside the patient which is received by an implanted energy transforming device located inside the patient, the implanted energy transforming device being connected to the device 10 for directly or indirectly supplying received energy thereto. The system is further adapted to determine an energy balance between the energy received by the implanted energy transforming device and the energy used for the device 10, and control the transmission of wireless energy E from the external energy source, based on the determined energy balance.

The functional parameter of the device is correlated to the transfer of energy for charging the internal energy source.

In yet an alternative embodiment, the external source of energy is controlled from outside the patient's body to release electromagnetic wireless energy, and released electromagnetic wireless energy is used for operating the device 10.

In another embodiment, the external source of energy is controlling from outside the patient's body to release non-magnetic wireless energy, and released non-magnetic wireless energy is used for operating the device 10.

Those skilled in the art will realize that the above various embodiments according to FIGS. 14-26 could be combined in many different ways. For example, the electric switch 38 operated polarized energy could be incorporated in any of the embodiments of FIGS. 12, 15-21, the hydraulic valve shilling device 54 could be incorporated in the embodiment of FIG. 24, and the gearbox 74 could be incorporated in the embodiment of FIG. 33. It should be noted that the switch simply could mean any electronic circuit or component.

Wireless transfer of energy for operating the movement restriction device 10 has been described to enable non-invasive operation. It will be appreciated that the device 10 can be operated with wire bound energy as well. One such example is shown in FIG. 26, wherein an external switch 84 is interconnected between the external energy source 34a and an operation device, such as an electric motor regulating the device 10, by means of power lines 86 and 88. An external control unit 34b controls the operation of the external switch to effect proper operation of the device 10. Hydraulic or Pneumatic Powering FIGS. 28-31 show in more detail block diagrams of four different ways of hydraulically or pneumatically powering a movement restriction device according to the invention.

Figure 28:
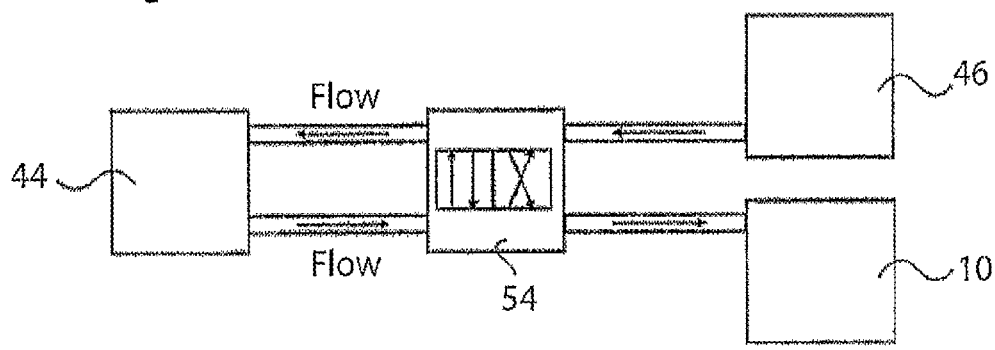
FIGS. 28-34 are schematic views of various ways of arranging the hydraulic or pneumatic powering of an apparatus of the invention for treating Gastro Esophageal Reflux Disease.

FIG. 28 shows a system for treating reflux disease as described above with. The system comprises a device 10 and further a separate regulation reservoir 46, a one way pump 44 and an alternate valve 54.

Figure 29:
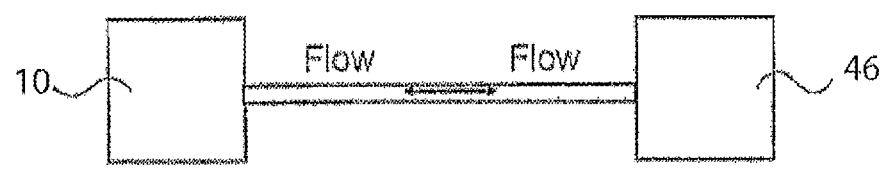

FIG. 29 shows the device 10 and a fluid reservoir 46. By moving the wall of the regulation reservoir or changing the size of the same in any other different way, the adjustment of the device may be performed without any valve, just free passage of fluid any time by moving the reservoir wall.

Figure 30:
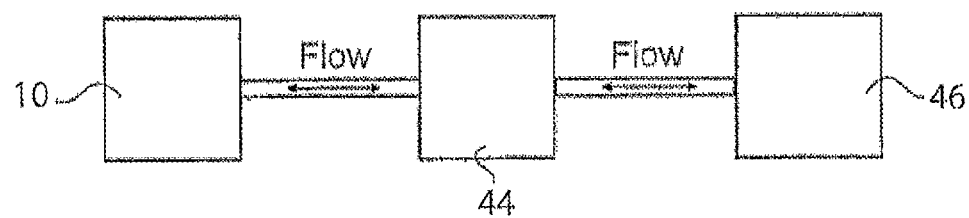

FIG. 30 shows the device 10, a two way pump 44 and the regulation reservoir 46.

Figure 31:
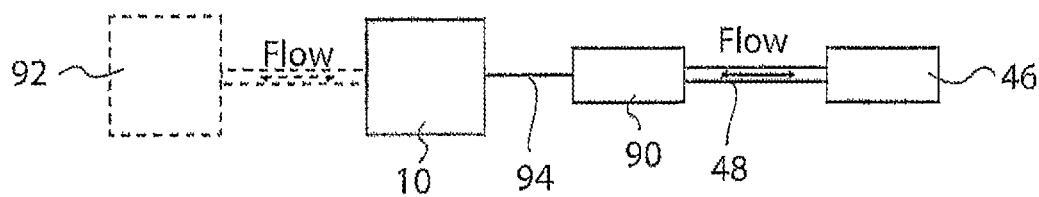

FIG. 31 shows a block diagram of a reversed servo system with a first closed system controlling a second closed system. The servo system comprises a regulation reservoir 46 and a servo reservoir 90. The servo reservoir 90 mechanically controls a movement restriction device 10 via a mechanical interconnection 94. The device 10 has an expandable/contactable cavity. This cavity is preferably expanded or contracted by supplying hydraulic fluid from the larger adjustable reservoir 92 in fluid connection with the device 10. Alternatively, the cavity contains compressible gas, which can be compressed and expanded under the control of the servo reservoir 90.

The servo reservoir 90 can also be part of the device itself.

Figure 32:
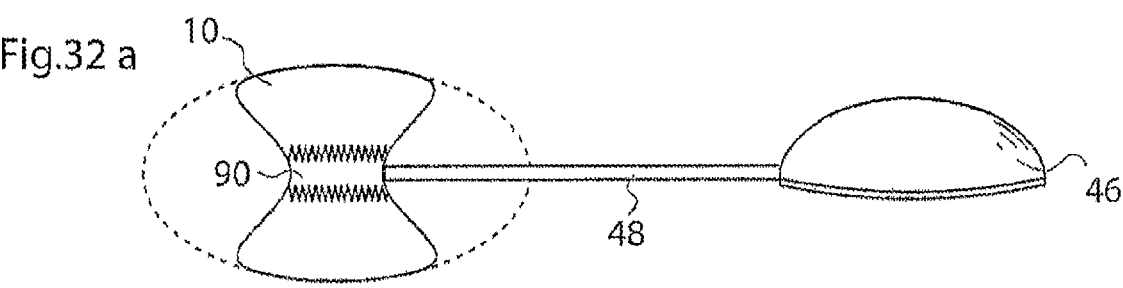
Figure 32:
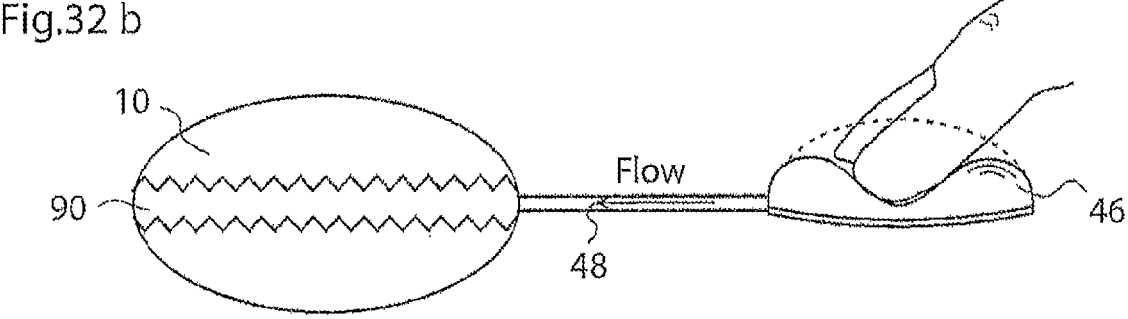
Figure 32:
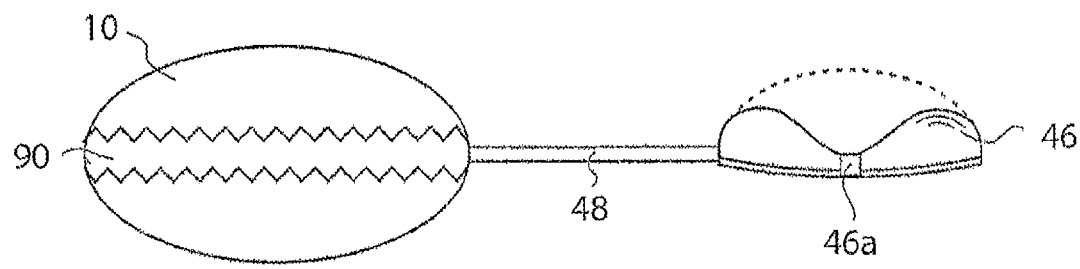

In one embodiment, the regulation reservoir is placed subcutaneous under the patient's skin and is operated by pushing the outer surface thereof by means of a finger. This reflux disease treatment system is illustrated in FIGS. 32-c. In FIG. 31, a flexible subcutaneous regulation reservoir 46 is shown connected to a bulge shaped servo reservoir 90 by means of a conduit 48. This bellow shaped servo reservoir 90 is comprised in a flexible movement restriction device 10. In the state shown in FIG. 32, the servo reservoir 90 contains a minimum of fluid and most fluid is found in the regulation reservoir 46. Due to the mechanical interconnection between the servo reservoir 90 and the device 10, the outer shape of the device 10 is contracted, i.e., it occupies less than its maximum volume. This maximum volume is shown with dashed lines in the figure.

FIG. 32 shows a state wherein a user, such as the patient in with the device is implanted, presses the regulation reservoir 46 so that fluid contained therein is brought to flow through the conduit 48 and into the servo reservoir 90, which, thanks to its bellow shape, expands longitudinally. This expansion in turn expands the device 10 so that it occupies its maximum volume, thereby stretching the stomach wall (not shown), which it contacts.

The regulation reservoir 46 is preferably provided with means 46a for keeping its shape after compression. This means, which is schematically shown in the figure, will thus keep the device 10 in a stretched position also when the user releases the regulation reservoir. In this way, the regulation reservoir essentially operates as an on/off switch for the reflux disease treatment system.

Figure 33:
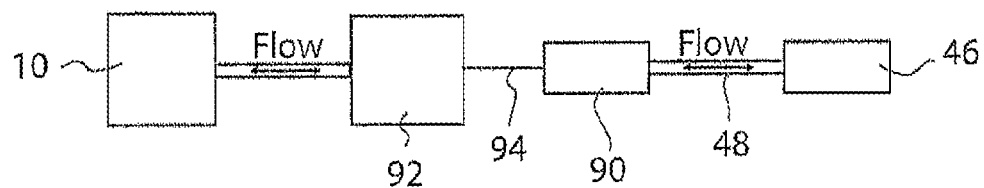
Figure 34:
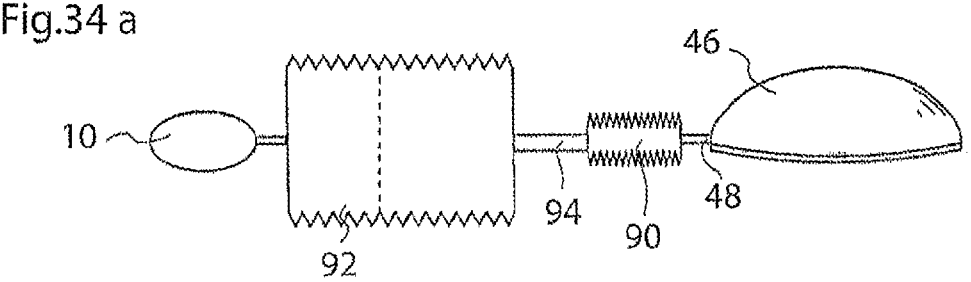
Figure 34:
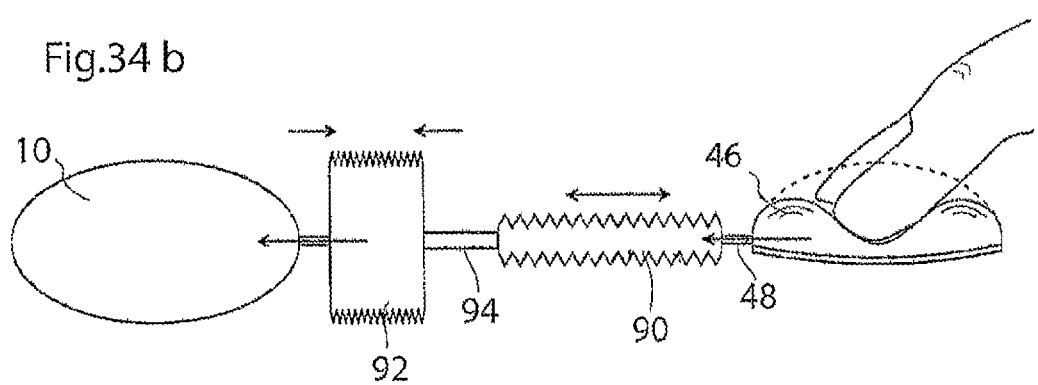
Figure 34:
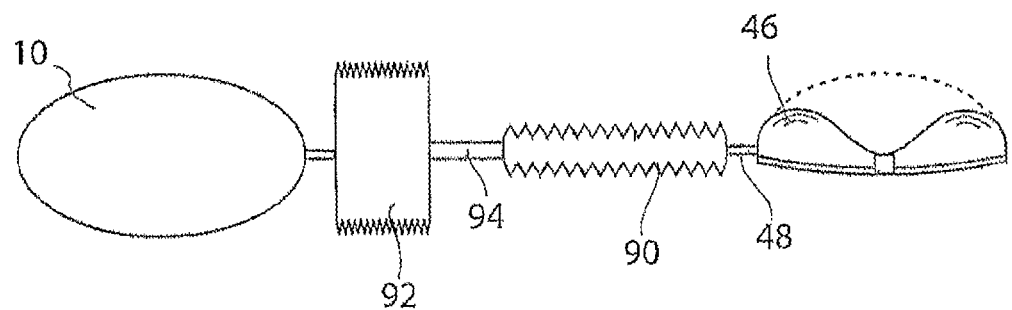

An alternative embodiment of hydraulic or pneumatic operation will now be described with reference to FIGS. 33 and 34. The block diagram shown in FIG. 33 comprises with a first closed system controlling a second closed system. The first system comprises a regulation reservoir 46 and a servo reservoir 90. The servo reservoir 90 mechanically controls a larger adjustable reservoir 92 via a mechanical interconnection 94. A movement restriction device 10 having an expandable/contactable cavity is in turn controlled by the larger adjustable reservoir 92 by supply of hydraulic fluid from the larger adjustable reservoir 92 in fluid connection with the device 10.

An example of this embodiment will now be described with reference to FIG. 34. Like in the previous embodiment, the regulation reservoir is placed subcutaneous under the patient's skin and is operated by pushing the outer surface thereof by means of a finger. The regulation reservoir 46 is in fluid connection with a bellow shaped servo reservoir 90 by means of a conduit 48. In the first closed system 46, 48, 90 shown in FIG. 32a, the servo reservoir 90 contains a minimum of fluid and most fluid is found in the regulation reservoir 46.

The servo reservoir 90 is mechanically connected to a larger adjustable reservoir 92, in this example also having a bellow shape but with a larger diameter than the servo reservoir 90. The larger adjustable reservoir 92 is in fluid connection with the device 10. This means that when a user pushes the regulation reservoir 46, thereby displacing fluid from the regulation reservoir 46 to the servo reservoir 90, the expansion of the servo reservoir 90 will displace a larger volume of fluid from the larger adjustable reservoir 92 to the device 10. In other words, in this reversed servo, a small volume in the regulation reservoir is compressed with a higher force and this creates a movement of a larger total area with less force per area unit.

Like in the previous embodiment described above with reference to FIGS. 32a-c, the regulation reservoir 46 is preferably provided with means 46a for keeping its shape after compression. This means, which is schematically shown in the figure, will thus keep the device 10 in a stretched position also when the user releases the regulation reservoir. In this way, the regulation reservoir essentially operates as an on/off switch for the reflux disease treatment system.

Figure 35:
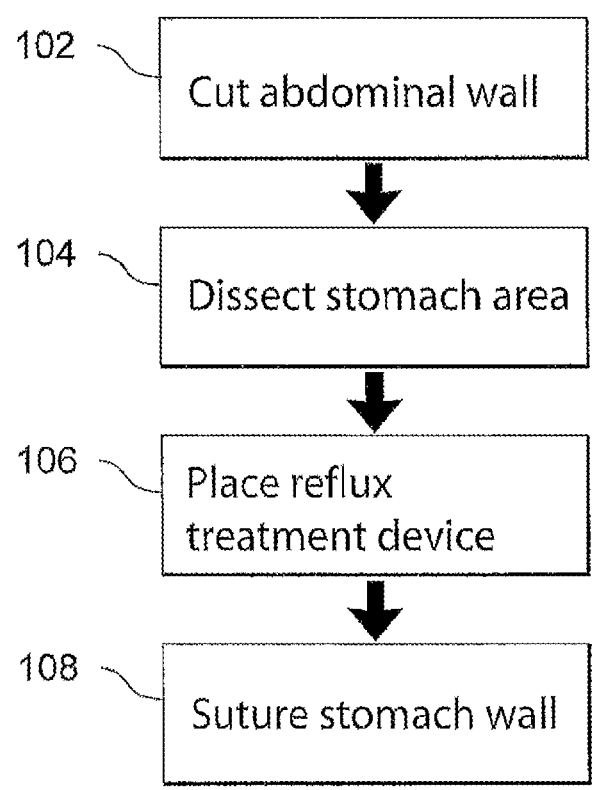
FIG. 35 is a flowchart illustrating steps performed when implanting a movement restriction device for treating Gastro Esophageal Reflux Disease.

In FIG. 35, a flow chart illustrating steps performed when implanting a device in accordance with the present invention. First in a step 102, an opening is cut in the abdominal wall. Next, in a step 104 an area around the stomach is dissected. Thereupon, in a step 106 at least one movement restriction device in accordance with the invention is placed in contact with the stomach wall, in particular the fundus wall. The stomach wall is then sutured in a step 108.

Method for the Restoration of the Location of the Cardia and the Fundus

Figure 36:
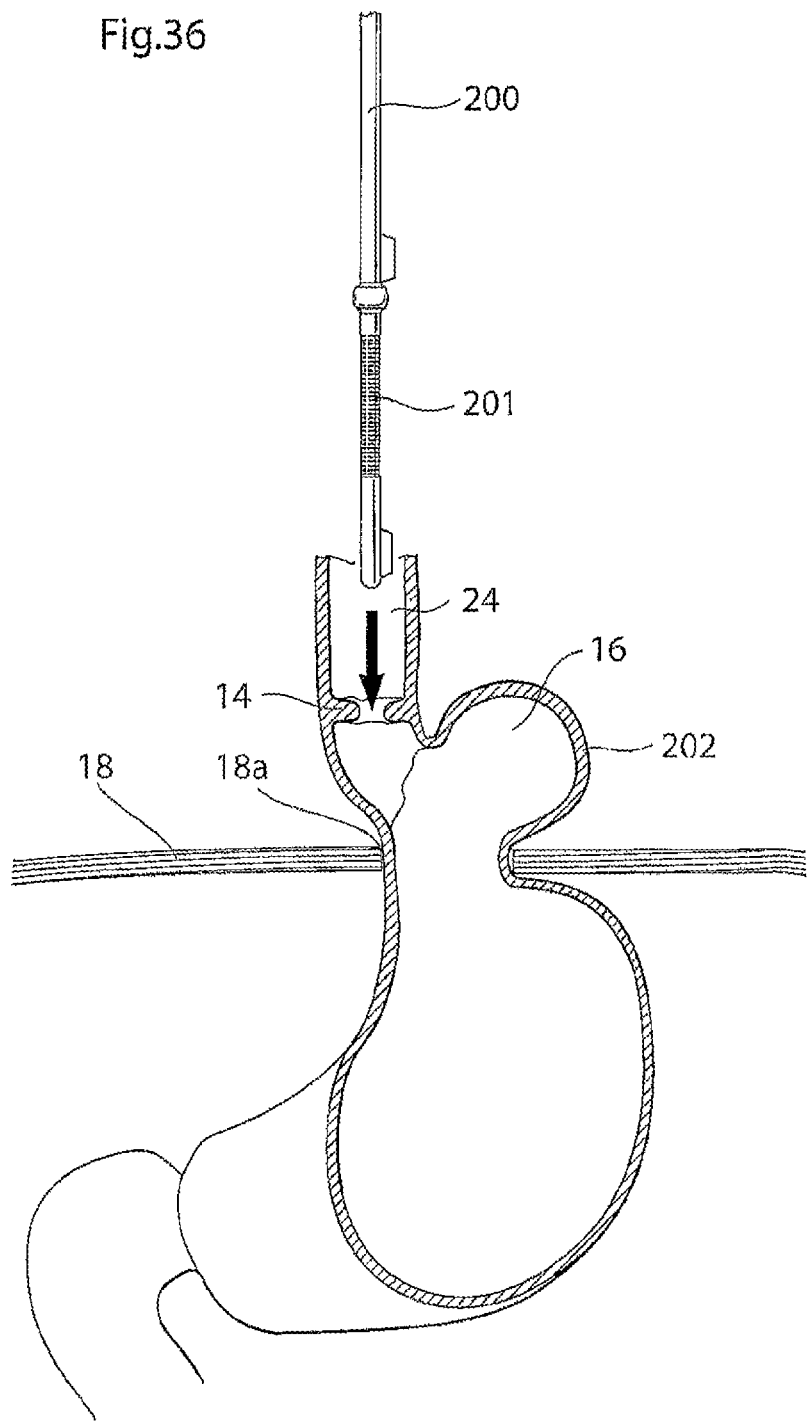
FIGS. 36-41 show methods for restoring the location of the cardia and the fundus in a patient suffering from Gastro Esophageal Reflux Disease.

FIG. 36 shows how an instrument 200 having at least one flexible part 201 is introduced into the esophagus 24 of a patient that is suffering from a hiatal hernia 202 where a part of the esophagus 24 and fundus 16 that is supposed to be located below the diaphragm 18 has moved through the hiatus opening 18a to a position above the diaphragm 18.

Figure 37:
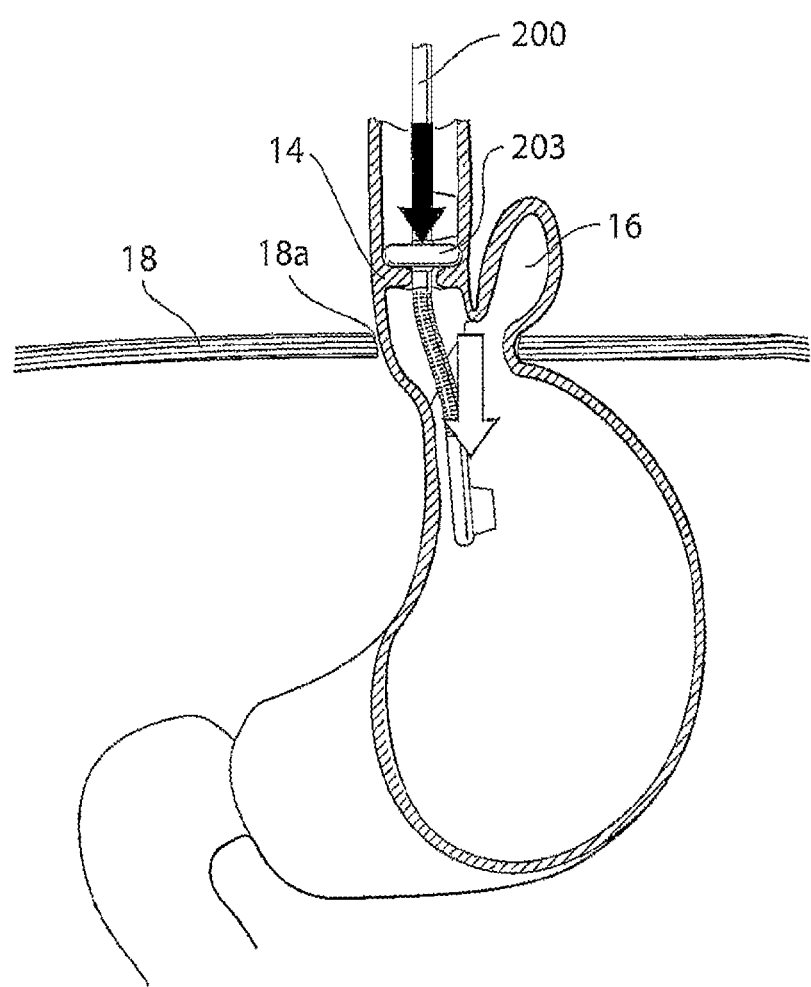

In FIG. 37 it is shown how, in a subsequent step, a member 203 having a larger cross sectional area than said instrument 200 is released from the instrument 200. The member 203 is adapted as to have a cross-sectional that is larger than the opening of the cardia 14. This can be achieved by radial expansion of the member 203. The instrument 200 is then pushed in a proximal direction so that the cardia 14 and the fundus 16, or part of fundus 16, incorrectly located above diaphragm 18, slide through the hiatus opening 18a back to a correct position below the diaphragm 18.

Figure 38:
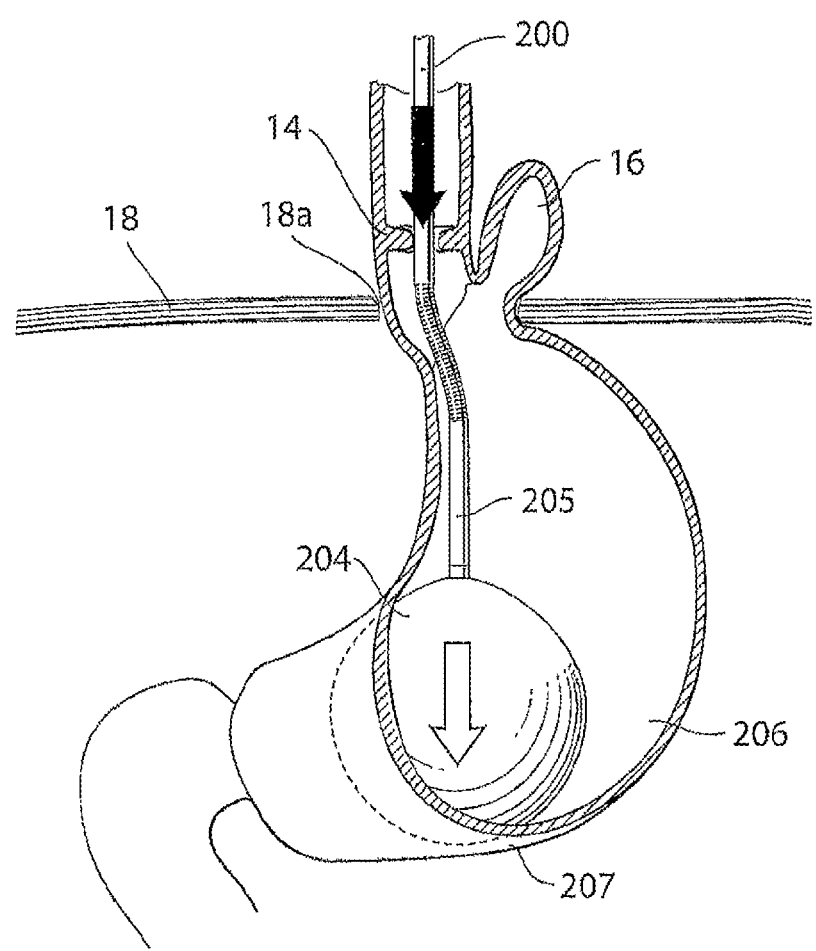

FIG. 38 shows an alternative method to the one shown in FIG. 37 which is an embodiment of the invention. In many aspects, this figure is similar to FIG. 37. In FIG. 38, the instrument 200 is adapted to release a balloon member 204 at the proximal end 205 of the instrument 200 in the lower part of the stomach 206, and using the balloon member 204 to push the instrument 200 against the lower wall part of the stomach 207 so that the cardia 14 and the fundus 16 or part of fundus 16 slide through the hiatus opening 18a to a position below the diaphragm 18.

Figure 39:
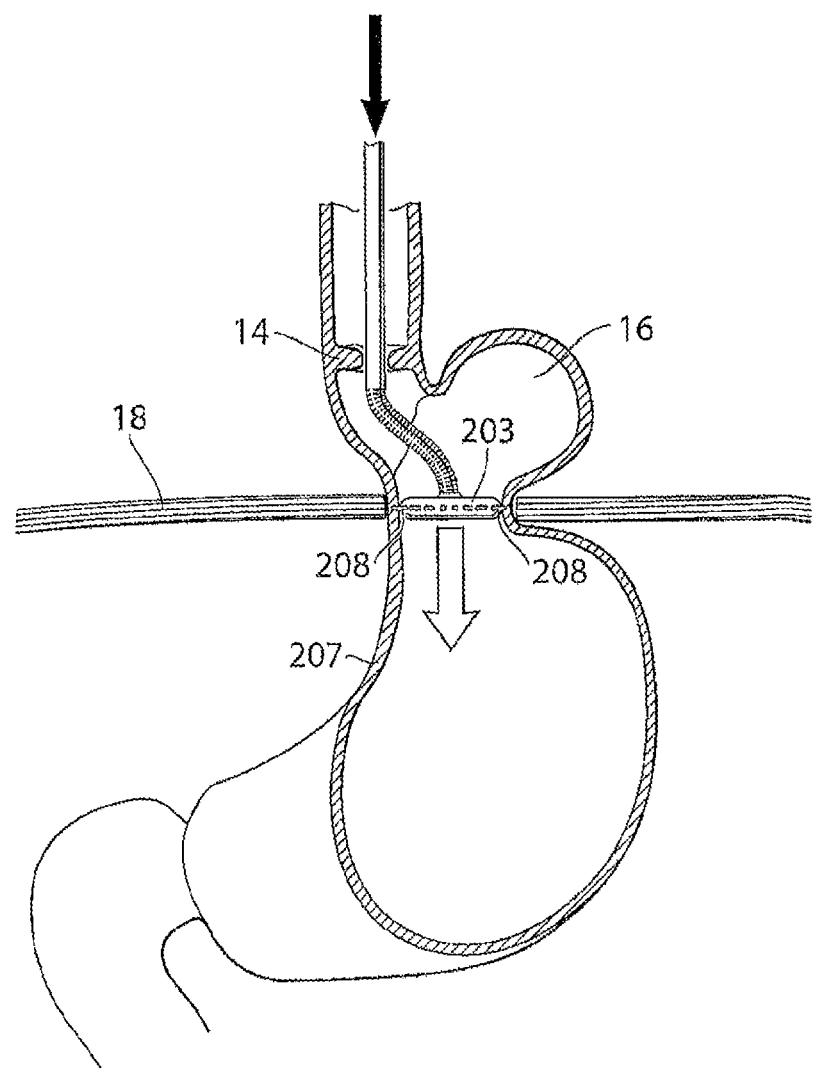

FIG. 39 shows yet an alternative method which is an embodiment of the invention. Again, this figure is in many aspects similar to FIG. 37. However, in FIG. 39 the method involves attaching the member 203 to the wall of the stomach 207 by a fixation 208. As described above the instrument is then pushed in a proximal direction so the cardia 14 and the fundus 16 or, part of fundus 16, slides below the diaphragm 18.

Figure 40:
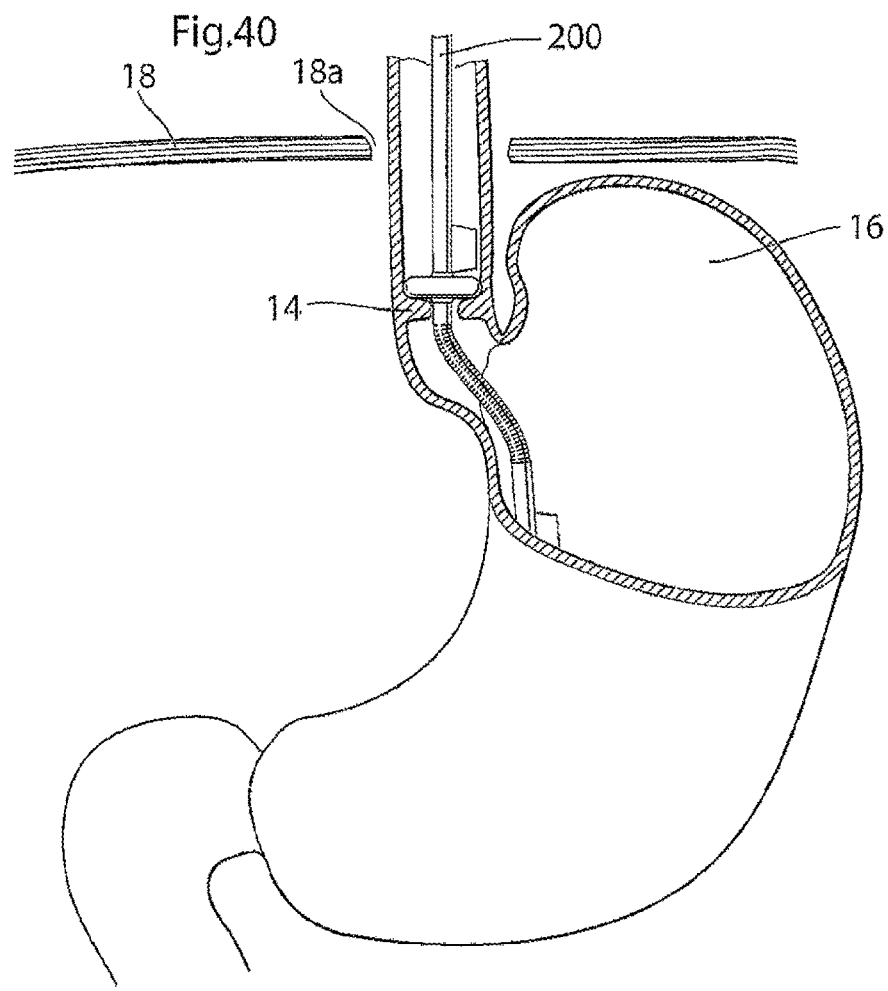

FIG. 40 shows how the fundus 16 and cardia 14 is located in a position below the diaphragm 18 after having been pushed through the hiatal opening 18a by the instrument 200.

Figure 41:
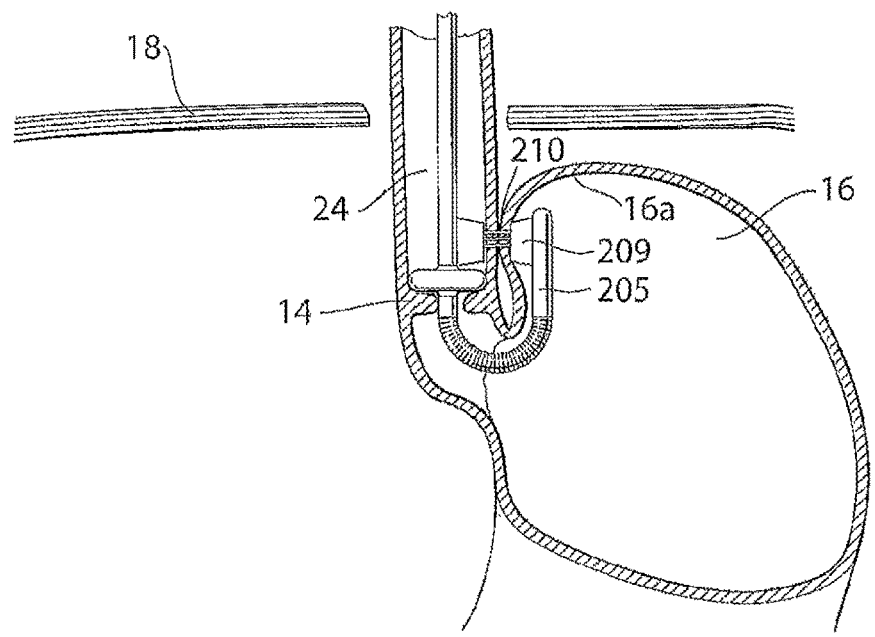

FIG. 41 shows a subsequent step of the method. After the fundus 16 and cardia 14 has been pushed into its correct position below the diaphragm 18, the wall of the fundus 16a is affixed to the lower part of the esophagus 24. This is carried out by using a member 209 in the proximal part 205 of the instrument 200 which is capable of providing sutures or staples 210. The fixation hinders the movement of the cardia 14 and the fundus 16 to a position above the diaphragm 18.

Other methods according to the invention are briefly described below.

A method of treating reflux disease of a patient comprises the step of implanting a reflux disease treatment system according to the invention into the patient's body.

A method of using the system for treating reflux disease according to the invention comprises the step of regulating the device postoperatively to prevent reflux.

A method for surgically placing a movement restriction device according to the invention in a patient comprises the steps of cutting an opening in the abdominal wall of the patient, dissecting the area around the stomach, placing a movement restriction device attached to the stomach wall, and suturing the stomach wall.

A method of using a reflux disease treatment system, postoperatively controlled from outside the body, regulating the device, comprises the steps of filling out a volume attached to a part of the stomach wall, and regulating the device from outside the patient's body to affect the reflux of the patient.

A method of using a movement restriction device comprises the steps of filling out a volume in a first part of the stomach wall by placing a first part of the device, filling out a volume in a second part of the stomach wall by placing a second part of the device, and regulating the devices from outside the patient's body to affect the reflux of the patient.

A method of treating reflux disease in a patient comprises the steps of inserting a needle or a tube like instrument into the abdomen of the patient's body, using the needle or tube like instrument to fill the patient's abdomen with gas thereby expanding the abdominal cavity, placing at least two laparoscopic trocars in the patient's body, inserting a camera through one of the laparoscopic trocars into the patient's abdomen, inserting at least one dissecting tool through one of said at least two laparoscopic trocars and dissecting an intended placement area of at least one portion of the stomach of the patient, placing a movement restriction device according to the invention on the stomach fundus wall, invaginating the device in the stomach fundus wall, suturing the stomach wall to itself to keep the device in place, suturing the fundus of the stomach towards the lower part of the esophagus, and preventing the cardia to slide up through the diaphragm into the thorax. Using the method and device as described herein will provide a treatment of Gastro Esophageal Reflux Disease which is very effective and which does not suffer from complications such as damaging of tissue and undesired migration of non tissue into tissue.

The filling body of the device can be adapted to be pushed or pulled through a trocar for laparoscopic use, where the trocar has a diameter that is smaller than the relaxed diameter of the body. The filling body can include an outer wall and a hollow gas filled inner part that allows the body to pass through the trocar. Alternatively, the filling body can include an outer wall and a hollow fluid filled inner part that allow the body to pass through the trocar. In this latter case, the fluid can be a gel. The filling body can further include multiple park that can be inserted into the trocar, and that can then be put together into one unitary piece inside the patient's body, allowing the filling body to pass through the trocar. The filling body can include an outer wall and a hollow compressed inner part that is filled with a fluid or gel after insertion into the patient's body. The can further include an injection port that can be used to fill the filling body with a fluid after insertion into the patient's body through the injection port.

The filling body of the device can be an elastic compressible material, allowing the filling body to pass through the trocar. The filling body can be made from a material that is softer than 25 shure, or even 15 shure.

The filling body can also include an outer wall substantially taking the shape of a ball. The filling body can also include at least one holding device adapted to be used for pushing or pulling the filling body through a trocar for laparoscopic use. The holding device can be adapted to hold a prolongation of the device that is adapted to be held by a surgical instrument. The holding device can also hold a tread or band inserted through the holding device. The holding device can also be at least partly placed inside the outer wall of the filling body. The filling body of the device can preferably has a size that is larger than the intestinal outlet from the stomach to avoid ileus if the ball, as a complication, should enter into the stomach Preferably, the body has a smallest outer diameter between 30 mm and 40 mm or larger. Preferably, the body has a smallest outer circumference between 30 mm and 150 mm.

Preferred embodiments of a device for treating reflux disease, a system comprising a device for treating reflux disease, and a method according to the invention have been described. A person skilled in the art realizes that these could be varied within the scope of the appended claims. Thus, although the different features have been described in specific embodiments, it will be appreciated that they can be combined in different configurations when applicable. For example, although hydraulic control has been described in association with the device configuration of FIG. 4 A-B, it can also be applied to the device configurations of FIGS. 2 A-B and 3A-B.

Figure 42:
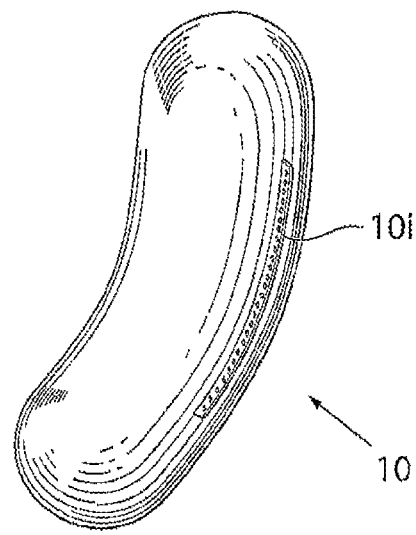
FIGS. 42-46 show different shapes and features of a reflux treatment device comprised in an apparatus according to the invention.

It is important that the implanted reflux treatment device is firmly kept in place in the stomach wall in which it is invaginated. To this end, the reflux treatment device can be provided with one or more through holes adapted for receiving sutures or staples used for fixation of the invagination. Such an embodiment is shown in FIG. 42, where the reflux treatment device 10 is provided with a row of holes 10i provided on a protruding flange-like protrusion on the reflux treatment device. In this embodiment, the row of holes extend along the longitudinal axis of the reflux treatment device.

Figure 43:
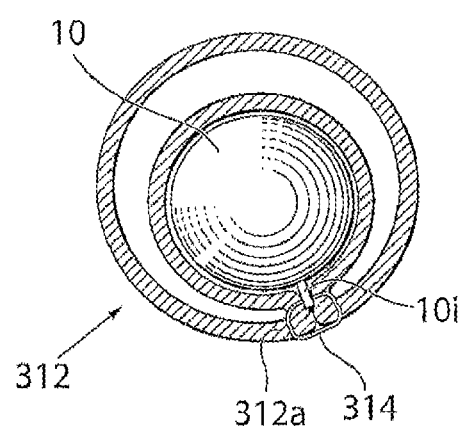

FIG. 43 illustrates how sutures 314 are provided so that they run through the stomach wall 12a and through the holes 10*i*. In this way, the reflux treatment device is fixed in place in the pouch created from the stomach wall and will thus be prevented from sliding.

Although a plurality of holes is illustrated in the FIG. 42, it will be appreciated that one single hole is sufficient to obtain improved fixation of the reflux treatment device 10.

Figure 44:
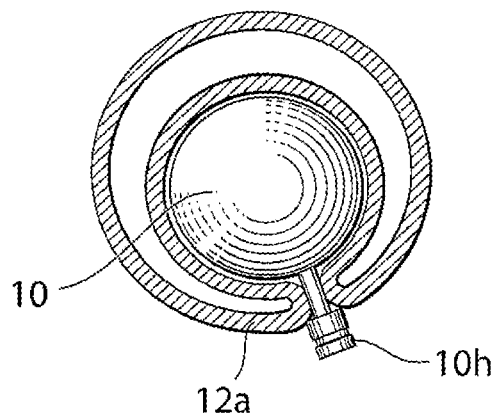

FIG. 44 illustrates a reflux treatment device provided with an inlet port 10*h*. The reflux treatment device is invaginated in the stomach wall and the inlet port 10*h* is available for connection to a tube or the like from the abdominal area of the patient.

Figure 45:
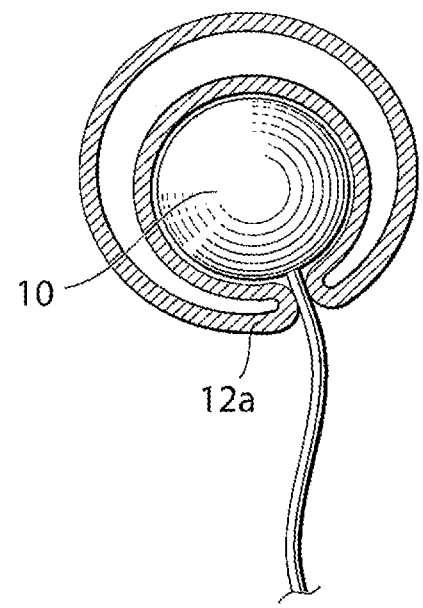

FIG. 45 illustrates an invaginated reflux treatment device wherein, instead of an inlet port, a fixed tube 10*g* extends into the abdominal area of the patient.

Figure 46:
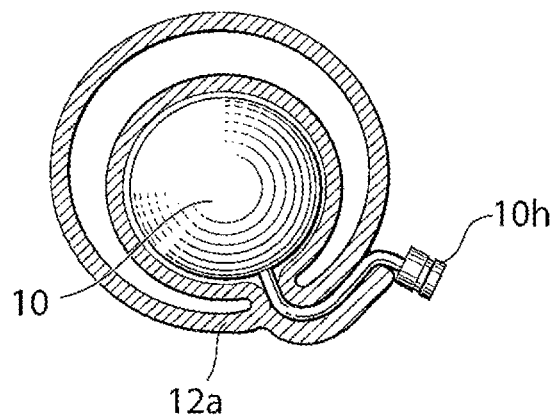

FIG. 46 is a figure similar to FIG. 44 but also illustrating tunneling of a connection tube 10*g* in the stomach wall between the inlet port 10*h* and the reflux treatment device 10.

It has been shown that the shape of the reflux treatment device can take many different forms. It will be appreciated that also the material of the reflux treatment device can vary. It is preferred that the reflux treatment device is provided with a coating, such as a Parylene, polytetrafluoroethylene (PTFE), or polyurethane coating, or a combination of such coatings, i.e., a multi-layer coating. This coating or multi-layer coating improves the properties of the reflux treatment device, such as its resistance to wear.

In one embodiment, the reflux treatment device comprises an inflatable device expandable to an expanded state. In this case, the inflatable device is provided with an inlet port for a fluid and is adapted to be connected to a gastroscopic instrument. This embodiment will now be described in detail with reference to FIGS. 47*a*-47*d*.

Figure 47A:
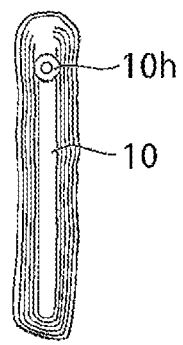
FIGS. 47a-d show a deflated inflatable reflux treatment device comprised in an apparatus according to the invention and an instrument for placing the reflux treatment device on the outside of the stomach wall of the patient.

An inflatable reflux treatment device in it non-expanded state is shown in FIG. 47*a*. It is essentially a balloon-like, deflated device 10 having an inlet port 10*h*. In this state, the inflatable device has a diameter of a few millimeters at the most, allowing it to be inserted into the stomach through the esophagus of the patient by means of a gastroscopic, tube-like instrument 600, depicted in FIG. 47*b*. The instrument comprises an outer sleeve 600*a* and an inner sleeve 600*b* which can be displaced longitudinally relatively to the outer sleeve. The inner sleeve is provided with a cutter in the form of a cutting edge 615 at the distal end thereof. This cutting edge can be used for cutting a hole in the stomach wall, as will be explained in detail in the following.

Figure 47B:
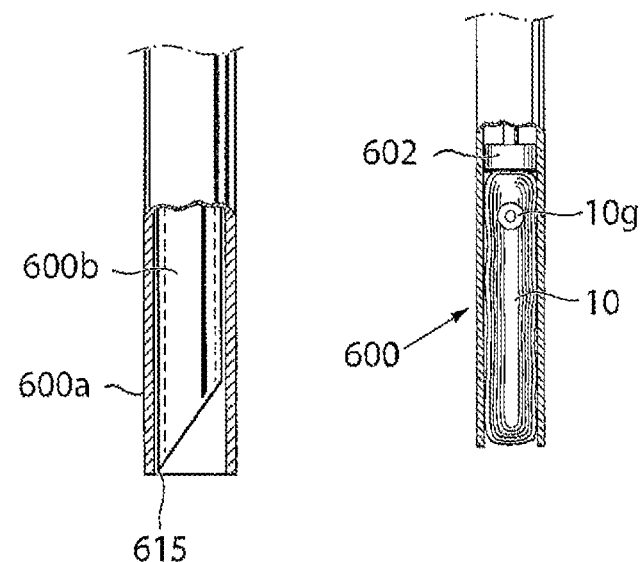
Figure 47C:
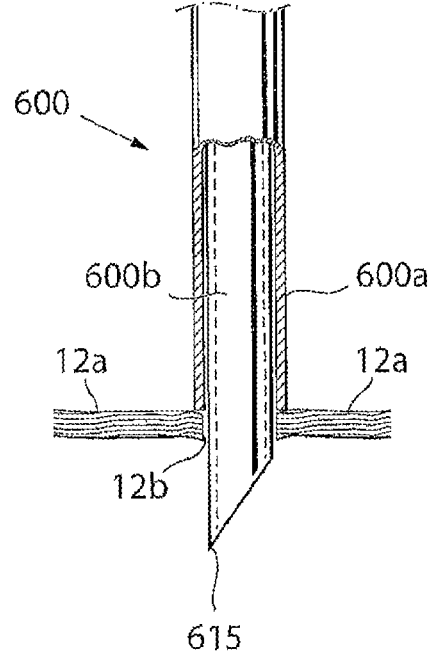
Figure 47D:
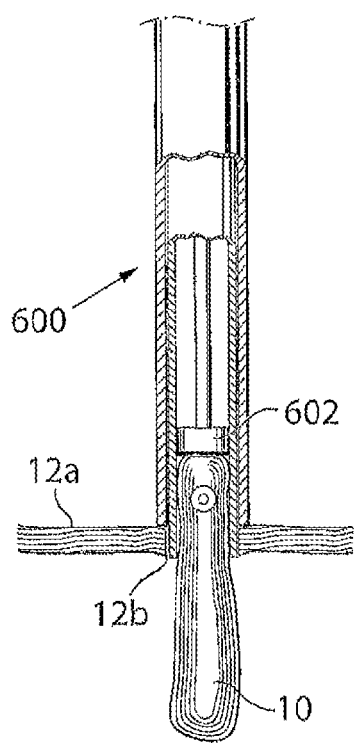

When the instrument reaches a stomach wall, see FIG. 47*c*, the inner sleeve is brought forward from its position in the outer sleeve and into contact with the stomach wall 12*a*. The cutting edge 615 of the inner sleeve then cuts a hole in the stomach wall so as to allow subsequent insertion of the reflux treatment device 10 into and through this hole, see FIG. 47*d*. In order to push the reflux treatment device through the hole, a piston 602 may be provided in the instrument. Thus, the instrument further comprises a piston 602 adapted for pushing a deflated reflux treatment device 10 out from a position in the inner sleeve, this position being shown in FIG. 47*b*, to a position outside of the inner sleeve, this being shown in FIG. 47*d*.

In order to protect the deflated reflux treatment device 10 from the cutting edge 615 of the inner sleeve, a further protective sleeve (not shown) can be provided around the reflux treatment device.

An intraluminar method of invaginating a reflux treatment device 10 on the outside of the stomach wall 12*a* will now be described with reference to FIGS. 48*a*-*i*. Initially, an instrument 600, preferably a gastroscopic instrument, is inserted into the mouth of the patient, see FIG. 48*a*. The instrument comprises an injection device 601, 602 for injecting either fluid or a device into the stomach of the patient. The instrument 600 further comprises a control unit 606 adapted for controlling the operation of the instrument. To this end, the control unit 606 comprises one or more steering devices, in the embodiment shown in the figure in the form of two joysticks 603 and two control buttons 604. A display 605 is provided for displaying the image provided by a camera (not shown) arranged at the outer end of the elongated member 607, see FIGS. 48*e*-*i*. The camera may be assisted by a light source (not shown).

Figure 48A:
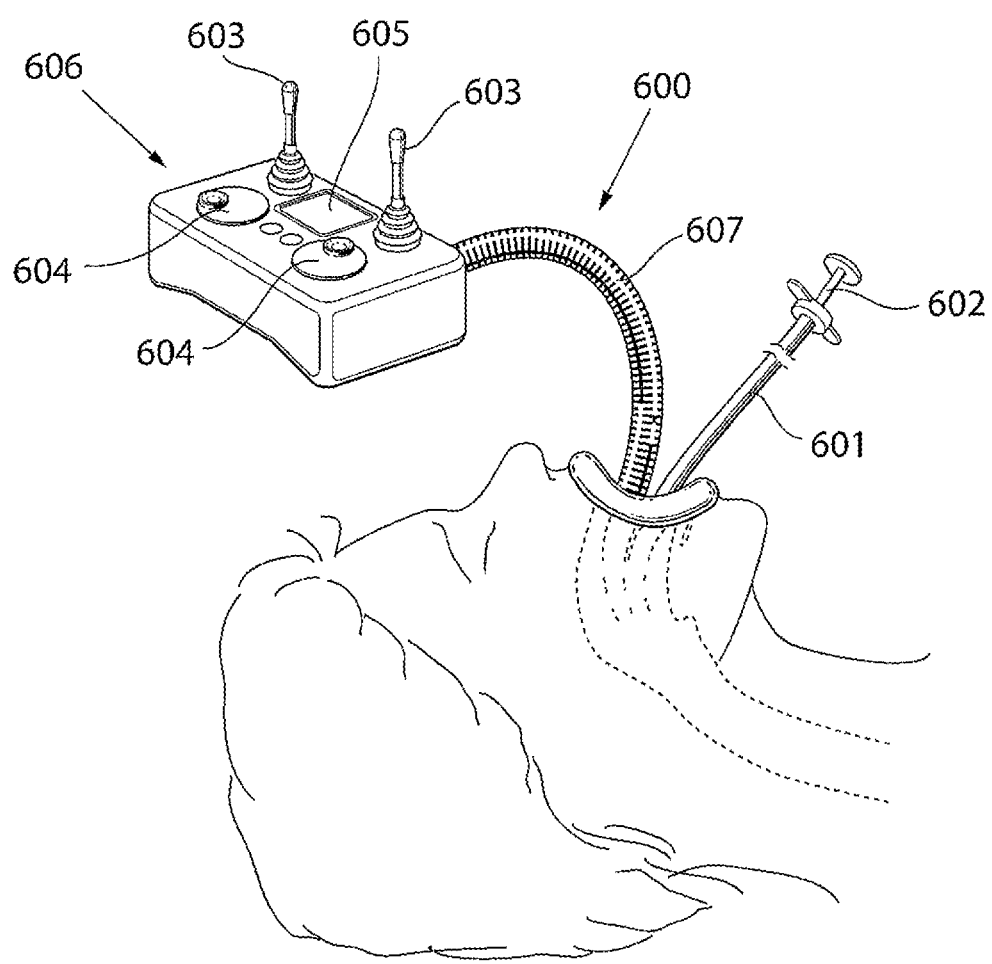
FIGS. 48a-i illustrate different steps of invaginating the inflatable device of FIG. 47a on the outside of a stomach wall of a patient.
Figure 48B:
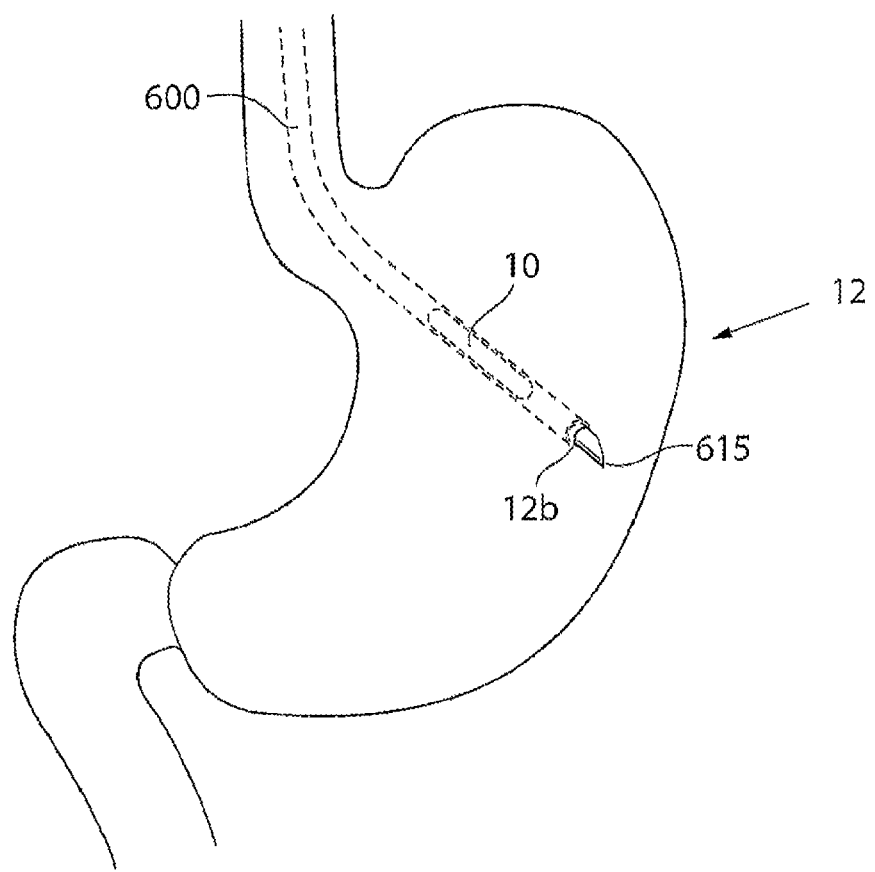

The instrument is further inserted into the esophagus and into the stomach of the patient, see FIG. 48*b*. By means of the instrument 600, a hole 12*b* is created in the wall of the stomach 12. To this end, the instrument is provided with one or more cutters 615 at the distal end thereof, for example in the way described above with reference to FIGS. 47*a*-*d*. These cutters can of course be designed in different ways, such as a toothed drum cutter rotating about the center axis of the tube-like instrument. The instrument 600 is hollow providing a space for the reflux treatment device 10 in its deflated state.

Figure 48C:
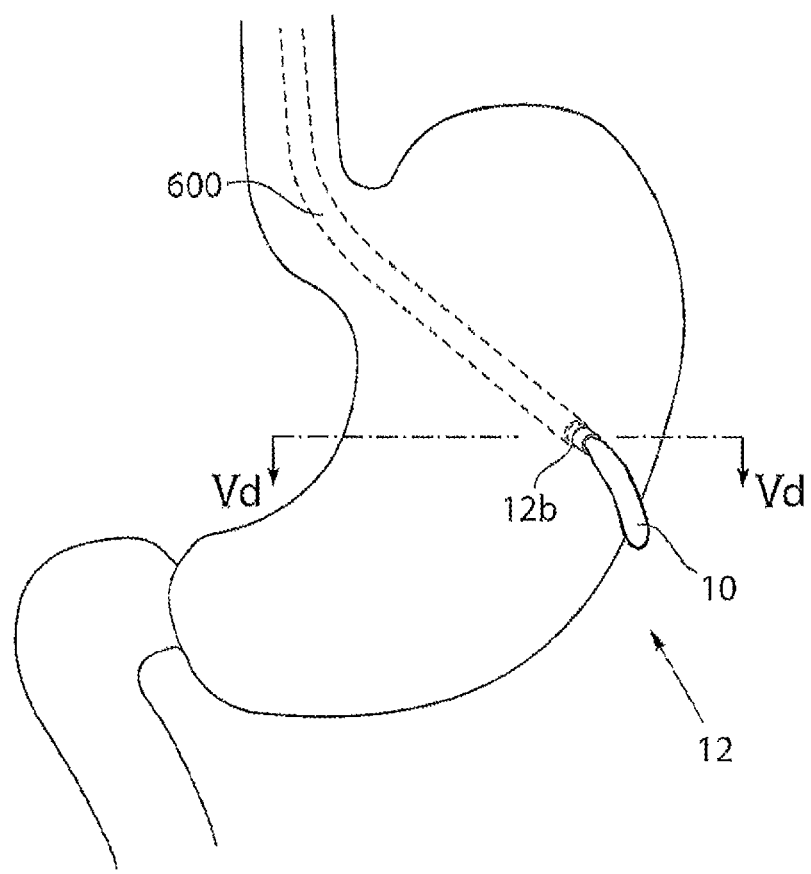
Figure 48D:
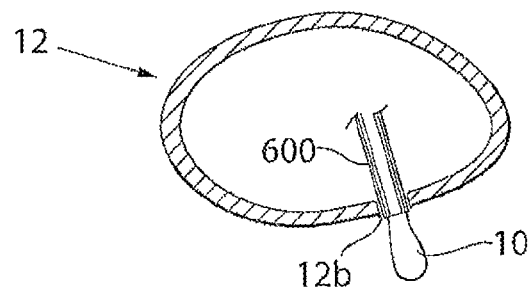
Figure 48E:
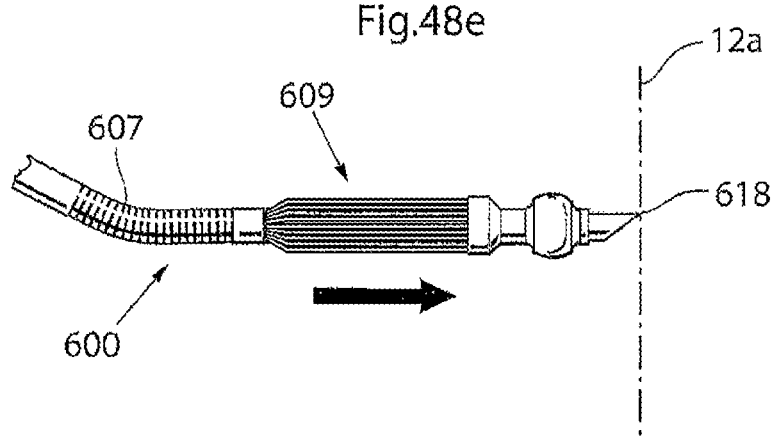
Figure 48F:
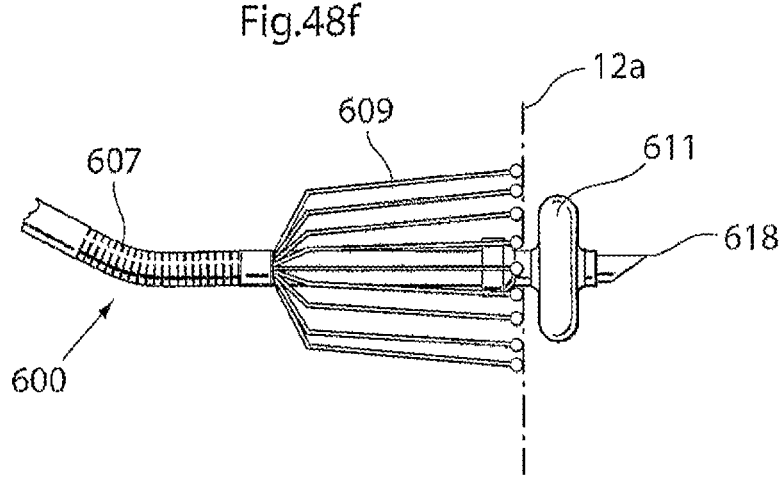

After cutting a hole in the stomach wall, the distal end of the instrument 600 is inserted into and through the hole 12*b* so that it ends up outside the stomach wall 12*a*. This is shown in FIG. 48*c*, showing a side view of the stomach 12, and FIG. 48*d*, which is a sectional view through the stomach of FIG. 48*c* taken along the lines Vd-Vd. The deflated reflux treatment device 10 is then inserted in the abdominal area.

The instrument 600 is adapted to create a "pocket" or "pouch" on the outside of the stomach 12 around the hole 12*b* in the stomach wall. Such an instrument and the method of providing the pouch will now be described.

FIGS. 48*e*-*i* shows a gastroscopic or laparoscopic instrument for invaginating a reflux treatment device 10 in the stomach wall 12*a* of the patient by creating a pouch of stomach wall 12*a* material in which the reflux treatment device is placed. The instrument, generally designated 600, and which may comprise the features described above with reference to FIGS. 47*a*-*d*, comprises an elongated member 607 having a proximal end and a distal end, the elongated member 607 having a diameter less than that of the patient's esophagus and being flexible such as to allow introduction of the flexible elongated member 607 with its distal end first through the patient's throat, esophagus and into the stomach 12 to the stomach wall 12*a*.

The stomach penetration device or cutter 615 is provided on the elongated member 607 at the distal en thereof for penetrating the stomach wall 12*a* so as to create a hole in the stomach wall 12*a*, to allow introduction of the elongated member 607 through the hole. The stomach penetration device 615 could be adapted to be operable for retracting said stomach penetration device 615 after the stomach fundus wall 12*a* has been penetrated, for not further damaging tissue within the body. The instrument further comprises a special holding device 609 provided on the elongated member 607 on the proximal side to the penetration device 615.

The elongated member further comprises an expandable member 611 which is adapted to be expanded after the elongated member has penetrated the stomach wall 12*a* and thereby assist in the creation of a cavity or pouch adapted to hold the reflux treatment device 610. The expandable member 611 may comprise an inflatable circular balloon provided circumferentially around the distal end portion of the flexible elongated member 607.

The method steps when invaginating the reflux treatment device will now be described in detail. After the instrument 600 has been inserted into the stomach 12, the stomach penetration device 615 is placed into contact with the stomach wall 12a, see FIG. 48e. The stomach penetration device or cutter 615 is then brought to create the hole 12b in the stomach wall, whereafter at least the expandable member 611 is brought through the hole 12b in the stomach wall. The special holding device 609 is in this step brought to a holding state wherein it expands radially so as to form an essentially circular abutment surface to the stomach wall 12a, see FIG. 48f. In this way, the insertion of the stomach penetration device 615 and the expandable member 611 through the hole 12a in the stomach wall is limited to the position shown in FIG. 48f.

The expandable member 611 is then expanded. In the case the expandable member comprises a balloon or the like, air or other fluid is injected into it.

Figure 48G:
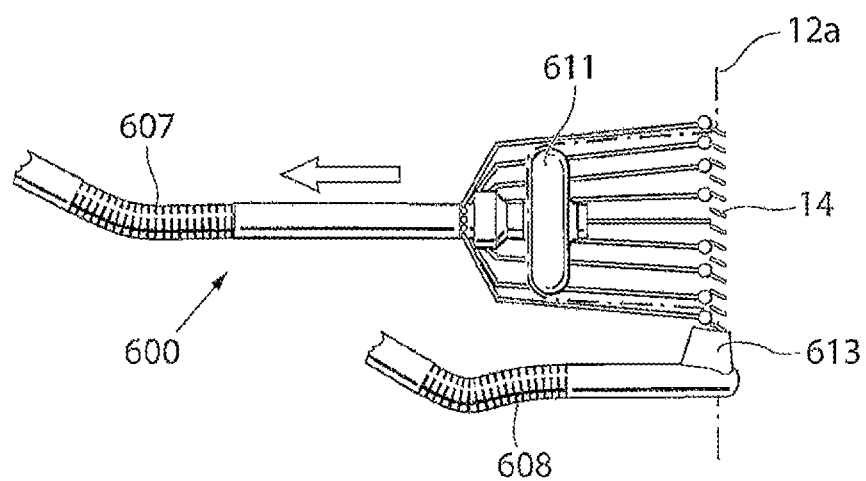

The part of the elongated member 607 comprising the expandable member 611 is then retracted in the proximal direction, as indicated by the arrow in FIG. 48g, thereby pulling the stomach wall 612 into a basket like structure created by the special holding device 609.

A suturing or stapling device 608 is further provided, either as a device connected to the elongated member 607 or as a separate instrument. The suturing or stapling member comprises a suturing or stapling end 613 which is adapted to close the cavity or pouch by means of stomach to stomach sutures or staples 14.

Figure 48H:
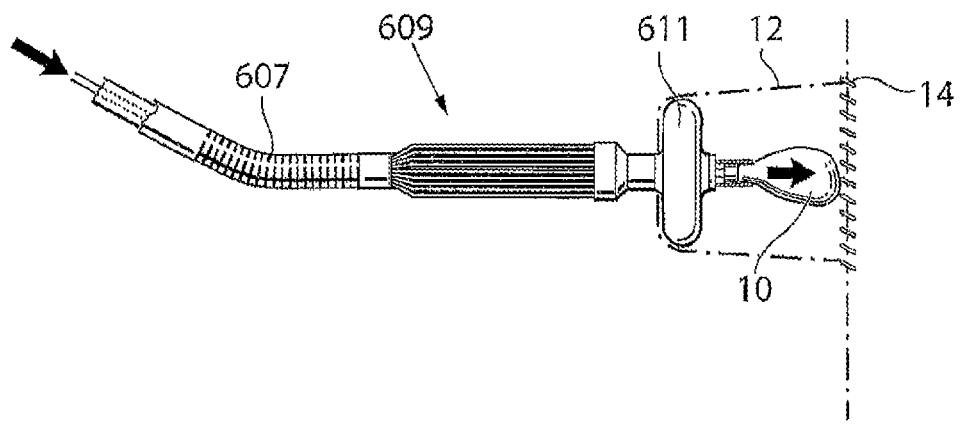
Figure 48I:
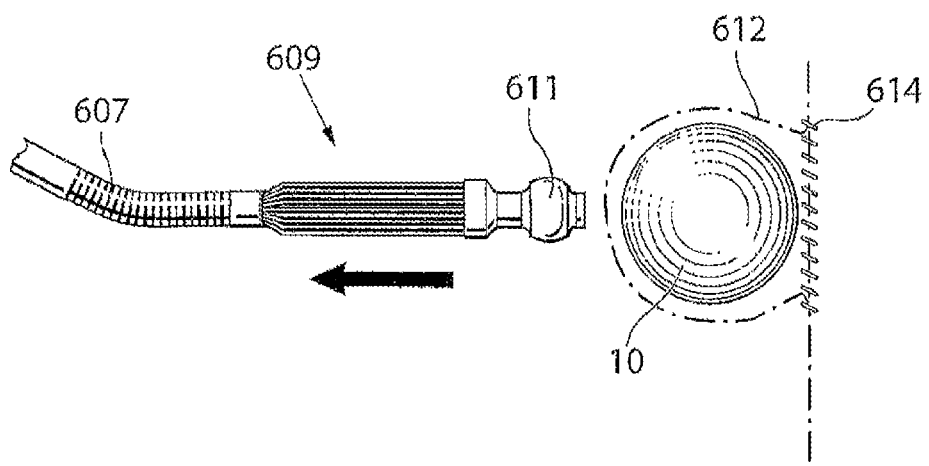

In a further step, illustrated in FIG. 48h, an inflatable reflux treatment device 10 is placed in its deflated state in the basket like structure. The reflux treatment device 10 is then inflated to its inflated or expanded state, see FIG. 48i. This inflation of the reflux treatment device 10 can be accomplished by injecting a fluid or a gel into the deflated reflux treatment device. It can also be accomplished by injecting a material which is allowed to cure, thereby forming a solid device 10. Thus, the reflux treatment device 10 shown in FIGS. 48h and 48i can illustrate either a balloon-like device which is subsequently filled with fluid or gel or alternatively a material which is simply injected into the basket like structure formed by the stomach wall 12a.

The fluid which is used to fill the reflux treatment device 10 could be any suitable fluid suitable to fill the inflatable device 10, such as a salt solution. In another embodiment, when this fluid is a fluid which is adapted to be transformed into solid state, the fluid could be liquid polyurethane.

In order to minimize or entirely eliminate leakage, the fluid is iso-tonic, i.e., it has the same osmolarity as human body fluids. Another way of preventing diffusion is to provide a fluid which comprises large molecules, such as iodine molecules.

The stomach-to-stomach sutures or staples are preferably provided with fixation portions exhibiting a structure, such as a netlike structure, adapted to be in contact with the stomach wall to promote growth in of human tissue to secure the long term placement of the reflux treatment device attached to the stomach wall.

After the inflatable device 10 has been inflated, partly or fully, the inlet port 10b (not shown in FIGS. 48h and 48i) of the reflux treatment device 10, is sealed and the instrument 600 is retracted from the hole 12b, which is subsequently closed in some suitable way, such as by means of the instrument 600. The instrument is then removed from the stomach 600 and the inflatable device 10 in its inflated or expanded state is invaginated by a stomach wall portion of the patient on the outside of the stomach wall. During one or more of the above described steps, the stomach may be inflated with gas, preferably by means of the gastroscopic instrument.

The reflux treatment device 10 described above with reference to FIGS. 48a-i has been described as an inflatable reflux treatment device. It will be appreciated that is also can be an elastic reflux treatment device with an elasticity allowing compression so as to be inserted into a gastroscopic instrument and which expands to an expanded state after leaving the instrument.

The apparatus for treating reflux can have the additional functionality of treating obesity. In such an embodiment, the reflux treatment device may be a volume filling device that fills a volume of the stomach and thereby creating satiety.

Figure 49A:
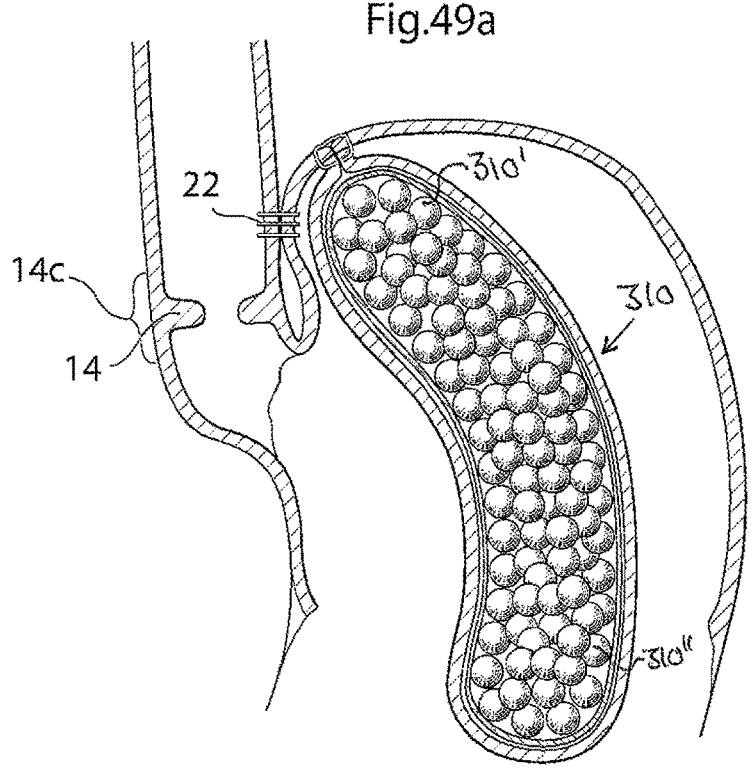
FIG. 49a shows an embodiment wherein the reflux treatment apparatus is also adaptable to treat obesity and comprises a plurality of movement restriction device segments.

The embodiment shown in FIG. 49a shows an elongated movement restriction device 310 having a proximal part 310' and a distal part 310". The device 310 is invaginated in the stomach wall with its proximal part 310' close to and at least partially above the patient's cardia 14 when the patient is in a standing position and is fixed to a position above the cardia area 14c by a fixation, such as sutures or staples 22. For example a direct or indirect fixation to the diaphragm muscle or other muscle tissue may be provided. As an alternative a direct or indirect fixation to the esophagus above and close to the angle o His can be provided. In this embodiment, the proximal part of the device 310' rests in a position against stomach wall of the fundus when implanted and which also fills a volume above the cardia area 14c between the cardia and the diaphragm muscle so that the cardia is prevented from slipping up into the thorax cavity, whereby reflux disease is prevented. The distal part 310" stabilizes and holds the proximal part and has sufficient length to exert the stabilizing effect. The distal part 310" also has a sufficient volume to reduce the food cavity volume and thereby the device obtains an additional functionality of treating obesity.

In this preferred embodiment, the apparatus for treating reflux disease comprises two or more movement restriction device segments adapted to form the movement restriction device 310. In this embodiment, there are a plurality of spherical movement restriction device segments in the form of small balls which are contained in a movement restriction device segment in the form of an outer layer or shell, which preferably is elastic or flexible. In this way, the outer layer can be inserted into the stomach as a separate part, which subsequently is filled with a plurality of small, preferably spherical or polyhedral movement restriction device segments. This method will be explained below with reference to FIGS. 117a-c.

By providing a movement restriction device 310 with a plurality of movement restriction device segments, the movement restriction device 310 easily adapts to the movement of the stomach into which it is invaginated.

Figure 49B:
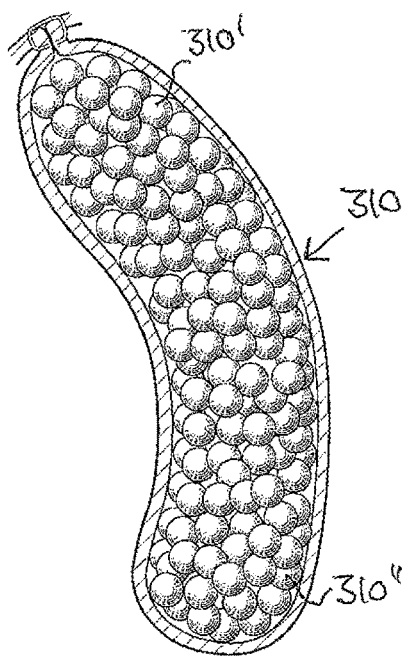
FIG. 49b shows an embodiment wherein the plurality of movement restriction device segments is provided in a pouch created by part of the stomach wall without any containing outer layer.

In an alternative embodiment, the small movement restriction device segments are inserted or injected into a pouch previously created by part of the stomach wall of the patient without any collecting outer layer or shell. This embodiment is illustrated in FIG. 49b and corresponds to the method described below with reference to FIG. 117a-c.

Figure 49C:
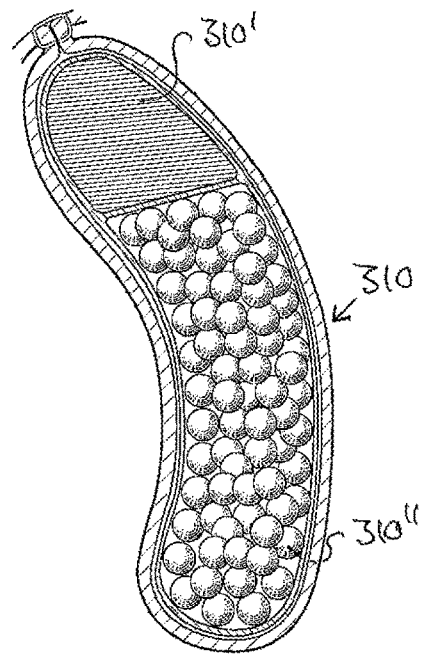
FIG. 49c shows an embodiment similar to the one shown in FIG. 49b but wherein proximal part of the combined reflux and obesity treatment apparatus has a different composition from the distal part the combined reflux and obesity treatment apparatus.

In order to provide a movement restriction device which is more stable in the proximal part 310', this part can be made of a different configuration from the distal part 310". Thus, in an embodiment shown in FIG. 49c, the proximal part 310', which is fixed to a position above the cardia area 14c, comprises a larger ball shaped part or segment, while the distal part 310" comprises a plurality of small movement restriction device segments. This embodiment combines the advantages of a stable proximal part 310' used for preventing reflux with a more adaptable distal part 310" used as a volume filling device for treating obesity. Generally, the proximal and distal parts can have different configurations and contents, independent of each other. This content can be a mixture of solid and fluid content, such as friction enhancing or reducing fluid.

Such a device 310 may be used for keeping electronics and/or an energy source and/or hydraulic fluid. Hydraulic fluid from that device may be distributed to several smaller inflatable device areas to vary the stretching area from time to time avoiding any possible more permanent stretching effect of the stomach wall. Even mechanically several stretching areas may be used.

Figure 50:
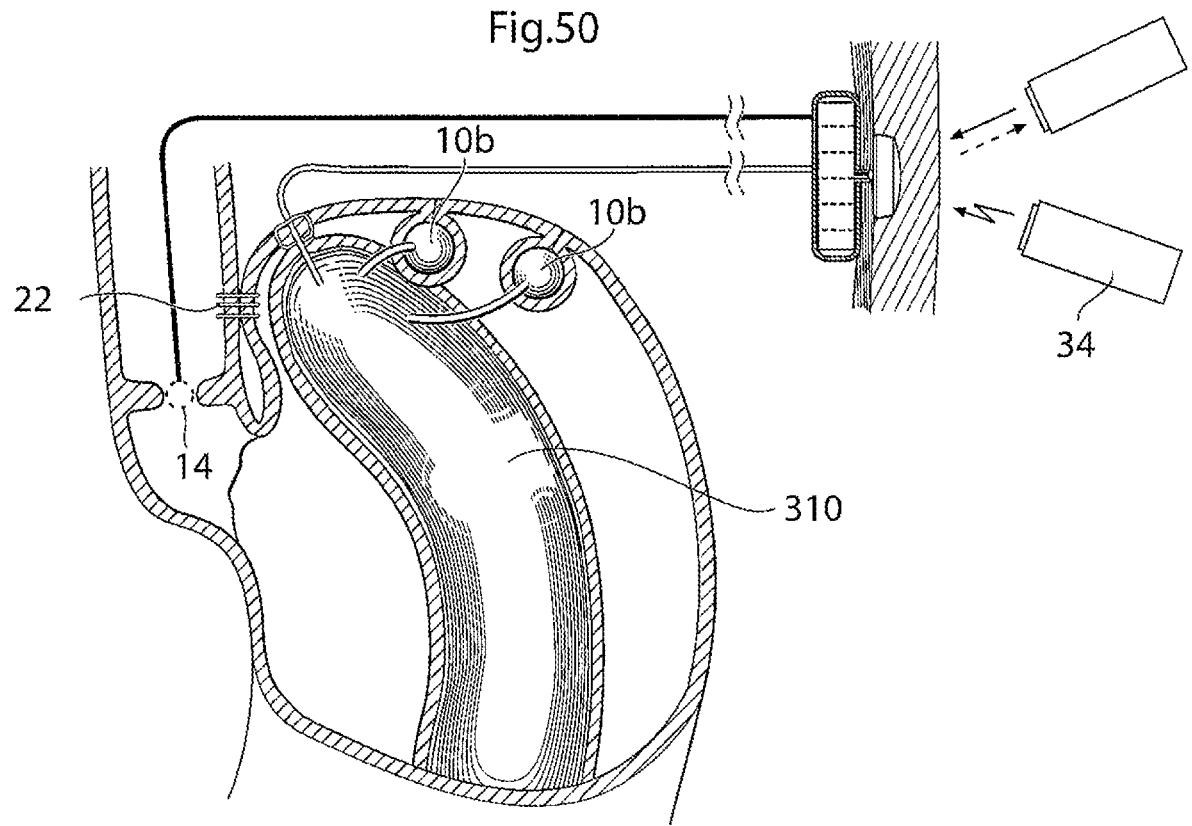
FIGS. 50-51 show an embodiment wherein the reflux treatment apparatus adaptable also for treating obesity.

In an alternative embodiment, which is shown in FIG. 50, the volume of an inflatable reflux treatment device 310 may be in fluid connection with one or more preferably smaller inflatable devices or chambers 10b. These chambers are adapted to communicate with fluid or air being moved between the chambers.

Thus, the large chamber 310 is adapted to, with its main volume to be a reflux treatment device for reducing the size of the food cavity and for treating reflux disease and the one or several small chambers are adapted to function as the inflatable devices to treat obesity, wherein the main chamber is adapted to communicate with fluid or air to the small chambers causing a stretching effect in the stomach wall thereby further treating obesity.

Figure 51:
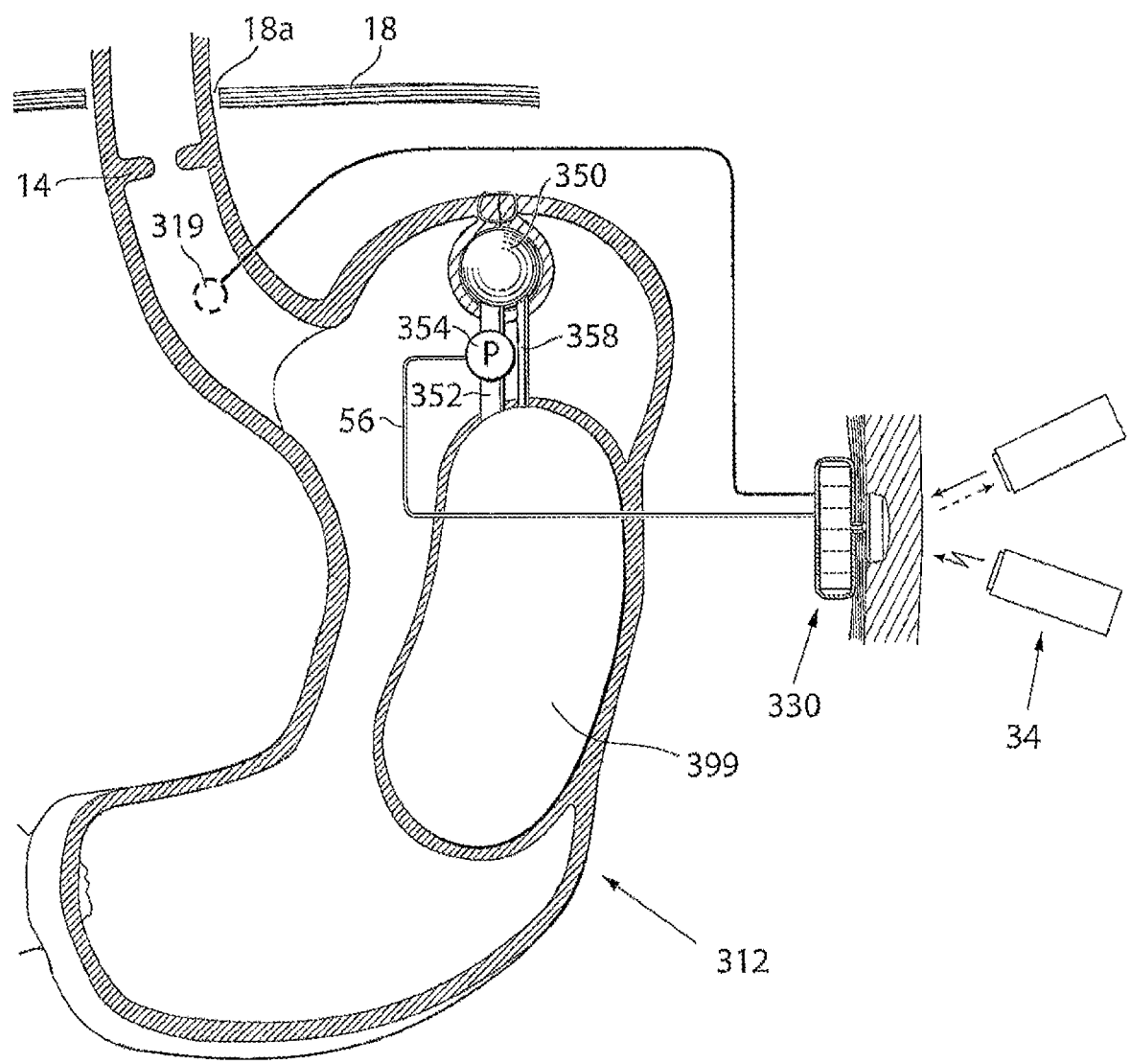

FIG. 51 show an embodiment with a combination of a volume filling device invaginated in the central or lower portion of the stomach and a stretching device invaginated in the upper portion or fundus of the patient's stomach. These two devices serve to treat obesity.

The volume filling device 399 fills a volume of the stomach creating satiety. The stretching device stretches the wall of the stomach. This stretches the tissue setting off an endogenous signaling that creates satiety. This mimics the stretching effect of filling the stomach with food. Thus, in FIG. 51 there is shown an adjustable volume filling device 399, which is invaginated in the stomach wall of a patient's stomach 312. Additionally, an adjustable stretching device 350 with the previously described function is invaginated in the stomach fundus wall of the patient. It is preferred that the volume filling device 399 is substantially larger than the stretching device 350.

The volume filling device 399 and the stretching device 350 can be adapted to treat reflux. In one embodiment, the volume filling device and the stretching device are positioned to prevent the cardia 14 from slipping upwards trough the opening of the hernia 18a to a position above the diaphragm 18.

The volume filling device 399 and the stretching device 350 are in fluid communication with each other via a first fluid tube 352, in which a pump 354 is provided. The pump 354 is under the control from an energy transforming device 330, which is adapted to supply the pump 350 with energy via a power supply line 356. The energy transforming device 330 is also connected to a sensor 319 provided in the esophagus of the patient so that food intake can be detected.

The reflux treatment device 10 and the stretching device 350 are also in fluid communication with each other via a second fluid tube 358, which preferably has a smaller cross-sectional area than the first fluid tube 352.

The operation of this arrangement is as follows. The volume filling device 399 functions as in the above described embodiments, i.e., it reduces the size of the food cavity of the patient's stomach 12. Additionally, when the stretching device 350 is enlarged by pumping fluid from the volume filling device 10 and to the stretching device 350 by means of the pump 354, the stomach fundus wall is stretched, creating a feeling of satiety for the patient. Thus, for example when food intake is detected by means of the sensor 319, fluid is automatically pumped into the stretching device 350 to increase the feeling of satiety and thereby limit the food intake.

When fluid has been injected into the stretching device 350, the internal pressure therein is higher than the internal pressure in the reflux treatment device 399. This difference in pressure will create a flow of fluid in the second, preferably narrower tube 358 from the stretching device 350 to the reflux treatment device 399. The flow rate will be determined by among other things the difference in pressure and the cross-sectional area of the second tube 358. It is preferred that the second tube is so dimensioned, that the pressures in the volume filing device 399 and the stretching device 350 will return to equilibrium after 3 hours after fluid has been injected into the stretching device 350 to create the feeling of satiety.

In this embodiment, the function of the second tube 358 is to allow fluid to return from the stretching device 350 to the volume filling device 399. It will be appreciated that this function also can be performed by the pump 354 in the first tube 352 and that the second tube 358 then can be omitted.

FIG. 51b illustrates an embodiment similar to the one illustrated in FIG. 51a. Thus, there is provided an adjustable volume filling device 310, which is invaginated in the stomach wall of a patient's stomach 312. Additionally, an adjustable stretching device 350 with the previously described function is invaginated in the stomach fundus wall of the patient. It is preferred that the volume filling device 310 is substantially larger than the stretching device 350.

The volume filling device 310 and the stretching device 350 are in fluid communication with each other via a first fluid tube 352, and a second fluid tube, which preferably has a smaller cross-sectional area than the first tube. However, instead of a pump, there is provided a non-return valve 360 in the first fluid tube 352 instead of an energized pump. This non-return valve 360 allows fluid to flow in the direction from the volume filling device 310 and to the stretching device 10 but not vice versa. This means that this embodiment may be entirely non-energized. Instead, it operates according to the following principles.

When the food cavity of the stomach 312 is essentially empty, there is a state of equilibrium between the internal pressure of the volume filling device 310 and the stretching device 350. In this state, the stretching device is in a non-stretch state, i.e., it does not stretch a part of the stomach fundus wall and thus does not create a feeling of satiety.

When the patient starts to eat, food will enter the food cavity of the stomach 312. This will create increased pressure on the stomach wall in which the volume filling device 310 is invaginated and the internal pressure therein will increase. Also, the stomach wall muscles will begin to process the food in the food cavity by contraction, which also contributes to an increased internal pressure in the volume filling device 310.

Since the internal pressure in the stretching device 350 will remain essentially unchanged, because it is located in the upper part of the stomach 312 where no food is exerting a pressure on the stomach wall, a fluid flow will be created through the first and second fluid tubes 352, 358 in the direction from the volume filling device 310 and to the stretching device 350. This in turn will increase the volume of the stretching device 350, which, by stretching the stomach fundus wall, will provide a feeling of satiety to the patient.

Figure 51C:
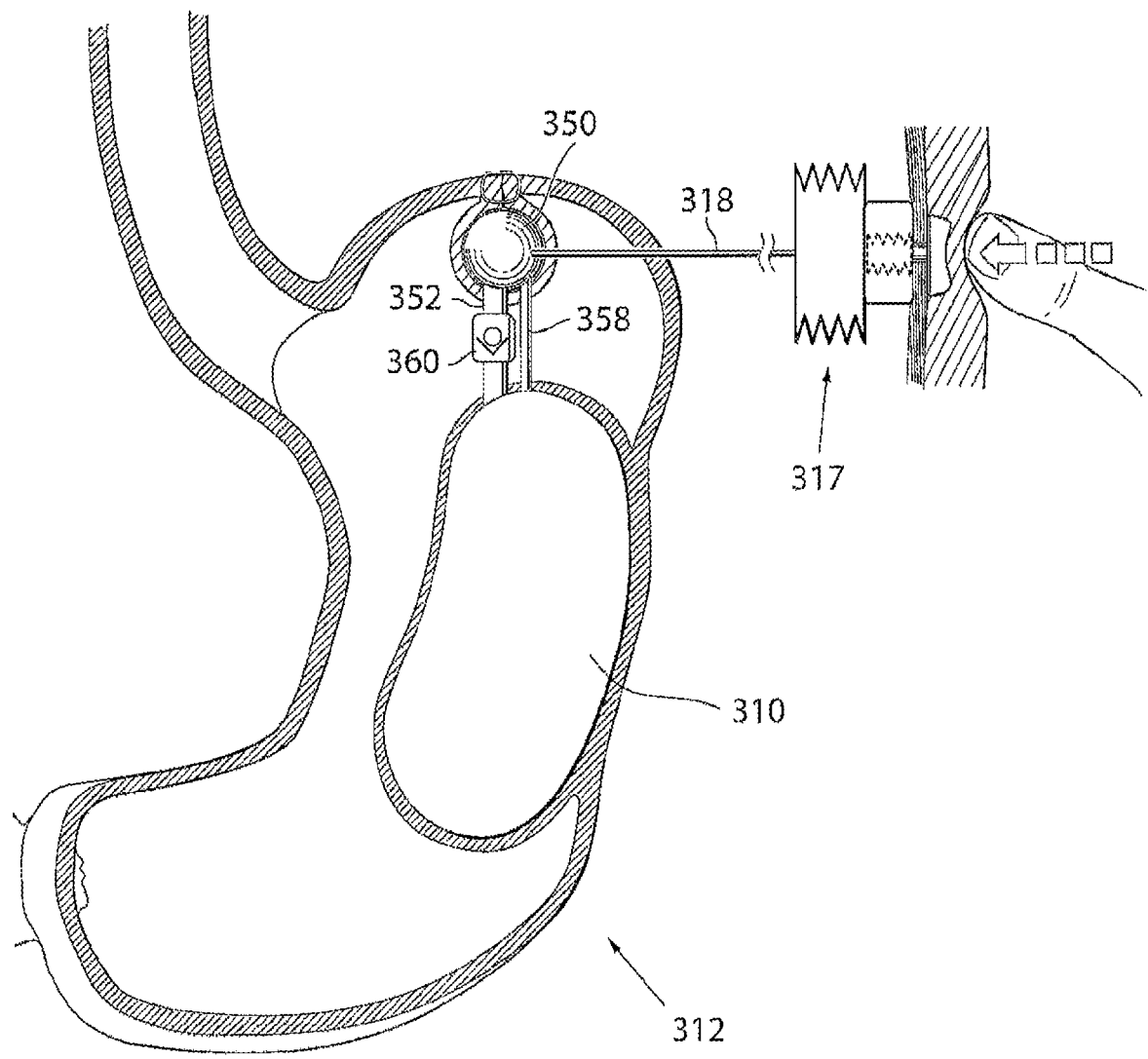

A fluid flow from the stretching device 350 to the volume filling device 310 through the second tube 358 will return the pressure of these devices to equilibrium as described above with reference to FIG. 51a Similarly, FIG. 51c illustrates an embodiment wherein the stretching device 350 can be actively regulated by manually pressing an adjustment reservoir which is provided subcutaneously below the patient's skin. Thus, a regulation reservoir 317 for fluids is connected to the inflatable device by means of a conduit 318 in the form of a tube. The stretching device 350 is thereby adapted to be regulated, non-invasively, by moving liquid or air from the regulation reservoir 317 to the chamber formed by the inflatable device. The regulation of the stretching device 350 preferably comprises a reversed servo, i.e., a small volume is actuated for example by the patient's finger and this small volume is in connection with a larger volume.

The volume filling device 310 preferably has an essentially round shape to not damage the stomach wall. An example thereof is shown in FIG. 51-3a, wherein the volume filling device is essentially egg-shaped. In another preferred embodiment, the volume filling device is slightly bent, such as the embodiment shown in FIG. 51-3b. However, since the stomach wall is strong many different shapes, forms, and dimensions may be used. In one embodiment, the volume filling device has a diameter of about 40 millimeters and a length of about 120 millimeters, resulting in a volume that is about half the volume of the patient's stomach. However, it is preferred that the maximum circumference of the volume filling device is at least 30 millimeters, more preferably at least 50 millimeters, and even more preferably at least 80 millimeters.

It is not necessary that the volume filling device is elongated. In the embodiment shown in FIG. 51-3c, the volume filling device 310 is essentially spherical or ball-shaped. In order to fill out the stomach, two or more such volume filling devices may be combined to achieve the desired decrease of the food cavity of the patient's stomach.

It has been mentioned that the volume filling device is secured by the stomach-to-stomach sutures or staples. In order to further improve the fixation, the volume filling device may be provided with a waist portion having smaller diameter that the maximum diameter of the volume filling device. Such volume filling device having a waist portion 10a is shown in FIG. 51-3d.

The volume filling device 10 may consist of at least two interconnectable portions so that each portion is easier to insert into the stomach and further through a hole in the stomach wall. Thus, FIG. 51-3e shows a volume filling device comprising two more or less spherical sub-parts 310b, 310c interconnected by a portion with which preferably has smaller diameter. The portion with smaller diameter may comprise an interconnection means with a reversible function allowing subsequent disconnection of the two interconnected sub-parts 310b, 310c. Such means may comprise a bayonet socket, a screw connection or the like, designated 310d in the figure. Alternatively, the portion with smaller diameter may comprise a fixed interconnection, such as resilient locking hooks provided on one of the sub-parts 310b, 310c and engaging the rim of a hole provided in the other one of the sub-parts 310b, 310c.

The configuration of the volume filling device 10 is not limited to one waist portion 310a. Thus, in FIG. 51-3f a volume filling device with two waist portions is shown In order to facilitate positioning of the volume filling device, an attachment means in the form of a handle or the like may be provided on the outer surface of the volume filling device. One example thereof is shown in FIG. 51-3g, wherein also a detail view of a handle 51-10e is shown. In a preferred embodiment, the attachment means is provide at an end portion of the volume filling device 310. In order to avoid protruding portion on the surface of the volume filling device 310, the handle 310e is provided flush with the outer surface of the volume filling device 310 and a recess 310f is arranged to allow a gripping tool or instrument (not shown in FIG. 51-3g) to achieve firm gripping around the handle 310e.

The volume filling device may comprise a tube for filling or emptying the volume filling device of a fluid or gel. By injecting fluid or gel into the volume filling device 310, the volume filling device is inflated to an inflated state, as will be described below. The size of the volume filling device can also be adjusted by moving fluid or gel therefrom to a different reservoir.

A volume filling device 310 adapted for this is shown in FIG. 51-3h. A tube 310g is fixedly attached to the volume filling device. This tube can be attached to a suitable instrument (not shown) or an injection port, which will be explained in detail below.

Instead of having a fixedly attached tube, the volume filling device 310 may comprise an inlet port 10h adapted for connection of a separate tube (not shown in this figure).

It is important that the implanted volume filling device is firmly kept in place in the stomach wall in which it is invaginated. To this end, the volume filling device can be provided with one or more through holes adapted for receiving sutures or staples used for fixation of the invagination. Such an embodiment is shown in FIG. 51-3j, where the volume filling device 310 is provided with a mw of holes 10i provided on a protruding flange-like protrusion on the volume filling device. In this embodiment, the row of holes extend along the longitudinal axis of the volume filling device.

Method for Placing a Reflux Treatment Device on the Inside of the Stomach Wall

In the following a method and an instrument for placing a reflux treatment device on the inside of the stomach wall will be described.

Figure 52A:
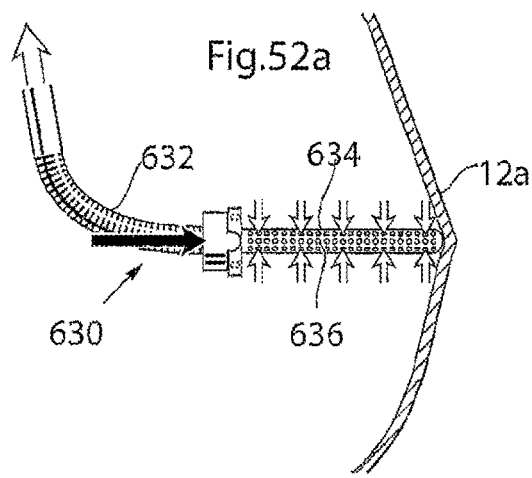
FIGS. 52a-h illustrate different steps of invaginating the inflatable device of FIG. 47a on the inside of a stomach wall of a patient.

The invagination instrument described in FIG. 52a-1 generally designated 630, comprises an elongated tube member 632 similar to the elongated member 607 described above with reference to FIGS. 48a-i. Thus, it can be connected to a control unit 606, see FIG. 48a. The invagination instrument 630 further comprises a perforated suction portion 634, which preferably is elongated. The suction portion 634 exhibits a plurality of small holes 636, into which air will be sucked by providing suction in the tube member 632. This suction effect will be used to create a "pocket" or "pouch" in a part of a stomach wall, generally designated 12a.

In other words, when the tip of the suction portion 634 is pressed against the stomach wall 12a, see FIG. 52a, a small recess will be formed therein. When the suction portion 634 is further pressed against the stomach wall 12a, see FIG. 52b, a larger recess will be formed. The part of the stomach wall 12a that forms the recess will, due to the suction effect, adhere to the suction portion 634 of the invagination instrument 630. As the suction portion 634 is further pressed into the stomach wall 12a, see FIG. 52c, a deeper recess will be formed until the entire suction portion 634 is embedded in the recess, see FIG. 18d.

Figure 52E:
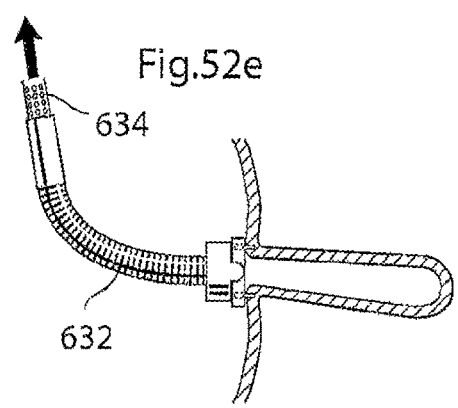
Figure 52B:
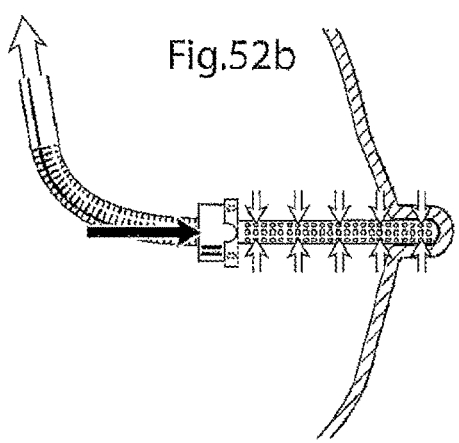
Figure 52F:
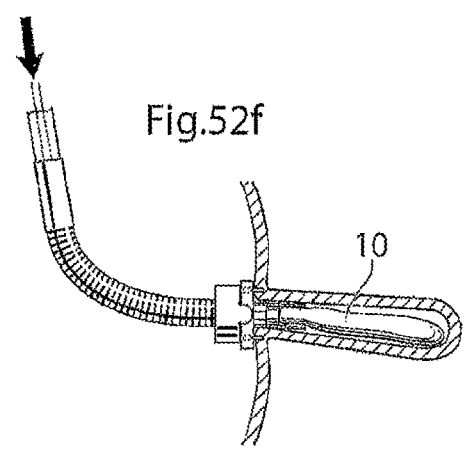
Figure 52C:
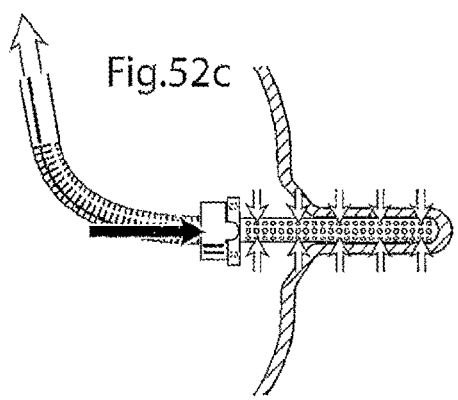
Figure 52G:
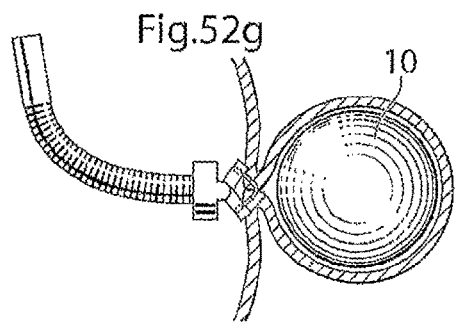
Figure 52D:
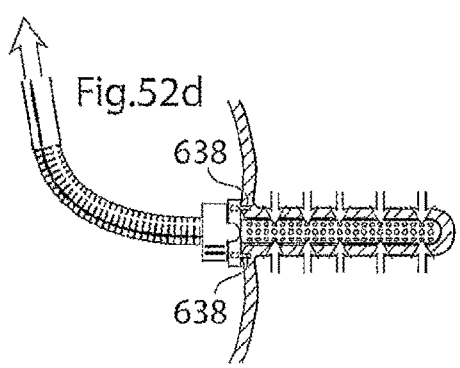
Figure 52H:
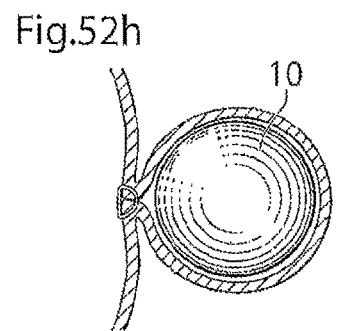

The rim of the recess will at this stage be fixated by means of fixation elements 638 and the suction portion be removed from the instrument, see FIG. 52e. A compressed elastic reflux treatment device 10 will subsequently be inserted into the recess, see FIG. 52f, for example in the way described above with reference to FIG. 47d. This compressed reflux treatment device is then expanded to its final shape, see FIG. 52g, where after the pouch is sealed by suturing or stapling by means of the fixations elements, see FIG. 52h.

All the alternatives described above with reference to FIGS. 1-51 are also applicable to the embodiment described with reference to FIGS. 52a-h, i.e., to the embodiment where the reflux treatment device is invaginated on the inside of the stomach wall.

Figure 53A:
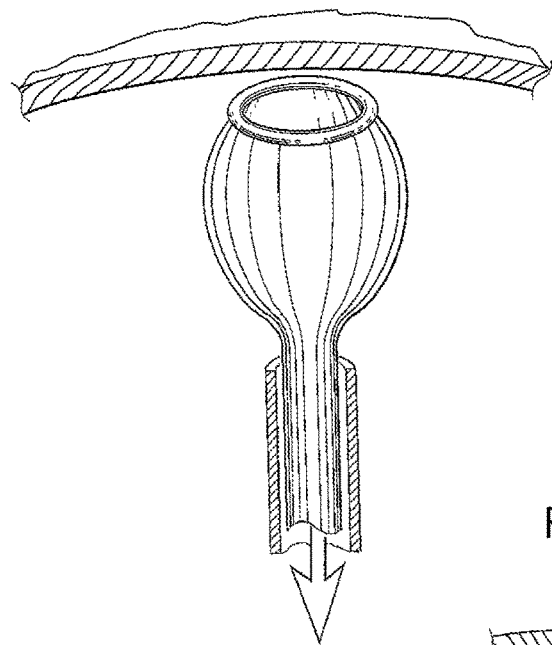
FIGS. 53a-c shows an instrument for creating an invagination of the wall of the stomach.
Figure 53B:
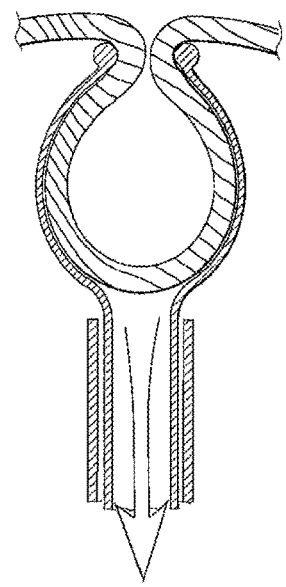
Figure 53C:
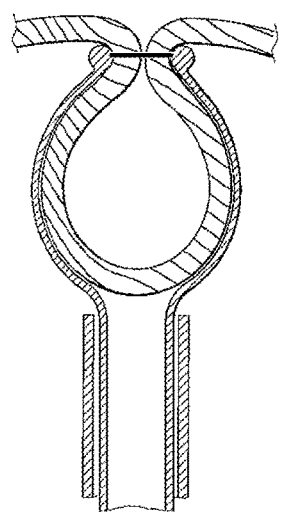

FIGS. 53 a-c show an instrument for creating an invagination of the wall of the stomach that can either be placed on the outside of the wall of the stomach or on the inside of the wall of the stomach depending if the reflux treatment device is place on the inside or the outside of the wall. The instrument uses vacuum to such a portion of the wall of the stomach into the cup of the instrument.

It has been described how the reflux treatment device 10 is invaginated in the stomach wall by means of a gastroscopic instrument. The gastroscopic instrument can be used for either placing the reflux treatment device on the outside of the wall of the stomach as shown in FIG. 1A or on the inside of the stomach as shown in FIG. 2A. In the latter case, the instruments will be used to make an incision in the wall of the stomach from the inside of the stomach.

Figure 54:
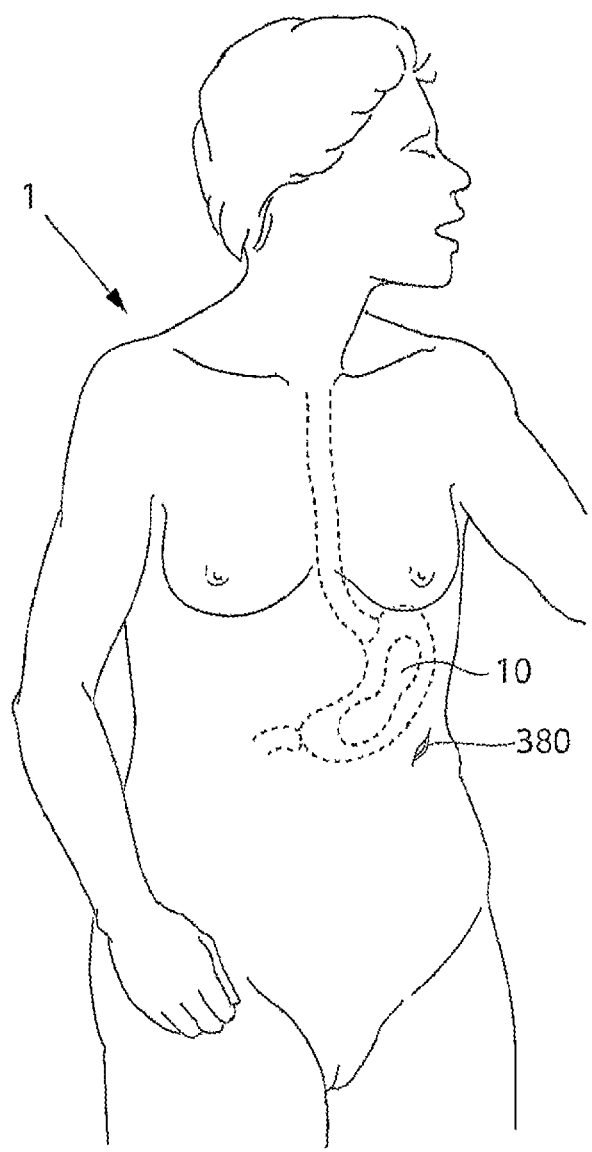
FIGS. 54-55 show an abdominal method for treating reflux disease.
Figure 55:
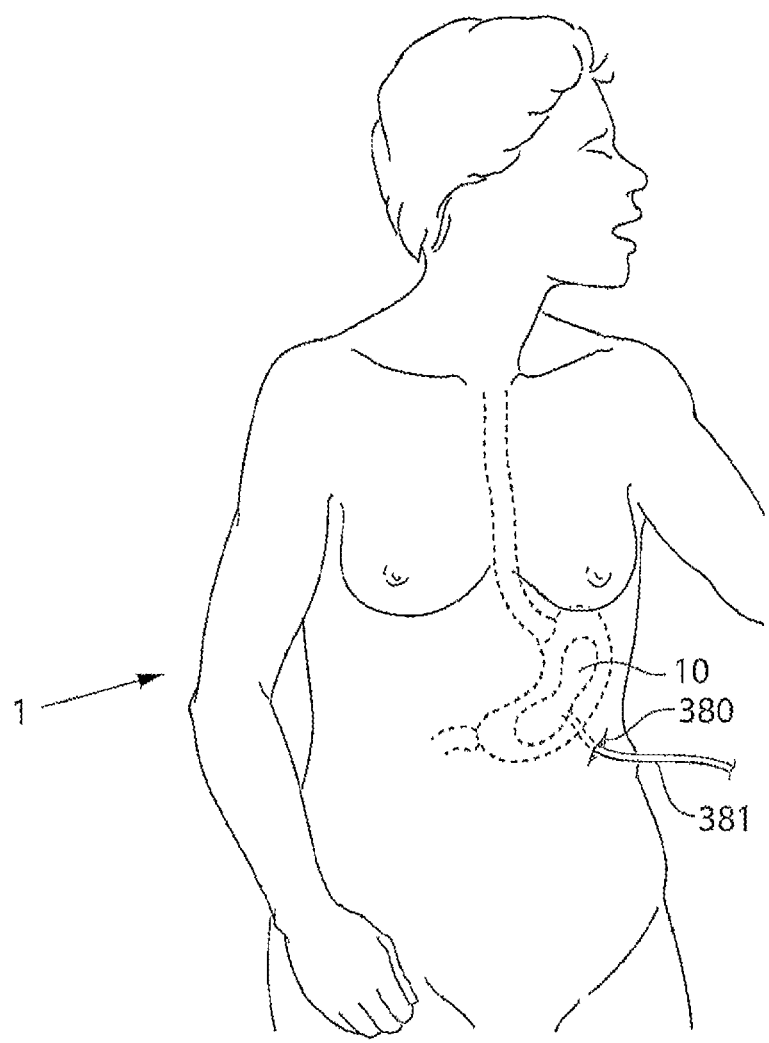
Figure 56:
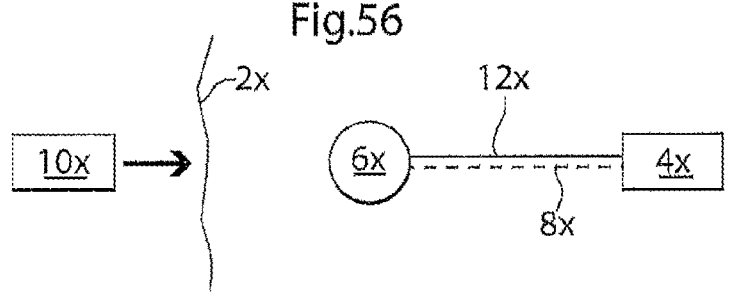
FIG. 56 is a schematic block diagram illustrating an embodiment of the reflux disease apparatus of the invention, in which wireless energy is released from an external source of energy for use in the power of a stimulation device.

It will be appreciated that abdominal operation methods can be used as well. Such methods will now be described in with reference to FIGS. 54-55. In FIG. 54 it is shown how the stomach is accessed by creating an incision 380 in the abdomen of the patient. In FIG. 55 it is shown how an instrument 381 is inserted into the abdomen of the patient. Any of the instrument and methods described can be selected an adapted for this purpose. Thus, for example, the reflux treatment device can be placed on the outside of the stomach as shown in FIG. 1A or on the inside as shown in FIG. 2A. In the later case an incision is made in the wall of the stomach Stimulation—Detailed Description FIG. 56 schematically shows an embodiment of the heartburn and reflux disease apparatus of the invention having some part implanted in a patient and other part located outside the patient's body. Thus, in FIG. 56 all part placed to the right of the patient's skin 2x are implanted and all part placed to the left of the skin 2x are located outside the patient's body. The apparatus of FIG. 56 comprises an implanted electric stimulation device 4, which engages the patient's cardia sphincter to provide electric connection thereto. An implanted control unit 6x controls the stimulation device 4x via a control line 8x. An external control unit 10x includes an external source of energy and a wireless remote control transmitting a control signal generated by the external source of energy. The control signal is received by a signal receiver incorporated in the implanted control unit 6x, whereby the control unit 6x controls the implanted stimulation device 4x in response to the control signal. The implanted control unit 6x also uses electric energy drawn from the control signal for powering the stimulation device 4x via a power supply line 12x.

Figure 57:
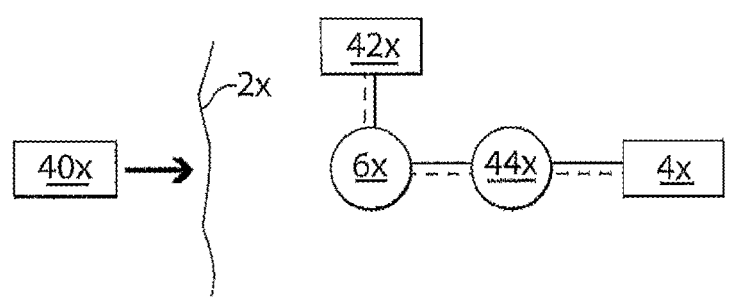
FIG. 57 is a schematic block diagram illustrating another embodiment of the invention, in which wireless energy is released from an internal source of energy.

FIG. 57 shows an embodiment of the invention identical to that of FIG. 56, except that an implanted internal electric source of energy in the form of a battery 42x is substituted for the external source of energy. Thus, an external control unit 40x without any source of energy is used in this embodiment. In response to a control signal from the external control unit 40x the implanted control unit 6x powers the stimulation device 4x with energy from the battery 42x.

Figure 58:
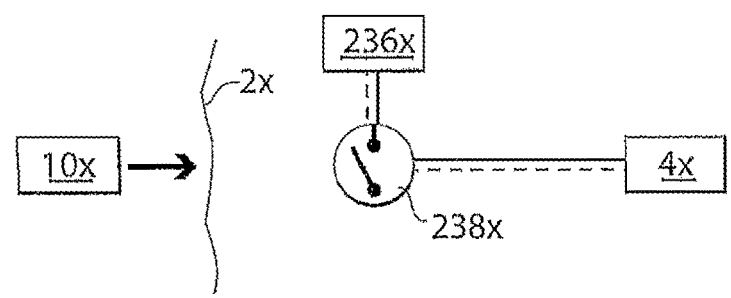
FIGS. 58 to 61 are schematic block diagrams illustrating four embodiments, respectively, of the invention, in which a switch is implanted in the patient for directly or indirectly switching the power of the stimulation device.

FIG. 58 shows an embodiment of the invention comprising the stimulation device 4x, the external control unit 10x, and an implanted source of energy 236x and an implanted switch 238x. The switch 238x is operated by wireless energy released from the external source of energy of the external control unit 6x to switch between an off mode, in which the implanted source of energy 236x is not in use, and an on mode, in which the implanted source of energy 236x supplies energy for the power of the stimulation device 4x.

Figure 59:
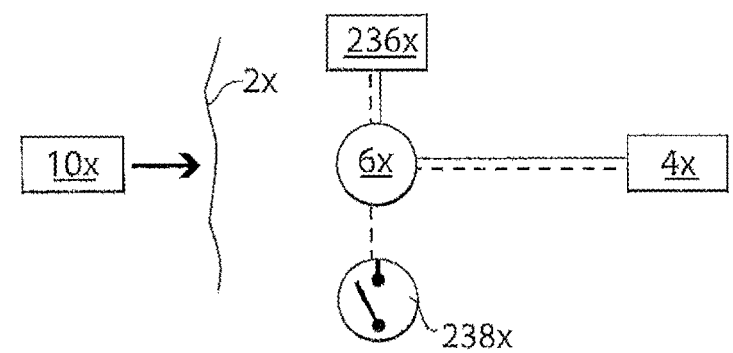

FIG. 59 shows an embodiment of the invention identical to that of FIG. 58, except that also the control unit 6x is implanted, in order to receive a control signal from the wireless remote control of the external control unit 10x. The switch 238x is operated by the wireless energy from the external source of energy 10x to switch between an off mode, in which the implanted source of energy 236x and the wireless remote control of the external control unit 10x are not in use, i.e. the control unit 6x is not capable of receiving the control signal, and a standby mode, in which the wireless remote control is permitted to control the internal source of energy 236x, via the implanted control unit 6x, to supply energy for the power of the stimulation device 4x.

Figure 60:
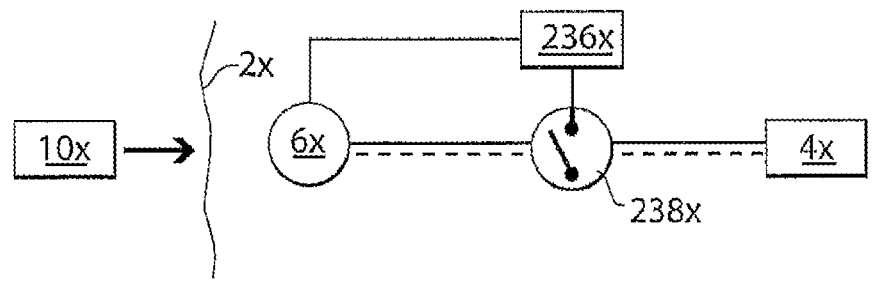

FIG. 60 shows an embodiment of the invention identical to that of FIG. 59, except that an energy transforming device for transforming the wireless energy into storable energy is incorporated in the implanted control unit 6x and that the implanted source of energy 236x is of a type that is capable of storing the storable energy. In this case, in response to a control signal from the external control unit 10x, the implanted control unit 6 controls the switch 238x to switch from an off mode, in which the implanted source of energy 236x is not in use, to an on mode, in which the source of energy 36x supplies energy for the power of the stimulation device 59x.

Figure 61:
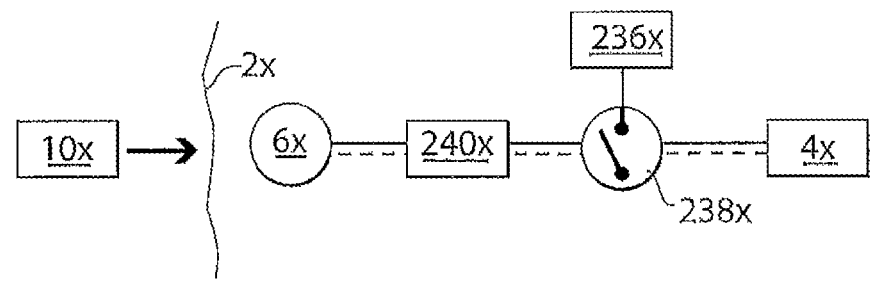

FIG. 61 shows an embodiment of the invention identical to that of FIG. 60, except that an energy storage device 240x also is implanted in the patient for storing the storable energy transformed from the wireless energy by the transforming device of the control unit 6x. In this case, the implanted control unit 6x controls the energy storage device 240 to operate the switch 238x to switch between an off mode, in which the implanted source of energy 236x is not in use, and an on mode, in which the implanted source of energy 236x supplies energy for the power of the stimulation device 4x.

Figure 62:
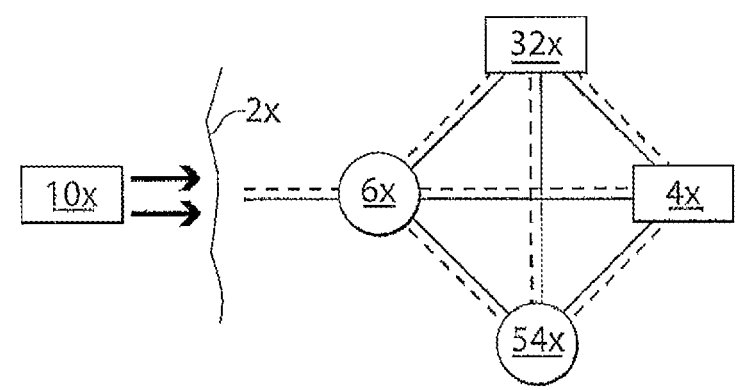
FIG. 62 is a schematic block diagram illustrating conceivable combinations of implantable components for achieving various communication options.

FIG. 62 schematically shows conceivable combinations of implanted components of the apparatus for achieving various communication possibilities. Basically, there are the implanted stimulation device 4x, the implanted control unit 6x and the external control unit 10x including the external source of energy and the wireless remote control. As already described above the remote control transmit a control signal generated by the external source of energy, and the control signal is received by a signal receiver incorporated in the implanted control unit 6x, whereby the control unit 6x controls the implanted stimulation device 4x in response to the control signal.

A sensor 54x may be implanted in the patient for sensing a physical parameter of the patient, such as the pressure in the esophagus. The control unit 6x, or alternatively the external control unit 10x, may control the stimulation device 4x in response to signals from the sensor 54x. A transceiver may be combined with the sensor 54x for sending information on the sensed physical parameter to the external control unit 10*x*. The wireless remote control of the external control unit 10*x* may comprise a signal transmitter or transceiver and the implanted control unit 6*x* may comprise a signal receiver or transceiver. Alternatively, the wireless remote control of the external control unit 10*x* may comprise a signal receiver or transceiver and the implanted control unit 6*x* may comprise a signal transmitter or transceiver. The above transceivers, transmitters and receivers may be used for sending information or data related to the stimulation device from inside the patient's body to the outside thereof. For example, the battery 32*x* may be equipped with a transceiver for sending information on the charge condition of the battery.

Those skilled in the art will realize that the above various embodiments according to FIGS. 56-61 could be combined in many different ways.

Figure 63:
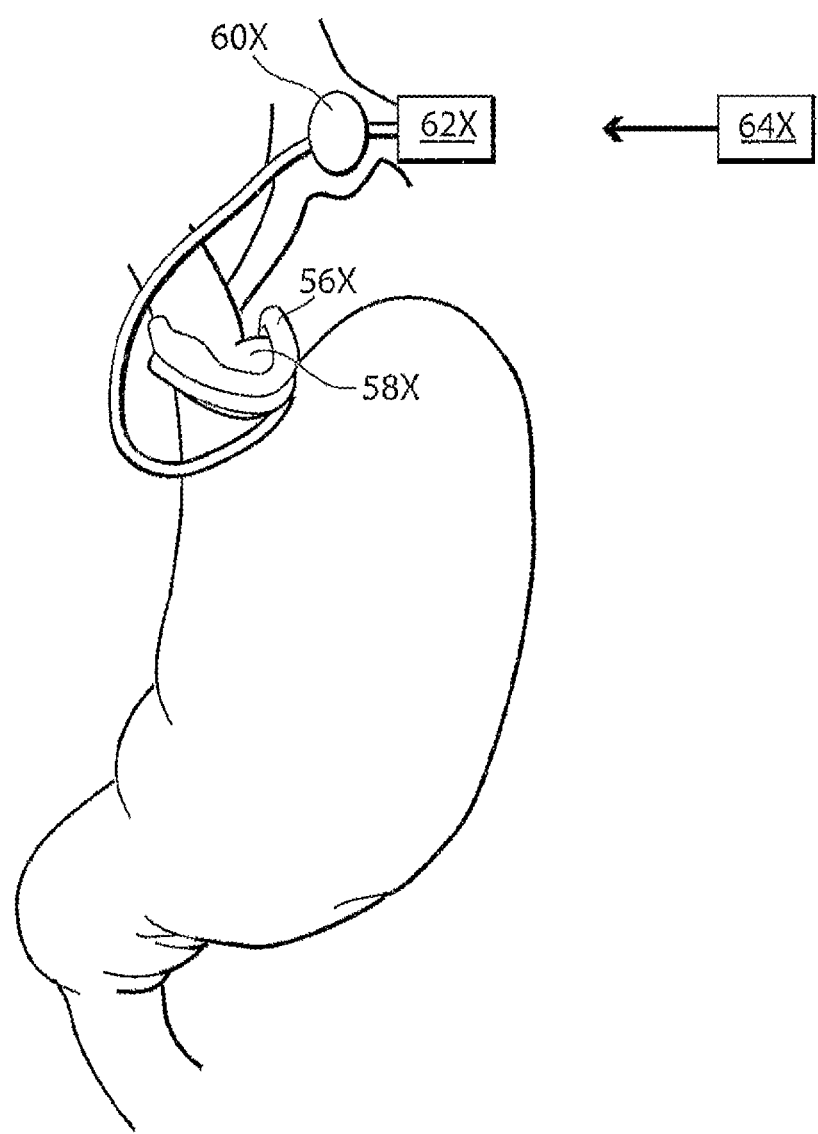
FIG. 63 illustrates the apparatus in accordance with the invention implanted in a patient.

FIG. 63 illustrates how any of the above-described embodiments of the heartburn and reflux disease treatment apparatus of the invention may be implanted in a patient. Thus, an assembly of the apparatus implanted in the patient comprises a stimulation device in the form of a band 56*x*, which is wrapped around the cardia 58*x*. The band 58*x* is provided with conductors that electrically contact the cardia sphincter and an operation device 60*x* for operating the stimulation device 56*x*. An implanted control unit 60*x* is provided for controlling the supply of electricity to the band 56*x*. There is an implanted energy transforming device 62*x* for transforming wireless energy into electric energy. The transforming device 62*x* also includes a signal receiver. An external control unit 64*x* includes a signal transmitter for transmitting a control signal to the signal receiver of the implanted transforming device 62*x*. The transforming device 62*x* is capable of transforming signal energy from the control signal into electric energy for powering the stimulation device 60*x* and for energizing other energy consuming implanted component of the apparatus.

Figure 64:
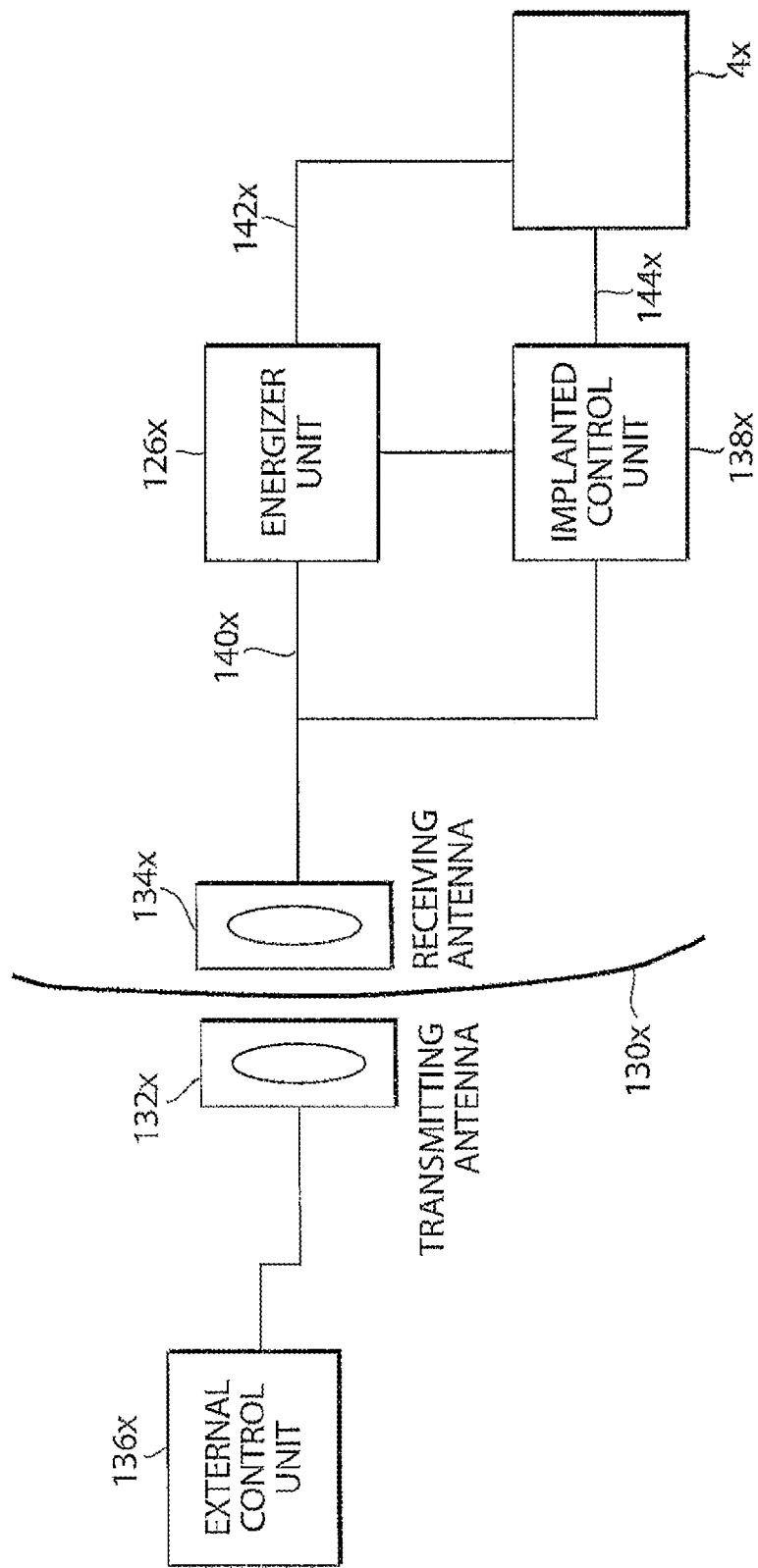
FIG. 64 is a block diagram illustrating remote control components of an embodiment of the invention.

FIG. 64 shows the basic parts of a wireless remote control of the apparatus of the invention including an implanted electric stimulation device 4*x*. In this case, the remote control is based on the transmission of electromagnetic wave signals, often of high frequencies in the order of 100 kHz-1 gHz, through the skin 130*x* of the patient. In FIG. 64, all park placed to the left of the skin 130*x* are located outside the patient's body and all park placed to the right of the skin 130*x* are implanted. Any suitable remote control system may be used.

An external signal transmitting antenna 132*x* is to be positioned close to a signal receiving antenna 134*x* implanted close to the skin 130*x*. As an alternative, the receiving antenna 134*x* may be placed for example inside the abdomen of the patient. The receiving antenna 134*x* comprises a coil, approximately 1-100 mm, preferably 25 mm in diameter, wound with a very thin wire and tuned with a capacitor to a specific high frequency. A small coil is chosen if it is to be implanted under the skin of the patient and a large coil is chosen if it is to be implanted in the abdomen of the patient. The transmitting antenna 132*x* comprises a coil having about the same size as the coil of the receiving antenna 134*x* but wound with a thick wire that can handle the larger current that is necessary. The coil of the transmitting antenna 132*x* is tuned to the same specific high frequency as the coil of the receiving antenna 134*x*.

An external control unit 136*x* comprises a microprocessor, a high frequency electromagnetic wave signal generator and a power amplifier. The microprocessor of the control unit 136*x* is adapted to switch the generator on/off and to modulate signals generated by the generator to send digital information via the power amplifier and the antennas 132*x*, 134*x* to an implanted control unit 138*x*. To avoid that accidental random high frequency fields trigger control commands, digital signal codes are used. A conventional keypad placed on the external control unit 136*x* is connected to the microprocessor thereof. The keypad is used to order the microprocessor to send digital signals to either power or not power the stimulation device. The microprocessor starts a command by applying a high frequency signal on the antenna 132*x*. After a short time, when the signal has energised the implanted parts of the control system, commands are sent to power the stimulation device. The commands are sent as digital packets in the form illustrated below.

| Start pattern, 8 bits | Command, 8 bits | Count, 8 bits | Checksum, 8 bits |
|---|---|---|---|

The commands may be sent continuously during a rather long time period. When a new power or not power step is desired the Count byte is increased by one to allow the implanted control unit 138*x* to decode and understand that another step is demanded by the external control unit 136*x*. If any part of the digital packet is erroneous, its content is simply ignored.

Through a line 140*x*, an implanted energizer unit 126*x* draws energy from the high frequency electromagnetic wave signals received by the receiving antenna 134*x*. The energizer unit 126 stores the energy in a power supply, such as a large capacitor, powers the control unit 138*x* and powers the electric stimulation device 4*x* via a line 142*x*.

The control unit 138*x* comprises a demodulator and a microprocessor. The demodulator demodulates digital signals sent from the external control unit 136*x*. The microprocessor of the control unit 138*x* receives the digital packet, decodes it and, provided that the power supply of the energizer unit 126*x* has sufficient energy stored, powers the stimulation device 4*x* via a line 144*x*.

Alternatively, the energy stored in the power supply of the energizer unit may only be used for powering a switch, and the energy for powering the stimulation device 4*x* may be obtained from another implanted power source of relatively high capacity, for example a battery. In this case the switch is adapted to connect said battery to the control unit 138*x* in an on mode when the switch is powered by the power supply and to keep the battery disconnected from the control unit in a standby mode when the switch is not powered.

Stretching—Detailed Description

Here follows detailed description of two embodiments of the invention where treatment of reflux is combined with treatment of obesity. First, embodiments showing a stretching device are shown Invaginated in the stomach wall is to be understood as an object being placed inside of a cavity made of stomach wall material. The invagination enables stomach to stomach sutures or staples which enables the object of be enclosed by means of the human tissue healing.

Figure 65:
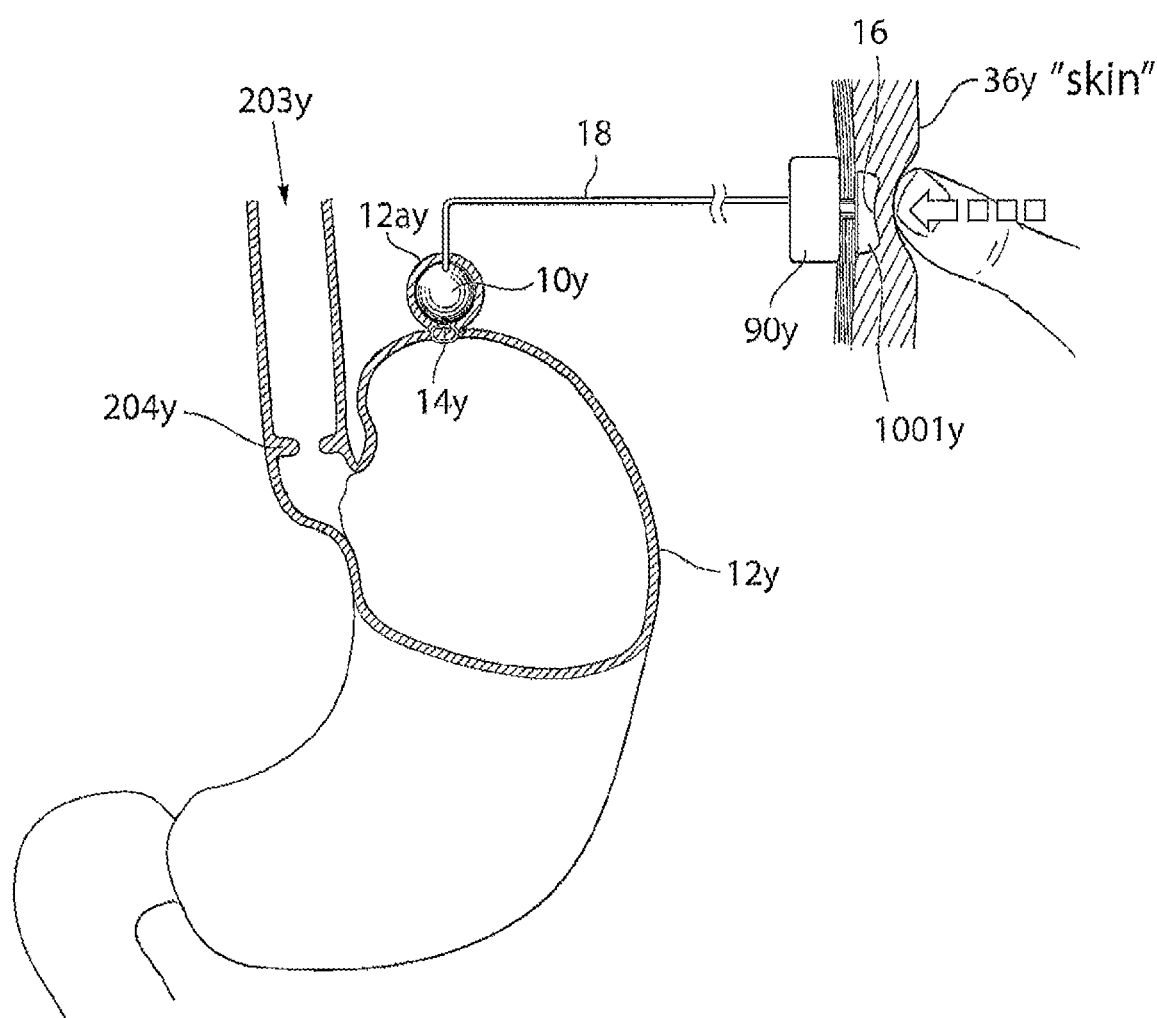
FIGS. 65-68 are views of embodiments of an apparatus for treating obesity by stretching the wall of the stomach that can be combined the reflux treatment apparatus implanted in a human patient.

FIG. 65 shows a first embodiment of an obesity treatment apparatus. The apparatus comprises a stretching device 10*y* implanted in a human patient In FIG. 65 the stretching device 10*y* is invaginated in the wall 12*y* of the patient's stomach 12*y* and the body of the stretching device 10*y* is shaped to rest against the wall 12*y* of the stomach 12*y* and further has an outer surface suitable to rest against this wall 12*y*. This means that the stretching device 10*y* preferably has an essentially round shape to not damage the stomach wall.

However, the stomach wall 12y is strong so many different shapes and forms may be used.

The stretching device 10y can be fixed to the wall 12ay of the stomach 12y in a number of different ways. In the embodiment shown in FIG. 65, the stretching device 10y is invaginated in the stomach wall 12ay. After invagination, a number of stomach-to-stomach sutures or staples 14y are applied to keep the invagination in the short term. This allows growth of human tissue, keeping the invagination in the long term.

By enlarging the size of the stretching device, the stomach wall 12y surrounding the stretching device 10y is stretched since the circumference of the stretching device 10y is increased. By this stretching, receptors in the stomach wall indicate that the stomach is full, thereby creating a feeling of satiety to the patient. Correspondingly, when the stretching device 10y is contracted, the receptors indicate that the stomach is not full, thereby returning the feeling of hunger.

The expansion and contraction of the stretching device 10y can be performed under direct control of the patient Alternatively, the expansion and contraction can be performed according to a pre-programmed schedule.

Returning to FIG. 65, this figure also shows a fluid operation device, i.e., a hydraulic or pneumatic operation device suited for operating the stretching device, which in the following will be described in detail.

The stretching device 10y forms a fluid chamber, in which fluid is allowed to flow. The stretching device 10y thus forms an expandable chamber that can change the volume it occupies in the stomach wall, thereby forming a hydraulically or pneumatically regulated stretching device 10y.

A regulation reservoir 16y for fluids is connected to the stretching device 10y by means of a conduit 18y in the form of a tube. The stretching device 10y is thereby adapted to be regulated, preferably non-invasively, by moving liquid or air from the regulation reservoir 16y to the chamber formed by the stretching device.

The regulation reservoir 16y can be regulated in several ways. In the embodiment shown in FIG. 65, the regulation reservoir 16y is regulated by manually pressing the regulation reservoir 16y. In other words, the regulation reservoir 16y is regulated by moving a wall of the reservoir. It is then preferred that the regulation reservoir 16y is placed subcutaneously and non-invasive regulation is thereby achieved.

When the regulation reservoir 16y is pressed, the volume thereof decreases and hydraulic fluid is moved from the reservoir to the chamber formed by the stretching device 10y via the conduit 18, enlarging or expanding the stretching device 10y. For filling and calibrating the fluid level of the apparatus an injection 1001y port is furthermore provided. The injection port preferably comprises self sealing membrane, such as a silicone membrane.

It will be appreciated that instead of hydraulic operation, pneumatic operation can be used, wherein air instead of hydraulic fluid is moved between the reservoir 16y and the chamber formed by the stretching device 10y. Preferable the reservoir has a locking position to keep it in the desired position. If the patient compresses the reservoir 16y it preferably stays compressed and releases after pressing again.

Any kind of hydraulic solution may be used for the stretching device. The hydraulic solution may be driven by both mechanically and be powered with any motor or pump as well as manually.

FIG. 65 further shows a reversed servo system which comprises a regulation reservoir 16y and a servo reservoir 90y. The servo reservoir 90y hydraulically controls a stretching device 10y via a conduit 18y. The reverse servo function is described in greater detail in FIGS. 97-100

Figure 66A:
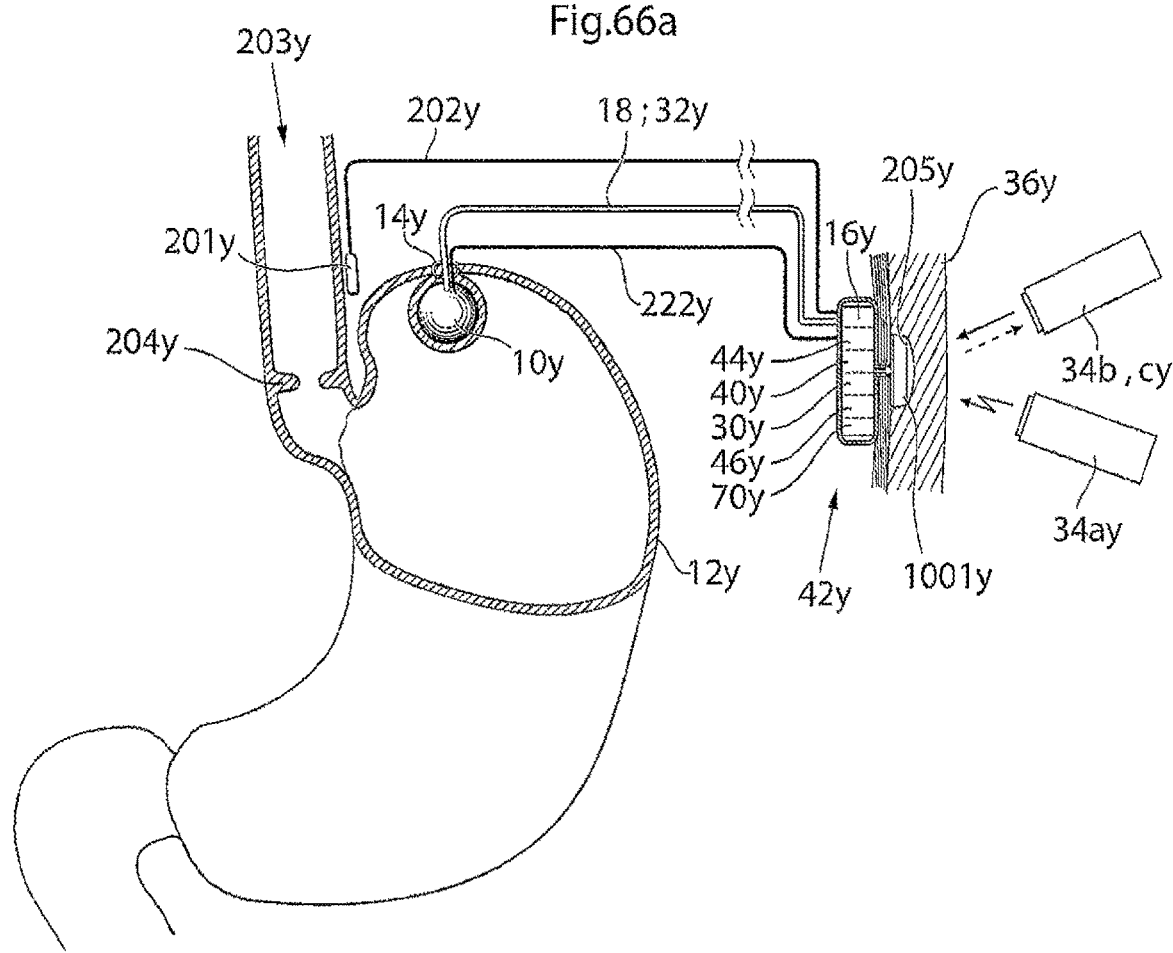

FIG. 66a shows the apparatus according to another embodiment in which a motor 40y is adapted to move a wall of the regulation reservoir 16y. The powered regulation reservoir 16y is then preferably placed in the abdomen of the patient In this embodiment, a wireless external remote control unit 34by,cy and an external energy transmission device 34ay can be provided to perform non-invasive regulation of the motor via an energy transforming device 30y, which is adapted to supply an energy consuming operation device, in the present example the motor 40y, with energy.

The remote control may comprise a wireless energy transmitter, 34ay which also can act as a regulation device for non-invasively regulating the stretching device. When the regulation is performed by means of a remote control 34y an internal power source 70y for powering the regulating device is provided. The internal energy source 70y can for example be a chargeable implanted battery or a capacitor or a device for receiving wireless energy transmitted from outside the body of the patient Different ways of regulating the stretching device 10y will be described below with reference to FIGS. 77-100.

The apparatus as shown in FIG. 66a further comprises a sensor 201y sensing a parameter of the patient or the apparatus preferably connected to the food intake of the patient. The sensor is connected to a control assembly 42y by means of a sensor signal transferring member 202y. The sensor can be used to regulate said apparatus in a completely automatic way, i.e. the apparatus responds to a sensor signal connected to the food intake of the patient, thereby affecting the control assembly to operate the stretching device 10y to stretch the stomach wall 12y and thereby creating a feeling of satiety in the patient. The sensor could be adapted to measure the food intake of the patient through any of temperature, blood pressure, blood flow, heartbeats, breathing and pressure and can be placed in the stomach 12y, esophagus 203y or in connection with the cardia 204y. According to one embodiment said sensor is a strain gauge measuring contraction and/or relaxation of the cardia 204y.

The apparatus as shown in FIG. 66a further comprises a second conduit 222y for backflow of hydraulic fluid. The backflow is adapted to create the desired feeling of satiety for a predetermined time whereafter the hydraulic fluid has flowed back in a quantity large enough for the stretching device not to stretch the stomach wall anymore and thereby the feeling of hunger returns to the patient. A suitable time for the process is between 1 and 6 hours. According to other embodiments the backflow takes place in the main conduit 18y by means of a valve system connected to said conduit 18y.

For filling and calibrating the fluid level of the apparatus an injection 1001y port is furthermore provided. The injection port 1001y preferably comprises self sealing membrane, such as a silicone membrane.

Figure 66B:
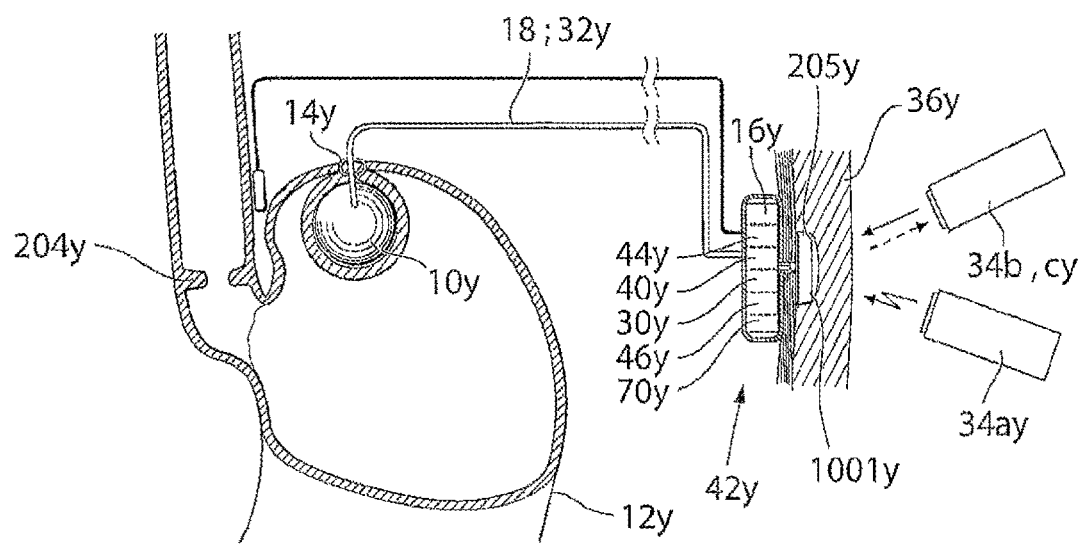

FIG. 66b shows the apparatus according to the embodiment of FIG. 66a, in a second state in which the stretching device 10y is expanded and thereby stretches the stomach wall 12y.

Figure 67A:
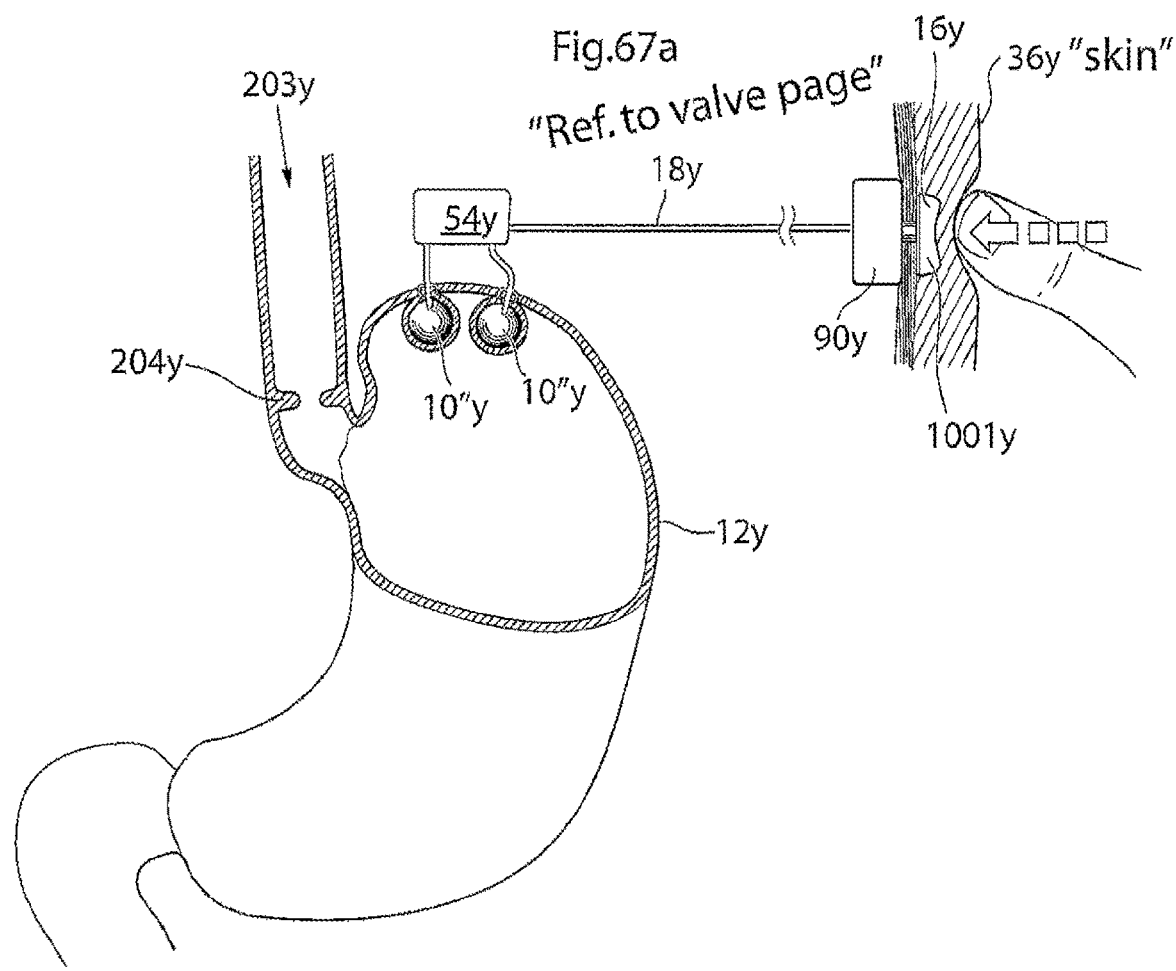

FIG. 67a shows an embodiment, wherein two stretching devices 10"y are provided. Both stretching devices 10"y work according to the principles described above with reference to FIG. 65. They can be adapted to postoperatively and non-invasively be regulated and adapted to from time to time regulate different stretching devices to at a first time stretch a first part of the stomach wall and at a second time stretch a second part of the stomach wall.

Such a stretching device 10y may be used for keeping electronics and/or an energy source and/or hydraulic fluid. Hydraulic fluid from that device may be distributed to several smaller stretching device areas to vary the stretching area from time to time avoiding any possible more permanent stretching effect of the stomach wall. Even mechanically several stretching areas may be used. The embodiment according to FIG. 67a further comprises a hydraulic valve shilling device 54y, implanted in the patient, for shilling between operating the first and the second stretching device 10"y. The alternating creates a more sustainable device since the receptors in the stomach wall is stimulated gets a longer time of recovery between the stretches.

Figure 67B:
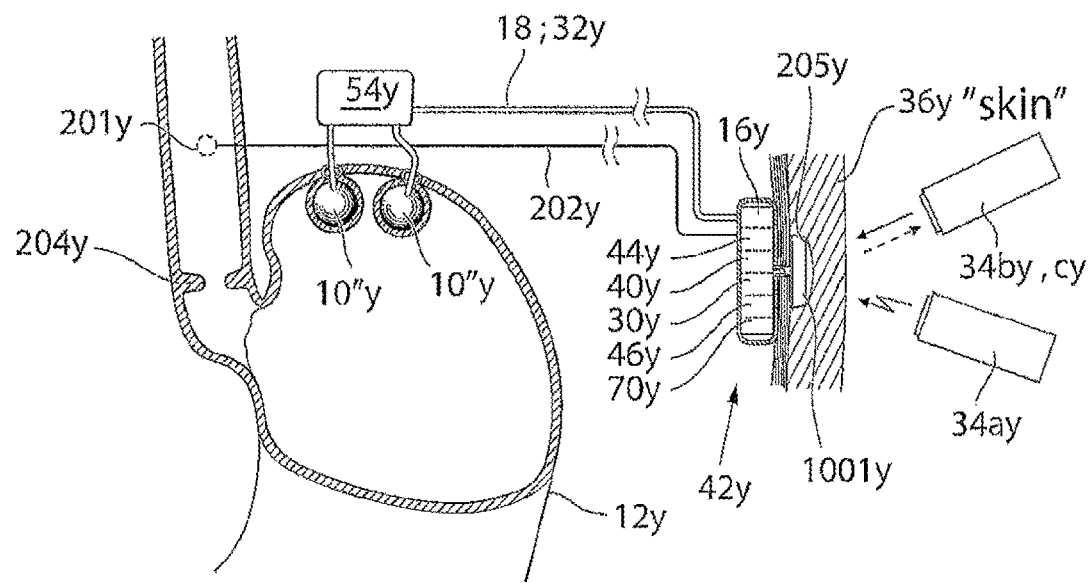

In FIG. 67a the system is a manual system controlled by the patient as described before with reference to FIG. 65, whereas in FIG. 67b the system is energized using wireless energy as described before with reference to FIG. 66a.

Figure 68A:
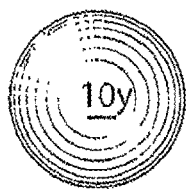
Figure 68E:
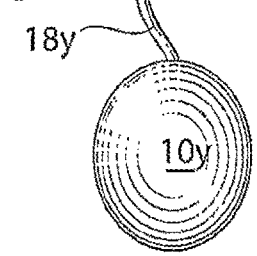
Figure 68B:
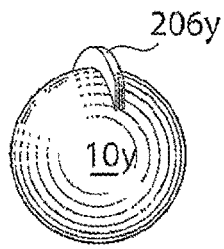
Figures 68F, 68G:
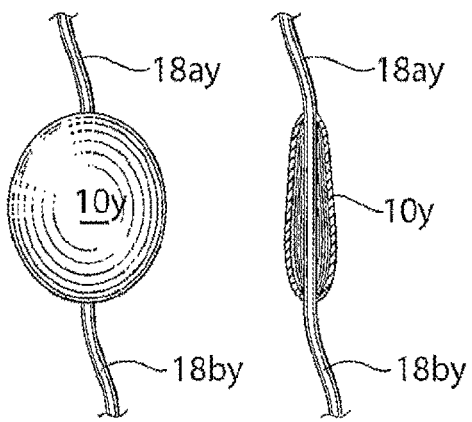
Figure 68C:
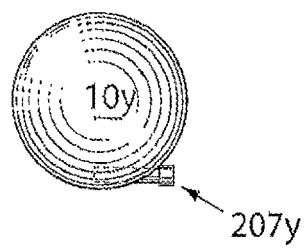
Figure 68H:
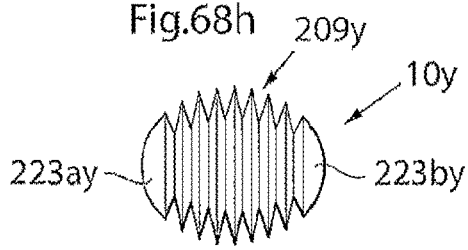
Figure 68D:
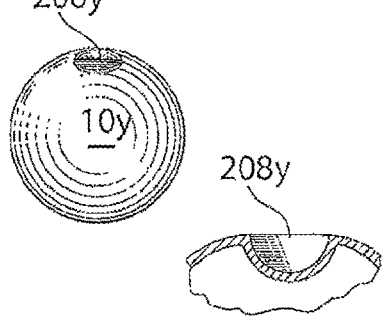
Figure 68I:
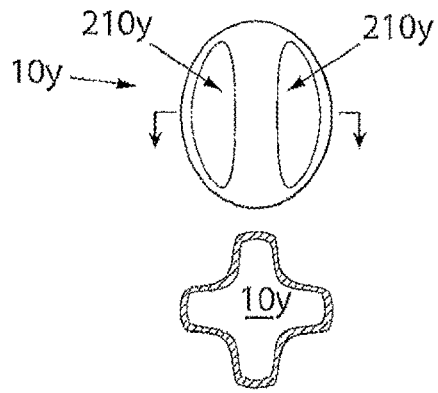

FIG. 68a-e shows different embodiments of the stretching device 10y adapted to be implanted in a patient. The stretching device 10y comprises a surface adapted to be in contact with the stomach wall 12y when the device is invaginated in the stomach wall. FIG. 68b shows an embodiment of the stretching device in which the stretching device comprises a fixating member 206y for suturing or stapling the stretching device to the stomach wall. The fixating member 206y could comprise holes for receiving said sutures or staples 14y, or the fixation device 206y could be penetratable such that the sutures or staples can penetrate the stomach wall and the fixation device 206y. 68c shows the stretching device 10y according to an embodiment in which the stretching device 10y comprises an inlet member 207y for filling said device with a fluid. Said inlet member is preferably connected to a hydraulic conduit 18y adapted to be invaginated in the stomach wall 12y. FIG. 68d shows the stretching device 10y according to an embodiment in which the stretching device 10y comprises a holding member 208 adapted to connect to an insertion device when said stretching device 10y is inserted into an invaginated pouch of the stomach wall 12y. FIG. 68e shows the stretching device 10y according to an embodiment in which the stretching device has a slightly oval or egg-shaped shape. FIG. 68e furthermore shows the hydraulic conduit 18 attached to said stretching device 10y. FIG. 68f shows the stretching device 10y according to an embodiment in which the stretching device is inflatable by a fluid transported through the conduit 18y. According to one embodiment shown in FIG. 68f the conduit comprises two sections 18ay, 18by wherein the first section 18ay is used to pull the stretching device 10y into place, and to fill the device 10y with a suitable fluid, whereas the second section 18by is used for the operation of said device 10y. FIG. 68g shows the stretching device 10y according to the embodiment of FIG. 68f in a deflated state. The stretching device 10y is inserted through a hole in the stomach wall 12y in its deflated state whereafter the device 10y is filled with a suitable fluid for operation. FIG. 68h shows the stretching device 10y according to an embodiment in which the stretching device 10y comprises two movable wall portion 223ay, 223by, which are moveable by means of a bellows structure 209y made of a flexible material. FIG. 68i shows the stretching device according to an embodiment where the stretching device is expandable by means of four expandable sections 210y symmetrically placed on four places along the surface of the stretching device, as shown in the section image of FIG. 68i. The expandable sections 210y are made of a flexible material for allowing said sections 210y to expand when said stretching device 10y is filled with a hydraulic fluid.

Surface Structure of Implants

The general structure of any implanted device of the invention will now be described with reference to FIG. 69 a-k. The present invention concerns an implant, adapted to post-operatively be adjustable and comprising at least one expandable section, wherein the implant is adapted to be adjustable between a first collapsed state and a second expanded state. In the first collapsed state the expandable section is collapsed, and in the second expanded state, the expandable section is expanded. The outer surface of said expandable section does at least partly comprise a surface structure having elevated areas alternating with lowered areas. The expandable section is adapted to have, in at least one of said first collapsed and second expanded states a first distance between adjacent elevated areas sufficiently extended to prevent growth of fibrotic tissue from directly interconnecting adjacent elevated areas to an extent that compromises the adjustability between a first collapsed and a second expanded state of said implant. The expandable section further comprising connecting areas between adjacent elevated and lowered areas, further adapted to have, in at least one of said first collapsed and second expanded states, a second distance between adjacent connecting areas sufficiently extended to prevent growth of fibrotic tissue from directly interconnecting adjacent connecting areas to an extent that compromises the adjustability between a first collapsed and a second expanded state of said implant.

According to one embodiment the expandable section is hollow or comprises a hollow body.

According to another embodiment the implant is substantially completely hollow or comprises a hollow body extending along substantially the complete length and/or complete volume of said implant.

Fibrotic tissue can often have an extension or thickness of about 0.5 mm to about 1.5 mm and hence the distances between relevant surfaces of the elements of the surface structure are suitably greater than about 3 mm, hence greater than about 2×1.5 mm. But depending on the circumstances also distances greater than about 1.0 mm to about 3 mm may be sufficient In cases where the fibrotic tissue can be expected to have an extension or thickness greater than about 1.5 mm the distances between relevant surfaces of the elements of the surface structure are adapted in a suitable manner.

The surface structure may comprise elevated and lowered areas and it may be suitable that also a distance between the different planes of the elevated and lowered areas is bigger than a certain threshold to facilitate the collapsible and/or expandable functionality of the implant. If said distance is too small, the collapsible and/or expandable functionality of the implant may be limited. A suitable interval for said distance is around 0.5 to 10 mm, more suitable around 2-8 mm and most suitable around 3-7 mm The surface structure may comprise different geometrical elements or shapes and any combination of such elements or shapes as long as the above mentioned conditions for the distances can be met. The surface structure may e.g. comprise ridges and grooves of different shapes. The ridges and grooves may each have a cross-section that is e.g. wedge-shaped, polygonal, square-formed, pyramidal-shaped, truncated pyramidal-shaped or. Further may the ridges and grooves have cross-sections of different shapes. The surface structure may as well in general comprise a bellows-shaped structure or a surface structure where geometrical objects of the same or different kind(s) are placed on a surface. The geometrical objects may be practically randomly placed on the surface or according to some scheme.

One type of implants where this type of surface structure may be suitable, is implants where the implant should have the ability to change shape and/or size substantially. Hence, this is a case where the presence of fibrotic tissue substantially could hinder or impede the function of the implant. But the surface structure may be used by any implant where the characteristics of the surface structure would be advantageous for the implant.

Figure 69A:
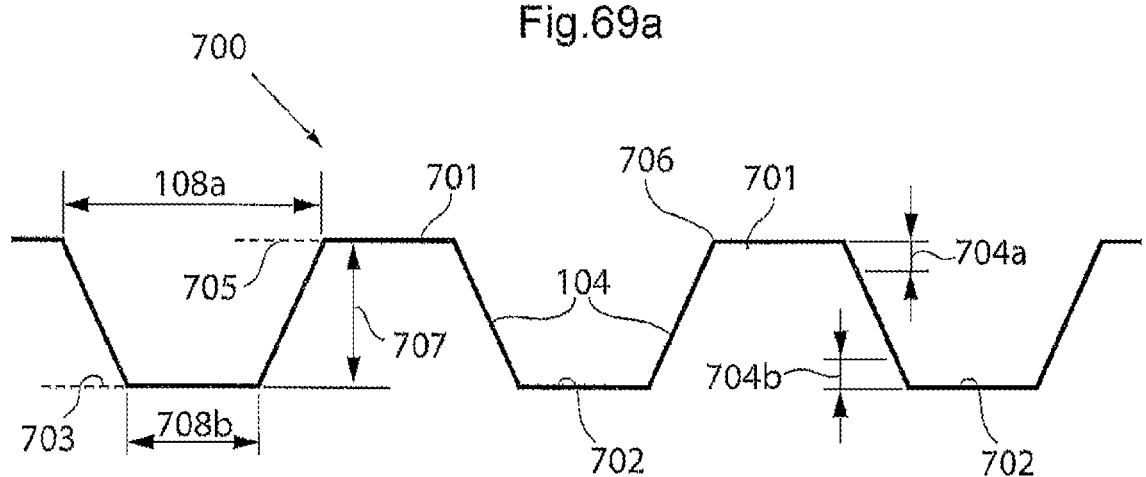
FIG. 69 is a general description of the surface structure of any implanted device of the invention.

A first distance 708a between two elevated areas 701, see FIG. 69a, is long enough so as to prevent growth of fibrotic tissue directly connecting two adjacent elevated areas 707. That is, it may be possible that fibrotic tissue grows on the surface of the elevated and lowered areas 701, 702 and the connecting areas 704. However, thanks to the extension of the first distance 708a, fibrotic tissue is prevented from growing directly from one elevated area 701 to another adjacent elevated area 701.

With the expression "growing directly from one elevated area 701 to another elevated area 701" it is e.g. meant that fibrotic tissue grows from one elevated area 701 to another while not or only to a small extent growing on a connecting area 704. As indicated at 704a in FIG. 69i, the first distance 708a may be measured within an interval 704a from the level of an elevated area 701. The expression "growing directly from one elevated area 701 to another elevated area 701" also includes the situation that fibrotic tissue grows on adjacent areas, e.g. two adjacent connecting areas 704, with such a thickness that the fibrotic tissue from each adjacent area meet and bridge the distance or space between two elevated areas 701. In such a situation the space between two elevated areas 701 may be partly or completely filled with fibrotic tissue.

It may be advantageous that also a second distance 708b corresponding to the extension of a lowered area 702 has an extension great enough so as to prevent fibrotic tissue from growing directly from one connecting area 704 to another connecting area 704. With the expression "growing directly from one connecting area 704 to another connecting area 704" it is meant that fibrotic tissue grows from one connecting area 704 to another while not or only to a small extent growing on a lowered area 702.

Figure 69B:
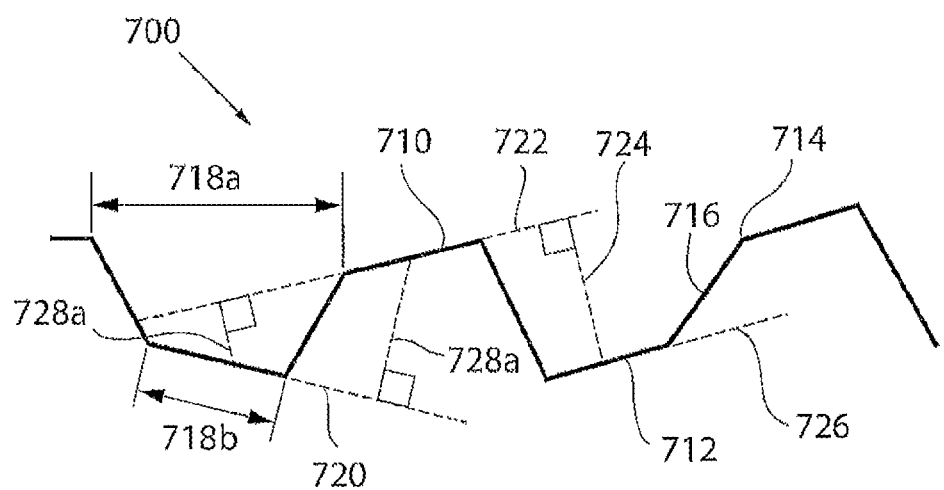
Figure 69C:
Figure 69D:
Figure 69E:
Figure 69F:
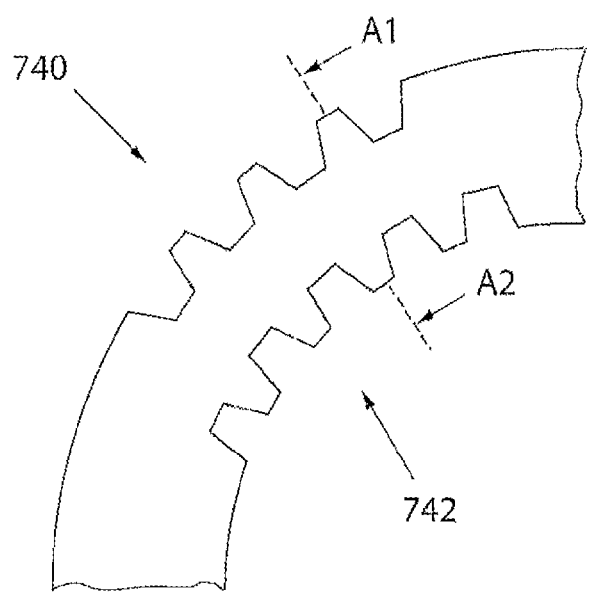
Figure 69G:
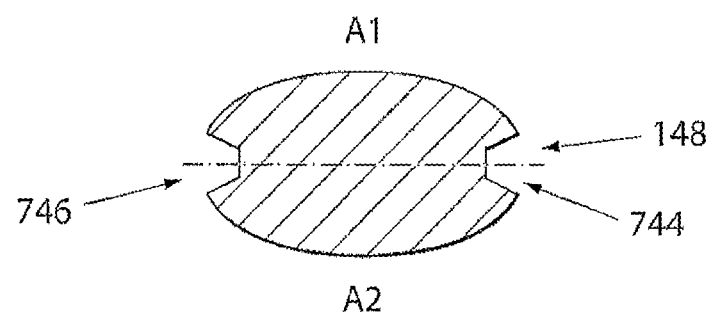
Figure 69H:
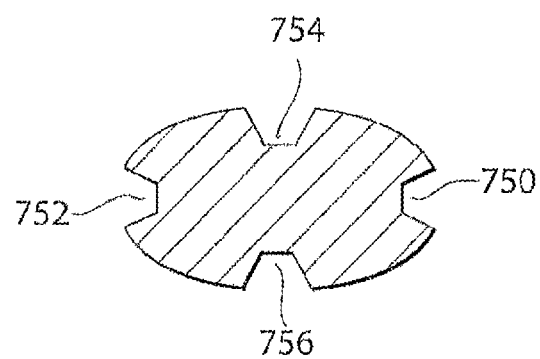
Figure 69I:
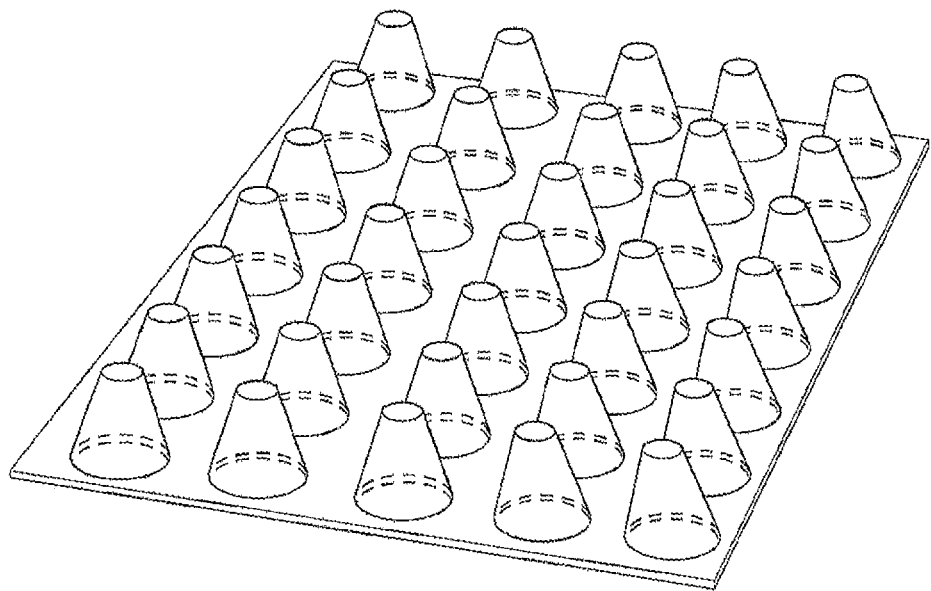

In FIG. 69i a surface structure comprising elevated and lowered areas has been shown, but apart from elevated and lowered areas also many other geometrical structures may be used where it is possible to fulfill the above mentioned prevention of growth of fibrotic tissue. In particular, the above mentioned prevention of growth of fibrotic tissue between elevated areas and between connecting areas.

Figure 69J:
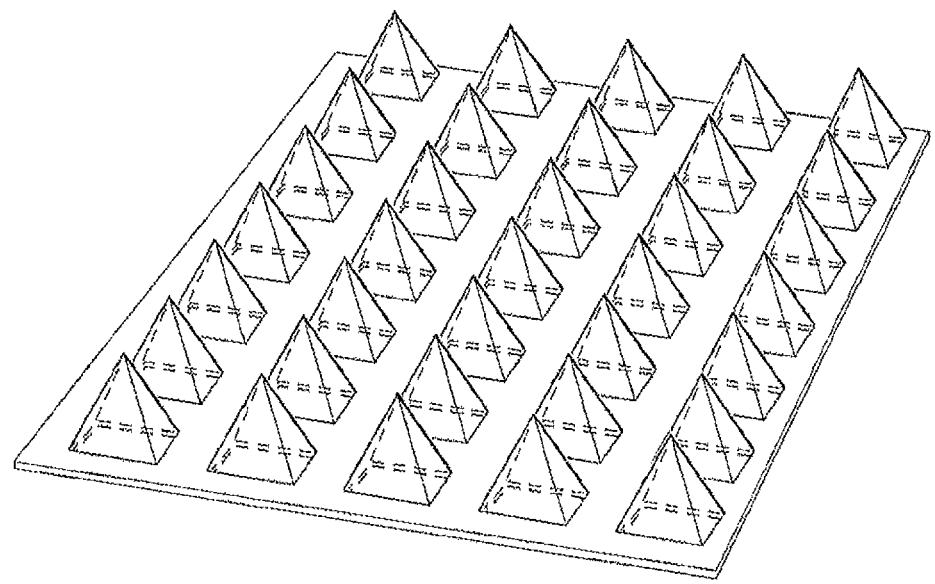
Figure 69K:
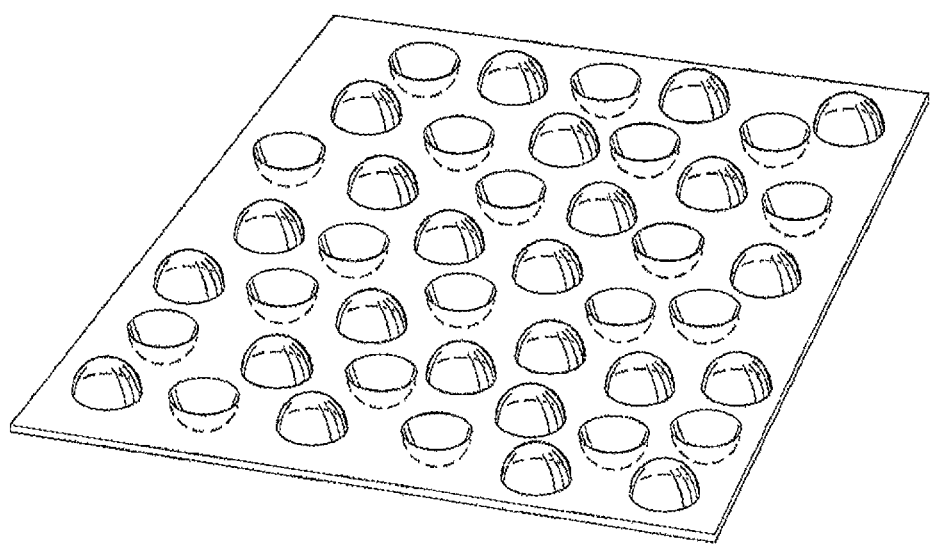

Some examples of such other geometrical structures are shown in FIGS. 69i-k. In a surface structure comprising ridges and grooves, the ridges and grooves may also have different sections, some examples are shown in FIGS. 69b-69e.

Referring mainly to FIGS. 69a and b some expressions and aspects will now be explained. In this application the concept of a first distance 708a, 718a between adjacent elevated areas 701, 710 is used. With such a first distance 708a, 718a it is meant a distance that is measured substantially from the edge 706, 714 of one elevated area 701, 710 to the edge 706, 714 of an adjacent elevated area 701, 710. Measured substantially from the edge means that the measurement may be done within a first interval 704a from the level of an elevated area 701, 710, the first interval 704a extending from the level of an elevated area 701, 710 towards the level of an adjacent lowered area 702, 712.

In this application also the concept of a second distance 708b, 718b between adjacent connecting areas 704, 716 is used. With such a second distance 708b, 718b it is meant a distance that is measured substantially from the connection point between a connecting area 704, 716 and a lowered area 702, 712 to another connection point involving an adjacent connecting area 704, 716. Measured substantially from the connection point means that the measurement may be done within a second interval 704b from the level of a lowered area 702, 712, the second interval 704b extending from the level of a lowered area 702, towards the level of an adjacent elevated area 701, 710.

With elevated and lowered areas it is meant areas that lie in different planes 703, 705, 720, 722 where the planes are separated by a distance 707, 724, 728. The planes may be parallel or substantially parallel but may also be non-parallel. If the planes are parallel, defining a distance between them is trivial. If the planes are non-parallel (as in FIG. 2a) a distance between the planes may be defined by a normal 724, 728 to one of the planes 720, 722 where the normal extend to a point on an area in another plane 722, 726 and the distance between the planes is equal to the extension of the normal 724, 728. As seen in FIG. 2a the normal 724, 728 extends from a plane 720, 722 to a point which is approximately equally distant from the edges of an area. There are two possible ways to define the normal or distance between the planes. Taking normal 728 as example, one may define the normal as in 728a or in 728b. It may be suitable to define the distance between two planes as the extension of the longest normal, the distance between the planes 720 and 722 would then be equal to the extension of normal 728a. This definition will be used hereafter.

The elevated and lowered areas may have different shapes, they may be plane or substantially plane but they may also have some kind of curved shape.

The elevated areas 701, 710 connect to adjacent lowered areas 702, 712 by means of connecting areas 704, 716. The connection between elevated/lowered areas and connecting areas 704, 716 may comprise a radius of different sizes, bigger or smaller radii. When the radius is very small there will substantially be an edge 706, 714 connecting the areas.

The expression "expandable section" implies that said section also is collapsible.

Suitably the implantable device 10 at least partly comprises materials which have a high degree of biocompatibility, such materials may be called physiologically inert, biologically inert or bio compatible.

Referring in particular to FIGS. 69a-b, in the surface structure 700 there may advantageously be a specified first distance 708a, 718a between adjacent elevated areas 701, 710. The distance between adjacent elevated areas 701, 710 is chosen so that fibrotic tissue cannot bridge the first distance 708a, 718a between adjacent elevated areas 701, 710. Hence, the first distance 708a, 718a between adjacent elevated areas 701, 710 is advantageously big enough to prevent the formation of fibrotic tissue that bridges adjacent elevated areas 701, 710.

As mentioned before, there may advantageously be a specified second distance 708b, 718b between adjacent connecting areas 704, 716. The second distance 708b, 718b between adjacent connecting areas 704, 716 is chosen so that fibrotic tissue cannot bridge the second distance 708b, 718b between adjacent connecting areas 704, 716. Hence, the second distance 708b, 718b between adjacent connecting areas 704, 716 is advantageously big enough to prevent the formation of fibrotic tissue that bridges adjacent connecting areas 704, 716.

It may also be advantageous that a third distance 707, 724, 728a between the different planes 703, 705, 720, 722, 726 of the elevated and lowered areas is bigger than a certain threshold to facilitate the collapsible and/or expandable functionality of the implant. If the third distance 707, 724, 728*a* is too small the collapsible and/or expandable functionality of the implant may be limited. A suitable interval for the third distance 707, 724, 728*a* is 0.5 to 10 mm, more suitable 2-8 mm and most suitable 3-7 mm. Also regarding the aspect that the fibrotic tissue should not impede the collapsible/expandable functionality of the implantable device it is advantageous that the distance 707, 724, 728*a* is not too small, but suitably in the interval/s as mentioned previously.

The surface structure 700 may include objects or element of different geometrical shapes, for example ridges of different shapes, embossments of different shapes and other objects which enable a surface structure as described herein. The area of the elevated areas 701, 710 may be very small while still resulting in a surface structure that has the desired functionality. The area of the elevated areas 701, 710 may even be almost zero, as exemplified in FIG. 2*d*. Whereas FIGS. 1 and 2*a*-2*d* show cross sections of examples of surface structures 700, FIGS. 69*i-k* show examples of different surface structures 700 in perspective. The objects or elements in the surface structure 700 may be placed in rows, ordered in some other way, or may be more or less randomly distributed over the surface of the implant Different types of objects may also be used together in the surface structure 700, e.g. a combination of pyramid shaped and cone shaped objects together with ridges of some shape.

In FIGS. 69*f-h* an embodiment of an implant 10 is shown where a surface structure 700 is used, the implant 10 is not shown in full. FIG. 69*f* shows a longitudinal section of the implant 10 where 740 denotes the surface structure on the upper side of the implant 10 and 742 denotes the surface structure on the underside of the implant 10. As shown in FIG. 69*f* the surface structure 742 on the underside may have a greater extension than the surface structure 740 on the upper side of the penile prosthesis. This gives the implant 10 an up-bent position when the implant 10 is expanded. The surface structures 140 and 142 are one example of a bending portion. FIG. 69*g* shows a cross section of the implant 10 where the implant 10 includes a waist portion 744, where the waist portion comprises waist surface structures 746 and 748. The waist portion with the waist surface structures 746 and 748 make the implant 10 expandable also in the radial direction. The implant 10 may also have a cross section as shown in FIG. 69*g* comprising a waist portion 744 having four waist surface structures 750, 752, 754, 756 further facilitating the ability of the implant 10 to be expandable also in the radial direction. The cross sections in FIGS. 69*g* and *h* are taken along the line A1-A2 in FIG. 69*f*.

Further Embodiments Comprising a Stretching Device.

Further embodiments of the inventions that disclose the treatment of obesity by stretching the stomach will now be described.

Figure 70A:
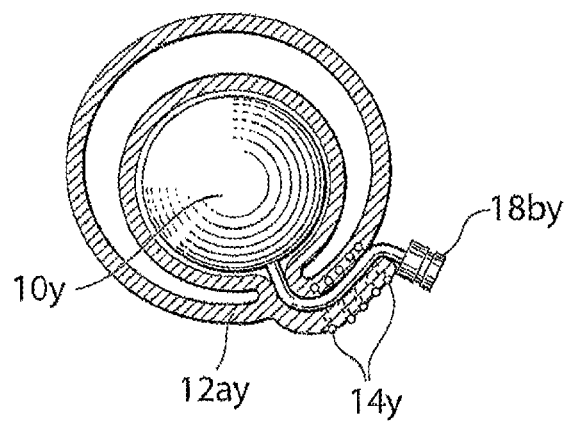

FIG. 70*a* illustrates a stretching device 10*y* provided with an inlet port 18*by*. The stretching device 10 is invaginated in the stomach wall 12*y* and the inlet port 18*by* is available for connection to a tube or the like from the abdominal area of the patient. The tube or conduit 18*y* can preferably be connected to the control unit 42*y* or an injection port 1001*y*.

Figure 70B:
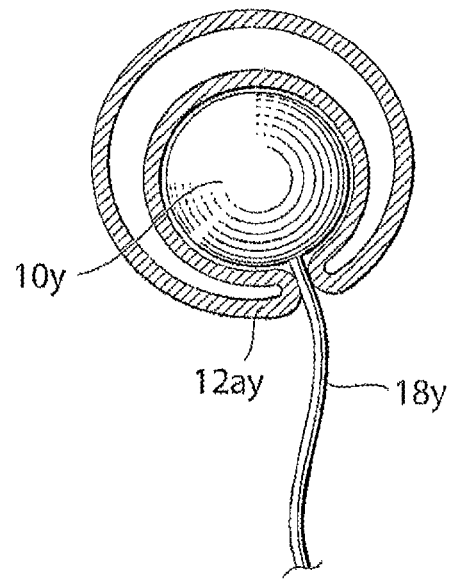

FIG. 70*b* illustrates an invaginated stretching device 10*y* wherein, instead of an inlet port, a conduit 18*y* or electrical lead extends into the abdominal area of the patient.

Figure 70C:
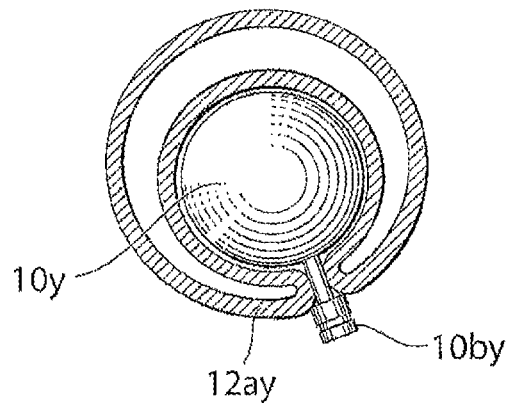

FIG. 70*c* shows a section of the stretching device 10*y* and part of the stomach in which the stretching device 10 is invaginated. The conduit 18*y* or electric lead is invaginated in the stomach wall 12*y* by means of stomach to stomach sutures or staples 14*y* which creates an entirely sealed pouch of stomach wall tissue in which the stretching device 10*y* is placed. The conduit 18*y* or electric lead is thereby tunneled in the stomach wall 12*y* between the inlet port 18*by* and the volume filling device 10*y*.

It has been shown that the shape of the stretching device 10*y* can take many different forms. It will be appreciated that also the material of the stretching device 10*y* can vary. It is preferred that the stretching device 10*y* is provided with a coating, such as a Parylene, polytetrafluoroethylene (PTFE), or polyurethane coating, or a combination of such coatings, i.e., a multi-layer coating. This coating or multi-layer coating improves the properties of the stretching device, such as its resistance to wear.

Figure 71:
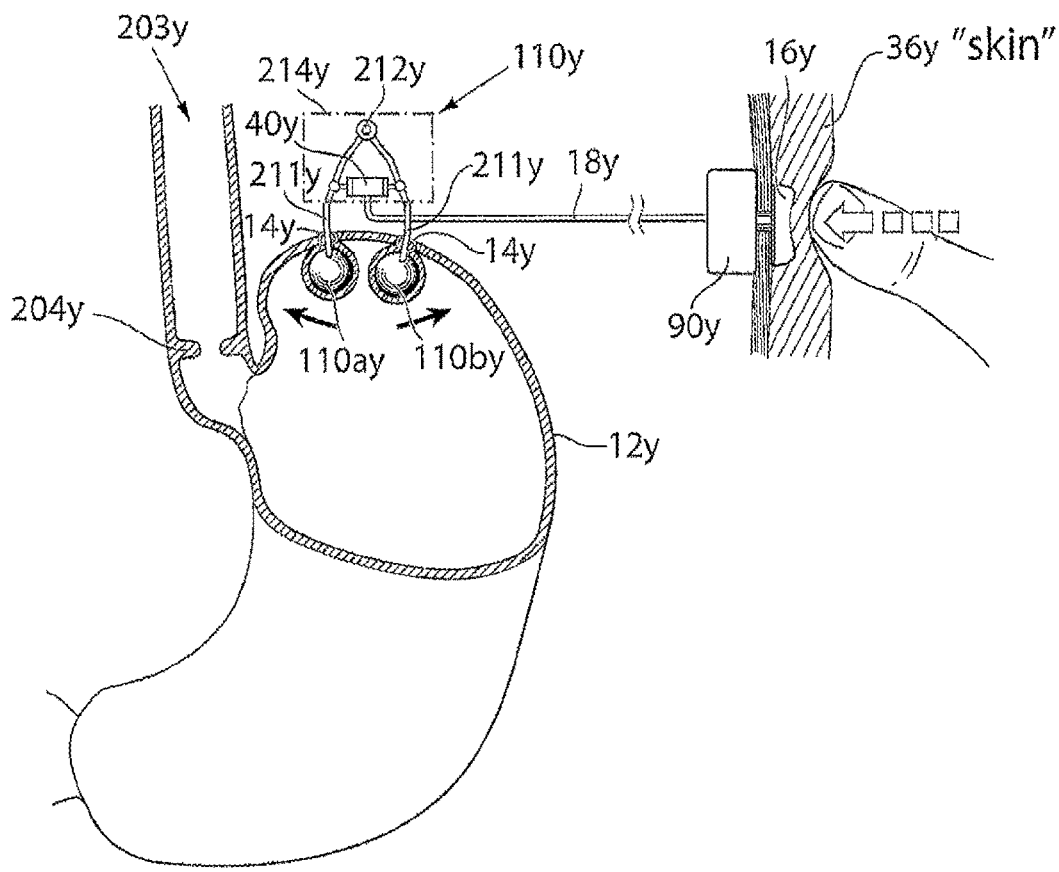

In another embodiment shown in FIG. 71, the stretching device 110*y* works according to a different principle from that described above with reference to FIGS. 65-70. The stretching device 110*y* here comprises a first fixation portion 110*ay* adapted to have a first fixation at a first position on the stomach wall 12*y* and a second fixation portion 110*by* adapted to have a second fixation at a second position on the stomach wall 12*y*. These fixation portions 110*ay,by*, which preferably have an essentially round shape and preferably are adapted to be invaginated in the stomach wall 12*y*, are attached to the distal end of a respective leg 211*y*, which in turn are attached at their respective proximal end to an operation device, such as a motor 40*y*. According to the embodiment shown in FIG. 71 the motor is a hydraulic motor, comprising a hydraulic piston, which is connected to a manual operation device described previously with reference to FIG. 65. The hydraulic piston affects the legs through their connection with a joint 212*y* placed in the extremity of the leg. The stretching device 110*y* is enclosed in a housing 214*y* protecting the device from the in growth of fibrotic tissue which potentially could damage the function of said device 110*y*. However it is equally conceivable that the motor is another hydraulic motor, a pneumatic motor or an electrical motor.

The stretching device 110*y* is adapted to increase the distance between the first position and the second position on the stomach wall 12*y*, thereby stretching the stomach wall 12*y*. The first and/or second fixation portions 110*ay*, 110*by* are adapted to at least partly be invaginated in the stomach wall 12*y* with stomach-to-stomach sutures or staples 14*y* holding the fixation portions 110*ay, by* in place in suspension in relation to the stomach wall 12*y*.

Of course the first and second positions may be sutured or fixated to the stomach wall in many possible ways and the invention covers all possibilities to distend the stomach wall by moving two portions of the stomach wall away from each other and thereby first fixating the device to at least two positions on the stomach wall. However, the soft suspended connection to the stomach wall 12*y* where fibrotic stomach-to-stomach tissue helps to give a long term stable position is to prefer.

Of course just expanding an invaginated part of the stomach also stretches away the stomach wall 12*y* which also may be achieved both mechanically, hydraulically, pneumatically and both being powered with a motor or pump or by manual force.

Any kind of mechanical construction may be used and the mechanical embodiment disclosed is one example. Any mechanical construction driven by mechanically or hydraulically or any pneumatic construction may be used. Any motor or any pump or moving material changing form when powered may be used to achieve the simple goal of stretching a part of the stomach wall by moving at least two portions of the stomach wall away from each other.

Figure 72:
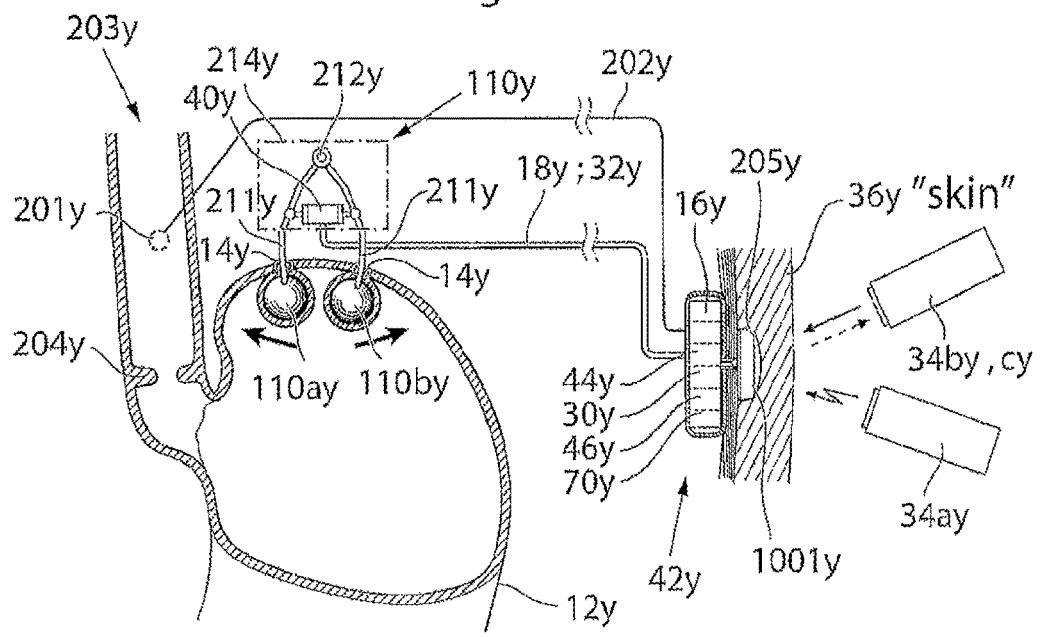

FIG. 72 shows the stretching device 110y according to an embodiment in which the stretching device is controlled from an implantable control assembly 42y to which sensor input, as described earlier, in received. The stretching device is then regulated through the conduit 18y using a pump 44y, connected to at least one fluid reservoir 16y, 46y, and powered from a energy transforming member 30y connected to an receiver of wireless energy 205y, placed under the skin 36y, or an implantable energy source 70y, such as a rechargeable battery.

In a variant, shown in FIG. 73a, the first and/or second fixation portions 210ay, 210by, respectively, exhibit a structure adapted to be in contact with the stomach wall 12y to promote growth in of human tissue to secure the long term placement of the stretching device 110y attached to the stomach wall 12y. This structure preferably comprises a netlike structure 213y. The fixation portions 210ay, 210by may be adapted to keep the stretching device 110y in place by sutures or staples between the fixation portion and the stomach wall 12y to secure the short term placement of the stretching device 110y. In turns of mechanical operation the stretching device 110y according to the embodiment shown in FIG. 73a functions in accordance with the device described with reference to FIG. 71. FIG. 9by shows a fixation device 213y comprising a netlike structure adapted to propagate the growth-in of fibrotic tissue to fixate the two fixating portions to the stomach wall 12y.

FIG. 73c shows the stretching device according to the embodiment of FIG. 73a in a second state, in which the two fixating portions have been separated from each other and the stomach 12y has been stretched.

Figure 74A:
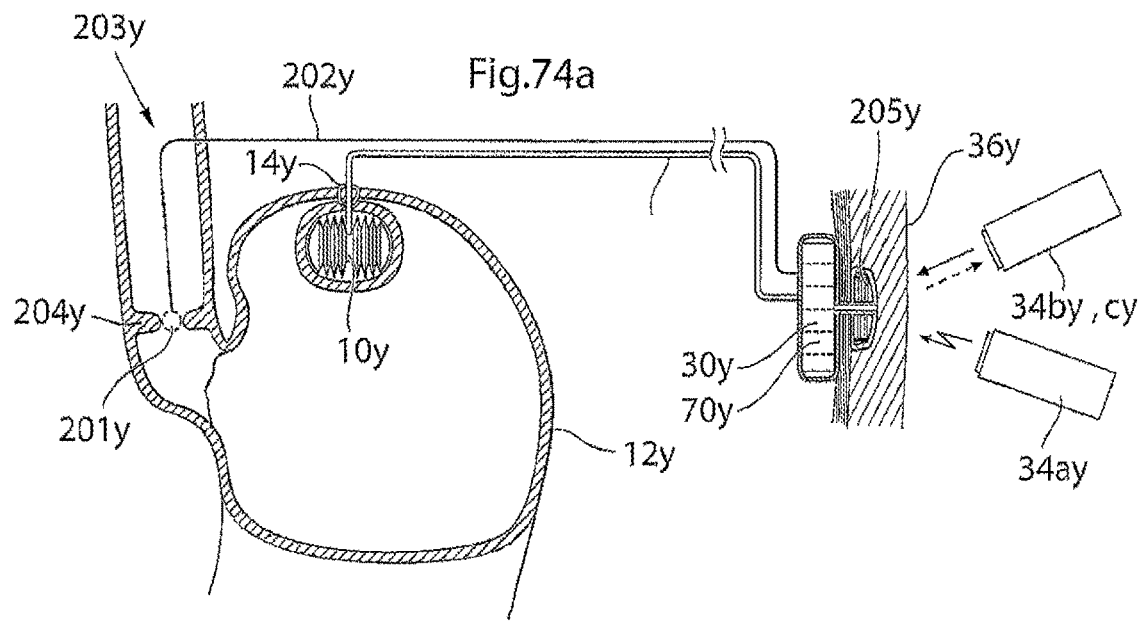

FIG. 74a shows the stretching device according to an embodiment in which the stretching device is an electrical mechanical stretching device connected to a control assembly 42y through a power supply line 32'y. The power supply line 32y is connected to a power transforming device 30y in contact with a receiver of wireless energy 205y, such as a coil, which receives energy from a transmitter of wireless energy 34ay. The control assembly may furthermore comprise a battery 70y for storing energy received from the wireless energy transmission device 34ay. The control assembly receives input from a sensor 201y, which according to this embodiment is a strain gauge measuring the contraction and/or relaxation of the cardia 204y.

Figure 74B:
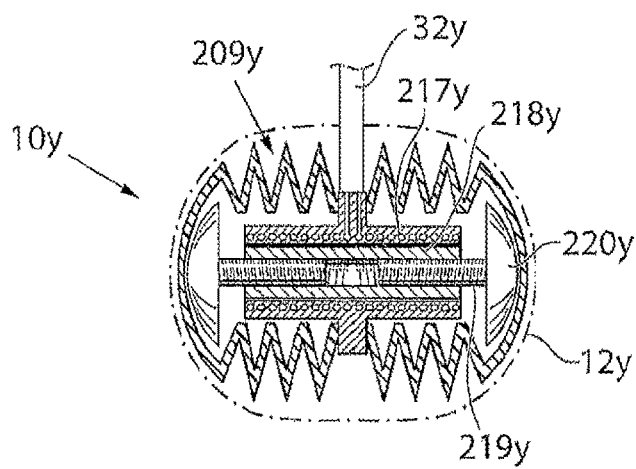

FIG. 74b shows the stretching device 10y in further detail. The stretching device 10y comprises a housing having a bellows structure 209y made of a flexible material so as to enable the wall portions to move. The power supply line 32y is connected to a stator 217y of an electrical motor, said motor further comprising a rotor 218y which comprises a thread that interacts with a displaceable member 219y comprising a corresponding thread. The displacing member is rotatably fixated to a housing contacting member 220y which pushes against the housing for affecting the volume of the stretching device and thereby stretching the stomach 12y.

Figure 74C:
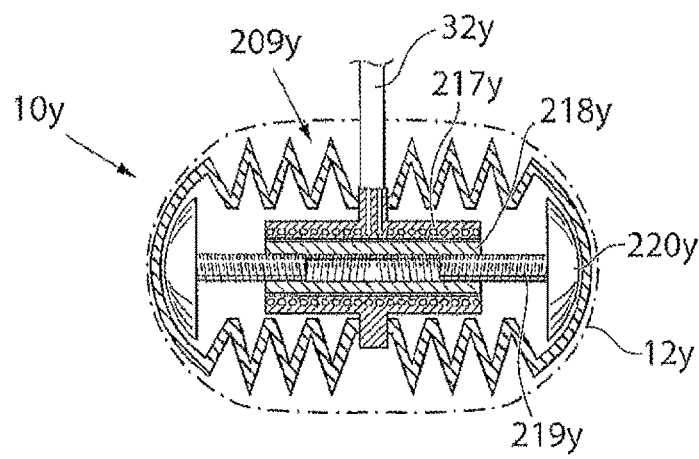

FIG. 74c shows the stretching device according to FIG. 10by in a second state, in which the stretching device is expanded and thereby stretches the stomach wall 12y.

Figure 75A:
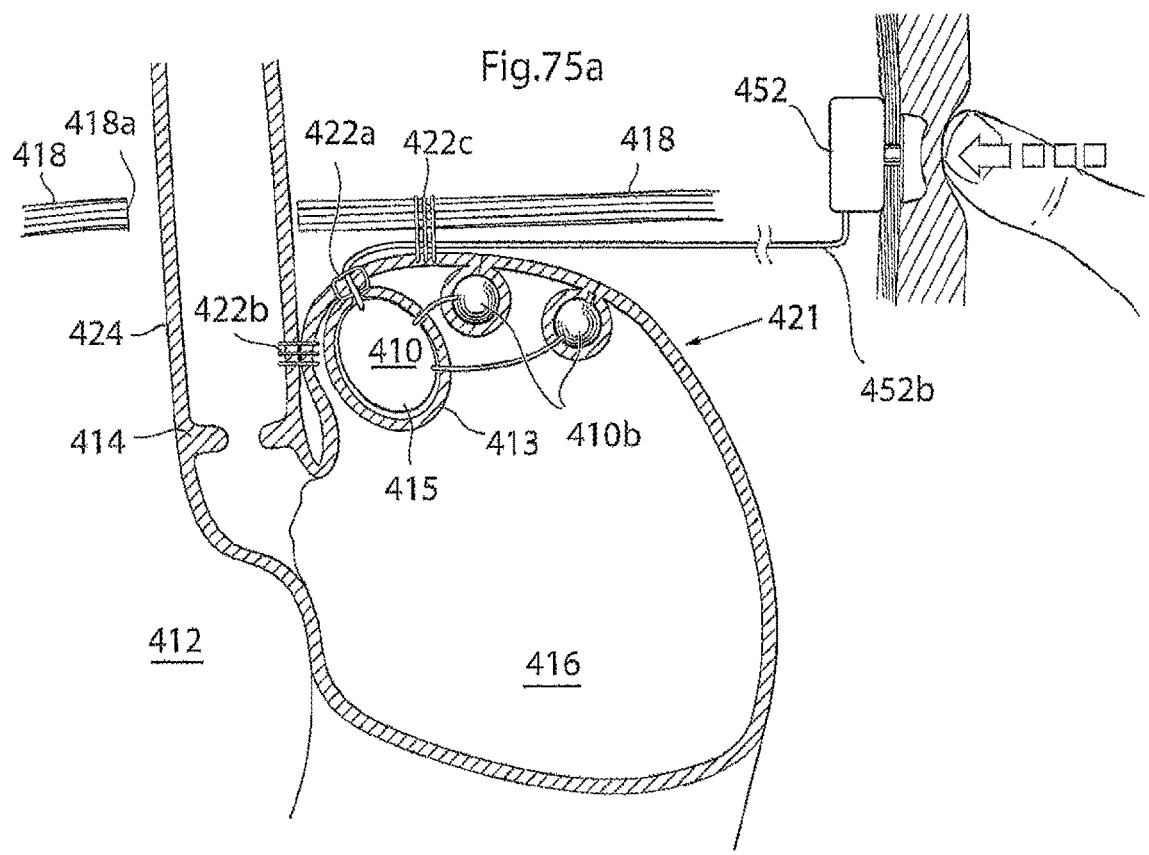

FIG. 75a shows an embodiment in which a device adapted to treat reflux disease is combined with the stretching device according to any of the embodiments above. After invagination of the device 410 in the fundus 416, a fixation consisting of a number of stomach-to-stomach sutures or staples 422a is applied to keep the invagination intact in the short term. A second fixation consisting of a number of sutures or staples 422b is provided to hold the device 410 in position above the cardia 414. The sutures or staples 422b are applied between the wall of the fundus 416 and the wall of the esophagus 424y. Additionally, a third fixation in the form of sutures or staples 422cy may be provided between the wall of the fundus 416 and the diaphragm 418, again, to hold the device 410 in position above the cardia 414.

In this fourth embodiment depicted in FIG. 75a, the size of the reflux disease treatment device 410 can be regulated while being implanted. The reflux disease treatment device 410 is associated with a subcutaneous hydraulic reservoir 452 connected to the reflux disease treatment device 410, by a lead 452b whereby a non-invasive regulation can be performed by manually pressing the reservoir 452. Pressing the reservoir 452 displaces hydraulic fluid from the reservoir 452 to the smaller chambers 410b via the lead 452b. The reflux disease treatment device 410 is, in turn, connected to one or more smaller chambers 410b. In this manner, the patient may adjust the size of the reflux treatment device 410 in a manner adapted to the treatment.

Furthermore, the embodiment above may alternatively be used to also treat obesity. The device may, in this embodiment, be adapted to treat obesity by using the volume of the reflux disease body to contain a fluid, and further using one or several smaller chambers 410b connected to the device body with a pump to be filled with fluid to expand and thereby stretch the fundus wall to create satiety. The small chambers 410b are also adapted to be invaginated to in the fundus stomach wall, and when filled with fluid, an expansion of the stomach occurs that results in human sensor feedback creating satiety. The subcutaneous hydraulic reservoir/pump enables the patient to conveniently pump hydraulic fluid to fill the small chambers 410b to create a feeling of satiety as he or she wishes.

Figure 75B:
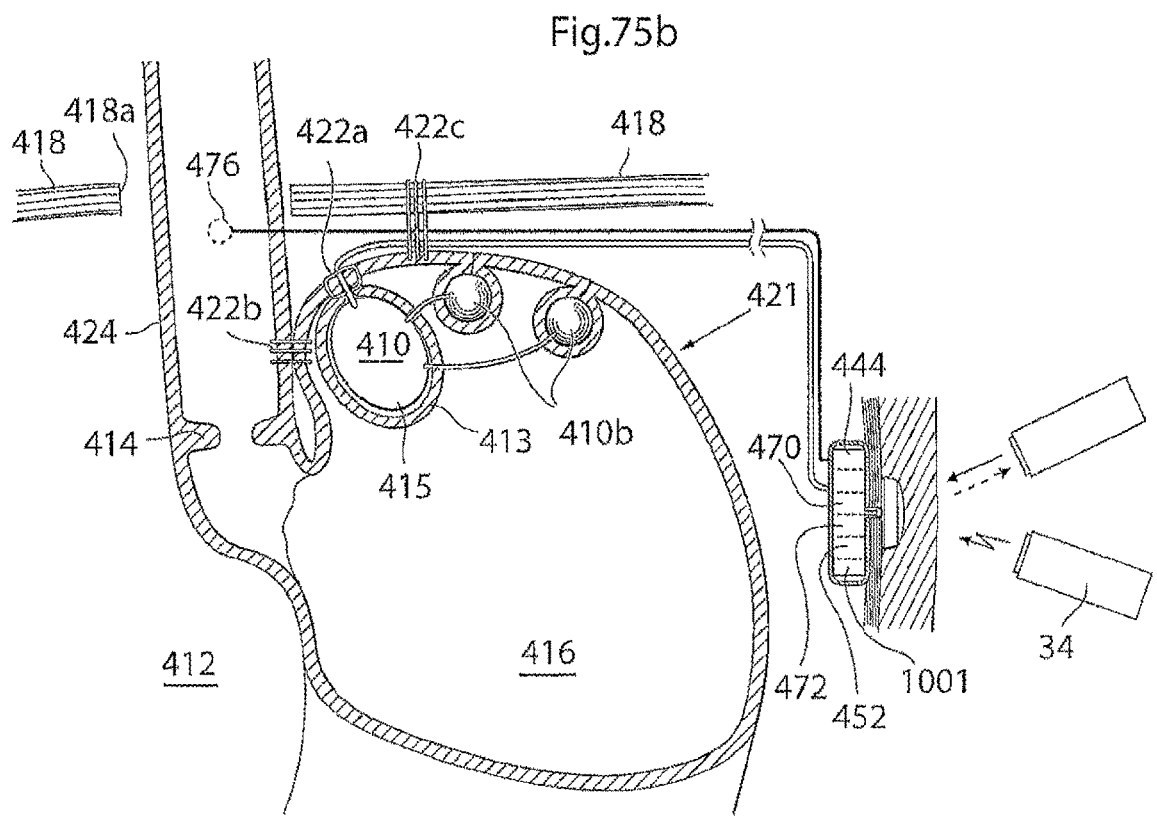

An alternative embodiment is shown in FIG. 75b. This embodiment is substantially similar to the one shown in FIG. 75a but differs in how the reflux treatment device 410 and chambers 410b are controlled. Here, the chambers 410b are not controlled by a subcutaneous pump but a powered internal control unit 456. The internal control unit 456 comprises means for the patient to control the device 410 in how it shall be used regarding treatment of reflux and/or obesity. It may also comprise means of supplying power to the device.

The internal control unit 456 may comprise a battery 470, an electric switch 472, a motor/pump 444, a reservoir 452, and an injection port 1001. An energy transmission device 34 with a remote control is adapted for controlling and powering the device. The items being selected depending on the circumstances, e.g. if the device is electrically, hydraulically, pneumatically or mechanically operated. The device 410 may be used for keeping electronics and/or an energy source and/or hydraulic fluid.

Figure 76A:
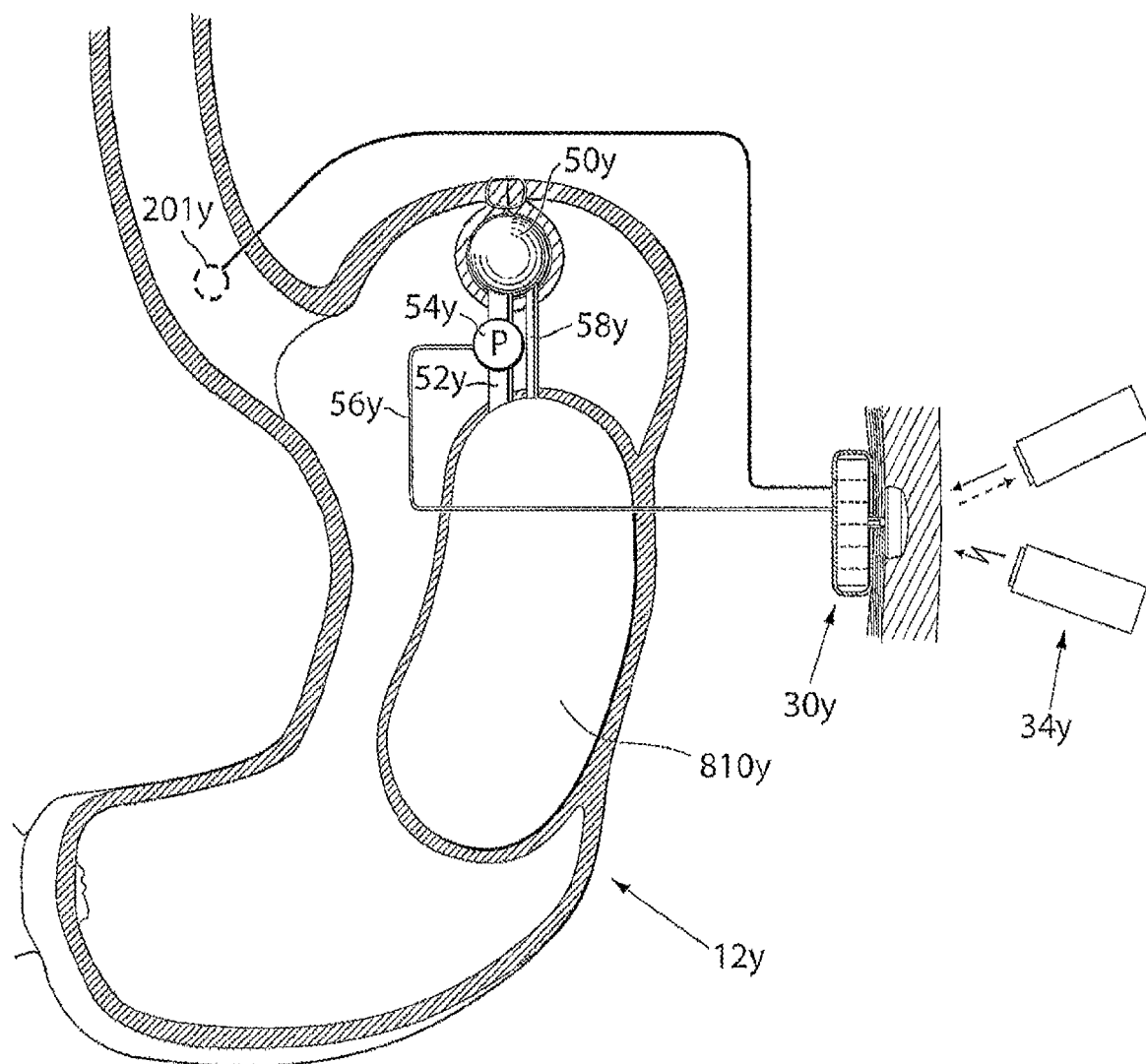

FIG. 76a shows an adjustable volume filling device 810y, which is invaginated in the stomach wall of a patient's stomach 12y. The volume filling device 810y is adapted to take up space in the stomach and thereby reduce the volume in which food can be placed. Additionally, an adjustable stretching device 10y according to any of the embodiments is invaginated in the stomach fundus wall of the patient his preferred that the volume filling device 810y is substantially larger than the stretching device 10y.

The volume filling device 810y and the stretching device 10y are in fluid communication with each other via a first fluid tube 52y, in which a pump 54y is provided. The pump 54y is under the control from an energy transforming device 30y, which is adapted to supply the pump 54y with energy via a power supply line 56. The energy transforming device 30 is also connected to a sensor 201y provided in the esophagus of the patient so that food intake can be detected.

The volume filling device 810y and the stretching device 10y are also in fluid communication with each other via a second fluid tube 58y, which preferably has a smaller cross-sectional area than the first fluid tube 52y.

The operation of this arrangement is as follows. The volume filling device 810y functions as in the above described embodiments, i.e., it reduces the size of the food cavity of the patient's stomach 12y. Additionally, when the stretching device 10y is enlarged by pumping fluid from the volume filling device 810y and to the stretching device 10y by means of the pump 54y, the stomach fundus wall is stretched, creating a feeling of satiety for the patient. Thus, for example when food intake is detected by means of the sensor 201y, fluid is automatically pumped into the stretching device 10y to increase the feeling of satiety and thereby limit the food intake.

When fluid has been injected into the stretching device 10y, the internal pressure therein is higher than the internal pressure in the volume filling device 810y. This difference in pressure will create a flow of fluid in the second, preferably narrower tube 58y from the stretching device 10y to the volume filling device 810y. The flow rate will be determined by among other things the difference in pressure and the cross-sectional area of the second tube 58y. This preferred that the second tube is so dimensioned, that the pressures in the volume filling device 810y and the stretching device 10y will return to equilibrium after 3 hours after fluid has been injected into the stretching device 10y to create the feeling of satiety.

In this embodiment, the function of the second tube 58y is to allow fluid to return from the stretching device 10y to the volume filling device 810y. It will be appreciated that this function also can be performed by the pump 54y in the first tube 52y and that the second tube 58y then can be omitted.

Figure 76B:
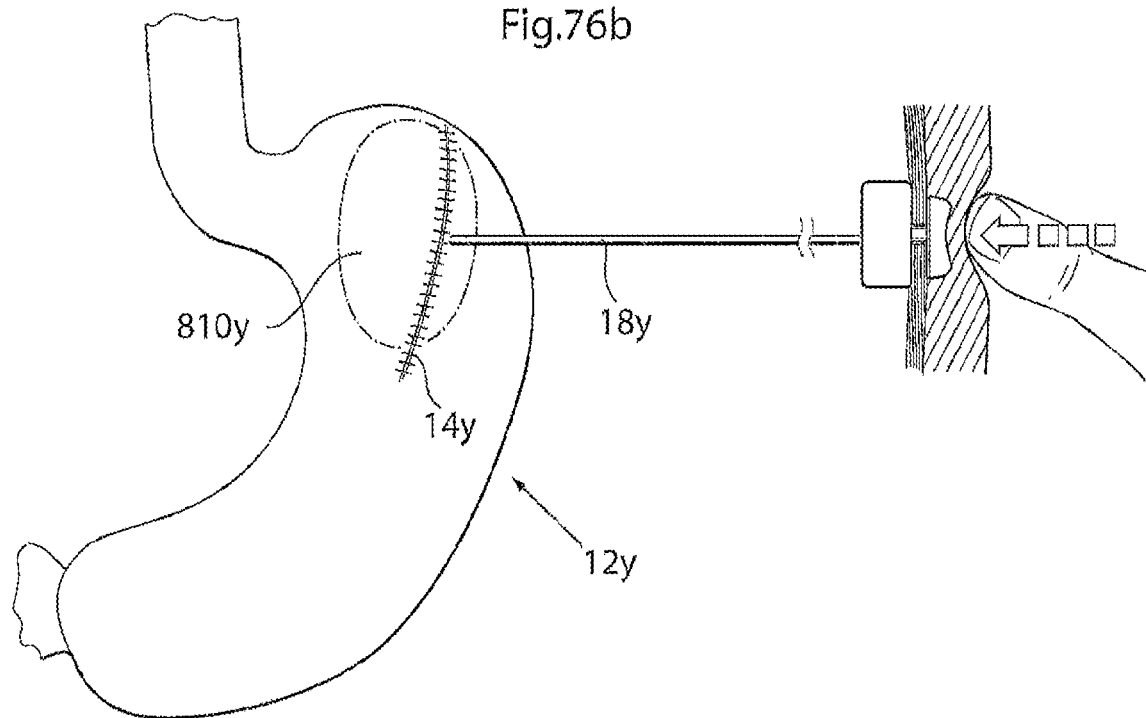

Yet an alternative embodiment of an apparatus for treating obesity will now be described with reference to FIG. 76b, which shows a stomach 12y of a patient who is treated for obesity. The apparatus comprises a volume filling device 810y in the form of an inflatable device 10y which is invaginated in the wall 12ay of the patient's stomach 12y. However, in this case the invagination has been performed in the fundus, i.e., the upper portion of the stomach, where the number of receptors in the stomach wall is large, and the inflatable device functions as a stretching device for part of the stomach fundus wall.

A regulation reservoir for fluids is connected to the inflatable device by means of a conduit 18y in the form of a tube. The inflatable device 810y is thereby adapted to be regulated, preferably non-invasively, by moving liquid or air from the regulation reservoir to the chamber formed by the inflatable device 810y. The regulation of the inflatable device 810y preferably comprises a reversed servo, i.e., a small volume is actuated for example by the patient's finger and this small volume is in connection with a larger volume, i.e., the regulation reservoir.

Thus, the inflatable device 810y is placed outside the stomach wall and is adapted to stretch a part of the stomach fundus wall, thereby affecting the patient's appetite. By enlarging the size of the stretching device, the stomach fundus wall surrounding the inflatable stretching device 810y is stretched since the circumference of the inflatable stretching device 810y is increased. By this stretching, the receptors in the stomach wall indicate that the stomach is full, thereby creating a feeling of satiety to the patient. Correspondingly, when the stretching device 810y is contracted, the receptors indicate that the stomach is not full, thereby returning the feeling of hunger. It will be appreciated that this embodiment combines the effects of both reducing the volume of the stomach food cavity and stretching part of the stomach wall 12y, thereby increasing the treatment effect.

The expansion and contraction of the stretching device 810y can be performed under direct control of the patient. Alternatively, the expansion and contraction can be performed according to a pre-programmed schedule.

Figure 76C:
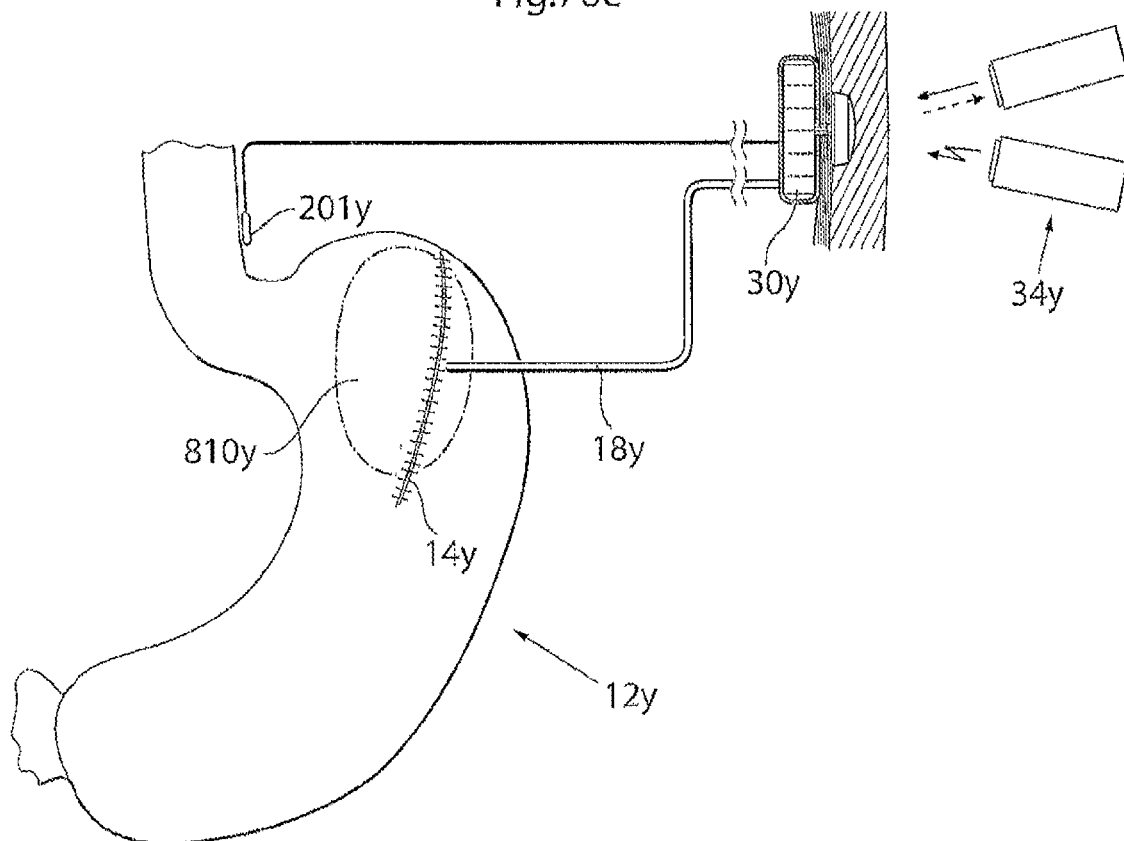

In a preferred embodiment, shown in FIG. 76c, a sensor 201y is provided at a suitable position, such as at the esophagus. The volume filling device 810y in the form of the inflatable stretching device is similar to the one shown in FIG. 76b. By providing one or more sensors, the apparatus for treating obesity can be automated in that the size of the volume filling device 810y in the form of the inflatable stretching device is adjusted depending on the amount of food entering the food cavity of the stomach. The fluid is thereby moved between the inflatable volume filling device 810y and a fluid reservoir.

System

A obesity treatment system that can be combined with the above-mentioned system for treating reflux, generally designated 28 and comprising a stretching device as described above will now be described with reference to FIGS. 77-93. The system 28 can be combined with or be the same as the system 28 for treating reflux in FIGS. 1-64.

The system of FIG. 77 comprises a stretching device 10y placed in the abdomen of the patient. An internal energy source in the form of an implanted energy transforming device 30 is adapted to supply energy consuming component of the obesity treatment system with energy via a power supply line 32. An external energy transmission device 34 includes a wireless remote control transmitting a wireless signal, which is received by a signal receiver, which may be incorporated in the implanted energy transforming device 30 or be separated therefrom. The implanted energy transforming device 30 transforms energy from the signal into electric energy which is supplied via the power supply line 32.

The system of FIG. 77 is shown in a more generalized block diagram form in FIG. 79, wherein the patient's skin 36, generally shown by a vertical line, separates the interior of the patient to the right of the line from the exterior to the left of the line.

FIG. 77 shows a simplified block diagram showing the stretching device 10y, the energy transforming device 30 powering the stretching device via power supply line 32, and the external energy transmission device 34.

Figure 81:
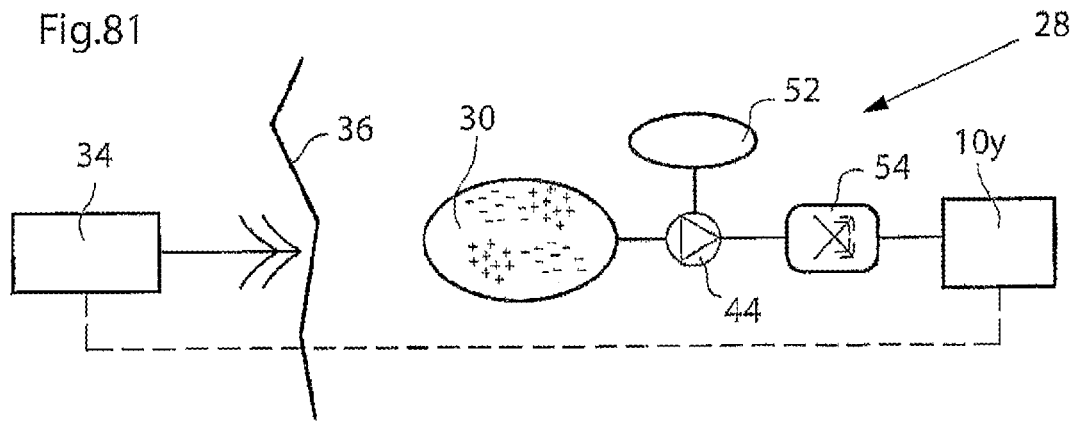

FIG. 78 shows an embodiment of the invention identical to that of FIG. 81, except that a reversing device in the form of an electric switch 38 operable by polarized energy also is implanted in the patient for reversing the stretching device 10y. The wireless remote control of the external energy transmission device 34 transmits a wireless signal that carries polarized energy and the implanted energy transforming device 30 transforms the wireless polarized energy into a polarized current for operating the electric switch 38. When the polarity of the current is shifted by the implanted energy transforming device 30 the electric switch 38 reverses the function performed by the stretching device 10y.

FIG. 79 shows an embodiment of the invention identical to that of FIG. 78, except that an operation device 40 implanted in the patient for regulating the stretching device 10y is provided between the implanted energy transforming device 30 and the stretching device 10y. This operation device can be in the form of a motor 40, such as an electric servomotor. The motor 40 is powered with energy from the implanted energy transforming device 30, as the remote control of the external energy transmission device 34 transmits a wireless signal to the receiver of the implanted energy transforming device 30.

FIG. 80 shows an embodiment of the invention identical to that of FIG. 81, except that it also comprises an operation device is in the form of an assembly 42 including a motor/pump unit 78 and a fluid reservoir 46 is implanted in the patient. In this case the stretching device 10y is hydraulically operated, i.e. hydraulic fluid is pumped by the motor/pump unit 44 from the fluid reservoir 46 through a conduit 48 to the stretching device 10y to operate the stitching device, and hydraulic fluid is pumped by the motor/pump unit 44 back from the stretching device 10y to the fluid reservoir 46 to return the stretching device to a starting position. The implanted energy transforming device 30 transforms wireless energy into a current, for example a polarized current, for powering the motor/pump unit 44 via an electric power supply line 50.

Instead of a hydraulically operated stretching device 10y, it is also envisaged that the operation device comprises a pneumatic operation device. In this case, pressurized air can be used for regulation and the fluid reservoir is replaced by an air chamber and the fluid is replaced by air.

In all of these embodiments the energy transforming device 30 may include a rechargeable accumulator like a battery or a capacitor to be charged by the wireless energy and supplies energy for any energy consuming part of the device.

The external energy transmission device 34 is preferably wireless and may include a remotely controlled control device for controlling the device from outside the human body.

Such a control device may include a wireless remote control as well as a manual control of any implanted part to make contact with by the patient's hand most likely indirect for example a button to press placed under the skin FIG. 81 shows an embodiment of the invention comprising the external energy transmission device 34 with its wireless remote control, the stretching device 10y, in this case hydraulically operated, and the implanted energy transforming device 30, and further comprising a hydraulic fluid reservoir 52, a motor/pump unit 44 and an reversing device in the form of a hydraulic valve shilling device 54, all implanted in the patient. Of course the hydraulic operation could easily be performed by just changing the pumping direction and the hydraulic valve may therefore be omitted. The remote control may be a device separated from the external energy transmission or included in the same. The motor of the motor/pump unit 44 is an electric motor. In response to a control signal from the wireless remote control of the external energy transmission device 34, the implanted energy transforming device 30 powers the motor/pump unit 44 with energy from the energy carried by the control signal, whereby the motor/pump unit 44 distributes hydraulic fluid between the hydraulic fluid reservoir 52 and the stretching device 10y. The remote control of the external energy transmission device 34 controls the hydraulic valve shilling device 54 to shift the hydraulic fluid flow direction between one direction in which the fluid is pumped by the motor/pump unit 44 from the hydraulic fluid reservoir 52 to the stretching device 10y to operate the stretching device, and another opposite direction in which the fluid is pumped by the motor/pump unit 44 back from the stretching device 10y to the hydraulic fluid reservoir 52 to return the stretching device to a starting position.

Figure 82:
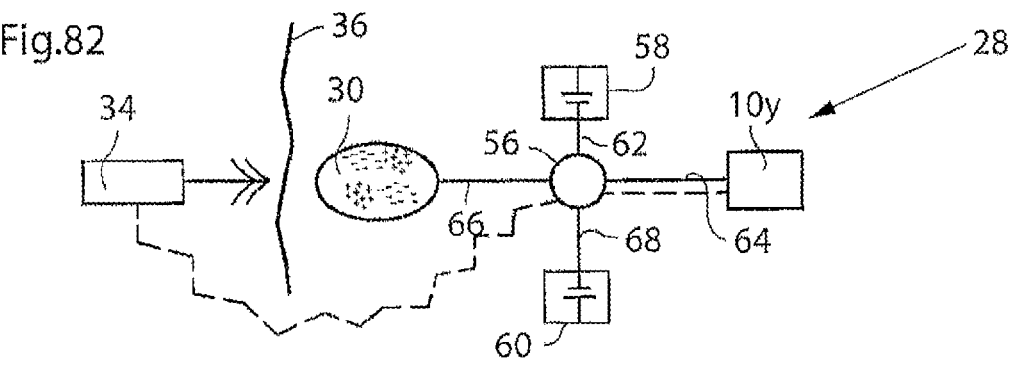

FIG. 82 shows an embodiment of the invention identical to that of FIG. 81, except that an internal control unit 56 controlled by the wireless remote control of the external energy transmission device 34, an accumulator 58 and a capacitor 60 also are implanted in the patient. The internal control unit 56 arranges storage of electric energy received from the implanted energy transforming device 30 in the accumulator 58, which supplies energy to the stretching device 10y. In response to a control signal from the wireless remote control of the external energy transmission device 34, the internal control unit 56 either releases electric energy from the accumulator 58 and transforms the released energy via power lines 62 and 64, or directly transforms electric energy from the implanted energy transforming device 30 via a power line 66, the capacitor 60, which stabilizes the electric current, a power line 68 and the power line 64, for the operation of the stretching device 10y.

The internal control unit is preferably programmable from outside the patient's body. In a preferred embodiment, the internal control unit is programmed to regulate the stretching device 10y to stretch the stomach according to a pre-programmed time-schedule or to input from any sensor sensing any possible physical parameter of the patient or any functional parameter of the device.

In accordance with an alternative, the capacitor 60 in the embodiment of FIG. 18 may be omitted. In accordance with another alternative, the accumulator 58 in this embodiment may be omitted.

Figure 83:
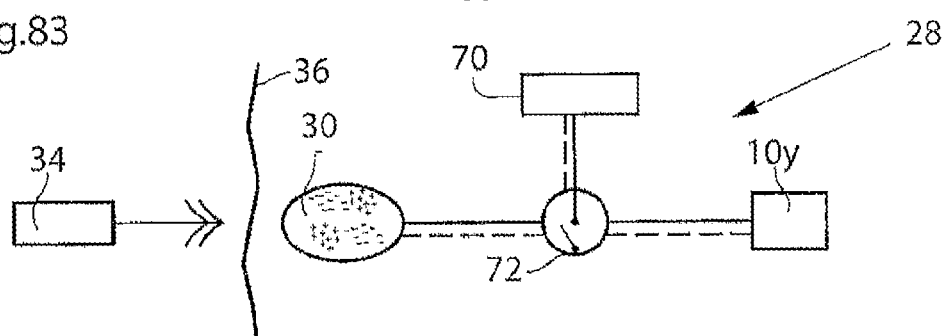

FIG. 83 shows an embodiment of the invention identical to that of FIG. 77, except that a battery 70 for supplying energy for the operation of the stretching device 10y and an electric switch 72 for switching the operation of the stretching device 10y also are implanted in the patient. The electric switch 72 is operated by the energy supplied by the implanted energy transforming device 30 to switch from an off mode, in which the battery 70 is not in use, to an on mode, in which the battery 70 supplies energy for the operation of the stretching device 10y.

Figure 84:
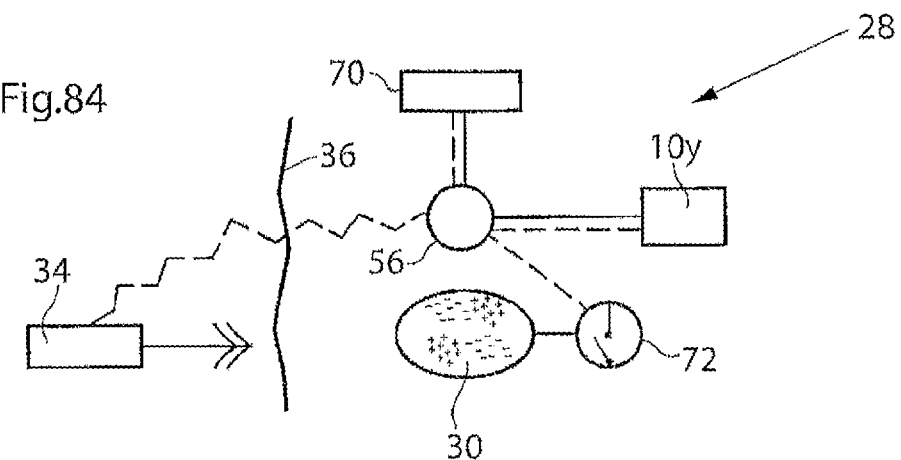

FIG. 84 shows an embodiment of the invention identical to that of FIG. 83, except that an internal control unit 56 controllable by the wireless remote control of the external energy transmission device 34 also is implanted in the patient. In this case, the electric switch 72 is operated by the energy supplied by the implanted energy transforming device 30 to switch from an off mode, in which the wireless remote control is prevented from controlling the internal control unit 56 and the battery is not in use, to a standby mode, in which the remote control is permitted to control the internal control unit 56 to release electric energy from the battery 70 for the operation of the stretching device 10y.

Figure 85:
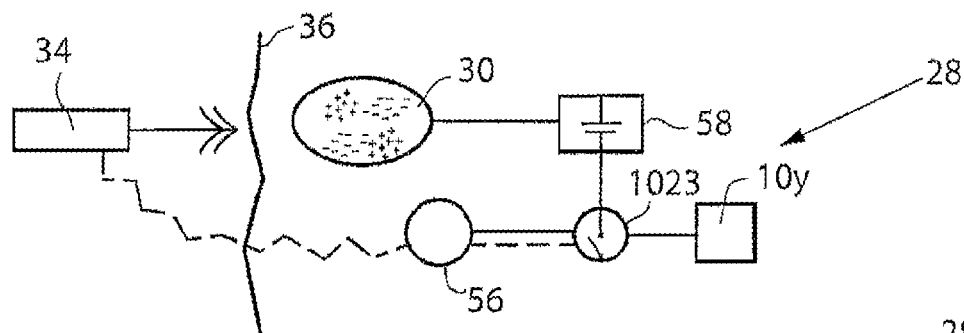

FIG. 85 shows an embodiment of the invention identical to that of FIG. 84, except that an accumulator 58 is substituted for the battery 70 and the implanted component are interconnected differently. In this case, the accumulator 58 stores energy from the implanted energy transforming device 30. In response to a control signal from the wireless remote control of the external energy transmission device 34, the internal control unit 56 controls the electric switch 72 to switch from an off mode, in which the accumulator 58 is not in use, to an on mode, in which the accumulator 58 supplies energy for the operation of the stretching device 10y.

Figure 86:
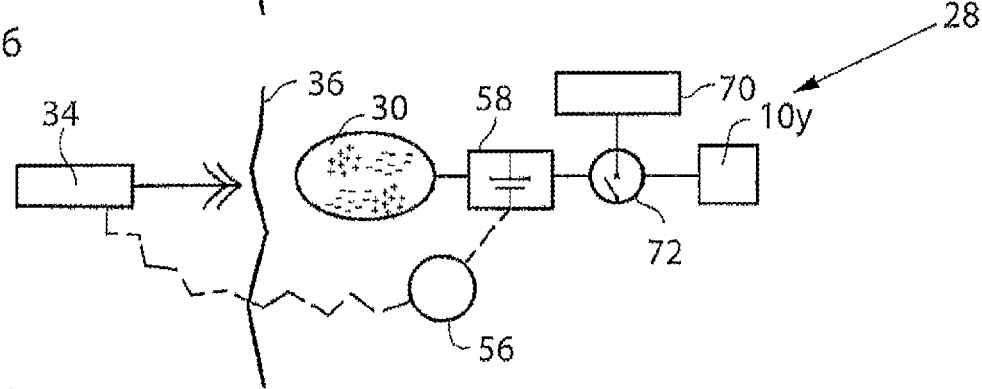

FIG. 86 shows an embodiment of the invention identical to that of FIG. 85, except that a battery 70 also is implanted in the patient and the implanted component are interconnected differently. In response to a control signal from the wireless remote control of the external energy transmission device 34, the internal control unit 56 controls the accumulator 58 to deliver energy for operating the electric switch 72 to switch from an off mode, in which the battery 70 is not in use, to an on mode, in which the battery 70 supplies electric energy for the operation of the stretching device 10y.

Alternatively, the electric switch 72 may be operated by energy supplied by the accumulator 58 to switch from an off mode, in which the wireless remote control is prevented from controlling the battery 70 to supply electric energy and is not in use, to a standby mode, in which the wireless remote control is permitted to control the battery 70 to supply electric energy for the operation of the stretching device 10y.

Figure 87:
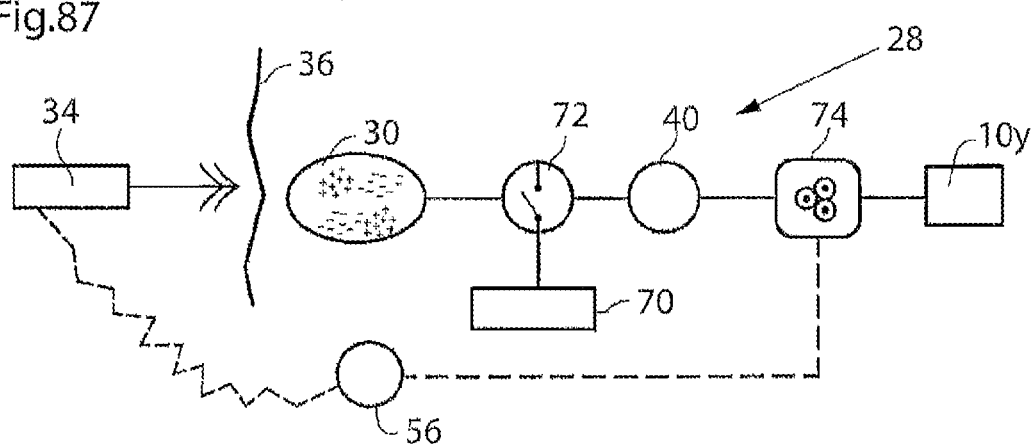

It should be understood that the switch should be interpreted in it broadest embodiment. This means an FPGA or a DA converter or any other electronic component or circuit may switch power on and off preferably being controlled from outside the body or by an internal control unit FIG. 87 shows an embodiment of the invention identical to that of FIG. 83, except that a motor 40, a mechanical reversing device in the form of a gear box 74, and an internal control unit 56 for controlling the gear box 74 also are implanted in the patient. The internal control unit 56 controls the gear box 74 to reverse the function performed by the stretching device 10y (mechanically operated). Even simpler is to switch the direction of the motor electronically.

Figure 88:
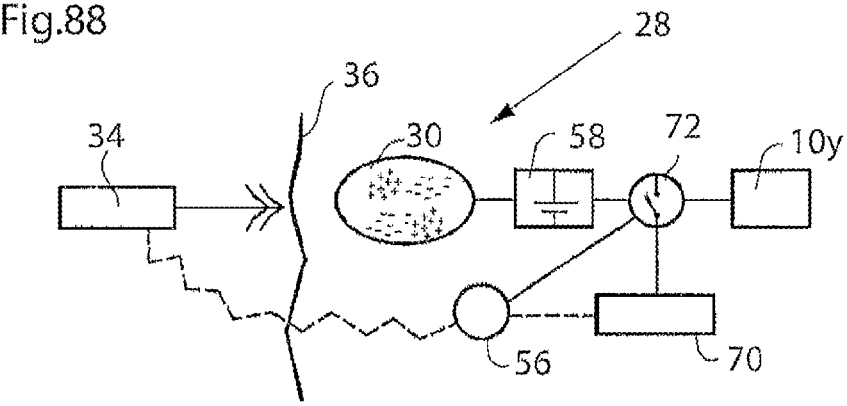

FIG. 88 shows an embodiment of the invention identical to that of FIG. 86 except that the implanted components are interconnected differently. Thus, in this case the internal control unit 56 is powered by the battery 70 when the accumulator 58, suitably a capacitor, activates the electric switch 72 to switch to an on mode. When the electric switch 72 is in it on mode the internal control unit 56 is permitted to control the battery 70 to supply, or not supply, energy for the operation of the stretching device 10y.

Figure 89:
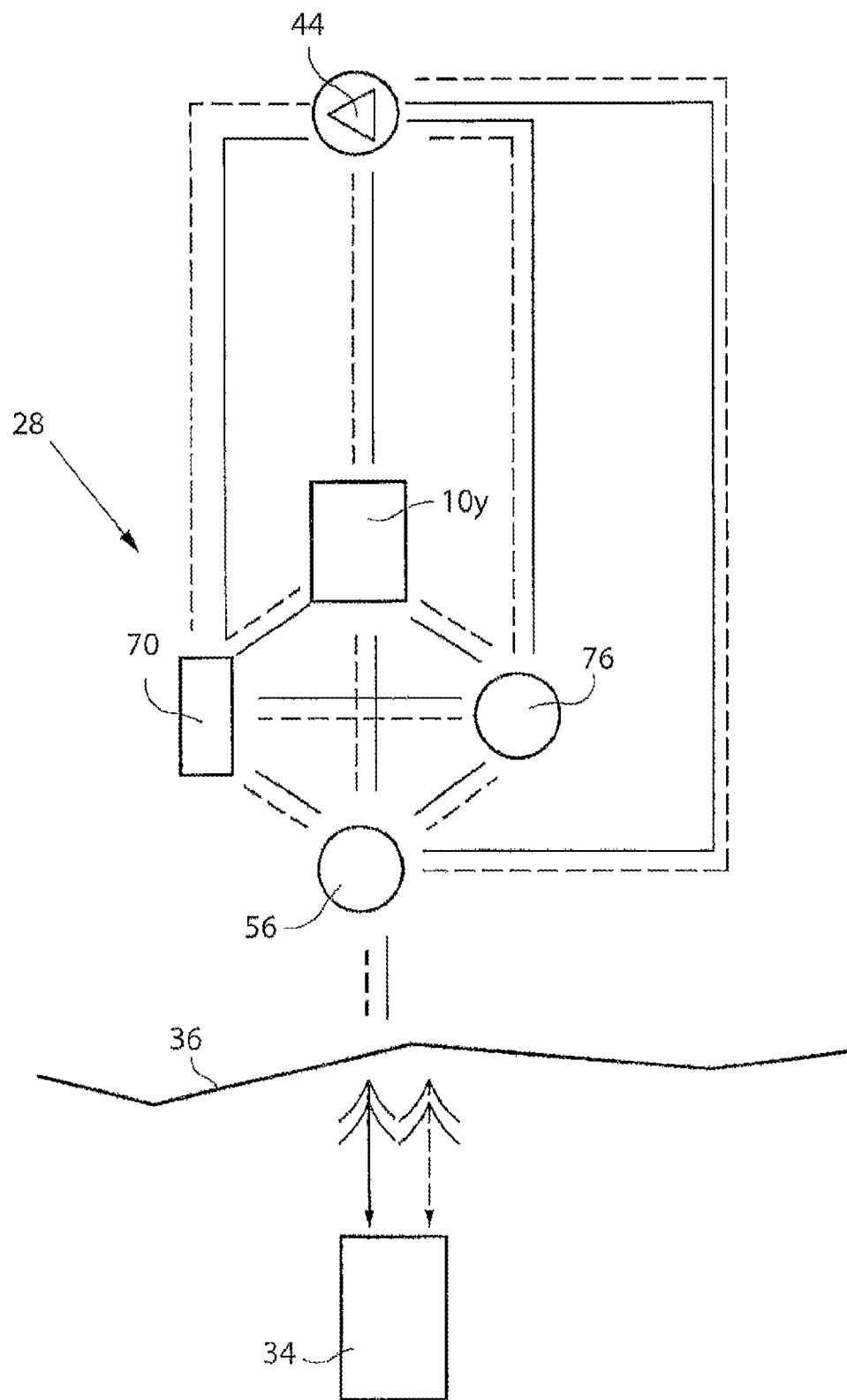

FIG. 89 schematically shows conceivable combinations of implanted components of the apparatus for achieving various communication options. Basically, there are the stretching device 10yy, the internal control unit 56, motor or pump unit 44, and the external energy transmission device 34 including the external wireless remote control. As already described above the wireless remote control transmit a control signal which is received by the internal control unit 56, which in turn controls the various implanted component of the apparatus.

A feedback device, preferably in the form of a sensor 76, may be implanted in the patient for sensing a physical parameter of the patient, such as a contraction wave in the esophagus 203 informing the patient is eating. The internal control unit 56, or alternatively the external wireless remote control of the external energy transmission device 34, may control the stretching device 10y in response to signals from the sensor 76. A transceiver may be combined with the sensor 76 for sending information on the sensed physical parameter to the external wireless remote control. The wireless remote control may comprise a signal transmitter or transceiver and the internal control unit 56 may comprise a signal receiver or transceiver. Alternatively, the wireless remote control may comprise a signal receiver or transceiver and the internal control unit 56 may comprise a signal transmitter or transceiver. The above transceivers, transmitters and receivers may be used for sending information or data related to the stretching device 10y from inside the patient's body to the outside thereof.

Alternatively, the sensor 76 may be arranged to sense a functional parameter of the stretching device 10y.

Where the motor/pump unit 44 and battery 70 for powering the motor/pump unit 44 are implanted, the battery 70 may be equipped with a transceiver for sending information on the condition of the battery 70. To be more precise, when charging a battery or accumulator with energy feedback information related to said charging process is sent and the energy supply is changed accordingly.

Figure 90:
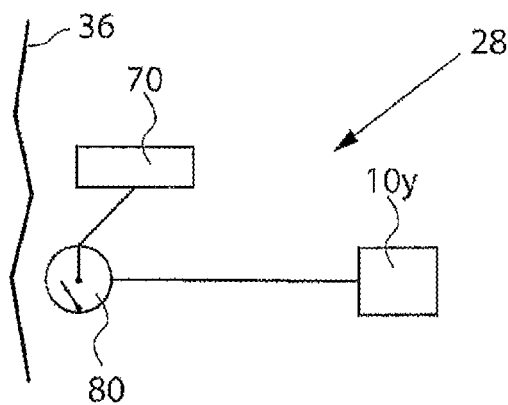
Figure 91:
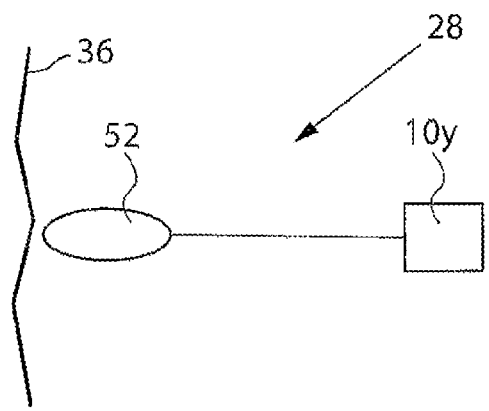

FIG. 90 shows an alternative embodiment wherein the stretching device 10y is regulated from outside the patient's body. The obesity treatment system 28 comprises a stretching device 10y connected to a battery 70 via a subcutaneous switch 80. Thus, the regulation of the stretching device 10y is performed non-invasively by manually pressing the subcutaneous switch, whereby the operation of the stretching device 10y is switched on and off. It will be appreciated that the shown embodiment is a simplification and that additional components, such as an internal control unit or any other part disclosed in the present application can be added to the obesity treatment system FIG. 91 shows an alternative embodiment, wherein the obesity treatment system 28 comprises a stretching device 10y in fluid connection with a hydraulic fluid reservoir 52. Non-invasive regulation is performed by manually pressing the hydraulic reservoir connected to the stretching device 10y.

A further embodiment of a system according to the invention comprises a feedback device for sending information from inside the patient's body to the outside thereof to give feedback information related to at least one functional parameter of the stretching device or system or a physical parameter of the patient, thereby optimizing the performance of the system.

One preferred functional parameter of the device is correlated to the transfer of energy for charging the internal energy source.

Figure 92:
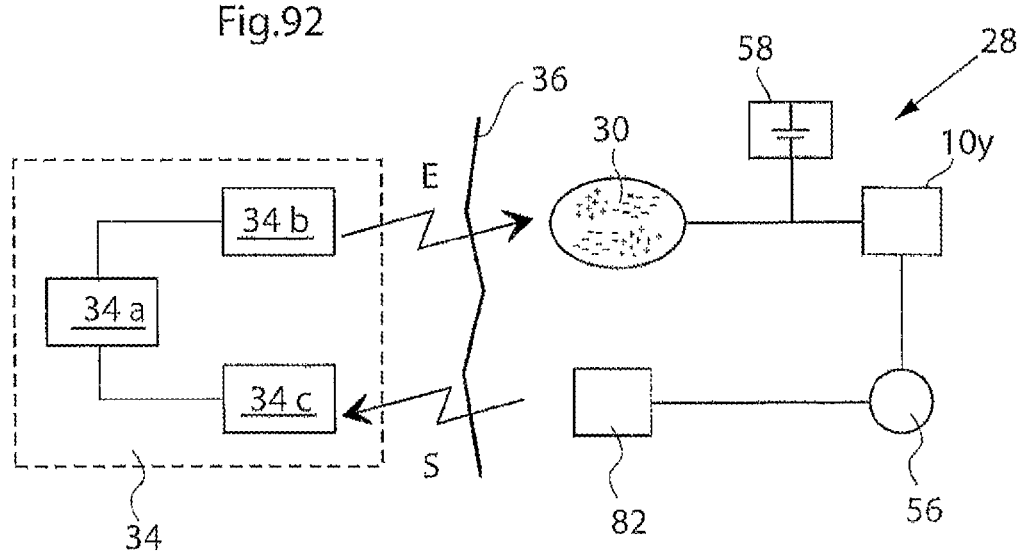

In FIG. 92, an arrangement is schematically illustrated for supplying an accurate amount of energy to an obesity treatment system 28 implanted in a patient, whose skin 36 is indicated by a vertical line. A stretching device 10y is connected to an implanted energy transforming device 30, likewise located inside the patient, preferably just beneath the patient's skin 36. Generally speaking, the implanted energy transforming device 30 may be placed in the abdomen, thorax, muscle fascia (e.g. in the abdominal wall), subcutaneously, or at any other suitable location. The implanted energy transforming device 30 is adapted to receive wireless energy E transmitted from an external energy source 34a provided in the external energy transmission device 34 located outside the patient's skin 36 in the vicinity of the implanted energy transforming device 30.

As is well known in the art, the wireless energy E may generally be transferred by means of any suitable Transcutaneous Energy Transfer (TET) device, such as a device including a primary coil arranged in the external energy source 34a and an adjacent secondary coil arranged in the implanted energy transforming device 30. When an electric current is fed through the primary coil, energy in the form of a voltage is induced in the secondary coil which can be used to operate a stretching device, e.g. after storing the incoming energy in an energy storing device or accumulator, such as a battery or a capacitor. However, the present invention is generally not limited to any particular energy transfer technique, TET devices or energy storing devices, and any kind of wireless energy may be used.

The amount of energy received inside the body to the device may be compared with the energy used by the device. The term used by the device is then understood to include also energy stored by the device. The amount of transferred energy can be regulated by means of an external control unit 34*b* controlling the external energy source 34*a* based on the determined energy balance, as described above. In order to transfer the correct amount of energy, the energy balance and the required amount of energy can be determined by means of an internal control unit 56 connected to the stretching device 10*y*. The internal control unit 56 may thus be arranged to receive various measurements obtained by suitable sensors or the like, not shown, measuring certain characteristics of the stretching device 10*y*, somehow reflecting the required amount of energy needed for proper operation of the stretching device 10*y*. Moreover, the current condition of the patient may also be detected by means of suitable measuring devices or sensors, in order to provide parameters reflecting the patient's condition. Hence, such characteristics and/or parameters may be related to the current state of the stretching device 10*y*, such as power consumption, operational mode and temperature, as well as the patient's condition reflected by, e.g., body temperature, blood pressure, heartbeats and breathing.

Furthermore, an energy storing device or accumulator 58 may optionally be connected to the implanted energy transforming device 30 for accumulating received energy for later use by the stretching device 10*y*. Alternatively or additionally, characteristics of such an accumulator, also reflecting the required amount of energy, may be measured as well. The accumulator may be replaced by a battery, and the measured characteristics may be related to the current state of the battery, such as voltage, temperature, etc. In order to provide sufficient voltage and current to the stretching device 10*y*, and also to avoid excessive heating, it is clearly understood that the battery should be charged optimally by receiving a correct amount of energy from the implanted energy transforming device 30, i.e. not too little or too much. The accumulator may also be a capacitor with corresponding characteristics.

For example, battery characteristics may be measured on a regular basis to determine the current state of the battery, which then may be stored as state information in a suitable storage means in the internal control unit 56. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 56 is adapted to determine the energy balance and/or the currently required amount of energy, (either energy per time unit or accumulated energy) based on measurements made by the above-mentioned sensors or measuring devices on the stretching device 10*y*, or the patient, or an energy storing device if used, or any combination thereof. The internal control unit 56 is further connected to an internal signal transmitter 82, arranged to transmit a control signal reflecting the determined required amount of energy, to an external signal receiver 34*c* connected to the external control unit 34*b*. The amount of energy transmitted from the external energy source 34*a* may then be regulated in response to the received control signal.

Alternatively, sensor measurements can be transmitted directly to the external control unit 34*b* wherein the energy balance and/or the currently required amount of energy can be determined by the external control unit 34*b*, thus integrating the above-described function of the internal control unit 56 in the external control unit 34*b*. In that case, the internal control unit 56 can be omitted and the sensor measurements are supplied directly to the internal signal transmitter 82 which sends the measurements over to the external signal receiver 34*c* and the external control unit 34*b*. The energy balance and the currently required amount of energy can then be determined by the external control unit 34*b* based on those sensor measurements.

Hence, the present solution employs the feedback of information indicating the required energy, which is more efficient than previous solutions because it is based on the actual use of energy that is compared to the received energy, e.g. with respect to the amount of energy, the energy difference, or the energy receiving rate as compared to the energy rate used by the stretching device. The stretching device may use the received energy either for consuming or for storing the energy in an energy storage device or the like. The different parameters discussed above would thus be used if relevant and needed and then as a tool for determining the actual energy balance. However, such parameters may also be needed per se for any actions taken internally to specifically operate the stretching device.

The internal signal transmitter 82 and the external signal receiver 34*c* may be implemented as separate unit using suitable signal transfer means, such as radio, IR (Infrared) or ultrasonic signals. Alternatively, the internal signal transmitter 82 and the external signal receiver 34*c* may be integrated in the implanted energy transforming device 30 and the external energy source 34*a*, respectively, so as to convey control signals in a reverse direction relative to the energy transfer, basically using the same transmission technique. The control signals may be modulated with respect to frequency, phase or amplitude.

To conclude, the energy supply arrangement illustrated in FIG. 28 may operate basically in the following manner. The energy balance is first determined by the internal control unit 56. A control signal reflecting the required amount of energy is also created by the internal control unit 56, and the control signal is transmitted from the internal signal transmitter 82 to the external signal receiver 34*c*. Alternatively, the energy balance can be determined by the external control unit 34*b* instead depending on the implementation, as mentioned above. In that case, the control signal may carry measurement results from various sensors. The amount of energy emitted from the external energy source 34*a* can then be regulated by the external control unit 34*b*, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 34*a*, such as voltage, current, amplitude, wave frequency and pulse characteristics.

A method is thus provided for controlling transmission of wireless energy supplied to an electrically operable stretching device implanted in a patient. The wireless energy E is transmitted from an external energy source located outside the patient and is received by an internal energy receiver located inside the patient, the internal energy receiver being connected to the stretching device for directly or indirectly supplying received energy thereto. An energy balance is determined between the energy received by the internal energy receiver and the energy used for the stretching device. The transmission of wireless energy E from the external energy source is then controlled based on the determined energy balance.

A system is also provided for controlling transmission of wireless energy supplied to an electrically operable stretching device implanted in a patient. The system is adapted to transmit the wireless energy E from an external energy source located outside the patient which is received by an implanted energy transforming device located inside the patient, the implanted energy transforming device being connected to the stretching device for directly or indirectly supplying received energy thereto. The system is further adapted to determine an energy balance between the energy received by the implanted energy transforming device and the energy used for the stretching device, and control the transmission of wireless energy E from the external energy source, based on the determined energy balance.

The functional parameter of the device is correlated to the transfer of energy for charging the internal energy source.

In yet an alternative embodiment, the external source of energy is controlled from outside the patient's body to release electromagnetic wireless energy, and released electromagnetic wireless energy is used for operating the stretching device.

In another embodiment, the external source of energy is controlling from outside the patient's body to release non-magnetic wireless energy, and released non-magnetic wireless energy is used for operating the stretching device.

Those skilled in the art will realize that the above various embodiments according to FIGS. 17-29 could be combined in many different ways. For example, the electric switch 38 operated polarized energy could be incorporated in any of the embodiments of FIGS. 11, 18-24, the hydraulic valve shilling device 54 could be incorporated in the embodiment of FIG. 16, and the gearbox 74 could be incorporated in the embodiment of FIG. 15. Please observe that the switch simply could mean any electronic circuit or component.

Figure 93:
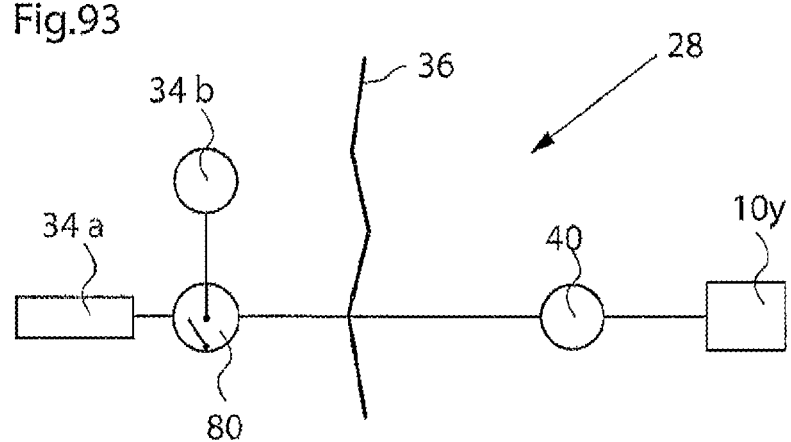

Wireless transfer of energy for operating the stretching device has been described to enable non-invasive operation. It will be appreciated that the stretching device can be operated with wire bound energy as well. One such example is shown in FIG. 93, wherein an external switch 84 is interconnected between the external energy source 34a and an operation device, such as an electric motor regulating the stretching device 10y, by means of power lines 86 and 88. An external control unit 34b controls the operation of the external switch to effect proper operation of the stretching device 10y.

Hydraulic or Pneumatic Powering

FIGS. 94-97 show in more detail block diagrams of four different ways of hydraulically or pneumatically powering an apparatus for treating obesity according to the invention.

Figure 94:
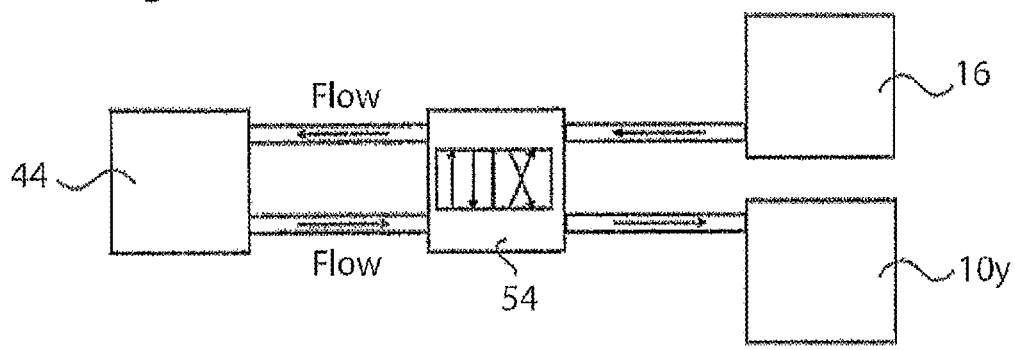
FIGS. 94-100 show various ways of arranging hydraulic or pneumatic powering of an apparatus for treating obesity implanted in a human patient.

FIG. 94 shows an apparatus for treating obesity as described above with reference to any of FIGS. 65-70. The apparatus comprises a stretching device 10y and further a separate regulation reservoir 16, a one way pump 44 and an alternate valve 54.

Figure 95:
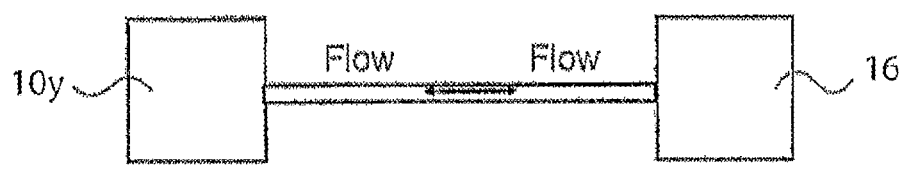

FIG. 95 shows the stretching device 10y and a fluid reservoir 16. By moving the wall of the regulation reservoir or changing the size of the same in any other different way, the adjustment of the stretching device may be performed without any valve, just free passage of fluid any time by moving the reservoir wall.

Figure 96:
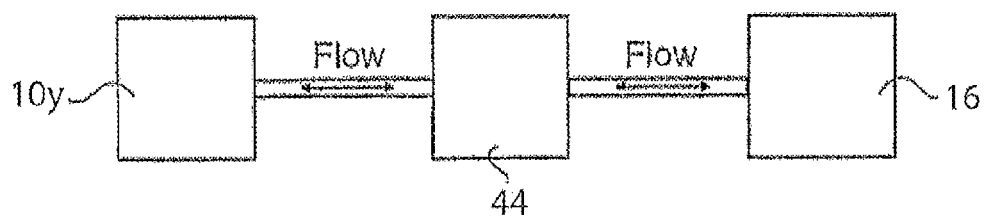

FIG. 96 shows the stretching device 10y, a two way pump 44 and the regulation reservoir 16.

Figure 97:
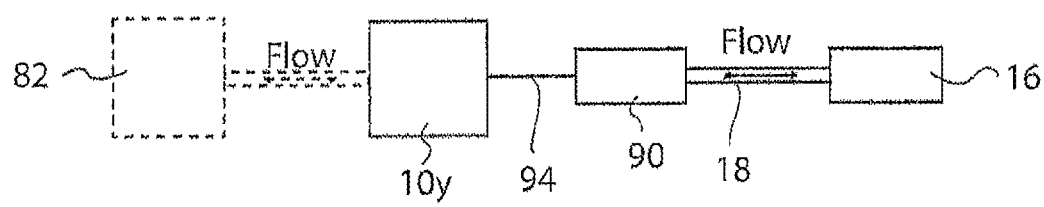
Figure 98:
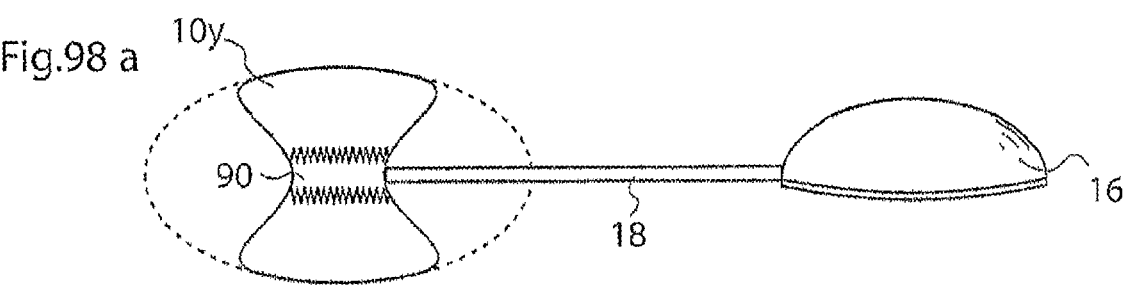
Figure 98:
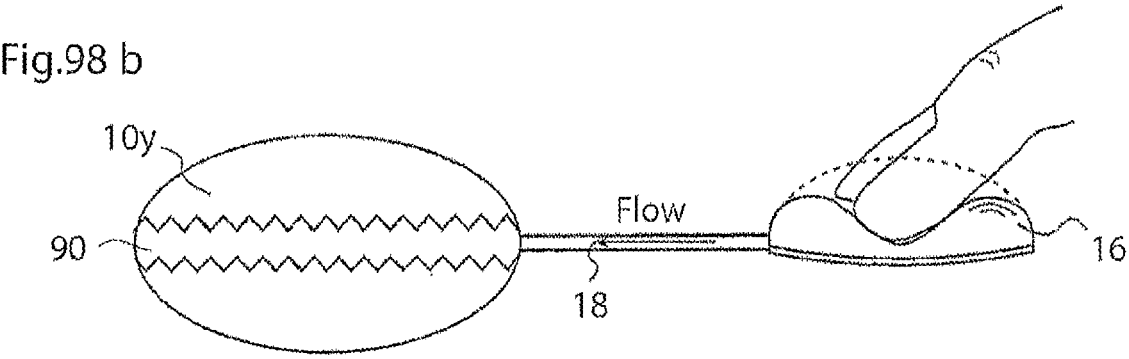
Figure 98:
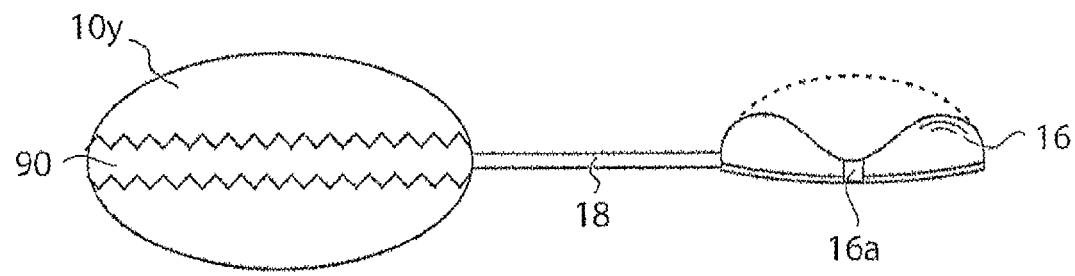
Figure 99:
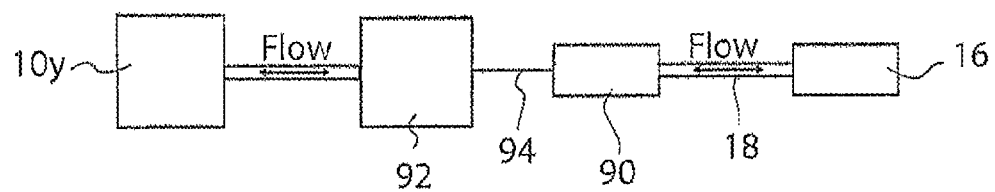

FIG. 97 shows a block diagram of a reversed servo system with a first closed system controlling a second closed system. The servo system comprises a regulation reservoir 16 and a servo reservoir 90. The servo reservoir 90 mechanically controls a stretching device 10y via a mechanical interconnection 94, the stretching device having an expandable/contactable cavity. This cavity is preferably expanded or contracted by supplying hydraulic fluid from the larger adjustable reservoir 92 in fluid connection with the stretching device 10y. Alternatively, the cavity contains compressible gas, which can be compressed and expanded under the control of the servo reservoir 90.

The servo reservoir 90 can also be part of the stretching device itself.

In one embodiment, the regulation reservoir is placed subcutaneous under the patient's skin 36 and is operated by pushing the outer surface thereof by means of a finger. This obesity treatment system is illustrated in FIGS. 98a-c. In FIG. 98a, a flexible subcutaneous regulation reservoir 16 is shown connected to a bulge shaped servo reservoir 90 by means of a conduit 18. This bellow shaped servo reservoir 90 is comprised in a flexible stretching device 10y. In state shown in FIG. 98a, the servo reservoir 90 contains a minimum of fluid and most fluid is found in the regulation reservoir 16. Due to the mechanical interconnection between the servo reservoir 90 and the stretching device 10y, the outer shape of the stretching device 10y is contracted, i.e., it occupies less than its maximum volume. This maximum volume is shown with dashed lines in the figure.

FIG. 98b shows a state wherein a user, such as the patient in with the stretching device is implanted, presses the regulation reservoir 16 so that fluid contained therein is brought to flow through the conduit 18 and into the servo reservoir 90, which, thanks to its bellow shape, expands longitudinally. This expansion in turn expands the stretching device 10y so that it occupies its maximum volume, thereby stretching the stomach wall (not shown) which it contact.

The regulation reservoir 16 is preferably provided with means for keeping its shape after compression. This means, which is schematically shown as 16a in the figure, will thus keep the stretching device 10y in a stretched position also when the user releases the regulation reservoir. In this way, the regulation reservoir essentially operates as an on/off switch for the obesity treatment system.

An alternative embodiment of hydraulic or pneumatic operation will now be described with reference to FIGS. 99 and 100a-c. The block diagram shown in FIG. 99 comprises with a first closed system controlling a second closed system. The first system comprises a regulation reservoir 16 and a servo reservoir 90. The servo reservoir 90 mechanically controls a larger adjustable reservoir 92 via a mechanical interconnection 94. A stretching device 10y having an expandable/contactable cavity is in turn controlled by the larger adjustable reservoir 92 by supply of hydraulic fluid from the larger adjustable reservoir 92 in fluid connection with the stretching device 10y.

Figure 100A:
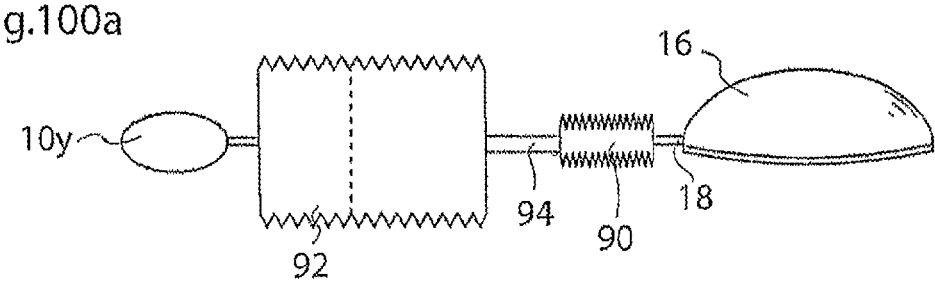
Figure 100B:
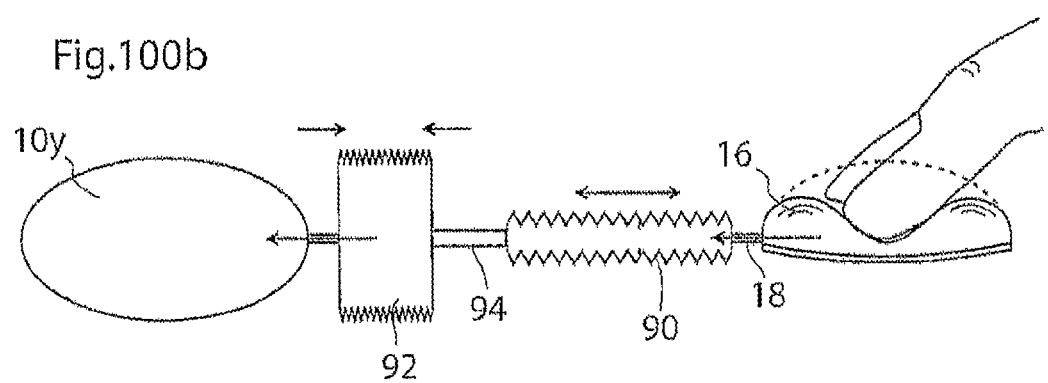
Figure 100C:
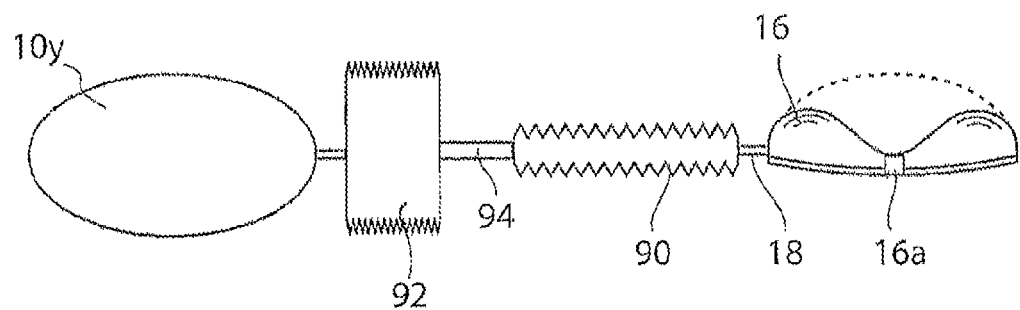

An example of this embodiment will now be described with reference to FIG. 100a-c. Like in the previous embodiment, the regulation reservoir is placed subcutaneous under the patient's skin and is operated by pushing the outer surface thereof by means of a finger. The regulation reservoir 16 is in fluid connection with a bellow shaped servo reservoir 90 by means of a conduit 18. In the first closed system 16, 18, 90 shown in FIG. 34a, the servo reservoir 90 contains a minimum of fluid and most fluid is found in the regulation reservoir 16.

The servo reservoir 90 is mechanically connected to a larger adjustable reservoir 92, in this example also having a bellow shape but with a larger diameter than the servo reservoir 90. The larger adjustable reservoir 92 is in fluid connection with the stretching device 10y. This means that when a user pushes the regulation reservoir 16, thereby displacing fluid from the regulation reservoir 16 to the servo reservoir 90, the expansion of the servo reservoir 90 will displace a larger volume of fluid from the larger adjustable reservoir 92 to the stretching device 10y. In other words, in this reversed servo, a small volume in the regulation reservoir is compressed with a higher force and this creates a movement of a larger total area with less force per area unit.

Like in the previous embodiment described above with reference to FIGS. 98a-c, the regulation reservoir 16 is preferably provided with means for keeping its shape after compression. This means, which is schematically shown as 16a in the figure, will thus keep the stretching device 10y in a stretched position also when the user releases the regulation reservoir. In this way, the regulation reservoir essentially operates as an on/off switch for the obesity treatment system.

Method for the Surgical Treatment of a Patient Suffering from Reflux and Obesity A method for surgically treating an obese patient that also suffers from reflux, the method comprising the steps of cutting an opening in the abdominal wall of the patient, dissecting an area around the stomach, placing an apparatus for treating to a part of the stomach wall of the patient, and suturing the stomach wall.

The apparatus for treating obesity and reflux is preferably placed in a patient via a laparoscopic abdominal approach, comprising the steps of inserting a needle or a tube like instrument into the abdomen of the patient's body, using the needle or a tube like instrument to fill the patient's abdomen with gas thereby expanding the patient's abdominal cavity, placing at least two laparoscopic trocars in the patient's body, inserting a camera through one of the laparoscopic trocars into the patient's abdomen, inserting at least one dissecting tool through one of said at least two laparoscopic trocars and dissecting an intended placement area of the patient, and placing an apparatus for treating obesity in connection with the stomach wall.

The methods could further comprise the step of postoperatively regulating the at least one stretching device to: stretch a part of the stomach wall and regulate the stretching device from outside the patient's body to affect the appetite of the patient.

Instruments

An intraluminar method of invaginating a stretching device 10 on the outside of the stomach wall 12 will now be described with reference to FIGS. 101a-i. Initially, an instrument 600, preferably a gastroscopic instrument, is inserted into the mouth of the patient, see FIG. 101a. The instrument comprises an injection device 601, 602 for injecting either fluid or a device into the stomach of the patient. The instrument 600 further comprises a control unit 606 adapted for controlling the operation of the instrument. To this end, the control unit 606 comprises one or more steering devices, in the embodiment shown in the figure in the form of two joysticks 603 and two control buttons 604. A display 605 is provided for displaying the image provided by an optical device for viewing inside the stomach, such as a camera (not shown) arranged at the outer end of the elongated member 607, see FIGS. 101e-i. The camera, which may comprise connecting electrical wires extending along the elongated member, may be assisted by a light source (not shown) placed distally on the elongated member for illuminating the inside of the stomach. The optical device may also comprise optical fibers placed along the elongated member and leading out from the patient's body for external viewing of the inside of the stomach.

Figure 101A:
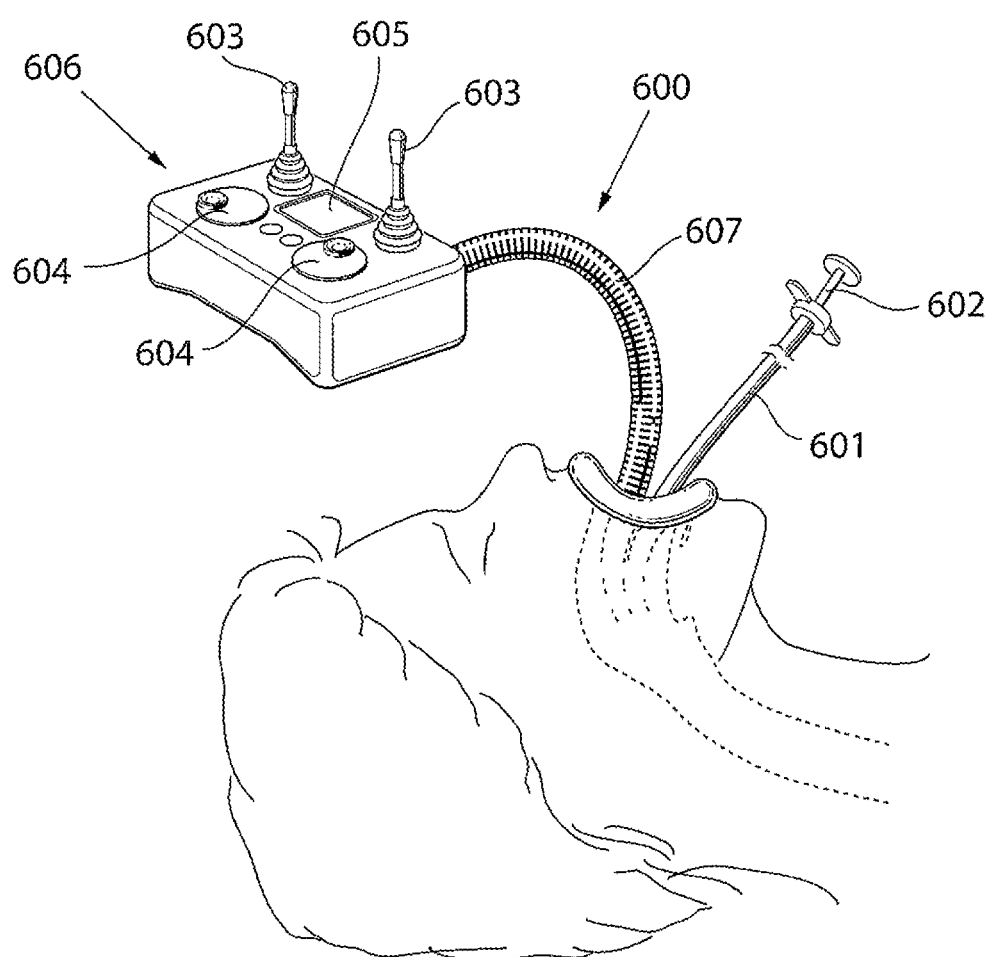
FIGS. 101-105 show various instruments for treating reflux and obesity.
Figure 101B:
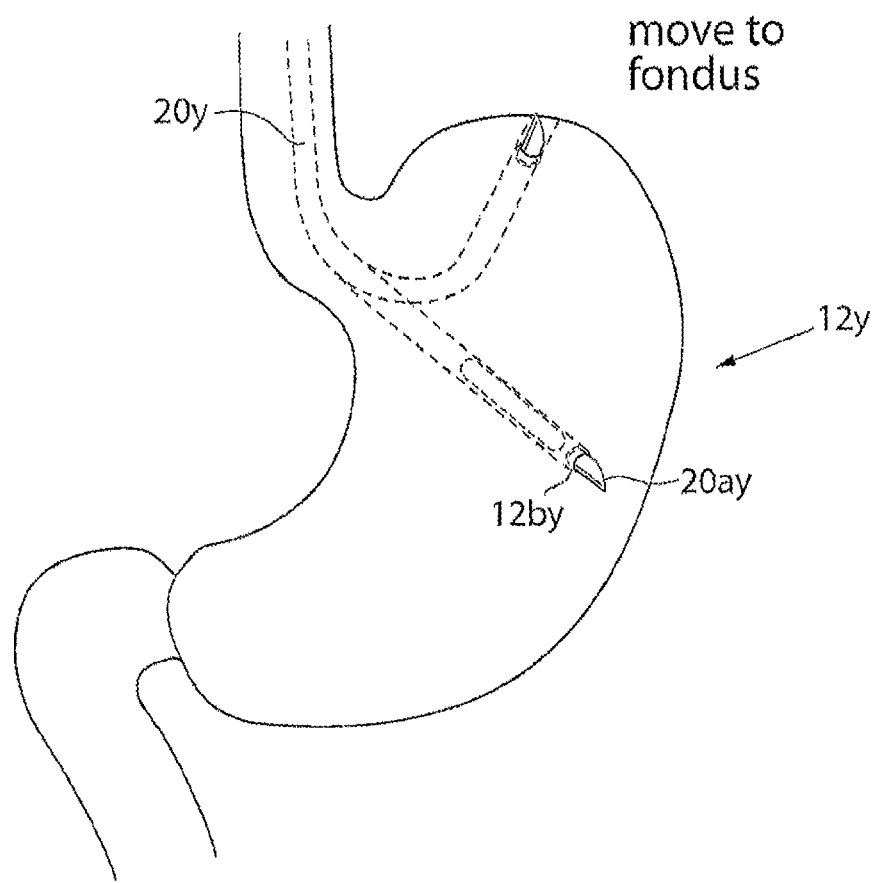

The instrument is further inserted into the esophagus and into the stomach of the patient, see FIG. 101b. By means of the instrument 600, a hole 12by is created in the wall of the stomach 12y. To this end, the instrument is provided with one or more cutters 615 at the distal end thereof. These cutters can of course be designed in different ways, such as a toothed drum cutter rotating about the center axis of the tube-like instrument.

Figure 101C:
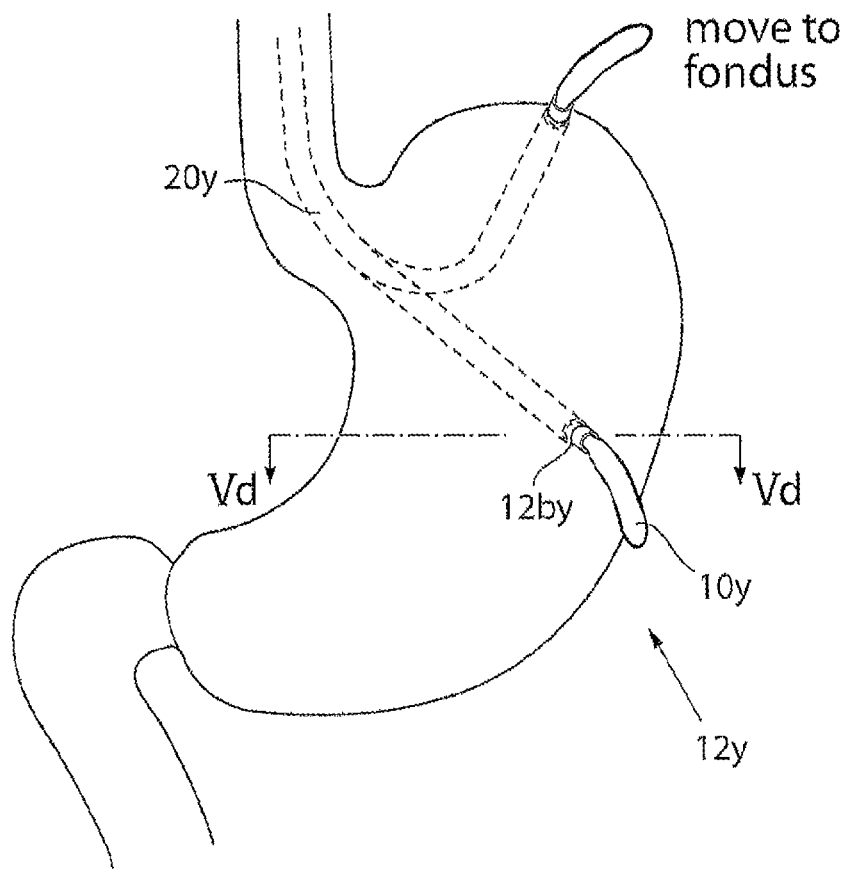
Figure 101D:
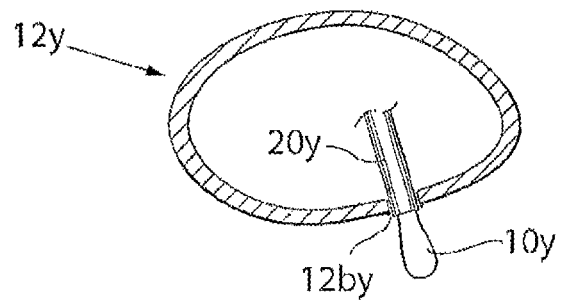
Figure 101E:
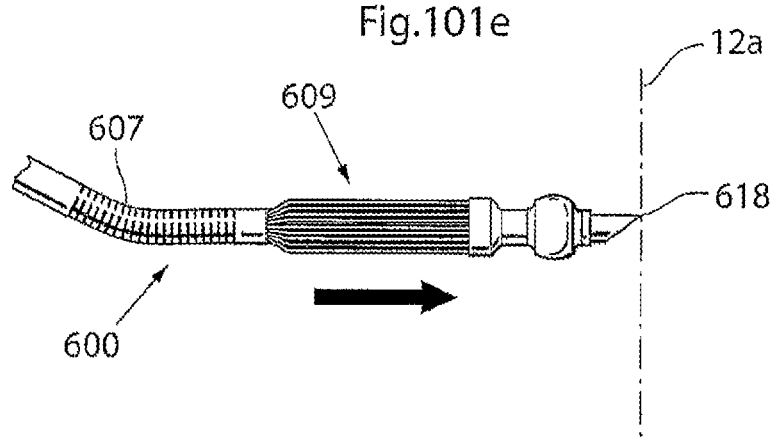
Figure 101F:
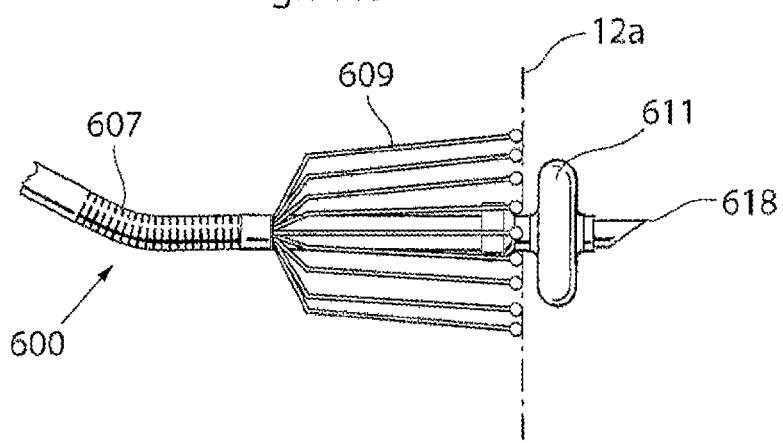

After cutting a hole in the stomach wall, the distal end of the instrument 600 is inserted into and through the hole 2by so that it ends up outside the stomach wall 12ay. This is shown in FIG. 101c, showing a side view of the stomach 12y, and FIG. 101d, which is a sectional view through the stomach of FIG. 101c taken along the lines Vd-Vd.

The instrument 600 is adapted to create a "cavity" or "pouch" on the outside of the stomach around the hole 12by in the stomach wall 12y. Such an instrument and the method of providing the pouch will now be described.

FIGS. 101e-i show a gastroscopic or laparoscopic instrument for invaginating a stretching device 10 in the stomach wall 12 of the patient by creating a pouch of stomach wall 12 material in which the stretching device 10 is placed. The instrument, generally designated 600, comprises an elongated member 607 having a proximal end and a distal end, the elongated member 607 having a diameter less than that of the patient's esophagus and being flexible such as to allow introduction of the flexible elongated member 607 with its distal end first through the patient's throat, esophagus and into the stomach 12 to the stomach wall 12a.

The stomach penetration device or cutter 615 is provided on the elongated member 607 at the distal en thereof for penetrating the stomach wall 12a so as to create a hole in the stomach wall 12a, to allow introduction of the elongated member 607 through the hole. The stomach penetration device 615 could be adapted to be operable for retracting said stomach penetration device 615 after the stomach fundus wall 12a has been penetrated, for not further damaging tissue within the body. The instrument further comprises a special holding device 609 provided on the elongated member 607 on the proximal side to the penetration device 615.

The elongated member further comprises an expandable member 611 which is adapted to be expanded after the elongated member has penetrated the stomach wall 12a and thereby assist in the creation of a cavity or pouch adapted to hold the volume filling device 610. The expandable member 611 may comprise an inflatable circular balloon provided circumferentially around the distal end portion of the flexible elongated member 607.

The method steps when invaginating the volume filling device will now be described in detail. After the instrument 600 has been inserted into the stomach 12, the stomach penetration device 615 is placed into contact with the stomach wall 12, see FIG. 101e. The stomach penetration device or cutter 615 is then brought to create the hole 12b in the stomach wall, whereafter at least the expandable member 611 is brought through the hole 12b in the stomach wall. The special holding device 609 is in this step brought to a holding state wherein it expands radially so as to form an essentially circular abutment surface to the stomach wall 12, see FIG. 101f. In this way, the insertion of the stomach penetration device 615 and the expandable member 611 through the hole 12 in the stomach wall is limited to the position shown in FIG. 101f.

The expandable member 611 is then expanded. In the case the expandable member comprises a balloon or the like, air or other fluid is injected into it.

Figure 101G:
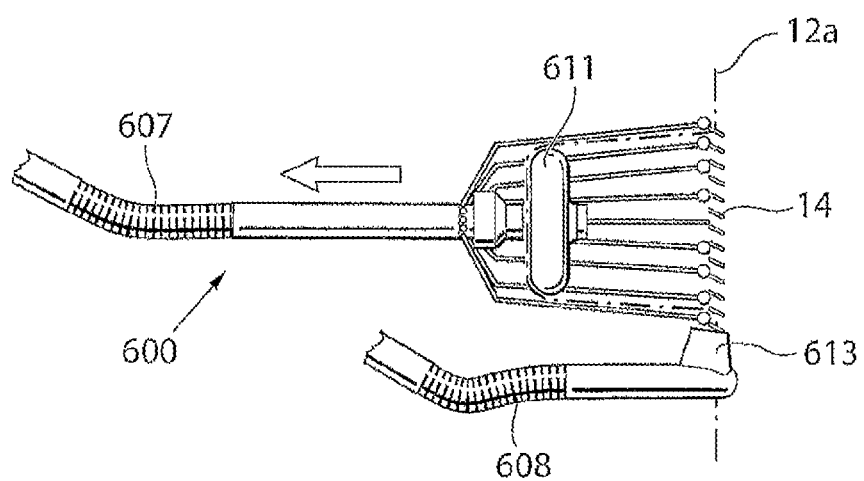

The part of the elongated member 607 comprising the expandable member 611 is then retracted in the proximal direction, as indicated by the arrow in FIG. 101g, thereby pulling the stomach wall 612 into a basket or cup like structure created by the special holding device 609.

A suturing or stapling device 608 is further provided, either as a device connected to the elongated member 607 or as a separate instrument The suturing or stapling member comprises a suturing or stapling end 613 which is adapted to close the cavity or pouch by means of stomach to stomach sutures or staples 14.

Figure 101H:
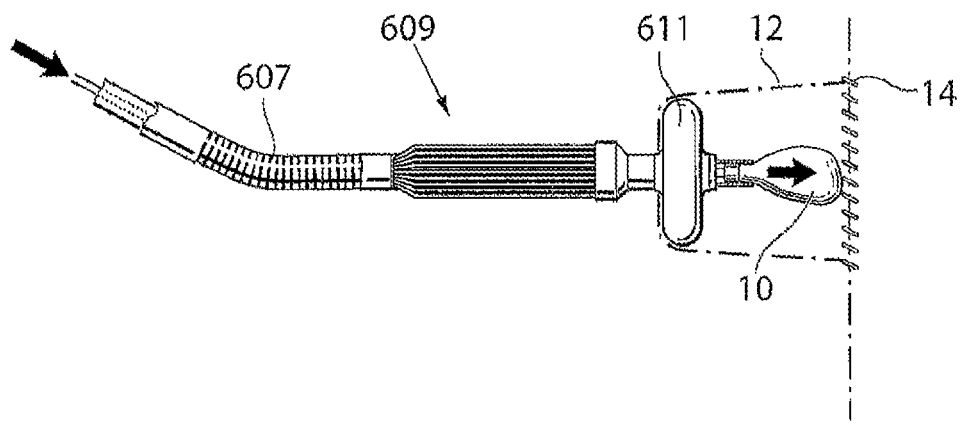
Figure 101I:
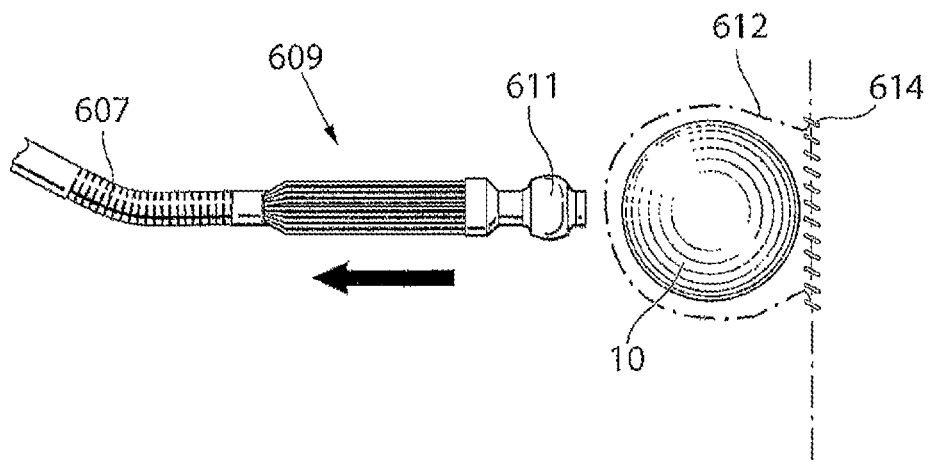

In a further step, illustrated in FIG. 101h, an inflatable stretching device 10 is placed in its deflated state in the cup like structure. The stretching device 10 is then inflated to its inflated or expanded state, see FIG. 101i. This inflation of the stretching device 10 can be accomplished by injecting a fluid or a gel into the deflated stretching device. It can also be accomplished by injecting a material which is allowed to cure, thereby forming a solid device 10. Thus, the stretching device 10 shown in FIGS. 101h and 101i can illustrate either a balloon-like device which is subsequently filled with fluid or gel or alternatively a material which is simply injected into the cup like structure formed by the stomach wall 12.

The fluid which is used to fill the stretching device 10 could be any suitable fluid suitable to fill the stretching device 10, such as a salt solution. In another embodiment, when this fluid is a fluid which is adapted to be transformed into solid state, the fluid could be liquid polyurethane.

In order to minimize or entirely eliminate leakage, the fluid is iso-tonic, i.e., it has the same osmolarity as human body fluids. Another way of preventing diffusion is to provide a fluid which comprises large molecules, such as iodine molecules.

The stomach-to-stomach sutures or staples 14 are preferably provided with fixation portions exhibiting a structure, such as a netlike structure, adapted to be in contact with the stomach wall 12 to promote growth in of human tissue to secure the long term placement of the stretching device attached to the stomach wall.

Thereby, the inflatable stretching device 10 will be in its inflated or expanded state invaginated by a stomach wall portion of the patient on the outside of the stomach wall 12.

During one or more of the above described steps, the stomach may be inflated with gas, preferably by means of the gastroscopic instrument.

The stretching device 10 described above with reference to FIGS. 101a-i has been described as an inflatable stretching device. It will be appreciated that it also can be an elastic stretching device with an elasticity allowing compression so as to be inserted into a gastroscopic instrument and which expands to an expanded state after leaving the instrument.

In one embodiment, the stretching device 10 comprises an inflatable stretching device 10 expandable to an expanded state. In this case, the inflatable stretching device 10 is provided with an inlet port 18b for a fluid and is adapted to be connected to a gastroscopic instrument. This embodiment will now be described in detail with reference to FIGS. 102a-102d.

Figure 102A:
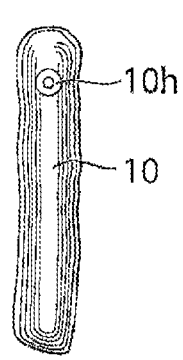

An inflatable stretching device in its non-expanded state is shown in FIG. 102a. It is essentially a balloon-like, deflated stretching device 10 having an inlet port 18b. In this state, the inflatable stretching device 10 has a diameter of a few millimeters at the most allowing it to be inserted into the stomach through the esophagus of the patient by means of a gastroscopic, tube-like instrument 600, or through a laparoscopic trocar in an abdominal laparoscopic method using a tube like instrument 600 depicted in FIG. 102b. The instrument comprises an outer sleeve 600a and an inner sleeve 600b which can be displaced longitudinally relatively to the outer sleeve. The inner sleeve is provided with a cutter in the form of a cutting edge 615 at the distal end thereof. This cutting edge can be used for cutting a hole in the stomach wall, as will be explained in detail in the following.

Figure 102B:
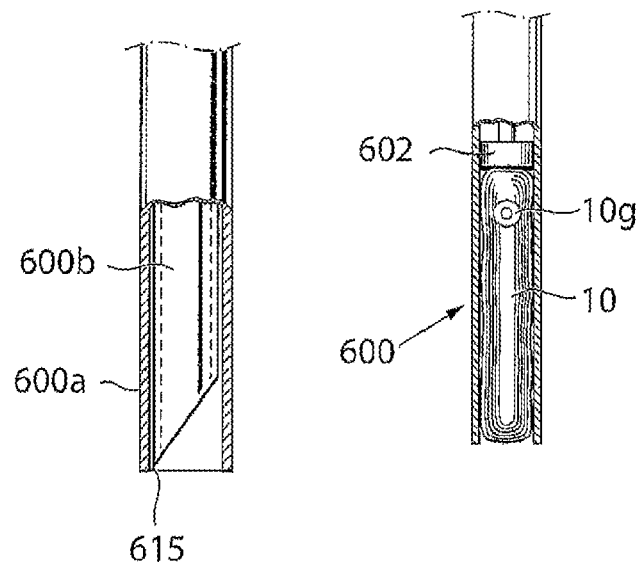
Figure 102C:
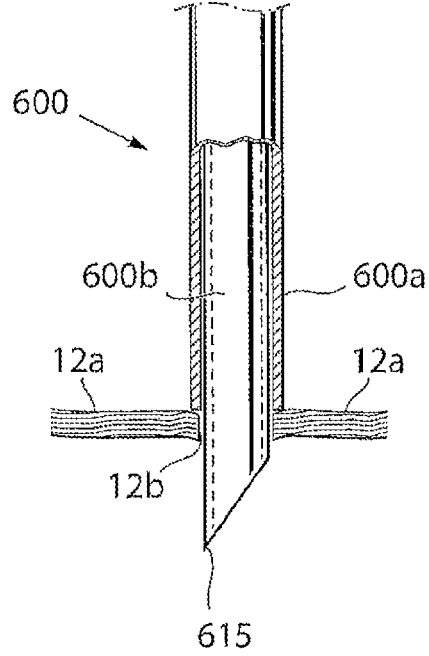

When the instrument reaches a stomach wall, from the inside or outside thereof, see FIG. 102c, the inner sleeve is brought forward from it position in the outer sleeve and into contact with the stomach wall 12a. The cutting edge 615 of the inner sleeve then cuts a hole in the stomach wall so as to allow subsequent insertion of the volume filling device 10 into and through this hole, see FIG. 102d. In order to push the stretching device through the hole, a piston 602 may be provided in the instrument. Thus, the instrument further comprises a piston 602 adapted for pushing a deflated stretching device 10 out from a position in the inner sleeve, this position being shown in FIG. 102b, to a position outside of the inner sleeve, this being shown in FIG. 102d.

In order to protect the deflated stretching device 10 from the cutting edge 615 of the inner sleeve, a further protective sleeve (not shown) can be provided around the stretching device.

Figure 102D:
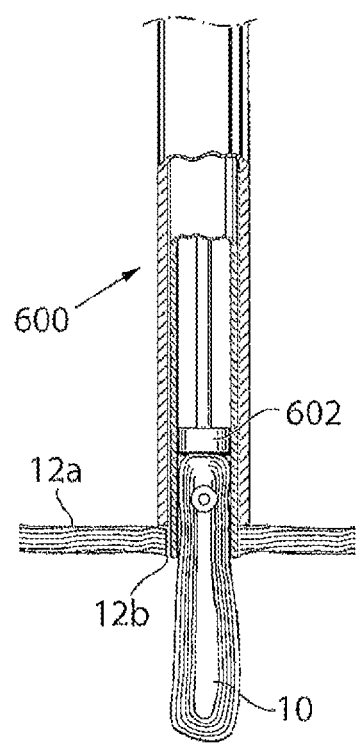

FIG. 102a-j shows an instrument for use in a method of engaging a stretching device 10 to the stomach wall 12 of a patient. The instrument is adapted to be inserted through a narrow tube shaped object such as a gastroscope, used in an intraluminar procedure, or a laparoscopic trocar used in a laparoscopic procedure. The instrument comprises an elongated member 650 which is adapted to be flexible by means of a construction comprising multiple ring shaped members, however it is equally conceivable that said elongated member 650 is adapted to be flexible by means of said elongated member 650 being made of a flexible or adjustable material. The elongated member 650 is inserted into the body and placed in proximity to the stomach wall 12 of the patient, from the outside or inside thereof. The elongated member 650 has a special holding device 651 adapted to hold the stomach by means of mechanical grabbing members or vacuum. The special holding device 651 comprises a first joint 652 and a second joint 653, which enables the special holding device 651 be operable in relation to the elongated member 650 and thereby place the part of the holding device 651 comprising the mechanical grabbing members or vacuum elements in contact with the stomach wall 12 of the patient. FIG. 102b shows the special holding device 651 when placed in contact with the stomach wall 12 of the human patient, after which the special holding member 651 connect to the stomach wall 12, for holding the stomach wall 12. FIG. 102c shows the instrument when the step of advancing a pushing rod 654 from the elongated member 650 is performed. The pushing rod 654 pushes the stomach wall 12 to create a cavity or pouch thereof. FIG. 102d shows the instrument turned 90° in relation to FIGS. 102a-c. This view shows the special holding members 651a,b operably attached to two sides of the elongated member 650 and being in contact with the stomach wall 12, holding the stomach wall 12 as the pushing rod 654 pushes to create a cavity or pouch. When the pushing rod 654 has pushed the stomach wall 12 to a desired position the special holding devices 651a,b moves towards the pushing rod 654 and thereby closes the cavity or pouch.

Figure 103A:
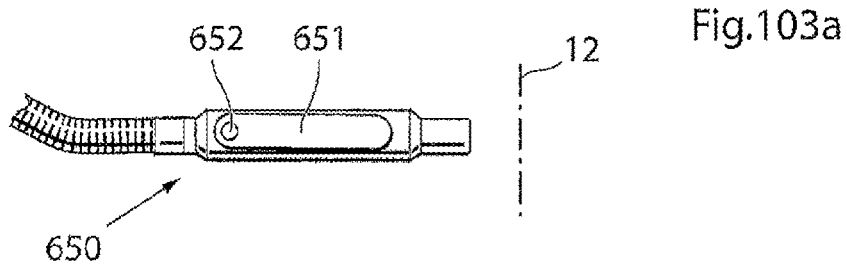
Figure 103B:
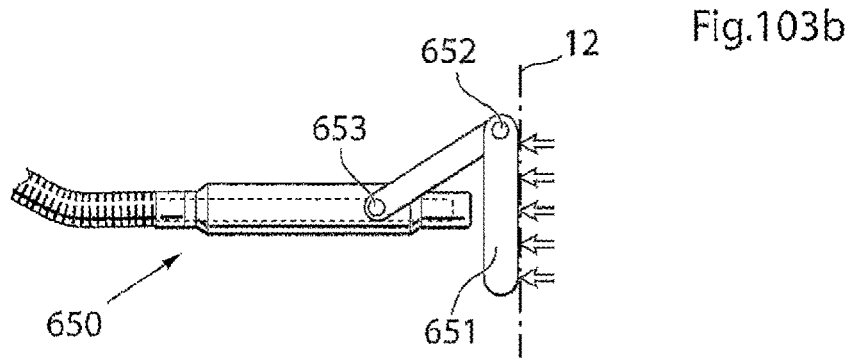
Figure 103C:
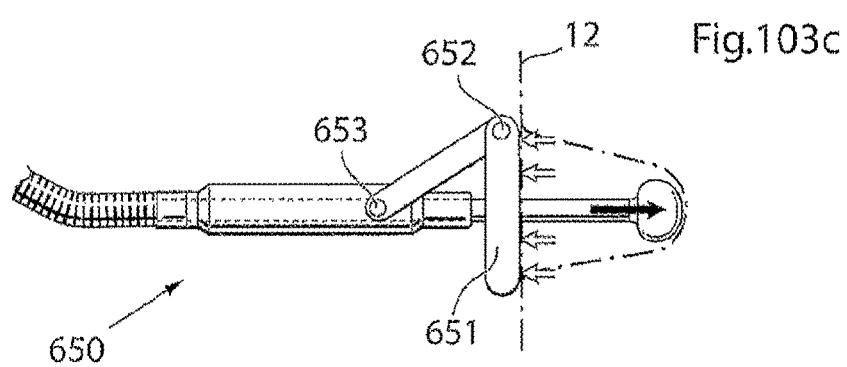
Figure 103D:
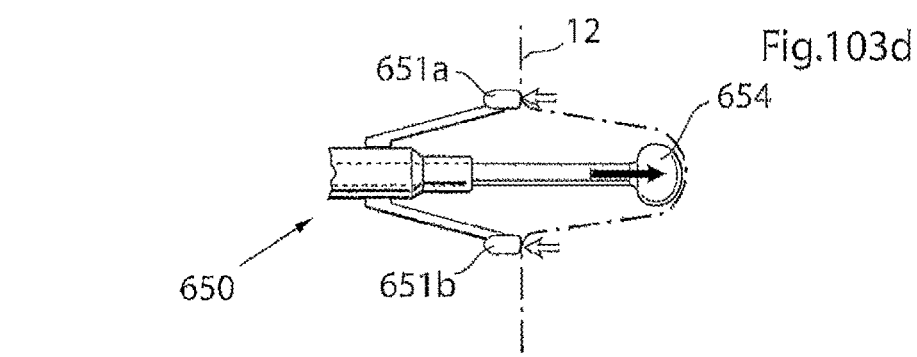
Figure 103E:
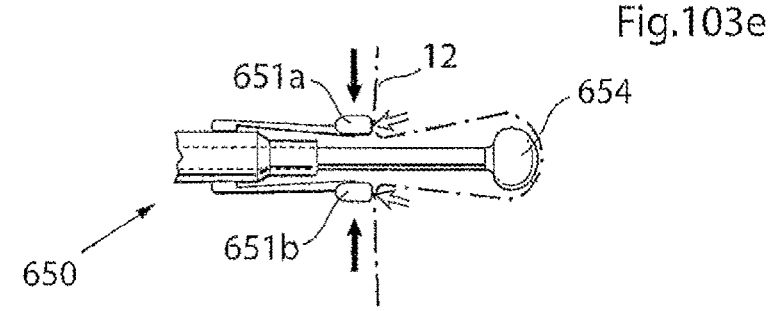
Figure 103F:
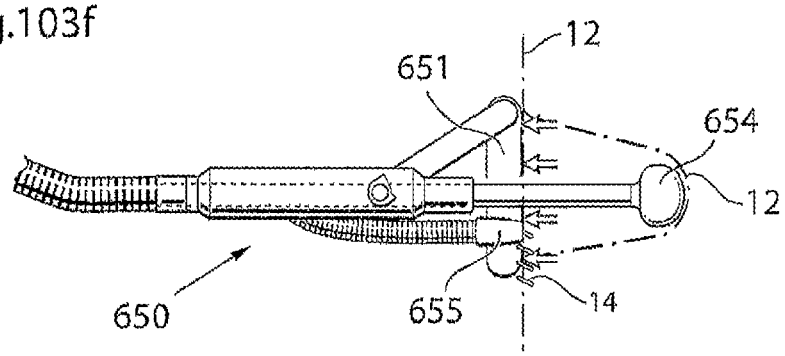
Figure 103G:
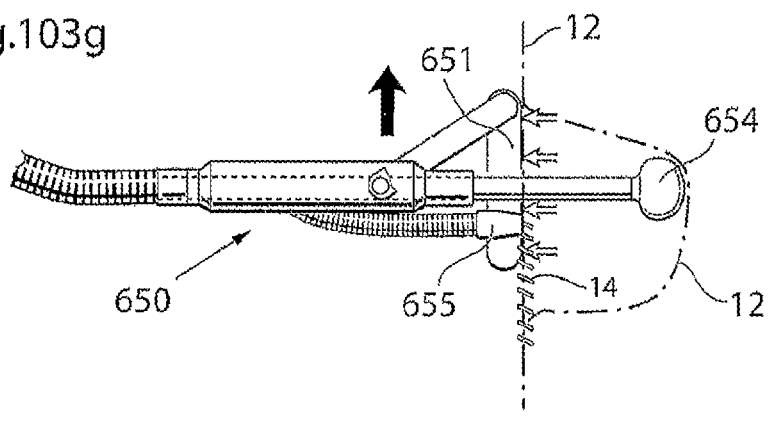
Figure 103H:
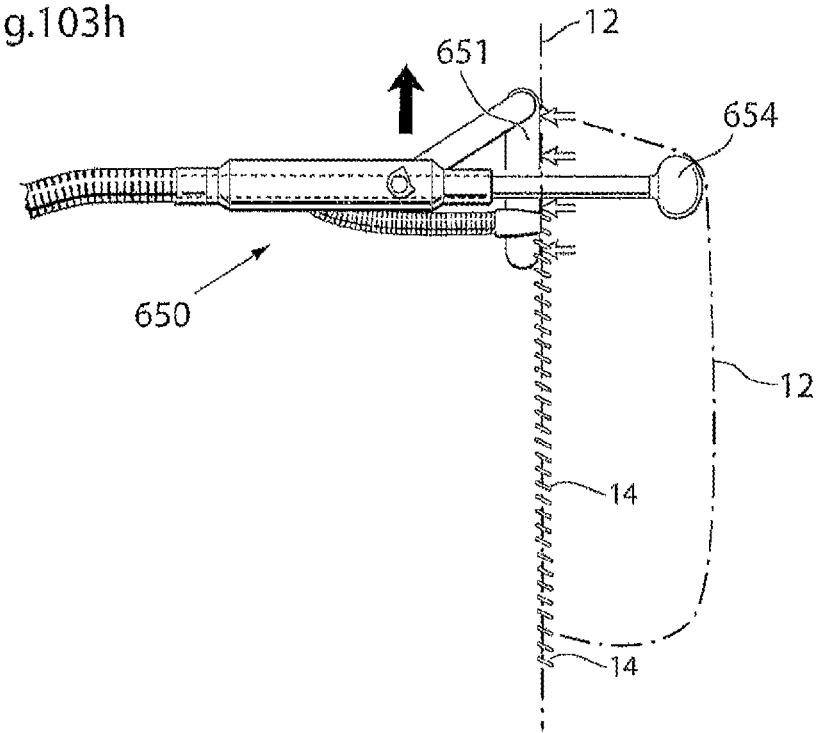
Figure 103I:
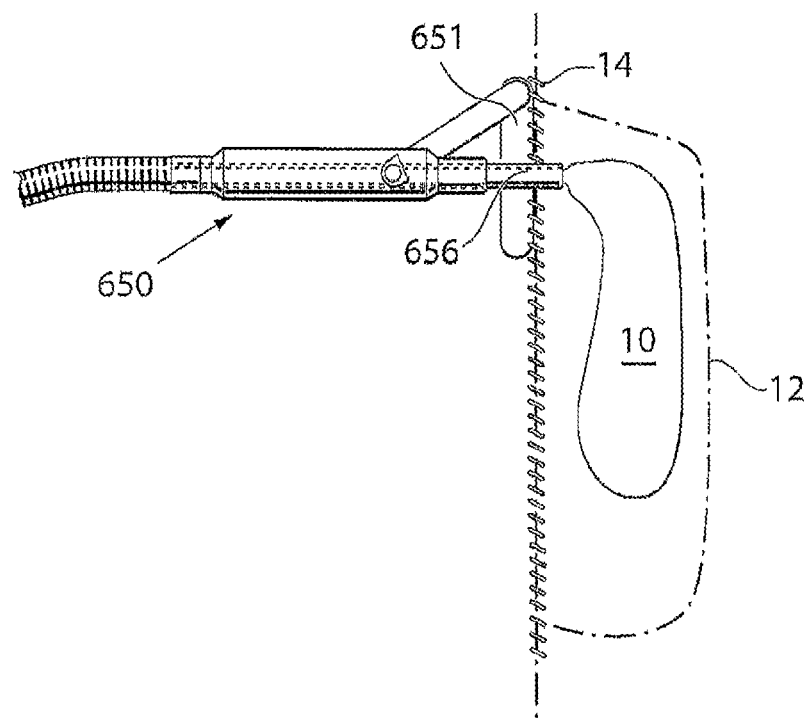
Figure 103J:
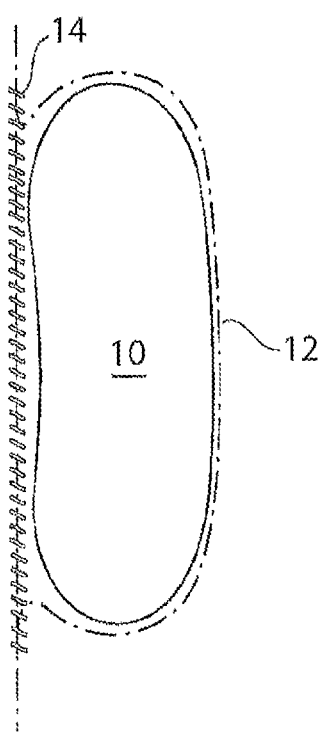

After the cavity or pouch has been created it needs to be sealed. FIG. 103f shows the advancement of a suturing or stapling device 655 from the elongated member 650. The suturing or stapling device 655 is positioned in connection with the stomach wall after which the suturing or stapling device commences with the suturing or stapling of the stomach wall 12, creating a seal of stomach to stomach sutures or staples 14. The instrument is moved along the stomach wall 12 of the patient and thereby a cavity or pouch is created and sealed using the instrument, as shown in FIGS. 103*g* and 103*h*. When a cavity or pouch or desired size has been created and sealed an inserting member 656 is advanced from the elongated member 650. The inserting member 656 is adapted to insert a stretching device 10 being inflatable, as described earlier in this application. After the inserting member 656 has been positioned in the cavity or pouch the stretching device 10 is inserted through the inserting member 656 and into the cavity or pouch by means of a pressurized fluid or gas, or a mechanical advancement member pushing said inflatable stretching device 10 into the cavity or pouch. The insertion member then inflates the inflatable stretching device with a fluid or gas and seals of the final section of the pouch using stomach to stomach sutures or staples 14. The embodiment described explains the process of inserting an inflatable stretching device, however it is equally conceivable that the stretching device 10 is expandable by means of the stretching device 10 being made of an elastic material.

Figure 104A:
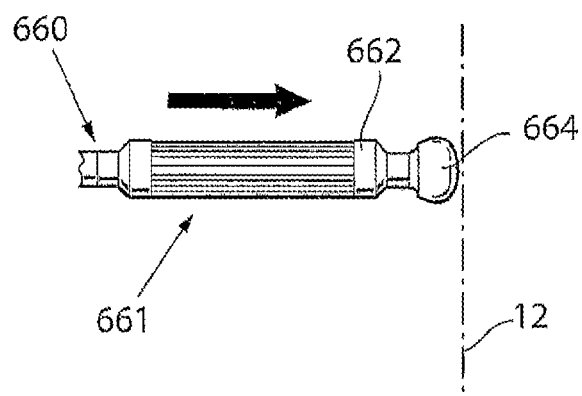
Figure 104B:
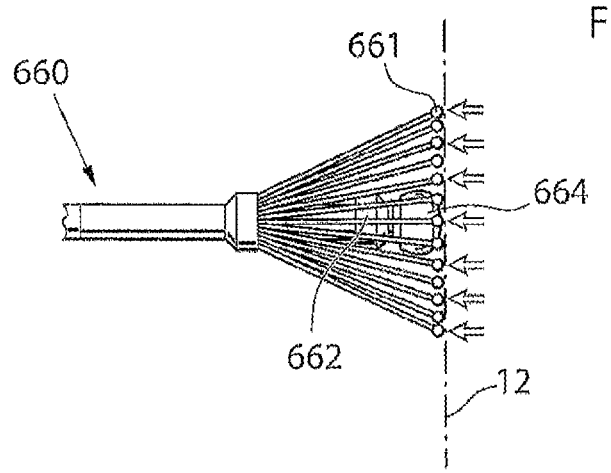
Figure 104C:
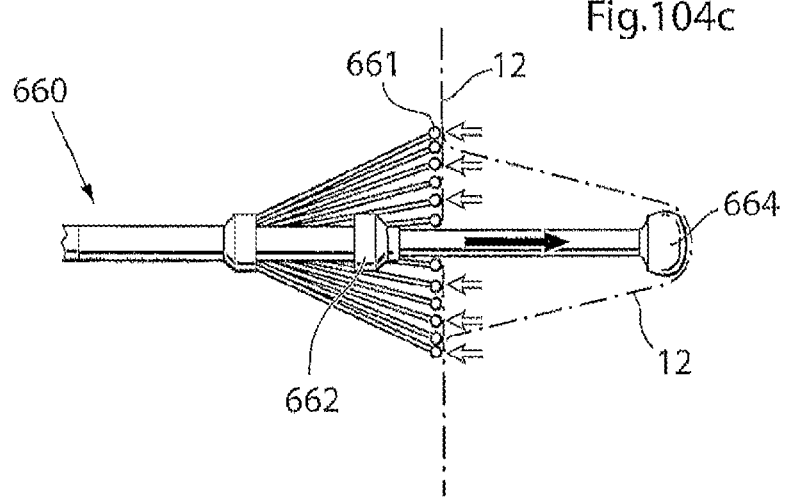

FIG. 104*a*-*f* shows an instrument for use in a method of engaging a stretching device 10 to the stomach wall 12 of a patient. The instrument is adapted to be inserted through a narrow tube shaped object such as a gastroscope, used in an intraluminar procedure, or a laparoscopic trocar used in a laparoscopic procedure. The instrument comprises an elongated member 660 which is adapted to be flexible by means of a construction comprising multiple ring shaped members, however it is equally conceivable that said elongated member 660 is adapted to be flexible by means of said elongated member 660 being made of a flexible or adjustable material. The elongated member 660 is inserted into the body and placed in proximity to the stomach wall 12 of the patient, from the outside or inside thereof. The elongated member 660 has multiple special holding devices 661 adapted to hold the stomach by means of mechanical grabbing members or vacuum. The special holding devices 661 are locked in a position alongside the elongated member 660 by means of a locking ring 662. The special holding devices are made of a flexible material end pre-bent to expand into a funnel-shaped device when said locking ring 662 is removed. The special holding device in its funnel shaped expandable state is shown in FIG. 104*b*. FIG. 104*b* further shows the special holding device 661 when placed in contact with the stomach wall 12 of the human patient, after which the special holding member 661 connects to the stomach wall 12, for holding the stomach wall 12. FIG. 104*c* shows the instrument when the step of advancing a pushing rod 664 from the elongated member 660 is performed. The pushing rod 664 pushes the stomach wall 12 to create a cavity or pouch thereof. When the pushing rod 664 has pushed the stomach wall 12 to a desired position the special holding devices 661 moves towards the pushing rod 664 and thereby closes the cavity or pouch.

Figure 104D:
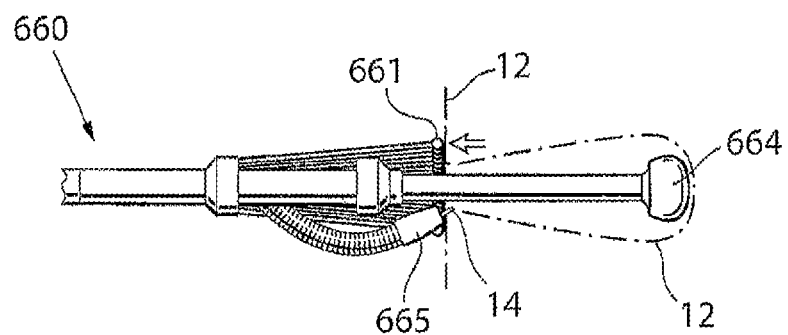
Figure 104E:
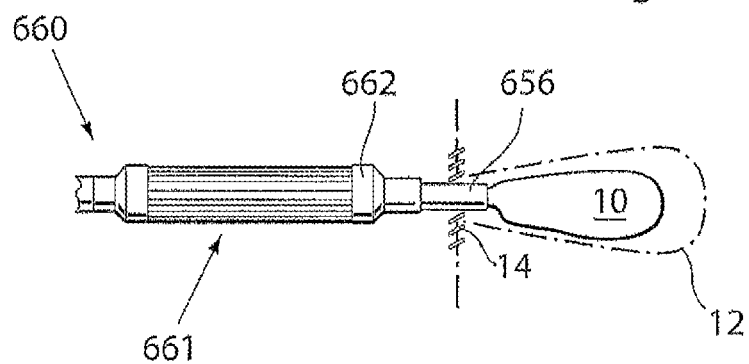
Figure 104F:
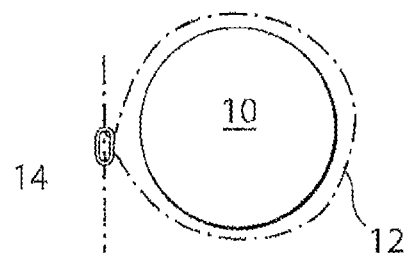

After the cavity or pouch has been created it needs to be sealed. FIG. 104*d* shows the advancement of a suturing or stapling device 665 from the elongated member 660. The suturing or stapling device 665 is positioned in connection with the stomach wall 12 after which the suturing or stapling device 665 commences with the suturing or stapling of the stomach wall 12, creating a seal of stomach to stomach sutures or staples 14. Thereafter an inserting member 666 is advanced from the elongated member 660 and the special holding devices 661 are retracted. The inserting member 666 is adapted to insert a stretching device 10 being inflatable, as described earlier in this application. After the inserting member 666 has been positioned in the cavity or pouch the stretching device 10 is inserted through the inserting member 666 and into the cavity or pouch by means of a pressurized fluid or gas, or a mechanical advancement member pushing said inflatable stretching device 10 into the cavity or pouch. The insertion member 656 then inflates the inflatable stretching device with a fluid or gas and seals of the final section of the pouch using stomach to stomach sutures or staples 14. The embodiment described explains the process of inserting an inflatable stretching device 10, however it is equally conceivable that the stretching device 10 is expandable by means of the stretching device 10 being made of an elastic material. FIG. 40 *f* shows the stretching device 10 as the stretching device 10 is invaginated in the stomach wall 12, in a cavity or pouch sealed with stomach to stomach sutures or staples 14.

Figure 105A:
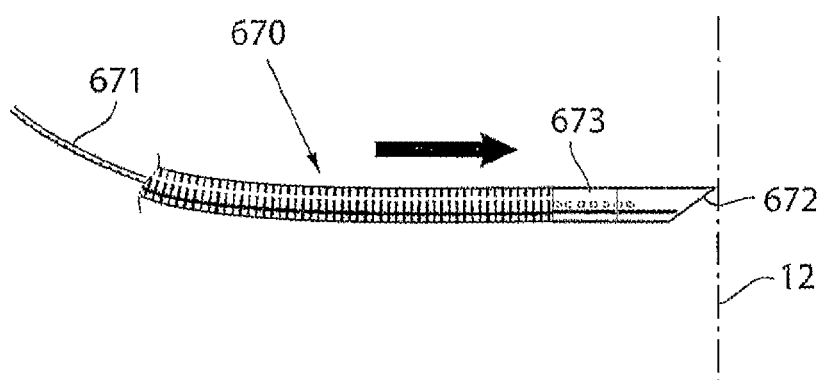

FIG. 105*a* shows an instrument used in a method of engaging the stretching device according to any of the embodiments of the application to the stomach wall 12. The instrument comprises an elongated member 670 which is adapted to be flexible by means of a construction comprising multiple ring shaped members, however it is equally conceivable that said elongated member 670 is adapted to be flexible by means of said elongated member 670 being made of a flexible or adjustable material. The elongated member 670 is inserted into the body and placed in proximity to the stomach wall 12 of the patient, from the inside thereof. A stomach penetrating member 672 is placed in the distal end of the elongated member 670, retractably fixated to a protective sleeve 673 adapted to protect the tissue of the body from the sharp penetrating member 672 or cutter 672 after the cutting operation has been performed.

Figure 105B:
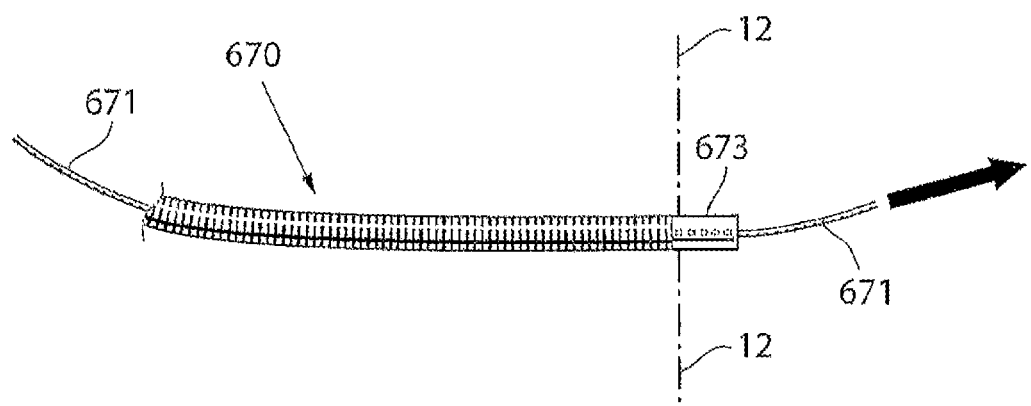

FIG. 105*b* shows the instrument comprising the elongated member 670 after the cutting operation has been performed and the stomach penetrating member or cutter 672 has been retracted into the protective sleeve 673. A guiding wire 671 is pushed through the elongated member 670, through the hole made in the stomach wall 12 and out through the abdomen and placed on the inside of the patient skin, which is penetrated from the outside to enable the guiding wire 671 to exit the abdomen. The guiding wire 671 can then be used to guide a conduit 18 or a lead attached to the stretching device 10 being placed in the stomach from the inside thereof. The stretching device 10 with the conduit 18 or electrical lead being a stretching device 10 according to any of the embodiments of this application. The guiding of the conduit 18 or electrical lead enables the attachment of the conduit 18 or electrical lead to a control unit 42 placed subcutaneously in the patient from the outside of the abdomen.

Figure 106:
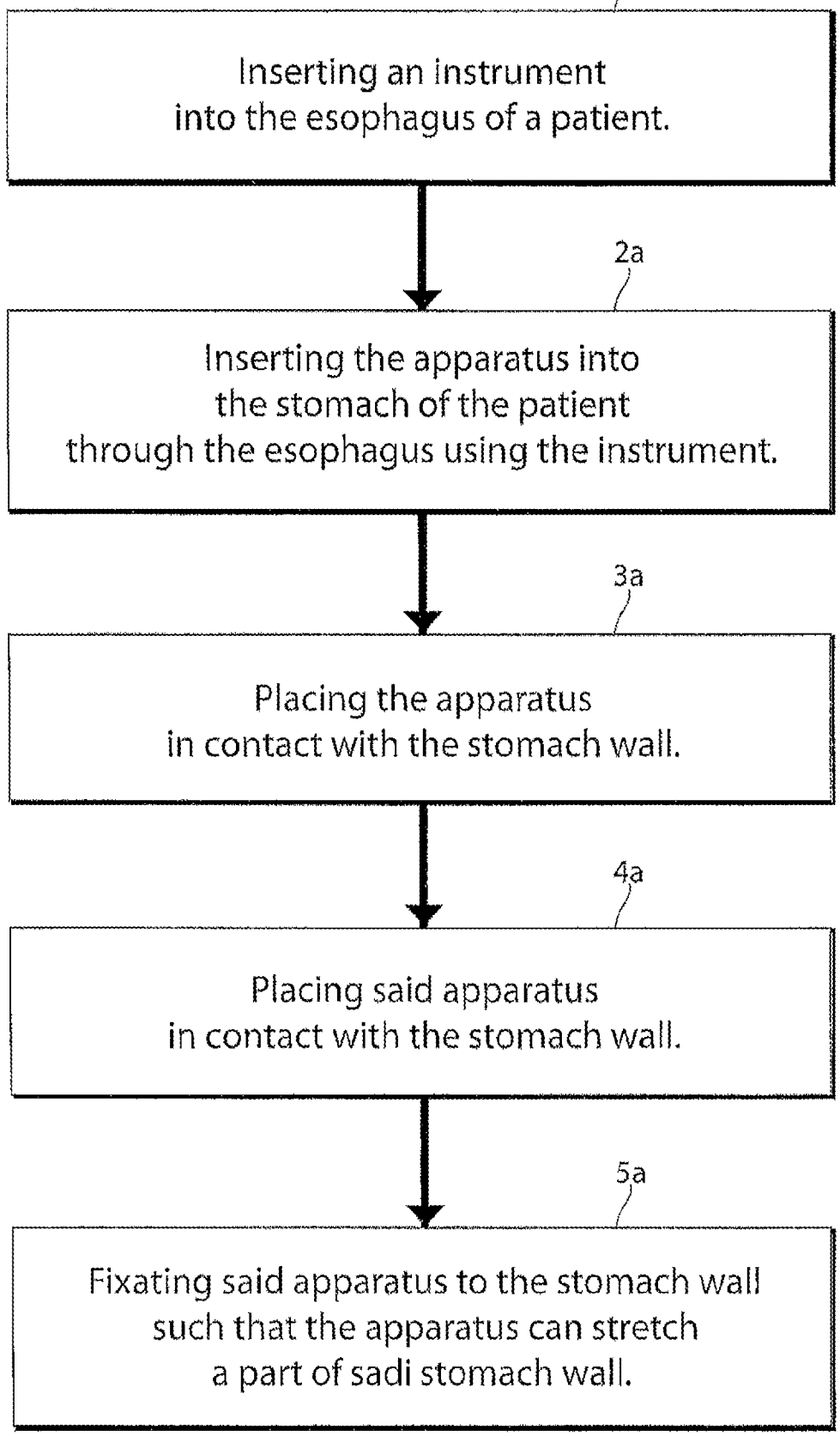
FIGS. 106-107 show methods for surgery for treating reflux and obesity.

FIG. 106 shows a flowchart describing the steps needed in an intraluminar method of inserting an apparatus for stretching a portion of the stomach wall, the method comprises the steps of inserting an instrument into the esophagus 203 of the patient, step 1*a*, inserting an apparatus into the stomach of the patient through the esophagus 203 using the instrument, step 2*a*, placing the apparatus 10 in contact with the stomach wall 12, step 3*a*, fixating the apparatus to the stomach wall 12 such that the apparatus can stretch a part of the stomach wall 12. The method described could further comprise the step of non-invasively regulating the device after the placing of the apparatus has been completed.

Figure 107:
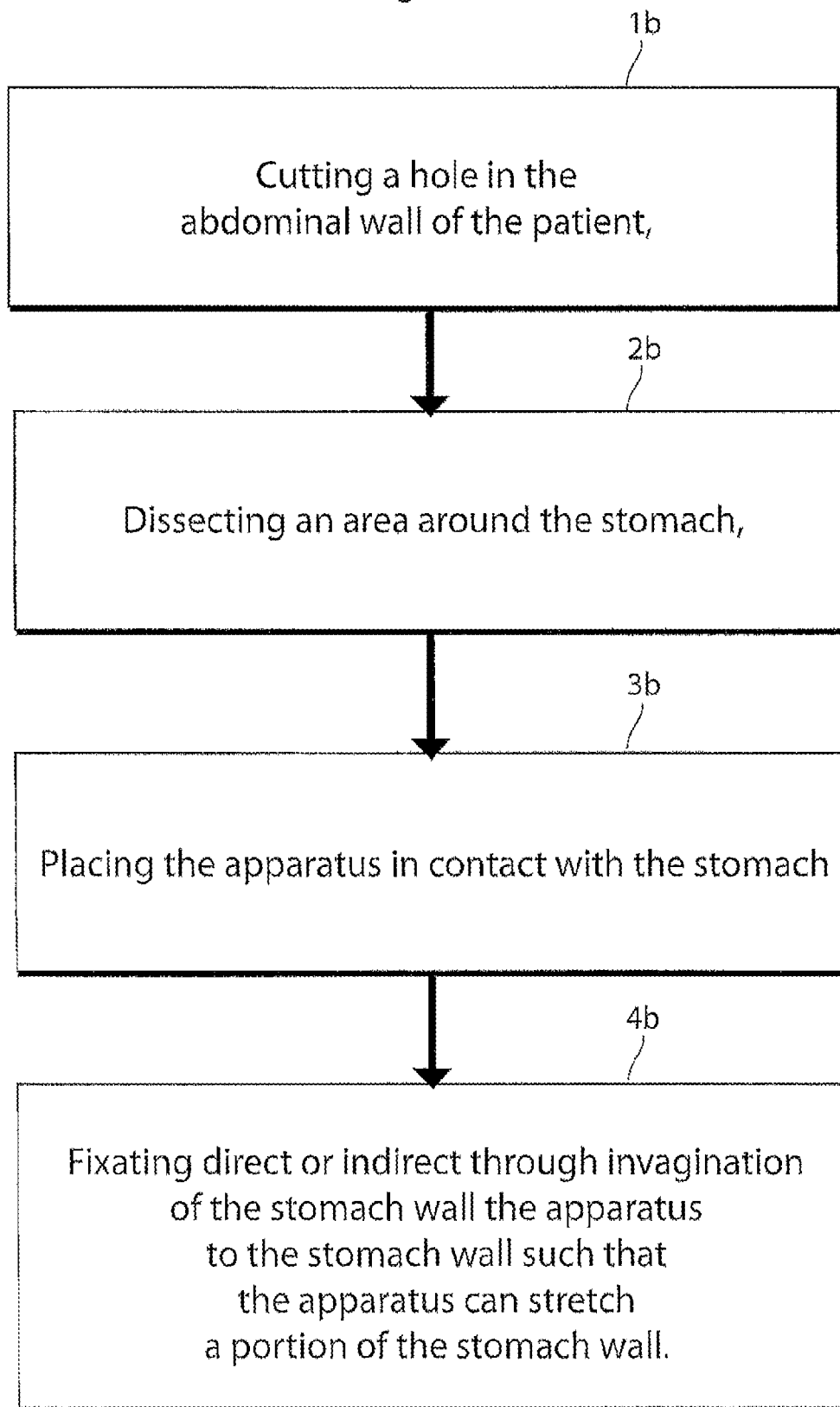

FIG. 107 shows a flowchart describing the steps needed in an abdominal method of inserting an apparatus for stretching a portion of the stomach wall, the method comprises the steps of cutting a hole in the abdominal wall of said patient, step 1b, dissecting an area around the stomach, step 2b, placing said apparatus in contact with the stomach, step 3b and fixating direct or indirect through invagination of the stomach wall the apparatus to the stomach wall such that the apparatus can stretch a portion of said stomach wall, step 4b. The method described could further comprise the steps of closing the hole in the abdomen using sutures or staples 14 and non-invasively regulating the device after the placing of the apparatus has been completed.

Figure 108:
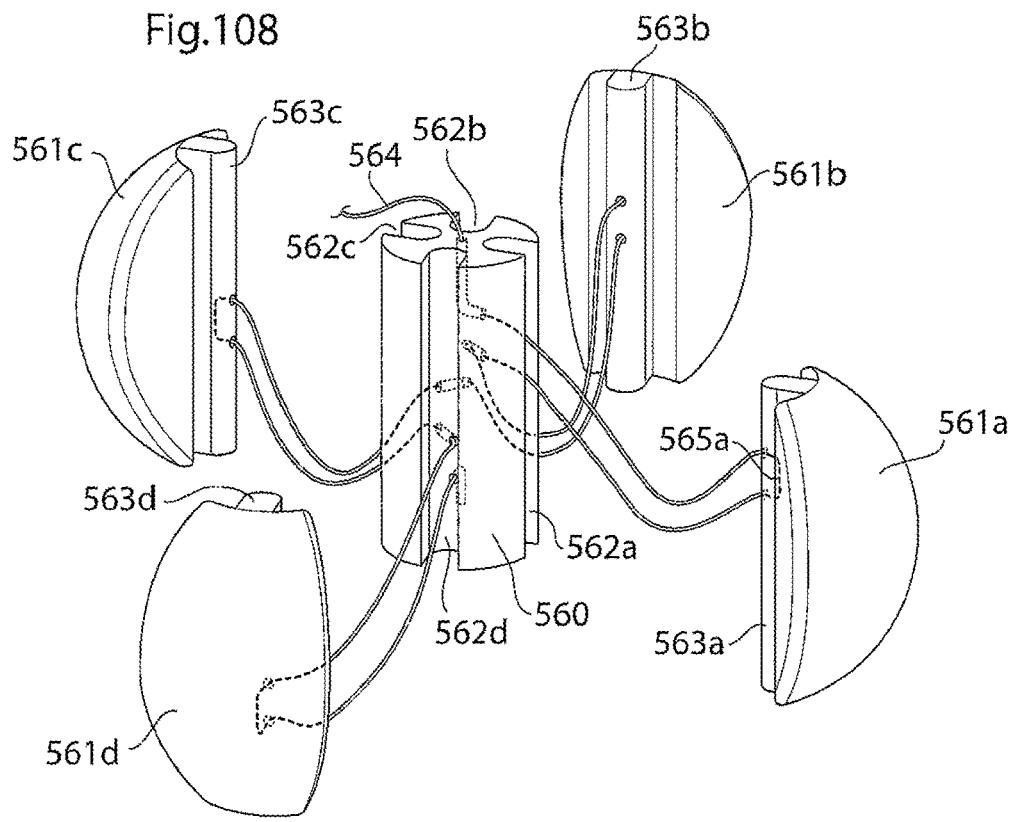
FIG. 108 shows an embodiment of the movement restriction device in segments before assembly.
Figure 109:
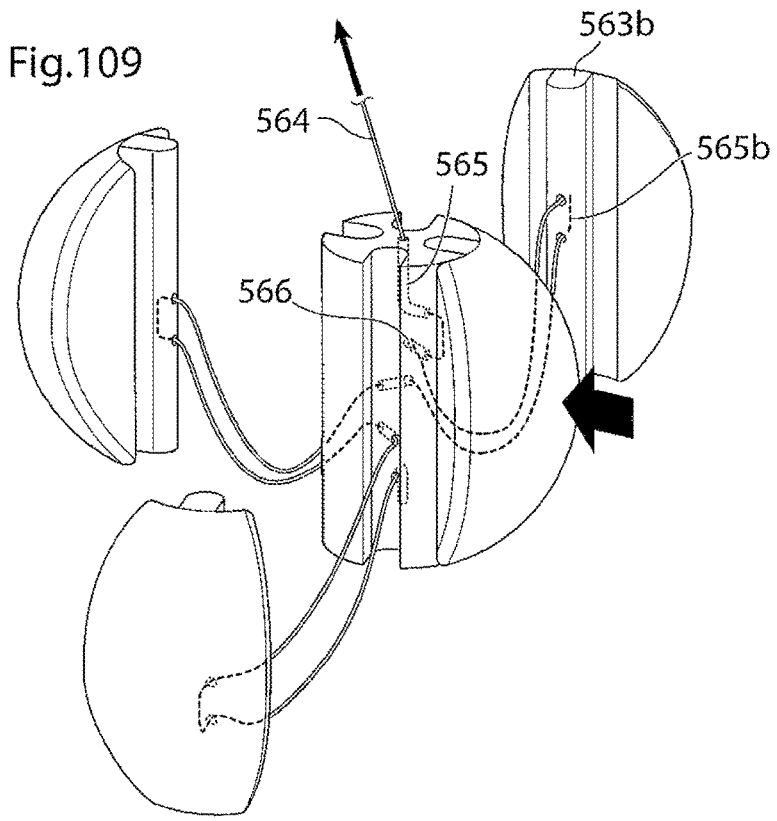
FIG. 109 shows an embodiment of the movement restriction device when first part and second part are assembled.
Figure 110:
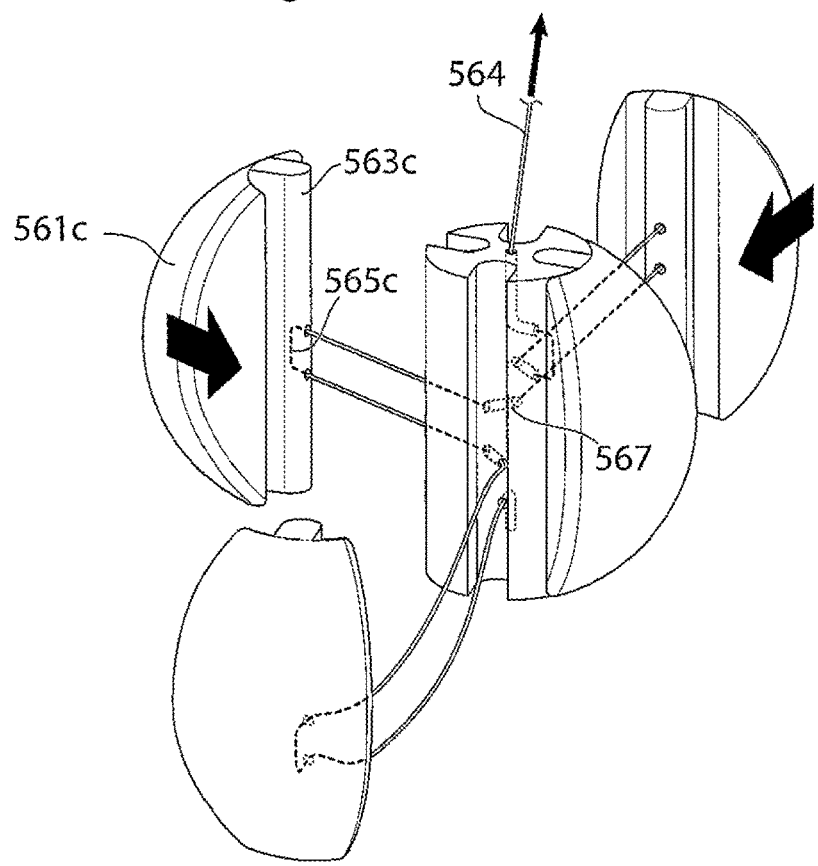
FIG. 110 shows the embodiment of FIG. 109 when a third and a fourth part is assembled.
Figure 111:
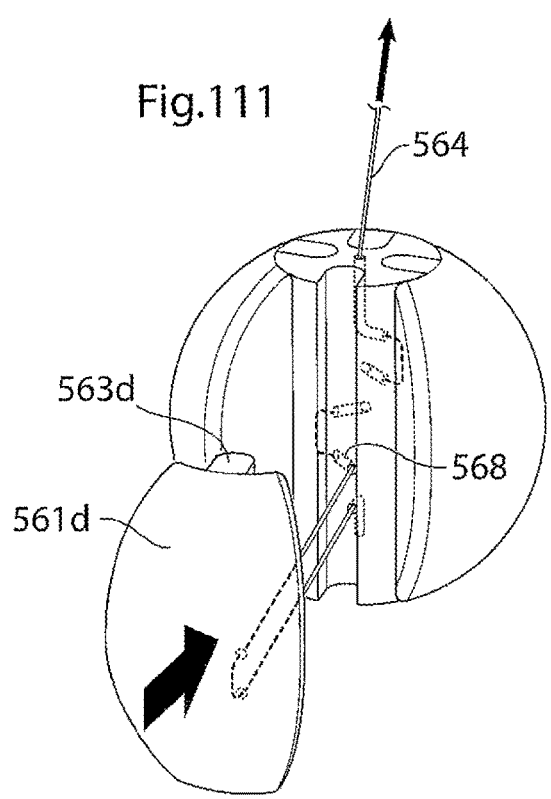
FIG. 111 shows the embodiment of FIG. 110 when assembling the final part.
Figure 112:
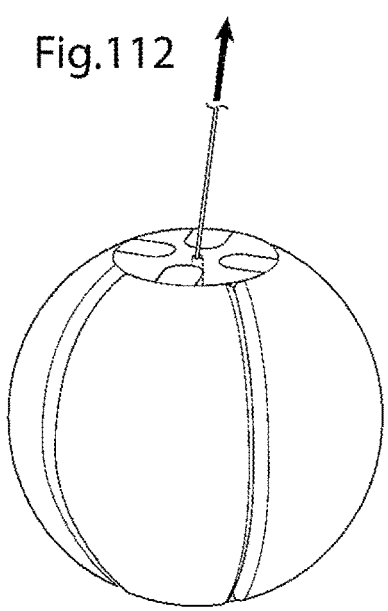
FIG. 112 shows the embodiment of FIGS. 108-111 when finally assembled.
Figure 113A:
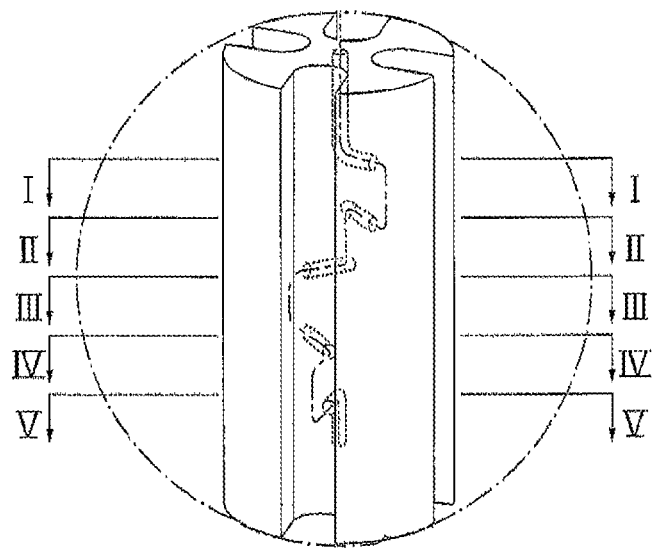
FIG. 113a shows the core part of the embodiment of FIG. 108 with the operation channels.
Figure 113B:
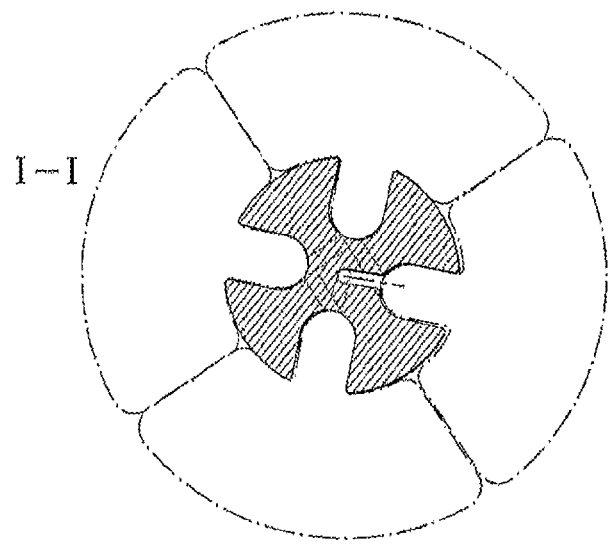
FIGS. 113b to 113f show cross sectional views of the core part of FIG. 113a according to planes I-I; II-II, III-III, IV-IV, respectively.
Figure 113C:
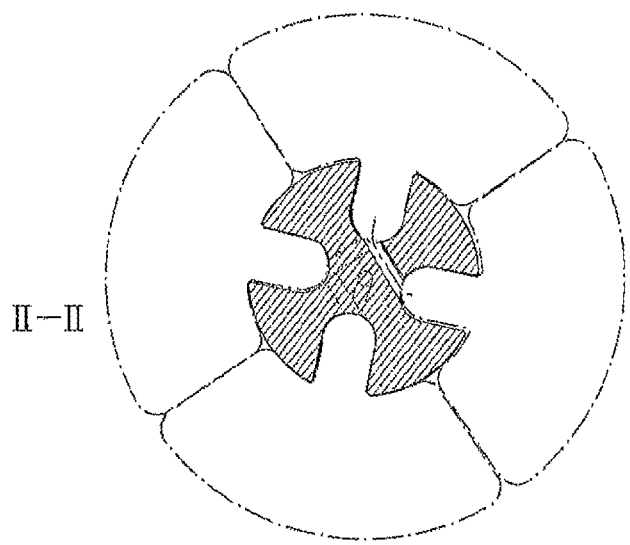
Figure 113D:
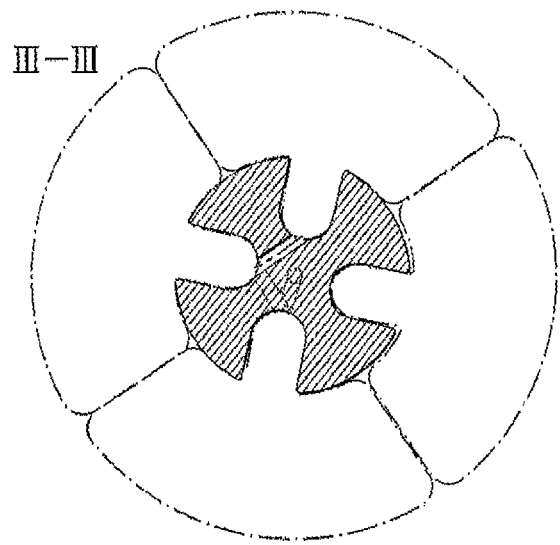
Figure 113E:
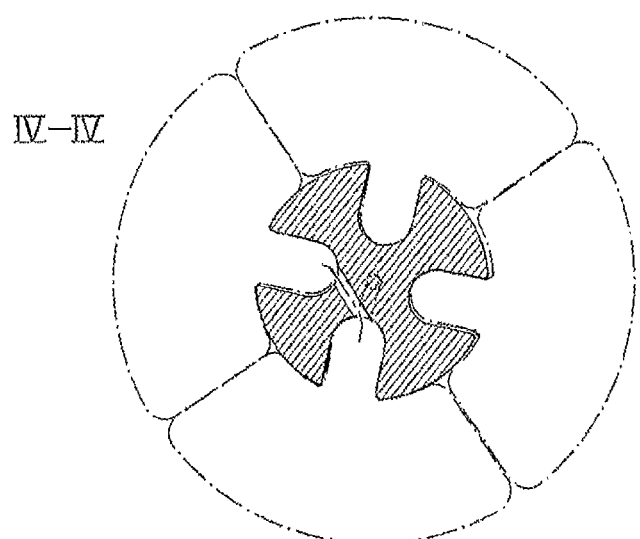
Figure 113F:
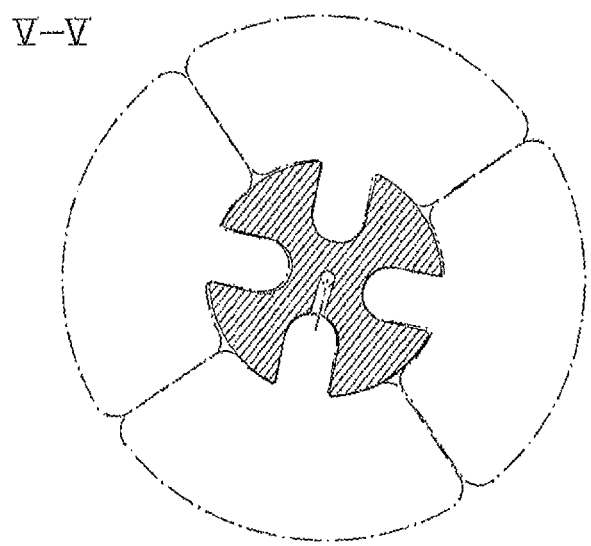

FIG. 108 shows an embodiment of an apparatus according to the invention FIG. 108 shows the segments of a movement restriction device to be assembled before implantation in a patient in the need of treatment for a reflux disease. The movement restriction device segments include a core part 560 and four outer part 561a-561d. The generally cylindrical core part is provided with an upper part 560' and is provided with four slits 562a-562d which are symmetrically distributed end extend along the peripheral outside of the core part, The outer part 561a-561s are shown as generally being a part of sphere having an inner and outer surface and each part is provided with a protruding flange 563a-563d extending along the inner surface. The flanges 563a-563d matches the slits 562a-562d in the depicted embodiment, but can be arranged with loose fits between flanges and slits so the assembled movement restriction device sufficiently is assembled at its implanted target position above the cardia. IC the movement restriction device inadvertently is displaced from this position to the stomach cavity, a loose fit arrangement contributes to a more rapid disassembly its segments. The core part is connected to a guiding wire 564 which extends through first channel 565 in the core part through a corresponding channel 565a between two neighboring orifices in the protrusion 563a in the first outer part 561a. When operating on the guiding wire 564 by displacing it away from the core part upper surface 560' the first outer part 561a will be displaced towards the core part and the flange 563a meets the slit 562a so the first outer part is assembled to the core part 560. As demonstrated in FIG. 109, this performance is repeated with the second outer part, now by the guiding wire 564 through the second channel 566 connected to a corresponding channel in the flange 563b of second outer part 561b. FIG. 110 shows this performance again for assembling the third outer part 561c and third channel 567 connecting the guiding wire 564 to flange 563c. FIG. 111 shows the fourth and last outer part 561d being assembled through flange 563d and channel 568. FIG. 112 shows the finally assembled movement restriction device. FIG. 113a is a more detailed view of the core part showing the system of channels for the guiding wire. FIG. 113b to 113d are crossectional views of planes I-I, II-II, III-III and IV-IV, respectively each at the level for four channels.

The guiding wire is made of a biodegradable material that is degraded so the segments readily become disassembled if the movement restriction device accidently becomes displaced from its implanted position. The segments depicted are made from a biocompatible solid material and are each of size and shape so they readily pass through the gastrointestinal system if the movement restriction device is disassembled. When implanting the so assembled movement restriction device any of the previously described methods will be suitable.

Figure 114:
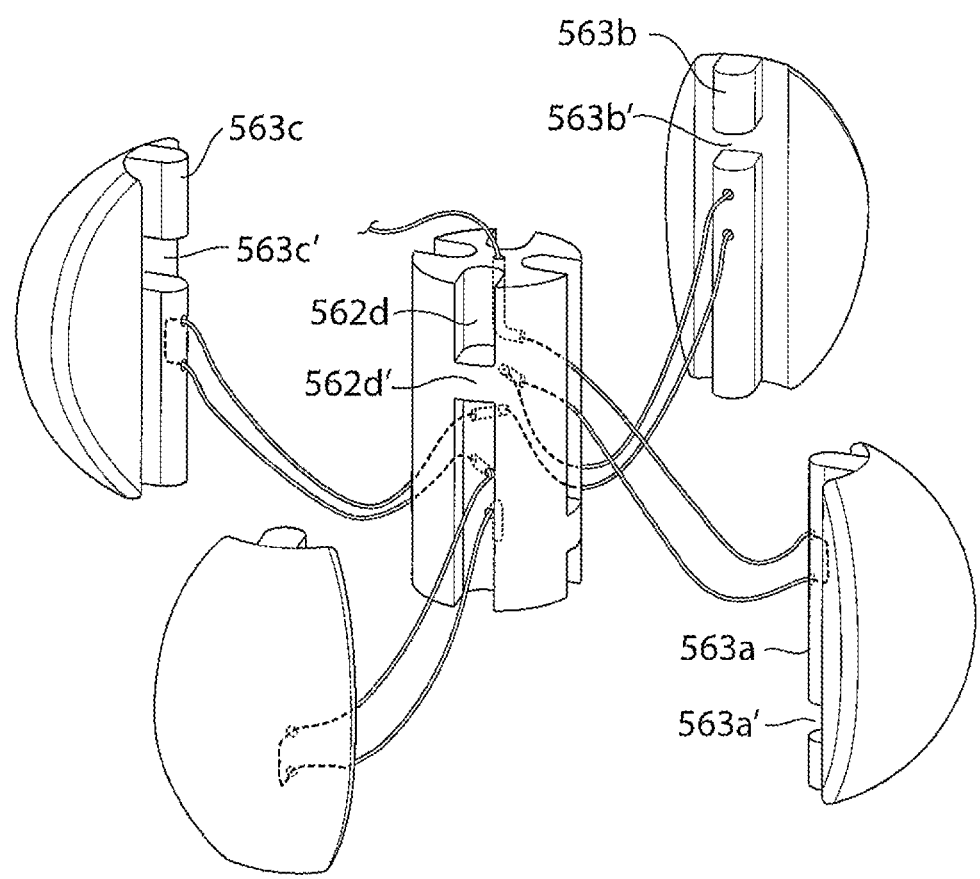
FIGS. 114 and 115 show alternative embodiments of the device as shown in FIG. 108.
Figure 115:
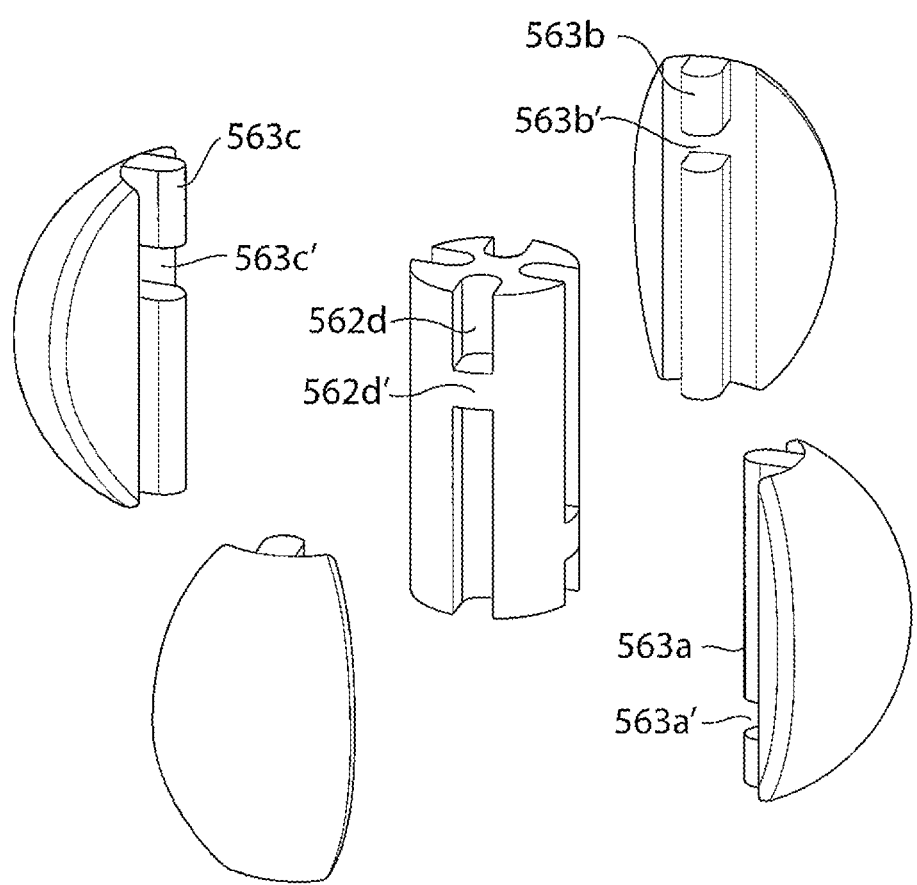

FIG. 114 shows an embodiment of the movement restriction device to be assembled. The outline of the core part and the segments is identical as has been shown in FIG. 108, but the flanges of the segments 563a-d are provided with recesses 563'a-d that match protrusions 562'a-d of the slits 562a-d of the core part so the assembled movement device becomes locked along two different planes. In this embodiment, these planes are perpendicularly arranged. FIG. 115 shows another embodiment of the movement restriction device according to FIG. 114 without any guiding wire and without any features for the guiding wire in the segments. This embodiment requires that matching element locking elements are adapted to assist with the disassembly if the movement restriction device inadvertently becomes displaced from its implanted position.

Figure 116A:
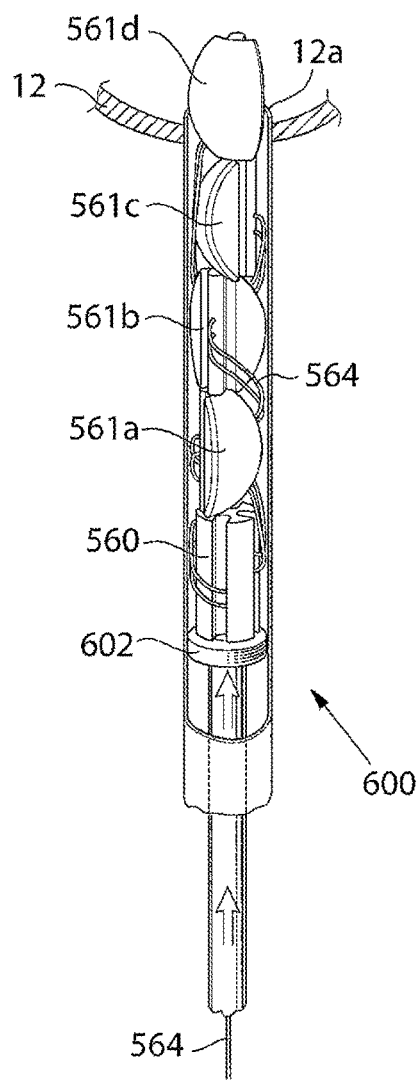
FIGS. 116a-d illustrate the insertion of the movement restriction device segments shown in FIG. 114 by means of an instrument.

A method of injecting or inserting a plurality of movement restriction device segments into a pouch formed by a part of a stomach wall will now be described with reference to FIGS. 116a-d. In this example, a movement restriction device as described above with reference to FIG. 50 will be used. A tube-like instrument, generally designated 600, such as the one also depicted in FIG. 4b, comprises a sleeve 600a having a cross-sectional diameter and shape so as to allow the passage of the core part 560 and the four outer part 561a-561d. A piston 602 is provided to displace the movement restriction device segments through the sleeve 600a and into a space, wherein the movement restriction device segments are to be assembled into or form a movement restriction device. As shown in FIG. 116a, in this example the instrument 600 is used to insert or inject the movement restriction device segments through a hole 12a in a stomach wall portion 12 of a patient.

Figure 116B:
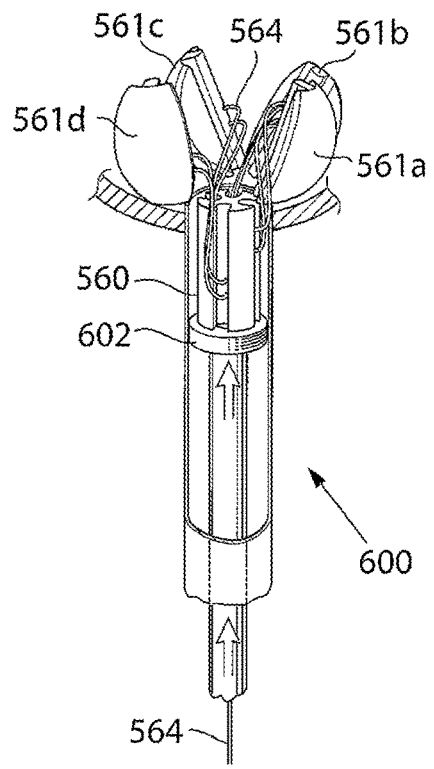
Figure 116C:
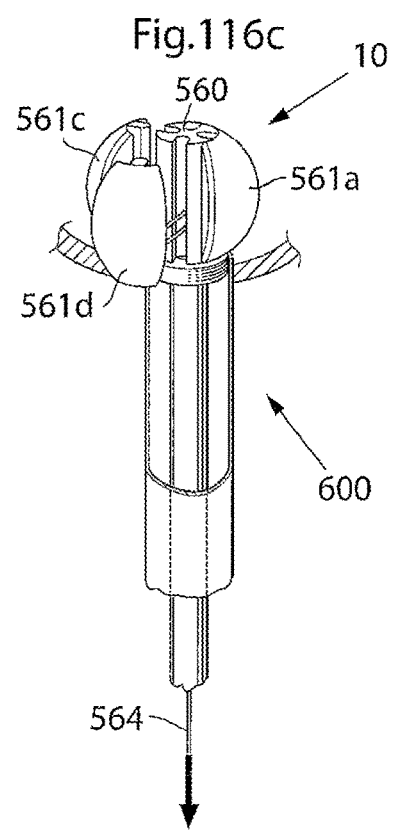

As shown in FIG. 116b, the guiding wire 564 forces the outer part 561a-d to take a respective position like petals to allow the core part 560 to take a position allowing the outer parts 561a-d and the core part 560 to assemble into an essentially spherical movement restriction device 10. By pulling the guiding wire 564, see FIG. 116c, the outer parts 561a-d are moved into engagement with the core part 560, being kept in position by means of the interlocking flanges 563a-d.

Figure 116D:
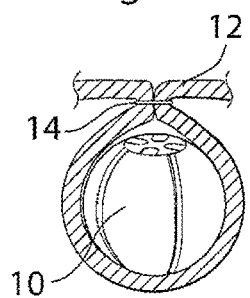

After being fully assembled, see FIG. 116d, the essentially spherical movement restriction device 10 is invaginated in part of the stomach wall 12 by means of sutures or staples 14. The limited space of the pouch formed by the stomach wall prevents the movement restriction device 10 from falling apart, even after the biodegradable guiding wire 564 has been degraded. However, in the event that movement restriction device 10 comes loose, such as by the sutures or staples 14 breaking, the movement restriction device 10 falls apart so that the different segments, each being smaller than the assembled movement restriction device 10, can pass through the gastrointestinal system.

It is evident from the general description and the appended claims that many of other ways designing the movement restriction device is possible without departing from the inventive concept. One such way is to let a plurality of relatively small movement restriction device segments form a movement restriction device, which will now be described with reference to FIGS. 117a-c.

Figure 117A:
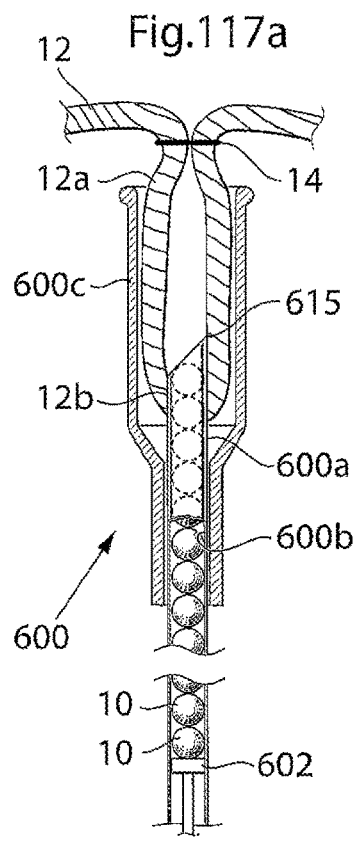
FIGS. 117a-c illustrate a preferred method of invaginating a plurality of movement restriction device segments into a stomach wall using an instrument.

This method of injecting or inserting movement restriction device segments into a pouch is similar to the one described above with reference to FIGS. 47a-d, after a pouch has been created in the stomach wall. Thus, FIG. 117a illustrates a stomach wall portion 12a after sutures or staples 14 have been applied to create a pouch in the stomach wall. The pouch can be provided by using the method described above with reference to FIGS. 48a-i.

Movement restriction device segments 10 are inserted or injected into the pouch by means of a gastroscopic or laparoscopic, tube-like instrument 600, such as the one also depicted in FIG. 47b. The instrument comprises an outer sleeve and an inner sleeve, see FIG. 47b, which can be displaced longitudinally relatively to the outer sleeve. The inner sleeve is provided with a cutter in the form of a cutting edge 615 at the distal end thereof. This cutting edge can be used for cutting a hole in the stomach wall, as will be explained in detail in the following.

When the instrument reaches a stomach wall, the inner sleeve is brought forward from its position in the outer sleeve and into contact with the stomach wall 12a. The cutting edge 615 of the inner sleeve then cuts a hole in the stomach wall so as to allow subsequent insertion of the movement restriction devices 10 into and through this hole, see FIG. 117b. In order to push the movement restriction device through the hole, a piston 602 may be provided in the instrument. Thus, the instrument further comprises a piston 602 adapted for pushing a plurality of movement restriction devices 10 out from a position in the inner sleeve, this position being shown in FIG. 117a, to a position outside of the inner sleeve, this being shown in FIG. 117b.

In order to protect the deflated movement restriction device 10 from the cutting edge 615 of the inner sleeve, a further protective sleeve (not shown) can be provided around the movement restriction device.

The tube-like instrument 600 is in the shown embodiment provided with a cup-shaped extension keeping the pouch in place during the insertion of the movement restriction device segments 10 into the pouch. By gradually withdrawing the tube-like instrument 600 during this process, see FIG. 117b, the pouch can be filled with movement restriction device segments 10 in a controlled way.

Figure 117B:
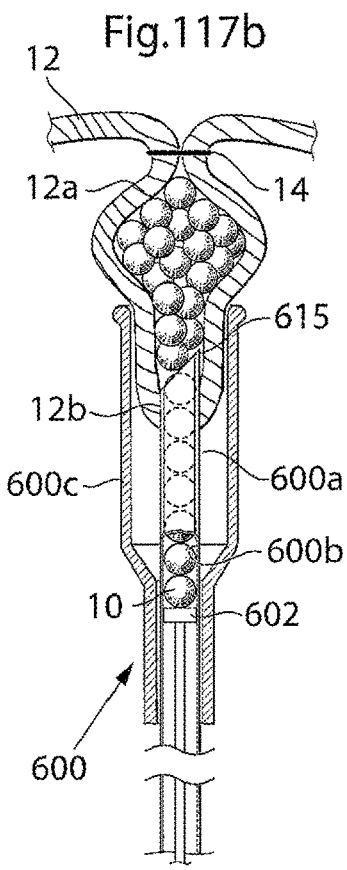
Figure 117C:
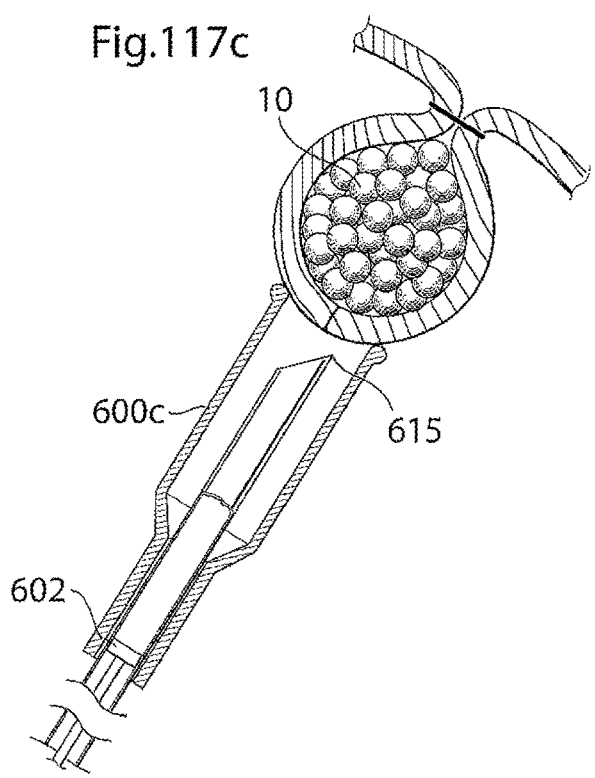
Figure 119A:
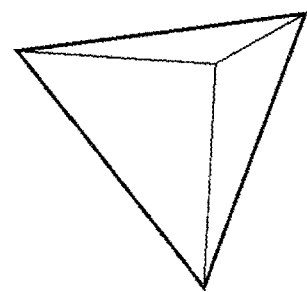
FIGS. 119a-e illustrate different shapes of movement restriction devices when using a plurality of movement restriction device segments to form a movement restriction device.
Figure 119B:
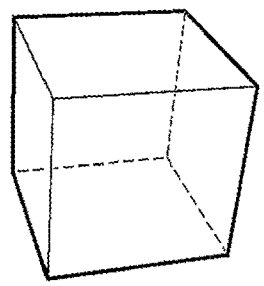
Figure 119C:
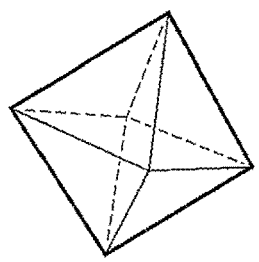
Figure 119D:
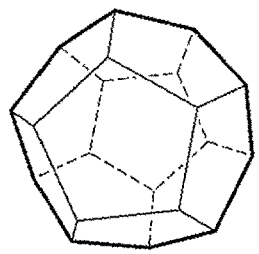
Figure 119E:
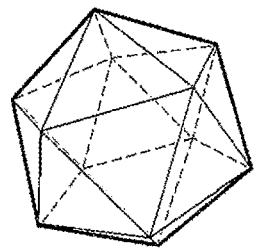

After the pouch has been filled with movement restriction device segment to a desired degree, see FIG. 117c, the hole 12b cut in the stomach wall 12a by means of the tube-shaped instrument 600 is permanently closed by means of suturing or stapling, for example.

Figure 118:
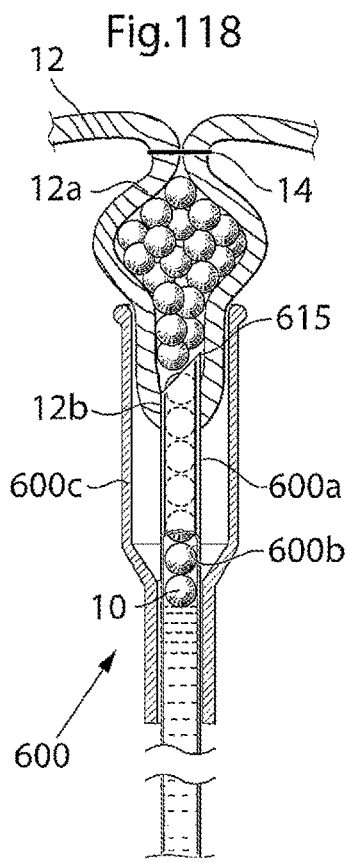
FIG. 118 illustrates an alternative instrument for invaginating a plurality of movement restriction device segments.

In the embodiment shown in FIGS. 117a-c, the tube-like instrument 600 comprises a piston 602 adapted to push or displace the movement restriction device segments 10 along the sleeve 600b. Alternatively, as shown in FIG. 118, pressure exerted by fluid can be used to push or displace the movement restriction device segments 10.

The movement restriction device segments 10 can take many different shapes. In the embodiments shown in FIGS. 117a-c and 118, they are essentially spherical. However, in alternative embodiments, they exhibit one or a plurality of flat or essentially flat surfaces. Preferably, they then take the shape of polyhedrons, such as tetrahedrons, hexahedrons, octahedrons, dodecahedrons or icosahedrons, i.e., regular polyhedrons with four, six, eight, twelve, and twenty flat surfaces, respectively. These examples of movement restriction device segments are shown in FIGS. 119a-e.

The movement restriction devices can additionally be kept in their mutual relationship by means of additional measures. For example, the surfaces of the movement restriction device segments can be provided with friction enhancing agent or material to minimize slipping of the movement restriction device segments. The friction enhancing agent can be some kind of glue or the like. Alternatively or additionally, the surface or surfaces of the movement restriction device segments can be given a rugged texture to increase the friction between adjacent movement restriction device segments.

Figure 120:
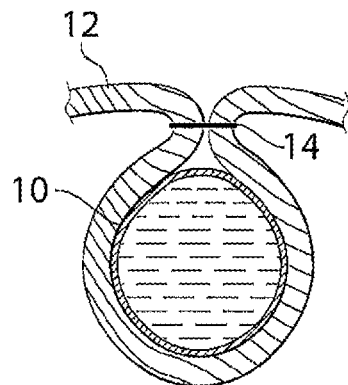
FIG. 120 is a sectional view of a movement restriction device comprising fluid.

As mentioned above, the movement restriction device 10 may be inflated with a gel or fluid supplied into a chamber defined by the movement restriction device 10, see FIG. 120.

Insertion or injection of a plurality of movement restriction device segments 10 into a natural pouch provided by a stomach wall portion 12 has been described above with reference to FIGS. 117a-d. However, in an alternative embodiment of an apparatus for treating obesity shown in FIG. 121, the movement restriction device segments can also comprise a movement restriction device segment for collecting two or more other movement restriction device segments, which are of a different kind. Thus, the apparatus comprises an expandable second movement restriction device segment 10' for collecting two or more first movement restriction device segments 10 different from the second movement restriction device segment, wherein the second movement restriction device segment and the first movement restriction device segments together form the movement restriction device. It is preferred that the second movement restriction device segment is flexible or stretchable.

Figure 122:
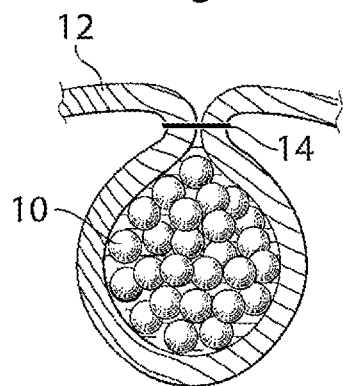
FIG. 122 is a view of a movement restriction device comprising a plurality of movement restriction device segments contained in a fluid.
Figure 123:
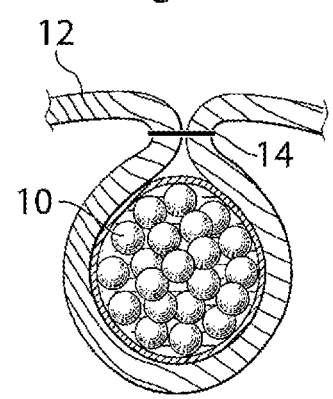
FIG. 123 is a sectional view of a movement restriction device defining a plurality of movement restriction device segments contained in a fluid.

In an alternative embodiment, to allow reshaping of the movement restriction device, there may be a friction reducing fluid to reduce the friction between adjacent movement restriction device segments. In FIG. 122, it is shown how a plurality of movement restriction device segments 10 are provided in a pouch created by part of a stomach wall 12 and a fluid has been injected into this pouch, which allows mutual movement between adjacent first movement restriction device segments so that the shape of the movement restriction device adapts to stomach wall movements, when said movement restriction device is invaginated in a stomach wall.

Figure 121:
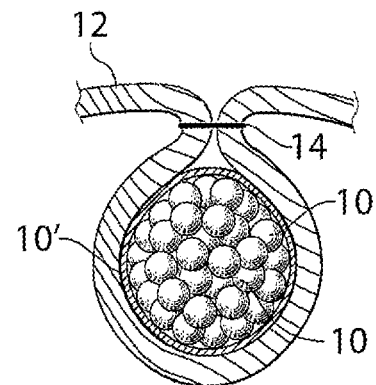
FIG. 121 is a sectional view of a movement restriction device defining a plurality of movement restriction device segments.

The embodiments of FIG. 121 and FIG. 122 may be combined, so that an outer movement restriction device segment 10' encloses both a plurality of different, in this case spherical, movement restriction device segments 10 as well as a fluid, which reduces the friction between the different movement restriction device segments.

The fluid described above may, instead of reducing the friction between adjacent movement restriction device segments, enhance the friction between adjacent movement restriction device segments, thus making the movement restriction device more stable. The friction enhancing material may also be a glue or an adhesive, i.e., a solidifying liquid.

Movement restriction device segments adapted to be used in a plurality to form a movement restriction device have been described above with reference to FIGS. 116a-c and 119a-e. It will be appreciated that these movement restriction device segments can be given the same properties as the movement restriction devices described earlier regarding materials, properties etc.

It is evident from the general description and the appended claims that many of other ways designing the movement restriction device is possible without departing from this concept.

Please note that all the embodiments or features of an embodiment as well as any method or step of a method could be combined in any way if such combination is not clearly contradictory. Please also note that the description in general should be seen as describing both an apparatus and a device adapted to perform a method as well as this method in itself.

A method or part of method to be used in any combination and using any apparatus or part of apparatus or any feature in any combination where the following method steps is applicable, wherein said method may comprise one or more of the following operational method steps:
    introducing said instrument into the throat,
    passing down the esophagus,
    placing an anvil or unit for delivery of fixating members in the esophagus between the cardia and the diaphragm level, for engaging in the fixation of the esophagus to the stomach tissue,
    passing down the esophagus and additionally further down into the stomach,
    filling the stomach with gas to expand the stomach,
    sucking fluid from the stomach,
    looking at a guiding vision when said instrument comprising a camera,
    engaging the instrument with the stomach,
    creating and suturing at least one pouch of the stomach wall,
    filling said at least one pouch with a fluid and/or volume filling device or two or more volume filling devices,
    deliver a plurality of volume filling devices into said pouch created in the stomach tissue through a tubular member,
    passing through the stomach wall with said instrument,
    passing through the stomach wall with said instrument for the placement of a volume filling device on the outside of the stomach wall,
    passing through the stomach wall with said instrument for the placement of a tube allowing placement of a subcutaneous injection port,
    placing an subcutaneous injection port,
    suturing or stapling the stomach wall from the inside thereof to the esophagus,
    suturing or stapling the stomach wall to stomach wall from the inside of the stomach,
    engaging the instrument with the esophagus,
    suturing or stapling one layer of stomach tissue to one layer of esophageal tissue,
    suturing or stapling two layers of stomach tissue to one layer of esophageal tissue,
    suturing or stapling three layers of stomach tissue to one layer of esophageal tissue,
    suturing or stapling four layers of stomach tissue to one layer of esophageal tissue,
    suturing or stapling one or more layers of stomach tissue to two or more positions on the esophageal tissue, the esophagus having an esophagus center axis, the esophagus further having an inner and outer substantially cylindrical surface extending radially in relation to the esophagus center axis and wherein the stomach tissue is attached to esophageal tissue both at a first point along a first esophagus surface length axis, substantially parallel to said esophagus center axis and at a second point along a second esophagus surface length axis, substantially parallel to said esophagus center axis, at a distance from said first esophagus surface length axis, radially in relation to said esophagus center axis,
    delivering fixating members by a unit placed on said instrument,
    penetrating at least one layer of stomach tissue and one layer of esophagus tissue with said fixating members,
    placing said fixating members above the gastro-esophageal junction for creating a tunnel between the esophagus and stomach above said junction,
    placing an esophagus part in the esophagus and a stomach part in the stomach,
    placing the fixating member substantially between the stomach and esophagus part,
    inserting said instrument into the main stomach cavity through the cardia and adapted to direct the instrument in cranial direction to reach a position of said unit above said junction,
    allowing the tunnel a substantially unrestricted contraction and release of the cardia closing sphincter muscle placed in said junction, when such a tunnel has been created.

A method or part of method to be used in any combination and using any apparatus or part of apparatus or any feature in any combination where the following method steps is applicable, wherein said method comprises one or more of the following operational method steps:
    cutting the skin of a patient
    creating an opening in the abdominal wall of the patient
    Introducing said instrument into the abdominal cavity through said opening in the abdominal wall,
    engaging the instrument with the stomach,
    pulling down into the stomach wall for creating at least one pre-shaped pouch of the stomach wall,
    clamping the stomach wall for creating at least one pre-shaped pouch of the stomach wall,
    suturing or stapling at least one pouch in the stomach wall,
    filling said at least one pouch with a fluid and/or volume filling device or two or more volume filling devices,
    deliver a plurality of volume filling devices into said pouch created in the stomach tissue through a tubular member,
    passing through the stomach wall into the stomach with said instrument,
    passing through the stomach wall with said instrument for the placement of a volume filling device on the inside of the stomach wall,
    passing through the stomach wall with said instrument for suturing the stomach wall to the esophagus wall,
    placing a volume filling device on the outside of the stomach wall,
    invaginating said volume filling device in the stomach wall
    placing a subcutaneous injection port,
    suturing or stapling the stomach wall to stomach wall from the outside of the stomach,
    suturing or stapling the stomach wall to stomach wall from the outside of the stomach without penetrating the mucosa,
    suturing or stapling two layers of stomach wall to one or two layers of stomach wall,
    engaging the instrument with the esophagus,
    clamping the on both sides of the esophagus for fixating one layer of esophageal wall to stomach tissue,
    clamping the on both sides of the esophagus and the stomach fundus wall for fixating one layer of esophageal wall to one or two layers of stomach tissue,
    introducing a tube or a gastroscopic instrument into the esophagus comprising an anvil member or a fixating delivery member involving in the fixation of the esophagus to the stomach,
    coordinating the position of the anvil member or a fixating delivery member inside the esophagus to said instrument clamping around the esophagus,
    suturing or stapling one layer of stomach tissue to one layer of esophageal tissue,
    suturing or stapling two layers of stomach tissue to one layer of esophageal tissue, suturing or stapling three layers of stomach tissue to one layer of esophageal tissue, suturing or stapling four layers of stomach tissue to one layer of esophageal tissue, stapling using staplers of different stapling depths at different positions in a stapler row, stapling stomach to esophagus with one first stapler depth and stapling stomach to stomach with a second smaller stapler depth, stapling a pouch with stomach to stomach sutures in a stapler row, further comprising stapling the esophagus with staplers of a larger depth included as a part of said stapler row, suturing or stapling one or more layers of stomach tissue to two or more positions on the esophageal tissue, the esophagus having an esophagus center axis, the esophagus further having an inner and outer substantially cylindrical surface extending radially in relation to the esophagus center axis and wherein the stomach tissue is attached to esophageal tissue both at a first point along a first esophagus surface length axis, substantially parallel to said esophagus center axis and at a second point along a second esophagus surface length axis, substantially parallel to said esophagus center axis, at a distance from said first esophagus surface length axis, radially in relation to said esophagus center axis, delivering fixating members by a unit placed on said instrument, penetrating at least one layer of stomach tissue and one layer of esophagus tissue with said fixating members, placing said fixating members above the gastro-esophageal junction for creating a tunnel between the esophagus and stomach above said junction, allowing the tunnel a substantially unrestricted contraction and release of the cardia closing sphincter muscle placed in said junction, when such a tunnel has been created, placing an esophagus part in the esophagus and a stomach part in the stomach via an introduction into the stomach cavity, placing the fixating member substantially between the stomach and esophagus part, inserting said instrument into the main stomach cavity below said junction and adapted to direct the instrument in cranial direction to reach a position of said unit above said junction, operating a joint comprised in said instrument, for enabling said instrument to be inserted into the main stomach cavity bending said joint in a direction to reach a position of said part of the unit in the esophagus above said junction.

A method or part of method to be used in any combination and using any apparatus or part of apparatus or any feature in any combination where the following method steps is applicable, wherein said method comprises one or more of the following laparoscopic operational method steps:

cutting the skin of a patient introducing a tube through the abdominal wall, filling a fluid or gas into the abdominal cavity, introducing two or more trocars into the abdominal cavity, introducing a camera into the abdominal cavity through one of the trocars, introducing said instrument into the abdominal cavity through a trocar, engaging the instrument with the stomach, pulling down into the stomach wall for creating at least one pre-shaped pouch of the stomach wall, clamping the stomach wall for creating at least one pre-shaped pouch of the stomach wall, suturing or stapling at least one pouch in the stomach wall, filling said at least one pouch with a fluid and/or a volume filling device or two or more volume filling devices, deliver a plurality of volume filling devices into said pouch created in the stomach tissue through a tubular member, passing through the stomach wall into the stomach with said instrument, passing through the stomach wall with said instrument for the placement of a volume filling device on the inside of the stomach wall, passing through the stomach wall with said instrument for suturing the stomach wall to the esophagus wall, placing a volume filling device on the outside of the stomach wall, invaginating said volume filling device in the stomach wall placing a subcutaneous injection port, suturing or stapling the stomach wall to stomach wall from the outside of the stomach, suturing or stapling two layers of stomach wall to one or two layers of stomach wall, suturing or stapling the stomach wall to stomach wall from the outside of the stomach without penetrating the mucosa, engaging the instrument with the esophagus, clamping the on both sides of the esophagus for fixating one layer of esophageal wall to stomach tissue, clamping the on both sides of the esophagus and the stomach fundus wall for fixating one layer of esophageal wall to one or two layers of stomach tissue, introducing a tube or a gastroscopic instrument into the esophagus comprising an anvil member or a fixating delivery member involving in the fixation of the esophagus to the stomach, coordinating the position of the anvil member or a fixating delivery member inside the esophagus to said instrument clamping around the esophagus, suturing or stapling one layer of stomach tissue to one layer of esophageal tissue, suturing or stapling two layers of stomach tissue to one layer of esophageal tissue, suturing or stapling three layers of stomach tissue to one layer of esophageal tissue, suturing or stapling four layers of stomach tissue to one layer of esophageal tissue, stapling using staplers of different stapling depths at different positions in a stapler row, stapling stomach to esophagus with one first stapler depth and stapling stomach to stomach with a second smaller stapler depth, stapling a pouch with stomach to stomach sutures in a stapler row, further comprising stapling the esophagus with staplers of a larger depth included as a part of said stapler row, suturing or stapling one or more layers of stomach tissue to two or more positions on the esophageal tissue, the esophagus having an esophagus center axis, the esophagus further having an inner and outer substantially cylindrical surface extending radially in relation to the esophagus center axis and wherein the stomach tissue is attached to esophageal tissue both at a first point along a first esophagus surface length axis, substantially parallel to said esophagus center axis and at a second point along a second esophagus surface length axis, substantially parallel to said esophagus center axis, at a distance from said first esophagus surface length axis, radially in relation to said esophagus center axis, delivering fixating members by a unit placed on said instrument, penetrating at least one layer of stomach tissue and one layer of esophagus tissue with said fixating members, placing said fixating members above the gastro-esophageal junction for creating a tunnel between the esophagus and stomach above said junction, allowing the tunnel a substantially unrestricted contraction and release of the cardia closing sphincter muscle placed in said junction, when such a tunnel has been created, placing an esophagus part in the esophagus and a stomach part in the stomach via an introduction into the stomach cavity, placing the fixating member substantially between the stomach and esophagus part, inserting said instrument into the main stomach cavity below said junction and adapted to direct the instrument in cranial direction to reach a position of said unit above said junction, operating a joint comprised in said instrument, for enabling said instrument to be inserted into the main stomach cavity bending said joint in a direction to reach a position of said part of the unit in the esophagus above said junction.

Please note that any embodiment or part of embodiment as well as any method or part of method or any apparatus or part of apparatus or any feature or part of feature or any system or part of system could be combined in any applicable way. All examples herein should be seen as part of the general description and therefore possible to combine in any way in general terms.

While specific embodiments of the invention have been illustrated and described herein, it is realized that numerous other embodiments may be envisaged and that numerous additional advantages, modifications and changes will readily occur to those skilled in the art without departing from the spirit and scope of the invention. Therefore, the invention in its broader aspects is not limited to the specific details, representative devices and illustrated examples shown and described herein. Accordingly, various modifications may be made without departing from the spirit or scope of the general inventive concept as defined by the appended claims and their equivalents. It is therefore to be understood that the appended claims are intended to cover all such modifications and changes as fall within a true spirit and scope of the invention. Numerous other embodiments may be envisaged without departing from the spirit and scope of the invention.

The invention claimed is:

1. An apparatus for treating reflux disease of a human patient, the apparatus comprising:

a first movement restriction device segment, and
a second movement restriction device segment,
wherein the first movement restriction device segment and the second movement restriction device segment are adapted to be directly connected, in the patient, to each other into an assembled, implantable movement restriction device, and wherein the first and second movement restriction device segments have a size and shape allowing them to be completely invaginated by a stomach fundus wall portion of the patient and to maintain a predefined shape when assembled and invaginated by the stomach fundus wall portion, without injuring the stomach fundus wall, in a position between the patient's diaphragm and the cardia sphincter, such that movement of the cardiac notch of the patient's stomach towards the patient's diaphragm is restricted to thereby prevent the cardia from sliding through the patient's diaphragm opening into the patient's thorax, wherein the assembled movement restriction device is configured to be disassembled into its movement restriction device segments if the movement restriction device leaves its invaginated stomach position, and wherein the movement restriction device segments are adapted to separately pass through the food passageway, thereby reducing risk for causing obstruction/ileus in the patient's intestine.

2. The apparatus according to claim 1, further comprising a fixation device adapted to secure the assembled movement restriction device in said position, when the movement restriction device is implanted.

3. The apparatus according to claim 2, wherein the fixation device comprises sutures or staples that are configured to attach together portions of the fundus stomach wall that enclose the assembled movement restriction device to secure the movement restriction device in said position.

4. The apparatus according to claim 3, wherein the sutures or staples are configured to attach together portions of the fundus stomach wall to invaginating the movement restriction device in the fundus stomach wall to thereby keep the movement restriction device in place.

5. The apparatus according to claim 3, wherein the sutures or staples are configured to attach together portions of the fundus stomach wall so at to invaginate the movement restriction device from inside of the patient's stomach wall.

6. The apparatus according to claim 3, wherein the sutures or staples are configured to attach together portions of the fundus stomach wall so at to invaginate the movement restriction device from outside of the patient's stomach wall.

7. The apparatus according to claim 1, further comprising at least one holding structure adapted to hold together said first and second movement restriction device segment.

8. The apparatus according to claim 7, wherein said at least one holding structure is a biodegradable holding structure adapted to degrade, such that the segments readily become disassembled if the movement restriction device accidently becomes displaced from its implanted position.

9. The apparatus according to claim 8, wherein said at least one holding structure is a biodegradable wire.

10. The apparatus according to claim 1, wherein movement restriction device having a size, when implanted and in function of at least 125 $mm^3$, and a circumference of at least 15 mm.

* * * * *